(12) United States Patent
Hornbeck et al.

(10) Patent No.: US 7,999,080 B2
(45) Date of Patent: Aug. 16, 2011

(54) REAGENTS FOR THE DETECTION OF PROTEIN PHOSPHORYLATION IN SIGNALING PATHWAYS

(75) Inventors: Peter Hornbeck, Magnolia, MA (US);
Valerie Goss, Seabrook, NH (US);
Kimberly Lee, Seattle, WA (US);
Ting-Lei Gu, Woburn, MA (US);
Albrecht Moritz, Salem, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 70 days.

(21) Appl. No.: 12/309,310

(22) PCT Filed: Jul. 13, 2007

(86) PCT No.: PCT/US2007/073540
§ 371 (c)(1),
(2), (4) Date: Jan. 13, 2009

(87) PCT Pub. No.: WO2008/009002
PCT Pub. Date: Jan. 17, 2008

(65) Prior Publication Data
US 2009/0258436 A1 Oct. 15, 2009

Related U.S. Application Data

(60) Provisional application No. 60/830,550, filed on Jul. 13, 2006.

(51) Int. Cl.
*C07K 16/18* (2006.01)

(52) U.S. Cl. .................................................... 530/387.9
(58) Field of Classification Search .................. None
See application file for complete search history.

(56) References Cited

OTHER PUBLICATIONS

Chen et al (Molecular and Cellular Biology, Jan. 2004, 24:320-329).*
Frodin et al (The EMBO Jounral, 2000, 19:2924-2934).*
Andrade et al (Biochemistry Journal, 2004, 381:437-446).*

* cited by examiner

*Primary Examiner* — Laura B Goddard
(74) *Attorney, Agent, or Firm* — Nancy Chiu Wilker

(57) ABSTRACT

The invention discloses novel phosphorylation sites identified in signal transduction proteins and pathways, and provides phosphorylation-site specific antibodies and heavy-isotope labeled peptides (AQUA peptides) for the selective detection and quantification of these phosphorylated sites/proteins, as well as methods of using the reagents for such purpose. Among the phosphorylation sites identified are sites occurring in the following protein types: adaptor/scaffold proteins, adhesion/extracellular matrix protein, apoptosis proteins, calcium binding proteins, cell cycle regulation proteins, chaperone proteins, chromatin, DNA binding/repair/replication proteins, cytoskeletal proteins, endoplasmic reticulum or golgi proteins, enzyme proteins, G/regulator proteins, inhibitor proteins, motor/contractile proteins, phosphatase, protease, Ser/Thr protein kinases, Protein kinase (Tyr)s, receptor/channel/cell surface proteins, RNA binding proteins, transcriptional regulators, tumor suppressor proteins, ubiquitan conjugating system proteins and proteins of unknown function.

2 Claims, 17 Drawing Sheets

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 2 | MTSS1 | NP_055566.3 | Adaptor / scaffold | Y390 | VTSVHLPDyAHYYTIGPGMFPSSQIPS | AML | KG-1 | SEQ ID NO: 1 |
| 3 | MTSS1 | NP_055566.3 | Adaptor / scaffold | Y393 | VTSVHLPDYAHyYTIGPGMFPSSQIPS | AML | KG-1 | SEQ ID NO: 2 |
| 4 | NCK2 | NP_003572.2 | Adaptor / scaffold | Y342 | VQLVDNYyCIGQR | ALL AML | CTV-1, KOPT-K1, RC-K8, RI-1, platelet | SEQ ID NO: 3 |
| 5 | NCK2 | NP_003572.2 | Adaptor / scaffold | Y50 | TGyVPSNYVER | AML CML glioblastoma | Baf3/E255K, Baf3/H396P, MO-91, T98G, ce042 | SEQ ID NO: 4 |
| 6 | NRAGE | NP_008917.3 | Adaptor / scaffold | Y126 | GPNAAyDFSQAATTGELAANKSEMAI | T cell leukemia | Jurkat | SEQ ID NO: 5 |
| 7 | NRAGE | NP_008917.3 | Adaptor / scaffold | Y161 | VGPNATyNFSQSLNANDLANSRPK | T cell leukemia | Jurkat | SEQ ID NO: 6 |
| 8 | NRAGE | NP_008917.3 | Adaptor / scaffold | Y481 | yLMLKDYTKVPIKR | T cell leukemia | Jurkat | SEQ ID NO: 7 |
| 9 | NUP62 | NP_036478.2 | Adaptor / scaffold | Y422 | EQSGTIyLQHADEER | T cell leukemia | Jurkat | SEQ ID NO: 8 |
| 10 | PAG | NP_060910.2 | Adaptor / scaffold | Y387 | TPNSTLPPAGRPSEEPEPDyEAIQTLN | AML NSCLC T cell lymphoma acute erythroblastic leukemia | H3255, HCC827, HEL, HU-3, KG-1, KG1-A, Mac1, Me-F2, VAL | SEQ ID NO: 9 |
| 11 | PHIP | NP_060404.3 | Adaptor / scaffold | Y235 | GHAAEISDMAVNyENTMIAAGSCDK | ALCL | TS | SEQ ID NO: 10 |
| 12 | PHIP | NP_060404.3 | Adaptor / scaffold | Y984 | KNKIySINPKK | AML SCLC | DMS 153, H69, Molm 14 | SEQ ID NO: 11 |
| 13 | RA70 | NP_003921.2 | Adaptor / scaffold | Y152 | TVFYYyGSDKDK | AML | AML-6735 | SEQ ID NO: 12 |
| 14 | RACK1 | NP_006089.1 | Adaptor / scaffold | Y52 | LTRDETNyGIPQR | CML | Baf3/E255K, Baf3/H396P, Baf3/p210wt, K562 | SEQ ID NO: 13 |
| 15 | RanBP2 | NP_006258.2 | Adaptor / scaffold | Y116 | AKyWLER | AML | KG1-A | SEQ ID NO: 14 |
| 16 | RanBP2 | NP_006258.2 | Adaptor / scaffold | Y1247 | ICANHyISPDMK | AML | KG-1, KG1-A | SEQ ID NO: 15 |
| 17 | RanBP2 | NP_006258.2 | Adaptor / scaffold | Y1271 | SFVWHALDyADELPKPEQLAIR | AML | KG-1, KG1-A | SEQ ID NO: 16 |
| 18 | RanBP2 | NP_006258.3 | Adaptor / scaffold | Y785 | STPSPTRySLSPSKSYKYSPK | AML | AML-6735 | SEQ ID NO: 17 |
| 19 | RanBP2 | NP_006258.3 | Adaptor / scaffold | Y793 | STPSPTRYSLSPSKSyKYSPK | AML | AML-6735 | SEQ ID NO: 18 |
| 20 | RanBP2 | NP_006258.3 | Adaptor / scaffold | Y795 | STPSPTRYSLSPSKSYKySPK | AML | AML-6735 | SEQ ID NO: 19 |
| 21 | SAMSN1 | NP_071419.3 | Adaptor / scaffold | Y130 | ASDSMDSLySGQSSSSGITSCSDGTS | AML | CTV-1, KG1-A | SEQ ID NO: 20 |
| 22 | SAP97 | NP_004078.1 | Adaptor / scaffold | Y606 | FIEAGQyNNHLYGTSVQSVR | T cell leukemia | Jurkat | SEQ ID NO: 21 |
| 23 | SG2NA | NP_001077362.1 | Adaptor / scaffold | Y374 | TKLyDMIADLGDDELPHIPSGIINQSR | AML | KG1-A | SEQ ID NO: 22 |
| 24 | SHEP1 | NP_005480.1 | Adaptor / scaffold | Y26 | AAGEPEAGSDyVK | B cell lymphoma | RI-1 | SEQ ID NO: 23 |
| 25 | SKAP55 | NP_003717.3 | Adaptor / scaffold | Y299 | GVDYASYyQGLWDCHGDGPDELSFC | AML | CTV-1 | SEQ ID NO: 24 |
| 26 | SLAP-130 | NP_001456.3 | Adaptor / scaffold | Y4 | yNTGGNPTEDVSVNSR | T cell leukemia | Jurkat | SEQ ID NO: 25 |
| 27 | SLAP-130 | NP_001456.3 | Adaptor / scaffold | Y801 | NEEGKyGYVLR | T cell leukemia | Jurkat | SEQ ID NO: 26 |
| 28 | SLAP-130 | NP_001456.3 | Adaptor / scaffold | Y803 | NEEGKYGyVLR | T cell leukemia | Jurkat | SEQ ID NO: 27 |
| 29 | N-cad | NP_001783.2 | Adhesion or extracell | Y785 | YDEEGGGEEDQDyDLSQLQQPDTVE | T cell leukemia | Jurkat, rat brain | SEQ ID NO: 28 |
| 30 | Plakophilin 4 | NP_003619.2 | Adhesion or extracell | Y425 | TYYSPVyRSPNHGTVELQGSQTALYR | CML | K562 | SEQ ID NO: 29 |
| 31 | ROBO2 | NP_002933.1 | Adhesion or extracell | Y65 | WyKDGER | T cell leukemia | Jurkat | SEQ ID NO: 30 |
| 32 | ROBO2 | NP_002933.1 | Adhesion or extracell | Y693 | GLSNyAVTFQR | AML | HU-3 | SEQ ID NO: 31 |
| 33 | Scribble | NP_056171.2 | Adhesion or extracell | Y834 | MVEPENAVTITPLRPEDDySPRER | T cell leukemia | Jurkat | SEQ ID NO: 32 |
| 34 | SDK2 | NP_061937.3 | Adhesion or extracell | Y914 | NGLVLGyKVMYKEK | multiple myeloma | RPMI8226 | SEQ ID NO: 33 |
| 35 | selectin P | NP_002996.1 | Adhesion or extracell | Y818 | CPLNPHSHLGTyGVFTNAAFDPSP | AML | CHRF | SEQ ID NO: 34 |
| 36 | SIGLEC5 | NP_003821.1 | Adhesion or extracell | Y544 | KSREPKDQEAPSTTEySEIKTSK | AML | CMK | SEQ ID NO: 35 |
| 37 | NCKAP1 | NP_038464.1 | Apoptosis | Y1116 | NAyHAVYKQSVTSSA | CML | K562 | SEQ ID NO: 36 |
| 38 | NCKAP1 | NP_038464.1 | Apoptosis | Y1120 | NAYHAVyKQSVTSSA | CML | K562 | SEQ ID NO: 37 |
| 39 | NCKAP1 | NP_038464.1 | Apoptosis | Y959 | VAMNVyELSSAAGLPCEIDPALVVALS | CML | K562 | SEQ ID NO: 38 |
| 40 | SART1 | NP_005137.1 | Apoptosis | Y783 | TPyIVLSGSGK | AML | MKPL-1 | SEQ ID NO: 39 |
| 41 | NASP | NP_002473.2 | Cell cycle regulation | Y148 | EQVyDAMGEK | T cell leukemia | Jurkat | SEQ ID NO: 40 |
| 42 | NOL1 | NP_006161.2 | Cell cycle regulation | Y438 | LGVTNTIISHyDGR | CML T cell leukemia breast cancer | BaF3-4ZF, HCC1806, Jurkat | SEQ ID NO: 41 |
| 43 | NuMA-1 | NP_006176.2 | Cell cycle regulation | Y1839 | KLDVEEPDSANSSFySTR | breast cancer | Jurkat | SEQ ID NO: 42 |
| 44 | OFD1 | NP_003602.1 | Cell cycle regulation | Y187 | LQLIDDQFADAyPQRIKFESLEIKLNEY | T cell leukemia | K562, MOLT15 | SEQ ID NO: 43 |
| 45 | OFD1 | NP_003602.1 | Cell cycle regulation | Y558 | QTQTALENEVyCNPK | CML T cell ALL | RC-K8 | SEQ ID NO: 44 |
| 46 | OFD1 | NP_003602.1 | Cell cycle regulation | Y611 | ITNyPTAWVEGSSPDSDLEFVANTK | AML | KG1-A | SEQ ID NO: 45 |
| 47 | ORC3L | NP_036513.2 | Cell cycle regulation | Y607 | IALHTALNNPyYYLXNEALK | AML | MKPL-1 | SEQ ID NO: 46 |
| 48 | ORC3L | NP_036513.2 | Cell cycle regulation | Y608 | IALHTALNNPYyYLX | AML | KG1-A | SEQ ID NO: 47 |
| 49 | PAFAH1B1 | NP_000421.1 | Cell cycle regulation | Y28 | SNGYEEAySVFKK | AML CML T cell ALL | Baf3/E255K, CTV-1, MKPL-1, MOLT15 | SEQ ID NO: 48 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 50 | PAFAH1B1 | NP_000421.1 | Cell cycle regulation | Y394 | TAPyVVTGSVDQTVK | CML | BaF3-10ZF BaF3-4ZF | SEQ ID NO: 49 |
| 51 | RASSF2 | NP_055552.1 | Cell cycle regulation | Y224 | FKIENSAEEFALyVVHTSGEK | T cell ALL | MOLT15 | SEQ ID NO: 50 |
| 52 | securin | NP_004210.1 | Cell cycle regulation | Y111 | SSVPASDDAyPEIEK | T cell leukemia gastric cancer | Jurkat NCI-N87 | SEQ ID NO: 51 |
| 53 | septin 7 | NP_001779.2 | Cell cycle regulation | Y22 | NLEGyVGFANLPNQVyR | T cell ALL | MOLT15 | SEQ ID NO: 52 |
| 54 | septin 7 | NP_001779.2 | Cell cycle regulation | Y61* | STLINSLFLTDLYSPEyPGPSHR | AML T cell ALL | CTV-1 MOLT15 HL55B | SEQ ID NO: 53 |
| 55 | PDIA5 | NP_006801.1 | Chaperone | Y178 | KEEKPLLIMFyAPWCSMCK | CLL | TRE-cll patient | SEQ ID NO: 54 |
| 56 | RP2 | NP_008846.1 | Chaperone | Y245 | QKSSDESCLVVLFAGDyTIANAR | T cell ALL | MOLT15 | SEQ ID NO: 55 |
| 57 | SGTA | NP_003012.1 | Chaperone | Y141 | LGNyAGAVQDCER | AML | CTV-1 MO-91 | SEQ ID NO: 56 |
| 58 | NEIL3 | NP_060718.1 | Chromatin, DNA-bind | Y246 | AGLALSKHyKVYK | multiple myeloma | RPMI8266 XG2 | SEQ ID NO: 57 |
| 59 | PARP1 | NP_001609.1 | Chromatin, DNA-bind | Y775 | VEMLDNLLDIEVAySLLR | AML | KG1-A | SEQ ID NO: 58 |
| 60 | PLSCR1 | NP_066928.1 | Chromatin, DNA-bind | Y74 | YNQPVyNQPVGA | AML | UT-7 | SEQ ID NO: 59 |
| 61 | POLB | NP_002681.1 | Chromatin, DNA-bind | Y250 | EyPHRRIDIRLIPK | ALL AML NSCLC SCLC breast cancer glioblastoma multiple myeloma transformed kidney | 293 T AML-6735 CHRF Calu-3 DBTRG-05MG DMS 153 DMS 79 DND41 ELF-153 GDM-1 H1734 H358 HCC1395 HL117B HL132B HL59b HL66B HL87A HL98A KMS11 LOU-NH91 M059K OPM-1 WSU-NHL XG2 cs037 | SEQ ID NO: 60 |
| 62 | POLE2 | NP_002683.2 | Chromatin, DNA-bind | Y99 | VyNSERKKFLPL | AML | CMK | SEQ ID NO: 61 |
| 63 | PURA | NP_005850.1 | Chromatin, DNA-bind | Y240 | FFFDVGSNKyGVFMR | AML | CTV-1 | SEQ ID NO: 62 |
| 64 | REV3 | NP_002903.2 | Chromatin, DNA-bind | Y2984 | LNATyYITK | | XG2 | SEQ ID NO: 63 |
| 65 | REV3 | NP_002903.2 | Chromatin, DNA-bind | Y2985 | LNATYyITK | | XG2 | SEQ ID NO: 64 |
| 66 | SAFB1 | NP_002958.2 | Chromatin, DNA-bind | Y723 | DDAyWPEAKR | AML | MKPL-1 | SEQ ID NO: 65 |
| 67 | SET | NP_003002.1 | Chromatin, DNA-bind | Y106 | ALLGEEDEEALHy | AML | UT-7 | SEQ ID NO: 66 |
| 68 | NEB | NP_004534.2 | Cytoskeletal protein | Y2144 | yILLPDAMNIELTR | T cell leukemia | Jurkat | SEQ ID NO: 67 |
| 69 | NEB | NP_004534.2 | Cytoskeletal protein | Y2647 | QAyDLQSDNLyKSDLQWLK | AML | KY821 | SEQ ID NO: 68 |
| 70 | NEB | NP_004534.2 | Cytoskeletal protein | Y2655 | QAYDLQSDNLyKSDLQWLK | AML | KY821 | SEQ ID NO: 69 |
| 71 | NEB | NP_004534.2 | Cytoskeletal protein | Y3742 | DyDLRADAISIKSAKASR | AML | KG1-A | SEQ ID NO: 70 |
| 72 | PDLIM3 | NP_055291.1 | Cytoskeletal protein | Y361 | TKPPEGYDTVTLyPKA | multiple myeloma | KMS18 | SEQ ID NO: 72 |
| 73 | plectin 1 | NP_000436.2 | Cytoskeletal protein | Y3667 | QQGLASyDYVR | T cell ALL | MOLT15 | SEQ ID NO: 73 |
| 74 | plectin 1 | NP_000436.2 | Cytoskeletal protein | Y286 | SIITYVSSLyDAMPR | AML CML T cell ALL | Baf3/E255K Baf3/M351T Baf3/Y253F CTV-1 MOLT15 rat brain | SEQ ID NO: 74 |
| 75 | PPHLN1 | NP_057572.5 | Cytoskeletal protein | Y162 | SySFHQSQHR | T cell leukemia | Jurkat | SEQ ID NO: 75 |
| 76 | PPHLN1 | NP_057572.5 | Cytoskeletal protein | Y52 | yYSHVDYR | T cell leukemia | Jurkat | SEQ ID NO: 76 |
| 77 | profilin 1 | NP_005013.1 | Cytoskeletal protein | Y60 | SSFyVNGLTLGGQK | T cell leukemia glioblastoma | Jurkat M059J | SEQ ID NO: 77 |
| 78 | SGCD | NP_000328.2 | Cytoskeletal protein | Y23 | STMPGSVGPQVyKVGIyGWRK | T cell leukemia | Jurkat | SEQ ID NO: 78 |
| 79 | SGCD | NP_000328.2 | Cytoskeletal protein | Y28 | STMPGSVGPQVYKVGIyGWRK | T cell leukemia | Jurkat | SEQ ID NO: 79 |
| 80 | RCN2 | NP_002893.1 | Endoplasmic reticulur | Y311 | QLHDDyFYHDEL | T cell leukemia | Jurkat | SEQ ID NO: 81 |
| 81 | MVD | NP_002452.1 | Enzyme, misc. | Y276 | DSNQFHATCLDTFPPISyLNAISWR | | K562 | SEQ ID NO: 82 |
| 82 | NANS | NP_018189.2 | Enzyme, misc. | Y188 | QVYQIVKPLNPNFCFLQCTSAyPLQPI | T cell ALL | MOLT15 | SEQ ID NO: 83 |
| 83 | NARG1 | NP_476516.1 | Enzyme, misc. | Y86 | SHVCWHVyGLLQR | T cell ALL | MOLT15 | SEQ ID NO: 84 |
| 84 | NARS | NP_004530.1 | Enzyme, misc. | Y539 | DVCLyPR | AML CML | BaF3-10ZF BaF3-4ZF BaF3-PRTK CTV-1 KG-1 | SEQ ID NO: 85 |
| 85 | NDUFA5 | NP_004991.1 | Enzyme, misc. | Y28 | ILyTKILDVLEEIPK | CML | K562 | SEQ ID NO: 86 |
| 86 | NDUFS1 | NP_004997.4 | Enzyme, misc. | Y316 | GLLTyTSWEDALSR | T cell ALL | MOLT15 | SEQ ID NO: 87 |
| 87 | NKEF-B | NP_005800.3 | Enzyme, misc. | Y193 | PGSDTIKPNVDDSKEyFSK | T cell leukemia | Jurkat | SEQ ID NO: 88 |
| 88 | NT5C | NP_055410.1 | Enzyme, misc. | Y65 | ALRPDLADKVASWyEAPGFFLDLEPIP | T cell ALL | MOLT15 | SEQ ID NO: 89 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 89 | OAS3 | NP_006178.2 | Enzyme, misc. | Y376 | SLNAVyPR | AML | CTV-1 | SEQ ID NO: 90 |
| 90 | p40phox | NP_000522.2 | Enzyme, misc. | Y243 | CyYYEDTISTIK | AML | KG-1 | SEQ ID NO: 91 |
| 91 | p47phox | NP_000256.3 | Enzyme, misc. | Y48 | FTElyEFHK | AML | Nomo-1 | SEQ ID NO: 92 |
| 92 | PARP4 | NP_006428.2 | Enzyme, misc. | Y17 | VKyLPQQQKK | ALCL | TS | SEQ ID NO: 93 |
| 93 | PARS2 | NP_689481.2 | Enzyme, misc. | Y430 | FGyPFVIAGK | ALCL | TS | SEQ ID NO: 94 |
| 94 | PCYT1A | NP_005008.2 | Enzyme, misc. | Y359 | AAAyDISEDEED | T cell leukemia | Jurkat | SEQ ID NO: 95 |
| 95 | PCYT2 | NP_002852.1 | Enzyme, misc. | Y170 | AHHSSQEMSSEyREYADSFGK | T cell leukemia | Jurkat | SEQ ID NO: 96 |
| 96 | PCYT2 | NP_002852.1 | Enzyme, misc. | Y173 | AHHSSQEMSSEYREyADSFGK | T cell leukemia | Jurkat | SEQ ID NO: 97 |
| 97 | PECI | NP_006108.2 | Enzyme, misc. | Y255 | ATFHTPFSHLGQSPEGCSSyTFPK | AML CML NSCLC breast cancer | H2030 HCC1806 K562 MDA-MB-453 OCI-M1 WSU-NHL | SEQ ID NO: 98 |
| 98 | PGAM-1 | NP_002620.1 | Enzyme, misc. | Y119 | RSyDVPPPPMEPDHPFYSNISK | AML CML multiple myeloma prostate cancer | BaF3-10ZF BaF3-FLT3(D842Y) BaF3-PRTK CHRF DU145 Molm 14 OPM-1 | SEQ ID NO: 99 |
| 99 | PGAM-1 | NP_002620.1 | Enzyme, misc. | Y133 | SYDVPPPPMEPDHPFySNISK | T cell ALL | MOLT15 | SEQ ID NO: 100 |
| 100 | PGK1 | NP_000282.1 | Enzyme, misc. | Y76 | SVVLMSHLGRPDGVPMPDKySLEPVI | T cell ALL | MOLT15 | SEQ ID NO: 101 |
| 101 | PGM3 | NP_056414.1 | Enzyme, misc. | Y347 | YLEEVMKVPVyCTK | T cell ALL | MOLT15 | SEQ ID NO: 102 |
| 102 | PIPMT | NP_079107.5 | Enzyme, misc. | Y67 | DSGNNSGDQATEEEEGGySCGTAEST | T cell leukemia | Jurkat | SEQ ID NO: 103 |
| 103 | PKM2 | NP_002645.3 | Enzyme, misc. | Y175 | VVEVGSKIyVDDGLISLQVK | AML CML | BaF3-10ZF BaF3-4ZF BaF3-PRTK KG1-A cs048 hl146a | SEQ ID NO: 104 |
| 104 | PLCD3 | NP_588614.1 | Enzyme, misc. | Y222 | SLLRMVNVDMNDMyAYLLFK | AML | KG1-A OCI-M1 | SEQ ID NO: 105 |
| 105 | PLCD3 | NP_588614.1 | Enzyme, misc. | Y224 | SLLRMVNVDMNDMYAyLLFK | AML | KG1-A OCI-M1 | SEQ ID NO: 106 |
| 106 | PLCG1 | NP_002651.2 | Enzyme, misc. | Y186 | NMLSQVNyRVPNMR | CML lymphoma | BaF3-10ZF BaF3-Tel/FGFR3 SUPT-13 | SEQ ID NO: 107 |
| 107 | PLCG1 | NP_002651.2 | Enzyme, misc. | Y210 | SGDiTyGQFAQLYR | AML CML | BaF3-10ZF MO-91 | SEQ ID NO: 108 |
| 108 | PLCG1 | NP_002651.2 | Enzyme, misc. | Y217 | SGDiTYGQFAQLyR | CML | BaF3-10ZF | SEQ ID NO: 109 |
| 109 | PLCG1 | NP_002651.2 | Enzyme, misc. | Y379 | CIELDCWDGPDGMPVIyHGHTLTTK | AML CML lymphoma | BaF3-10ZF BaF3-Tel/FGFR3 KG-1 MO-91 SUPT-13 | SEQ ID NO: 110 |
| 110 | PLCG1 | NP_002651.2 | Enzyme, misc. | Y428 | NMAQyFK | AML | MO-91 | SEQ ID NO: 111 |
| 111 | PLCG1 | NP_002651.2 | Enzyme, misc. | Y496 | NGIlyLEDPVNHEWYPHYFVLTSSK | CML | BaF3-10ZF BaF3-Tel/FGFR3 | SEQ ID NO: 112 |
| 112 | PLCG1 | NP_002651.2 | Enzyme, misc. | Y506 | NGILYLEDPVNHEWyPHYFVLTSSK | AML CML multiple myeloma | BaF3-4ZF BaF3-PRTK KG-1 KG1-A KMS11 | SEQ ID NO: 113 |
| 113 | PLCG1 | NP_002651.2 | Enzyme, misc. | Y509 | NGILYLEDPVNHEWYPHyFVLTSSK | CML | BaF3-10ZF BaF3-Tel/FGFR3 | SEQ ID NO: 114 |
| 114 | PLCG1 | NP_002651.2 | Enzyme, misc. | Y833 | SAIIQNVEKQEGGWWRGDyGGKK | AML | MO-91 | SEQ ID NO: 115 |
| 115 | PLCG2 | NP_002652.2 | Enzyme, misc. | Y1137 | FVVyEEDMFSDPNFLAHATYPIKAVK | AML | KG-1 | SEQ ID NO: 116 |
| 116 | PLCG2 | NP_002652.2 | Enzyme, misc. | Y482 | QQGELyMWDSIDQK | AML | KG-1 MO-91 RI-1 | SEQ ID NO: 117 |
| 117 | PLCG2 | NP_002652.2 | Enzyme, misc. | Y495 | HyCAIADAX | AML CML | 3T3 T×B BaF3-10ZF BaF3-4ZF BaF3-PRTK BaF3-Tel/FGFR3 MO-91 | SEQ ID NO: 118 |
| 118 | PLCG2 | NP_002652.2 | Enzyme, misc. | Y811 | GALIHNVSKEPGGWWKGDyGTR | AML CML | BaF3-Tel/FGFR3 MO-91 | SEQ ID NO: 119 |
| 119 | PLCG2 | NP_002652.2 | Enzyme, misc. | Y818 | QQyFPSNYVEDISTADFEELEK | AML | KG-1 MO-91 | SEQ ID NO: 120 |
| 120 | PLCL1 | NP_006217.1 | Enzyme, misc. | Y474 | MSVDyNGEQK | T cell leukemia | Jurkat | SEQ ID NO: 121 |
| 121 | PPIE | NP_006103.1 | Enzyme, misc. | Y143 | SNPQVyMDIK | ALCL | TS | SEQ ID NO: 122 |
| 122 | RARS | NP_002878.2 | Enzyme, misc. | Y291 | RAyQCVVLLQGKNPDITX | ALCL | TS | SEQ ID NO: 123 |
| 123 | RARS | NP_002878.2 | Enzyme, misc. | Y382 | SDGGyTYDTSDLAAIK | CML | BaF3-10ZF BaF3-4ZF BaF3-PRTK | SEQ ID NO: 124 |
| 124 | RENT1 | NP_002902.2 | Enzyme, misc. | Y1101 | SQIDVALSQDSTyQGER | T cell leukemia | Jurkat | SEQ ID NO: 125 |
| 125 | RENT1 | NP_002902.2 | Enzyme, misc. | Y1107 | AyQHGGVTGLSQY | T cell leukemia | Jurkat | SEQ ID NO: 126 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 126 | RENT1 | NP_002902.2 | Enzyme, misc. | Y1118 | AYQHGGVTGLSQy | T cell ALL / T cell leukemia | Jurkat / MOLT15 | SEQ ID NO: 127 |
| 127 | RENT1 | NP_002902.2 | Enzyme, misc. | Y858 | ARyGVIIVGNPK | ALCL | TS | SEQ ID NO: 128 |
| 128 | RENT1 | NP_002902.2 | Enzyme, misc. | Y935 | FMTTAMyDAR | T cell ALL / T cell leukemia | Jurkat / MOLT15 | SEQ ID NO: 129 |
| 129 | RENT1 | NP_002902.2 | Enzyme, misc. | Y947 | EAIIPGSVyDR | T cell leukemia | Jurkat | SEQ ID NO: 130 |
| 130 | RNASEH2A | NP_006388.2 | Enzyme, misc. | Y172 | AKADALyPVVSAASICAK | AML | KG-1 / KG1-A / MO-91 | SEQ ID NO: 131 |
| 131 | RNASEH2A | NP_006388.2 | Enzyme, misc. | Y208 | LQDLDTDyGSGYPNDPK | T cell leukemia | Jurkat | SEQ ID NO: 132 |
| 132 | RNASEH2A | NP_006388.2 | Enzyme, misc. | Y210 | LQDLDTDYGSGyPNDPK | ALL / AML / NSCLC / multiple myeloma | DND41 / H3255 / KG-1 / KG1-A / KY821 / Karpas-1106p / MO-91 / MV4-11 / Molm 14 / OPM-1 / PL21 / RI-1 | SEQ ID NO: 133 |
| 133 | RRM1 | NP_001024.1 | Enzyme, misc. | Y102 | KVFSDVMEDLyNYINPHNGK | AML / T cell ALL | CMK / CTV-1 / MKPL-1 / MOLT15 | SEQ ID NO: 134 |
| 134 | RRM1 | NP_001024.1 | Enzyme, misc. | Y104 | KVFSDVMEDLYNyINPHNGK | AML | MKPL-1 | SEQ ID NO: 135 |
| 135 | RRM2 | NP_001025.1 | Enzyme, misc. | Y221 | WIGDKEATyGEK | T cell ALL | MOLT15 | SEQ ID NO: 136 |
| 136 | RUVBL2 | NP_006657.1 | Enzyme, misc. | Y172 | TTEMETIyDLGTK | T cell leukemia | Jurkat | SEQ ID NO: 137 |
| 137 | RUVBL2 | NP_006657.1 | Enzyme, misc. | Y430 | RVySLFLDESR | ALCL | TS | SEQ ID NO: 138 |
| 138 | SETD8 | NP_065115.3 | Enzyme, misc. | Y57 | IYSyMSPNK | CML | K562 | SEQ ID NO: 139 |
| 139 | SGSH | NP_000190.1 | Enzyme, misc. | Y174 | PFFLyVAFHDPHR | B cell lymphoma | VAL | SEQ ID NO: 140 |
| 140 | SHMT2 | NP_005403.2 | Enzyme, misc. | Y228 | LIIAGTSAyAR | AML | CTV-1 | SEQ ID NO: 141 |
| 141 | MX2 | NP_002454.1 | G protein or regulator | Y355 | EITFFQTHPyFR | anaplastic lymphoma | Karpas 299 | SEQ ID NO: 142 |
| 142 | PSCD1 | NP_004753.1 | G protein or regulator | Y382 | AAISRDPFyEMLAAR | T cell leukemia | Jurkat | SEQ ID NO: 143 |
| 143 | RAB11A | NP_004654.1 | G protein or regulator | Y8 | DDEyDYLFK | T cell leukemia / breast cancer / AML | 3T3 TrkB / 3T3-TrkA / Jurkat / MDA-MB-453 / BaF3-FLT3(WT) | SEQ ID NO: 144 |
| 144 | RAB13 | NP_002861.1 | G protein or regulator | Y5 | AyDHLFK | neuroblastoma | SH-SY5Y | SEQ ID NO: 145 |
| 145 | RAB14 | NP_057406.2 | G protein or regulator | Y80 | FRAVTRSyYRGAAGALMVYDITRR | CLL | LUC-cll patient | SEQ ID NO: 146 |
| 146 | RAB14 | NP_057406.2 | G protein or regulator | Y81 | FRAVTRSYyRGAAGALMVYDITRR | CLL | LUC-cll patient | SEQ ID NO: 147 |
| 147 | RAB8A | NP_005361.2 | G protein or regulator | Y5 | TyDYLFK | AML | BaF3-FLT3(D842Y) / BaF3-FLT3(WT) / M-07e | SEQ ID NO: 148 |
| 148 | RAB9A | NP_004242.1 | G protein or regulator | Y107 | EFIyYADVKEPESFPFVILGNK | AML / CML / NSCLC | H1437 / K562 / KY821 / RC-K8 | SEQ ID NO: 149 |
| 149 | RAB9A | NP_004242.1 | G protein or regulator | Y108 | EFIYyADVKEPESFPFVILGNK | B cell lymphoma | SuDHL5 | SEQ ID NO: 150 |
| 150 | RanBP1 | NP_002873.1 | G protein or regulator | Y103 | ICANHyITPMMELKPNAGSDR | CML / transformed kidney | 293T / K562 | SEQ ID NO: 151 |
| 151 | Rap1a | NP_002875.1 | G protein or regulator | Y159 | INVNEIFyDLVR | AML / CML / T cell ALL | Baf3/E255K / Baf3/Y253F / CTV-1 / MOLT15 / rat brain | SEQ ID NO: 152 |
| 152 | Rap1b | NP_056461.1 | G protein or regulator | Y159 | SKINVNEIFyDLVR | AML / CML / T cell ALL | Baf3/E255K / Baf3/Y253F / CTV-1 / MOLT15 | SEQ ID NO: 153 |
| 153 | RapGEF1 | NP_005303.2 | G protein or regulator | Y329 | QDFDVDCyAQR | T cell leukemia | Jurkat | SEQ ID NO: 154 |
| 154 | RapGEF1 | NP_005303.2 | G protein or regulator | Y715 | KDLVLyCEAFLTTYR | | XG2 | SEQ ID NO: 155 |
| 155 | RapGEF1 | NP_005303.2 | G protein or regulator | Y723 | KDLVLYCEAFLTTyR | | XG2 | SEQ ID NO: 156 |
| 156 | RAPGEF4 | NP_008954.1 | G protein or regulator | Y857 | KFIKIAAHCKEyK | CML / acute erythroblastic leukemia / breast cancer / multiple myeloma | BaF3-PRTK / HCC1806 / HEL / K562 / KMS11 | SEQ ID NO: 157 |
| 157 | RAPGEF4 | NP_008954.1 | G protein or regulator | Y886 | SyVRQLNVIDNQR | T cell leukemia | Jurkat | SEQ ID NO: 158 |
| 158 | RasGAP 3 | NP_031394.2 | G protein or regulator | Y777 | SVYDGPEQEEYSTFVIDDPQETyKTLI | AML / CML | BaF3-FLT3(D842Y) / BaF3-FLT3(K663Q) / BaF3-FLT3(WT) / BaF3-PRTK | SEQ ID NO: 159 |
| 159 | RASGRP2 | NP_005816.2 | G protein or regulator | Y108 | MFLMMHPWyIPSSQLAAKLLHIYQQS | AML | OCI/AML3 | SEQ ID NO: 160 |
| 160 | RASGRP2 | NP_005816.2 | G protein or regulator | Y122 | MFLMMHPWYIPSSQLAAKLLHIyQQS | AML | OCI/AML3 | SEQ ID NO: 161 |
| 161 | RGL2 | NP_004752.1 | G protein or regulator | Y431 | GGGVVPyLGTFLK | ALCL | TS | SEQ ID NO: 162 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 162 | RICS | NP_055530.2 | G protein or regulator | Y1188 | YNTyVAPGR | AML / T cell leukemia / colon cancer / gastric cancer | Jurkat / MO-91 / NCI-N87 / VACO432 | SEQ ID NO: 163 |
| 163 | RICS | NP_055530.2 | G protein or regulator | Y1355 | SLYSyAGLAPRPR | AML | MO-91 | SEQ ID NO: 164 |
| 164 | RIP3 | NP_055949.2 | G protein or regulator | Y267 | VRVESGyFSLEK | AML | MKPL-1 | SEQ ID NO: 165 |
| 165 | RIP3 | NP_055949.2 | G protein or regulator | Y945 | YASDKYKDlyTELSIAK | CML / T cell ALL | Baf3/M351T / Baf3/T315I / Baf3/p210wt / K562 / MOLT15 | SEQ ID NO: 166 |
| 166 | SIPA1L1 | NP_056371.1 | G protein or regulator | Y1590 | TLSDESlyNSQR | T cell leukemia | Jurkat | SEQ ID NO: 167 |
| 167 | Nogo | NP_065393.1 | Inhibitor protein | Y384 | VAVEAPMREEyADFKPFER | T cell leukemia | Jurkat | SEQ ID NO: 168 |
| 168 | RKIP | NP_002558.1 | Inhibitor protein | Y181 | APVAGTCYQAEWDDYVPKLyEQLSGF | AML / NSCLC / T cell ALL | CTV-1 / H1993 / MOLT15 | SEQ ID NO: 169 |
| 169 | RKIP | NP_002558.1 | Inhibitor protein | Y64 | LyTLVLTDPDAPSRKDPKYR | CML | K562 | SEQ ID NO: 170 |
| 170 | RKIP | NP_002558.1 | Inhibitor protein | Y81 | LYTLVLTDPDAPSRKDPKyR | CML | K562 | SEQ ID NO: 171 |
| 171 | NM23 | NP_000260.1 | Kinase (non-protein) | Y52 | MQASEDLLKEHyVDLKDRPF | AML | CMK | SEQ ID NO: 172 |
| 172 | PFKFB3 | NP_004557.1 | Kinase (non-protein) | Y194 | ISCyEASYQPLDPDKCDR | ALCL / anaplastic lymphoma | Karpas 299 / RI-1 / TS | SEQ ID NO: 173 |
| 173 | PFKL | NP_002617.3 | Kinase (non-protein) | Y640 | CHDYYTTEFLyNLYSSEGK | AML / T cell ALL | CTV-1 / MOLT15 | SEQ ID NO: 174 |
| 174 | PFKP | NP_002618.1 | Kinase (non-protein) | Y447 | MLAlyDGFDGFAK | AML / T cell ALL | CTV-1 / MOLT15 | SEQ ID NO: 175 |
| 175 | PFKP | NP_002618.1 | Kinase (non-protein) | Y586 | IIETMGGyCGY | T cell ALL | DU-528 | SEQ ID NO: 176 |
| 176 | PIK3C2A | NP_002635.1 | Kinase (non-protein) | Y73 | AQVYNKQDyDLMVFPESDSQKR | T cell leukemia | Jurkat | SEQ ID NO: 177 |
| 177 | PIK3C2B | NP_002637.2 | Kinase (non-protein) | Y1541 | GLQLLQDGNDPDPyVK | AML | MO-91 | SEQ ID NO: 178 |
| 178 | PIK3CA | NP_006209.2 | Kinase (non-protein) | Y246 | LCVLEyQGKYILK | ALL | DND41 | SEQ ID NO: 179 |
| 179 | PIK3CA | NP_006209.2 | Kinase (non-protein) | Y361 | TGlyHGGEPLCDNVNTQR | lymphoma | SUPT-13 | SEQ ID NO: 180 |
| 180 | PIK3R1 | NP_852664.1 | Kinase (non-protein) | Y426 | LLyPVSK | AML / CML | BaF3-10ZF / KG-1 | SEQ ID NO: 181 |
| 181 | PIK3R1 | NP_852664.1 | Kinase (non-protein) | Y504 | IFEEQCQTQFRySKEYIEK | lymphoma | SUPT-13 | SEQ ID NO: 182 |
| 182 | PIK3R1 | NP_852664.1 | Kinase (non-protein) | Y657 | ESSKQGCyACSVVVDGEVK | AML | KG1-A | SEQ ID NO: 183 |
| 183 | PIK3R2 | NP_005018.1 | Kinase (non-protein) | Y423 | LLyPVSK | AML / CML | BaF3-10ZF / KG-1 | SEQ ID NO: 184 |
| 184 | PIK3R2 | NP_005018.1 | Kinase (non-protein) | Y577 | DQyLVWLTQKGARQKKINEWLGIK | AML | Monomac 6 | SEQ ID NO: 185 |
| 185 | PIK3R3 | NP_003620.2 | Kinase (non-protein) | Y184 | LQEyHSQYQEK | ALL / breast cancer / lymphoma | DND41 / MCF-10A (Y561F) / MCF-10A(Y969F) / SUPT-13 | SEQ ID NO: 186 |
| 186 | PIK3R3 | NP_003620.2 | Kinase (non-protein) | Y202 | SKEYDRLYEEyTR | CML | K562 | SEQ ID NO: 187 |
| 187 | PIK4CA | NP_477352.1 | Kinase (non-protein) | Y466 | yHSQYHTVAGNDIK | B cell lymphoma | RI-1 / VAL | SEQ ID NO: 188 |
| 188 | PIK4CA | NP_477352.1 | Kinase (non-protein) | Y973 | DQPyYDIPDAPYR | AML / NSCLC / breast cancer / T cell leukemia | H3255 / KG-1 / MDA-MB-453 / DU145 | SEQ ID NO: 189 |
| 189 | PIP5K1A | NP_003548.1 | Kinase (non-protein) | Y333 | EPLSSETQySVDTR | prostate cancer | Jurkat | SEQ ID NO: 190 |
| 190 | PIP5K1A | NP_003548.1 | Kinase (non-protein) | Y347 | ALySTAMESIQGEAR | T cell leukemia | Jurkat | SEQ ID NO: 191 |
| 191 | PIP5K2B | NP_003550.1 | Kinase (non-protein) | Y363 | KEVyFMAIIDILTPYDTKK | ALK | 293T NPM-ALK wt / 3YF SILAC | SEQ ID NO: 192 |
| 192 | PRPS2 | NP_002756.1 | Kinase (non-protein) | Y245 | LLSAGATKVyAILTHGIFSGPAISR | ALCL | TS | SEQ ID NO: 193 |
| 193 | SEPHS1 | NP_036379.2 | Kinase (non-protein) | Y345 | SPKyGEGHQAWIIGIVEK | AML | MKPL-1 | SEQ ID NO: 194 |
| 194 | OSBP | NP_002547.1 | Lipid binding protein | Y764 | ATEDGTPyDPYKALWFER | AML | CTV-1 | SEQ ID NO: 195 |
| 195 | PLCL2 | NP_055999.1 | Lipid binding protein | Y896 | ALIENADAVyEK | ALL / AML / T cell ALL | CTV-1 / KOPT-K1 / MOLT15 / RC-K8 / RI-1 / VAL | SEQ ID NO: 196 |
| 196 | PLEKHA1 | NP_067635.2 | Lipid binding protein | Y181 | SQSHLPyFTPKPPQDSAVIK | T cell leukemia | Jurkat | SEQ ID NO: 197 |
| 197 | NDUFB9 | NP_004996.1 | Mitochondrial protein | Y118 | AMYPDyFAKR | AML | OCI/AML2 | SEQ ID NO: 198 |
| 198 | MYH10 | NP_005955.1 | Motor or contractile p | Y13 | TGLEDPERyLFVDR | AML / T cell leukemia | Jurkat / MKPL-1 | SEQ ID NO: 199 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 199 | MYH10 | NP_005955.1 | Motor or contractile p | Y1415 | ALAyDKLEK | AML<br>NSCLC<br>T cell ALL | CTV-1<br>HL107A<br>HL107B<br>HL130A<br>HL131B<br>HL132B<br>HL133A<br>HL59A<br>HL59b<br>HL66B<br>HL84A<br>HL84B<br>MOLT15<br>cs042<br>gz74<br>hl144a | SEQ ID NO: 200 |
| 200 | MYH10 | NP_005955.1 | Motor or contractile p | Y194 | VIQyLAHVASSHK | CML | BaF3-4ZF<br>BaF3/H396P | SEQ ID NO: 201 |
| 201 | MYH9 | NP_002464.1 | Motor or contractile p | Y158 | HEMPPHIYAITDTAyR | CML | BaF3-4ZF | SEQ ID NO: 202 |
| 202 | MYH9 | NP_002464.1 | Motor or contractile p | Y278 | TFHIFyYLLSGAGEHLK | CML | BaF3-PRTK | SEQ ID NO: 203 |
| 203 | MYL6 | NP_066299.2 | Motor or contractile p | Y29 | ILySQCGDVMR | AML<br>CML<br>NSCLC<br>T cell ALL | BaF3-1U2F<br>BaF3-4ZF<br>BaF3-APR<br>BaF3-FLT3(D842Y)<br>BaF3-FLT3(K663Q)<br>BaF3-PRTK<br>BaF3-Tel/FGFR3<br>Baf3/E255K<br>Baf3/M351T<br>Baf3/T315I<br>Baf3/Y253F<br>Baf3/p210wt<br>CTV-1<br>HCC827<br>MO-91<br>MOLT15<br>RI-1<br>VAL<br>cs041<br>cs042<br>gzB1 | SEQ ID NO: 204 |
| 204 | MYO18B | NP_115997.5 | Motor or contractile p | Y1564 | LGELQSAyDGAK | AML<br>T cell ALL | CTV-1<br>MOLT15 | SEQ ID NO: 205 |
| 205 | MYO1D | NP_056009.1 | Motor or contractile p | Y114 | yIMQYIAAITNPSQR | T cell leukemia | Jurkat | SEQ ID NO: 206 |
| 206 | MYO1D | NP_056009.1 | Motor or contractile p | Y435 | HIDyFNNQIIVDLVEQQHK | AML | CHRF<br>Pfeiffer | SEQ ID NO: 207 |
| 207 | MYO9B | NP_004136.2 | Motor or contractile p | Y105 | RAQDEHPQEDGyYFLLQER | CML | BaF3-4ZF<br>BaF3-PRTK | SEQ ID NO: 208 |
| 208 | MYO9B | NP_004136.2 | Motor or contractile p | Y22 | EQAAYHLHIyPQLSTTESQASCR | AML | KG-1 | SEQ ID NO: 209 |
| 209 | MYPT1 | NP_002471.1 | Phosphatase | Y446 | TGSyGALAEITASK | T cell leukemia | Jurkat | SEQ ID NO: 210 |
| 210 | MYPT1 | NP_002471.1 | Phosphatase | Y669 | SyLTPVRDEESESQR | T cell leukemia | Jurkat | SEQ ID NO: 211 |
| 211 | MYPT1 | NP_002471.1 | Phosphatase | Y913 | SGSYSyLEER | AML<br>T cell leukemia | Jurkat<br>PL21 | SEQ ID NO: 212 |
| 212 | PHPT1 | NP_054891.2 | Phosphatase | Y91 | IHVyGYSMAYGPAQHAISTEK | AML | CTV-1 | SEQ ID NO: 213 |
| 213 | PHPT1 | NP_054891.2 | Phosphatase | Y93 | IHVYGySMAYGPAQHAISTEK | AML<br>NSCLC<br>T cell ALL<br>prostate cancer | CHRF<br>CTV-1<br>DU-528<br>DU145<br>H3255<br>MOLT15<br>RC-K8<br>cs042 | SEQ ID NO: 214 |
| 214 | PHPT1 | NP_054891.2 | Phosphatase | Y97 | IHVYGYSMAyGPAQHAISTEK | AML | KG-1 | SEQ ID NO: 215 |
| 215 | PPP1CA | NP_002699.1 | Phosphatase | Y78 | LFEyGGFPPESNYLFLGDYVDR | AML | KG1-A | SEQ ID NO: 216 |
| 216 | PPP2CA | NP_002706.1 | Phosphatase | Y265 | NVVTIFSAPNyCYR | ALCL | TS | SEQ ID NO: 217 |
| 217 | PPP2R4 | NP_056954.2 | Phosphatase | Y188 | yLEVMRKLQKTYR | CML | K562 | SEQ ID NO: 218 |
| 218 | PPP2R5D | NP_006236.1 | Phosphatase | Y488 | LFDDCTQQyK | CML | BaF3-Tel/FGFR3<br>Baf3/E255K<br>K562 | SEQ ID NO: 219 |
| 219 | PPP2R5D | NP_006236.1 | Phosphatase | Y580 | KSELPQDVyTIK | AML<br>T cell ALL | CTV-1<br>MOLT15 | SEQ ID NO: 220 |
| 220 | PPP5C | NP_006238.1 | Phosphatase | Y313 | GNHETDNMNQIyGFEGEVK | AML<br>T cell ALL | CTV-1<br>MOLT15 | SEQ ID NO: 221 |
| 221 | PPP5C | NP_006238.1 | Phosphatase | Y80 | TECYGyALGDATR | AML | KG1-A<br>MO-91 | SEQ ID NO: 222 |
| 222 | PPP6C | NP_002712.1 | Phosphatase | Y261 | LVTVWSAPNyCYR | ALCL<br>AML<br>T cell ALL | BaF3-FLT3(D842Y)<br>MOLT15<br>TS | SEQ ID NO: 223 |
| 223 | PTEN | NP_000305.3 | Phosphatase | Y174 | yVYYYSYLLK | ALL | GND41 | SEQ ID NO: 224 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 224 | PTEN | NP_000305.3 | Phosphatase | Y176 | YVyYYSYLLK | ALCL, AML, CML, NSCLC, breast cancer, glioblastoma, lung cancer, squamous cell carcinoma | H1651, H1975, H2170, H520, H810, HCC1143, HCC1500, HL129A, HL131B, HL132A, Human lung tumor, K562, KG1-A, MCF7, MV4-11, TS, U87 MG, cs001, cs018, cs019, cs024, cs029, cs048, cs057, gz30, gz41, gz7, h2228, hl144a, hl144b, hl145b, hl146a, hl148a, hl152b | SEQ ID NO: 225 |
| 225 | PTEN | NP_000305.3 | Phosphatase | Y177 | YVVyYSYLLK | ALL | DND41 | SEQ ID NO: 226 |
| 226 | PTEN | NP_000305.3 | Phosphatase | Y178 | YVVYySYLLK | ALCL, AML, CML, NSCLC, breast cancer, glioblastoma, lung cancer, squamous cell carcinoma | H1651, H1975, H2170, H520, H810, HCC1143, HCC1500, HL129A, HL131B, HL132A, Human lung tumor, K562, KG1-A, MCF7, MV4-11, TS, U87 MG, cs001, cs018, cs019, cs024, cs029, cs048, cs057, gz30, gz41, gz7, h2228, hl144a, hl144b, hl145b, hl146a, hl148a, hl152b | SEQ ID NO: 227 |
| 227 | PTEN | NP_000305.3 | Phosphatase | Y180 | YVVYYSySLLK | ALL | DND41 | SEQ ID NO: 228 |
| 228 | PTP4A2 | NP_536316.1 | Phosphatase | Y50 | VCDATyDKAPVEK | T cell leukemia | Jurkat | SEQ ID NO: 229 |
| 229 | PTPN23 | NP_056281.1 | Phosphatase | Y1229 | HQDVMPyDSNR | T cell leukemia | Jurkat | SEQ ID NO: 230 |
| 230 | PTPRD | NP_002830.1 | Phosphatase | Y954 | NGIITKyTLLYR | lymphoma | SUPT-13 | SEQ ID NO: 231 |
| 231 | PTPRD | NP_002830.1 | Phosphatase | Y958 | NGIITKYTLLyR | lymphoma | SUPT-13 | SEQ ID NO: 232 |
| 232 | PTPRK | NP_002835.2 | Phosphatase | Y917 | NRyGNIIAYDHSR | T cell leukemia | Jurkat | SEQ ID NO: 233 |
| 233 | PTPRK | NP_002835.2 | Phosphatase | Y923 | YGNIIAyDHSR | T cell leukemia | Jurkat | SEQ ID NO: 234 |
| 234 | PTPRK | NP_002835.2 | Phosphatase | Y941 | VILQPVEDDPSSDyINANYIDGYQR | T cell leukemia | Jurkat | SEQ ID NO: 235 |
| 235 | SHIP | NP_005532.2 | Phosphatase | Y555 | NQNyMNILR | AML | KG-1 | SEQ ID NO: 236 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 236 | SHIP | NP_005532.2 | Phosphatase | Y643 | VFLHFEEEEITFAPTyRFER | CML / T cell ALL | BaF3-PRTK / MOLT15 / NKM-1 | SEQ ID NO: 237 |
| 237 | SHIP | NP_005532.2 | Phosphatase | Y795 | LKPIISDPEyLLDQHILISIK | CML | BaF3-10ZF / KG-1 | SEQ ID NO: 238 |
| 238 | SHIP | NP_005532.2 | Phosphatase | Y943 | QTLSPDQQPTAWSyDQPPKDSPLGP | AML | RC-K8 | SEQ ID NO: 239 |
| 239 | SHIP-2 | NP_001558.2 | Phosphatase | Y190 | GSyGLDLEAVR | CML | K562 | SEQ ID NO: 240 |
| 240 | SHP-1 | NP_002822.2 | Phosphatase | Y301 | DSNIPGSDyINANYIK | T cell leukemia | Jurkat | SEQ ID NO: 241 |
| 241 | SHP-2 | NP_002825.3 | Phosphatase | Y511 | SGMVQTEACyR | CML / lymphoma | Baf3/E255K / K562 / SUPT-13 | SEQ ID NO: 242 |
| 242 | PREP | NP_002717.3 | Protease | Y71 | MTELyDYPKYSCHFKK | T cell ALL | MOLT15 | SEQ ID NO: 243 |
| 243 | PRSS15 | NP_004784.2 | Protease | Y186 | LKRDDSNESDVVESLDEIyHTGTF | AML | CMK | SEQ ID NO: 244 |
| 244 | PSMA3 | NP_002779.1 | Protease | Y105 | SNFGyNIPLK | CML | K562 | SEQ ID NO: 245 |
| 245 | PSMA6 | NP_002782.1 | Protease | Y23 | LyQVEYAFK | T cell ALL | MOLT15 | SEQ ID NO: 246 |
| 246 | PSMB1 | NP_002784.1 | Protease | Y150 | GAVySFDPVGSYQR | AML / T cell ALL | CTV-1 / MOLT15 | SEQ ID NO: 247 |
| 247 | PSMB3 | NP_002786.2 | Protease | Y103 | FGPyYTEPVIAGLDPK | AML / CML | BaF3-10ZF / BaF3-4ZF / BaF3-PRTK / BaF3-Tel/FGFR3 / KG-1 / KG1-A | SEQ ID NO: 248 |
| 248 | PSMB5 | NP_002788.1 | Protease | Y220 | RAIyQATYR | AML | CTV-1 | SEQ ID NO: 249 |
| 249 | PSMB8 | NP_004150.1 | Protease | Y122 | VIEINPYLLGTMSGCAADCQyWER | T cell ALL | MOLT15 | SEQ ID NO: 250 |
| 250 | PSMB8 | NP_004150.1 | Protease | Y181 | KGPGLYyVDEHGTR | AML / anaplastic lymphoma | CTV-1 / Karpas 299 / RI-1 | SEQ ID NO: 251 |
| 251 | PSMC6 | NP_002797.2 | Protease | Y173 | GCLLyGPPGTGK | AML / CML / T cell ALL | Baf3/E255K / Baf3/M351T / CTV-1 / K562 / MOLT15 | SEQ ID NO: 252 |
| 252 | PSMD10 | NP_002805.1 | Protease | Y138 | DHyEATAMHR | T cell leukemia | Jurkat | SEQ ID NO: 253 |
| 253 | PSMD3 | NP_002800.2 | Protease | Y264 | NYLHYSLyDQAEK | ALCL / CML | K562 / TS | SEQ ID NO: 254 |
| 254 | PSME2 | NP_002809.2 | Protease | Y239 | IVNPKGEEKPSMy | T cell leukemia | Jurkat | SEQ ID NO: 255 |
| 255 | RIOK1 | NP_113668.2 | Protein kinase | Y466 | LKEEDMAMNAQQDNILyQTVTGLKK | T cell leukemia | Jurkat | SEQ ID NO: 256 |
| 256 | RIOK2 | NP_060813.1 | Protein kinase | Y366 | NCLEESEGCyCR | T cell leukemia | Jurkat | SEQ ID NO: 257 |
| 257 | PHKA1 | NP_002628.1 | Protein kinase, regula | Y636 | LYSEDYDDNyDYLESGNWMNDYDST | T cell leukemia | Jurkat | SEQ ID NO: 258 |
| 258 | PHKA1 | NP_002628.1 | Protein kinase, regula | Y638 | LYSEDYDDNYDyLESGNWMNDYDST | T cell leukemia | Jurkat | SEQ ID NO: 259 |
| 259 | PKAR2A | NP_004148.1 | Protein kinase, regula | Y105 | RVSVCAETyNPDEEEEDTDPR | T cell leukemia | Jurkat / cs041 | SEQ ID NO: 260 |
| 260 | Nek9 | AAH93881.1 | Protein kinase, Ser/T | Y350 | TSEVyVWGGGK | B cell lymphoma | VAL | SEQ ID NO: 261 |
| 261 | PAK1 | NP_002567.3 | Protein kinase, Ser/T | Y142 | yMSFTDKSAEDYNSSNALNVK | T cell leukemia | Jurkat | SEQ ID NO: 262 |
| 262 | PAK1 | NP_002567.3 | Protein kinase, Ser/T | Y153 | YMSFTDKSAEDyNSSNALNVK | T cell leukemia | Jurkat | SEQ ID NO: 263 |
| 263 | PAK2 | NP_002568.2 | Protein kinase, Ser/T | Y252 | LRTIVSIGDPKKKYTRyEK | CML | BaF3-PRTK | SEQ ID NO: 264 |
| 264 | PERK | NP_004827.4 | Protein kinase, Ser/T | Y464 | FSHEEYSNGALSILQYPYDNGyYLPY | T cell leukemia | Jurkat | SEQ ID NO: 265 |
| 265 | PERK | NP_004827.4 | Protein kinase, Ser/T | Y481 | FSHEEYSNGALSILQYPYDNGyYLPY | T cell leukemia | Jurkat | SEQ ID NO: 266 |
| 266 | PERK | NP_004827.4 | Protein kinase, Ser/T | Y484 | FSHEEYSNGALSILQYPYDNGyYLPY | T cell leukemia | Jurkat | SEQ ID NO: 267 |
| 267 | PERK | NP_004827.4 | Protein kinase, Ser/T | Y485 | FSHEEYSNGALSILQYPYDNGyYLPY | T cell leukemia | Jurkat | SEQ ID NO: 268 |
| 268 | PKACb | NP_002722.1 | Protein kinase, Ser/T | Y69 | HKATEQyYAMK | AML / CML | BaF3-4ZF / BaF3-FLT3(K663Q) / BaF3-FLT3(D842V) / BaF3-FLT3(D842Y) / BaF3-FLT3(K663Q) / BaF3-FLT3(WT) / BaF3-FLT3/ITD | SEQ ID NO: 269 |
| 269 | PKCA | NP_002728.1 | Protein kinase, Ser/T | Y195 | NLIPMDPNGLSDPyVK | ALCL / AML | TS / rat brain | SEQ ID NO: 270 |
| 270 | PKCB | NP_002729.2 | Protein kinase, Ser/T | Y195 | NLVPMDPNGLSDPyVK | acute erythroblastic leukemia | HEL / gz68 / rat brain | SEQ ID NO: 271 |
| 271 | PKCT | NP_006248.1 | Protein kinase, Ser/T | Y545 | TNTFCGTPDyIAPEILLGQK | T cell leukemia | Jurkat | SEQ ID NO: 272 |
| 272 | PKD2 | NP_057541.2 | Protein kinase, Ser/T | Y246 | RPPPSSSSSSASSyTGRPIELQK | T cell leukemia | Jurkat | SEQ ID NO: 273 |
| 273 | PKD2 | NP_057541.2 | Protein kinase, Ser/T | Y717 | SVVGTPAyLAPEVLLNQGYNR | T cell leukemia | Jurkat | SEQ ID NO: 274 |
| 274 | PLK1 | NP_005021.2 | Protein kinase, Ser/T | Y217 | TLCGTPNyIAPEVLSK | CML | K562 | SEQ ID NO: 275 |
| 275 | QSK | NP_079440.2 | Protein kinase, Ser/T | Y1167 | HHTIQNSDDAyVQLDNLPGMSLVAGK | AML | KG1-A | SEQ ID NO: 276 |
| 276 | ROCK2 | NP_004841.2 | Protein kinase, Ser/T | Y722 | iyESIEEAK | T cell leukemia | Jurkat | SEQ ID NO: 277 |
| 277 | RSK2 | NP_004577.1 | Protein kinase, Ser/T | Y483 | DVyDDGKYVYVVTELMK | AML / CML | BaF3-10ZF / KG-1 / KG1-A | SEQ ID NO: 278 |
| 278 | RSK2 | NP_004577.1 | Protein kinase, Ser/T | Y488 | YGQHPNIITLKDVYDDGKyVYVVTEL | AML / CML | BaF3-10ZF / BaF3-Tel/FGFR3 / KG1-A | SEQ ID NO: 279 |
| 279 | RSK2 | NP_004577.1 | Protein kinase, Ser/T | Y490 | DVYDDGKYVyVVTELMK | CML | BaF3-4ZF | SEQ ID NO: 280 |
| 280 | RSK2 | NP_004577.1 | Protein kinase, Ser/T | Y529 | TVEyLHAQGVVHR | CML | BaF3-10ZF / BaF3-Tel/FGFR3 | SEQ ID NO: 281 |
| 281 | SgK269 | XP_370878.3 | Protein kinase, Ser/T | Y598 | FNSyNNAGMPPFPIIIHDEPTYAR | CML | K562 | SEQ ID NO: 282 |
| 282 | SgK269 | XP_370878.3 | Protein kinase, Ser/T | Y616 | FNSYNNAGMPPFPIIIHDEPTyAR | CML | K562 | SEQ ID NO: 283 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 283 | SgK307 | NP_112562.3 | Protein kinase, Ser/T | Y1141 | DISLTDIQDLSSISyEPDSSFKEASCKT | lymphoma | MC-116 | SEQ ID NO: 284 |
| 284 | NEO1 | NP_002490.1 | Receptor, channel, tr | Y1436 | MLEDSESSyEPDELTK | T cell leukemia | 3T3 TrkB Jurkat | SEQ ID NO: 285 |
| 285 | NMDAR2B | NP_000825.1 | Receptor, channel, tr | Y239 | CTKEEATyiFEVANSVGLTGYGYTW | AML | CMK | SEQ ID NO: 286 |
| 286 | NUP133 | NP_060700.2 | Receptor, channel, tr | Y1150 | ANyEyYVQGQI | AML | KG-1 | SEQ ID NO: 287 |
| 287 | NUP155 | NP_004289.1 | Receptor, channel, tr | Y1025 | yYEKNRSFSNAARVLSRLADMHSTEI | ALCL | TS | SEQ ID NO: 288 |
| 288 | NUP155 | NP_004289.1 | Receptor, channel, tr | Y1026 | YyEKNRSFSNAARVLSRLADMHSTEI | ALCL | TS | SEQ ID NO: 289 |
| 289 | NUP155 | NP_004289.1 | Receptor, channel, tr | Y867 | FyEGWELSLTAAEK | AML | Marimo | SEQ ID NO: 290 |
| 290 | NUP205 | NP_055950.1 | Receptor, channel, tr | Y581 | DLPSADSVQyR | CML T cell leukemia AML | Jurkat K562 K562 | SEQ ID NO: 291 |
| 291 | Nup214 | NP_005076.3 | Receptor, channel, tr | Y1145 | NNPATPSTAMGSSVPySTAK | CML | KG-1 | SEQ ID NO: 292 |
| 292 | Nup214 | NP_005076.3 | Receptor, channel, tr | Y502 | SSATVTGEPPSySSGSDSSK | CML | K562 | SEQ ID NO: 293 |
| 293 | NUP93 | NP_055484.2 | Receptor, channel, tr | Y155 | ILHTLLASGEDALDFTGESEPSyISDVi | CML | K562 | SEQ ID NO: 294 |
| 294 | NUP93 | NP_055484.2 | Receptor, channel, tr | Y185 | SSLDNIEMAyAR | T cell leukemia | Jurkat | SEQ ID NO: 295 |
| 295 | NUP93 | NP_055484.2 | Receptor, channel, tr | Y391 | AVyCIIGR | ALCL | TS | SEQ ID NO: 296 |
| 296 | OR2D3 | NP_001004684.1 | Receptor, channel, tr | Y266 | AFSTCGSHLIVVVLFyGSGIFTYMR | multiple myeloma | KMS18 | SEQ ID NO: 297 |
| 297 | OR2D3 | NP_001004684.1 | Receptor, channel, tr | Y275 | AFSTCGSHLIVVVLFYGSGIFTyMR | multiple myeloma | KMS18 | SEQ ID NO: 298 |
| 298 | OR4C3 | NP_001004702.1 | Receptor, channel, tr | Y300 | NMALFyGILTPMLNPLIYTLR | CML | K562 | SEQ ID NO: 299 |
| 299 | OR5F1 | NP_003688.1 | Receptor, channel, tr | Y141 | SRTVyLKMAAGAFAAGLL | T cell ALL | DU-528 | SEQ ID NO: 300 |
| 300 | PAR1 | NP_001983.1 | Receptor, channel, tr | Y397 | ESSDPSSyNSSGQLMASK | AML | M-07e | SEQ ID NO: 301 |
| 301 | PITPNA | NP_006215.1 | Receptor, channel, tr | Y140 | HVEAWyIDIADR | AML | CTV-1 | SEQ ID NO: 302 |
| 302 | RXR-alpha | NP_002948.1 | Receptor, channel, tr | Y150 | SSGKHYGVySCEGCK | T cell ALL | MOLT15 | SEQ ID NO: 303 |
| 303 | SIGIRR | NP_068577.1 | Receptor, channel, tr | Y402 | TDFyCLVSKDDM | T cell leukemia colon cancer | HT29 Jurkat | SEQ ID NO: 304 |
| 304 | SIGLEC12 | NP_201586.1 | Receptor, channel, tr | Y470 | ARPQYPQEQEAIGYEySEINIPK | AML | KY821 Me-F2 | SEQ ID NO: 305 |
| 305 | Siglec-9 | NP_055256.1 | Receptor, channel, tr | Y502 | RSSVGEGELQy | AML | UT-7 | SEQ ID NO: 306 |
| 306 | SLAMF6 | NP_443163.1 | Receptor, channel, tr | Y273 | NLEyVSVSPTNNTVYASVTHSNR | T cell leukemia | Jurkat | SEQ ID NO: 307 |
| 307 | NCBP2 | NP_031388.2 | RNA binding protein | Y14 | SDSyVELSQYR | AML | KG1-A | SEQ ID NO: 308 |
| 308 | NCL | NP_005372.2 | RNA binding protein | Y351 | KFGyVDFESAEDLEK | AML | KY821 | SEQ ID NO: 309 |
| 309 | NCL | NP_005372.2 | RNA binding protein | Y402 | NLPyKVTQDELKEVFEDAAEIR | AML | MKPL-1 | SEQ ID NO: 310 |
| 310 | NCL | NP_005372.2 | RNA binding protein | Y462 | SISLyYTGEKGQNQDYR | T cell ALL | MOLT15 | SEQ ID NO: 311 |
| 311 | NCL | NP_005372.2 | RNA binding protein | Y463 | SISLYyTGEK | lymphoma | SUPT-13 | SEQ ID NO: 312 |
| 312 | NCL | NP_005372.2 | RNA binding protein | Y525 | SKGyAFIEFASFEDAKEALNSCNKR | ALCL | TS | SEQ ID NO: 313 |
| 313 | NIFK | NP_115766.2 | RNA binding protein | Y183 | GIDyDFPSLILQK | T cell leukemia | Jurkat | SEQ ID NO: 314 |
| 314 | NIFK | NP_115766.2 | RNA binding protein | Y88 | TGNSKGyAFVEFESEDVAK | ALCL anaplastic lymphoma | Karpas 299 TS | SEQ ID NO: 315 |
| 315 | NOLA1 | NP_061856.1 | RNA binding protein | Y97 | CTTDENKVPyFNAPVYLENK | AML | MKPL-1 | SEQ ID NO: 316 |
| 316 | NONO | NP_031389.3 | RNA binding protein | Y265 | FAQPGSFEyEYAMR | T cell leukemia squamous cell carcinoma | H520 Jurkat | SEQ ID NO: 317 |
| 317 | NOP5 | NP_057018.1 | RNA binding protein | Y272 | TQLyEYLQNR | AML multiple myeloma | CMK KMS11 KY821 MKPL-1 | SEQ ID NO: 318 |
| 318 | NXF2 | NP_060279.2 | RNA binding protein | Y185 | iyDDENQKICIFVNHSTAPYSVKNK | T cell leukemia | Jurkat | SEQ ID NO: 319 |
| 319 | NXF2 | NP_060279.2 | RNA binding protein | Y203 | IYDDENQKICIFVNHSTAPySVKNK | T cell leukemia | Jurkat | SEQ ID NO: 320 |
| 320 | PABP 1 | NP_002559.2 | RNA binding protein | Y297 | YQGVNLyVK | CML T cell ALL | BaF3-10ZF BaF3-4ZF MOLT15 VAL | SEQ ID NO: 321 |
| 321 | PABP 1 | NP_002559.2 | RNA binding protein | Y382 | QAHLTNQyMQR | T cell leukemia | Jurkat | SEQ ID NO: 322 |
| 322 | PABP 4 | NP_003810.1 | RNA binding protein | Y382 | KAHLTNQyMQR | T cell ALL | MOLT15 | SEQ ID NO: 323 |
| 323 | PAI-RBP1 | NP_001018077.1 | RNA binding protein | Y244 | QISyNYSDLDQSNVTEETPEGEEHHP | T cell leukemia | Jurkat | SEQ ID NO: 324 |
| 324 | PAI-RBP1 | NP_001018077.1 | RNA binding protein | Y246 | QISYNySDLDQSNVTEETPEGEEHHP | T cell leukemia | Jurkat | SEQ ID NO: 325 |
| 325 | PHF5A | NP_116147.1 | RNA binding protein | Y36 | CDGKCVICDSyVR | acute erythroblastic leukemia multiple myeloma | HEL KMS18 | SEQ ID NO: 326 |
| 326 | PHF5A | NP_116147.1 | RNA binding protein | Y54 | ICDECNYGSyQGR | T cell leukemia | Jurkat | SEQ ID NO: 327 |
| 327 | PNPT1 | NP_149100.1 | RNA binding protein | Y459 | ALyPVIPR | ALCL AML | KG-1 TS | SEQ ID NO: 328 |
| 328 | PRPF8 | NP_006436.3 | RNA binding protein | Y1432 | HTLAyDKGWR | ALCL | TS | SEQ ID NO: 329 |
| 329 | PRPF8 | NP_006436.3 | RNA binding protein | Y2062 | TVNKHGDEIITSTTSNyETQTFSSK | T cell leukemia | Jurkat | SEQ ID NO: 330 |
| 330 | PRPF8 | NP_006436.3 | RNA binding protein | Y2091 | TNHIyVSSDDIK | ALCL AML | MV4-11 TS | SEQ ID NO: 331 |
| 331 | PRPF8 | NP_006436.3 | RNA binding protein | Y2102 | TNHIYVSSDDIKETGyTYILPK | AML | MKPL-1 | SEQ ID NO: 332 |
| 332 | PRPF8 | NP_006436.3 | RNA binding protein | Y394 | LKDTPLyTDNTANGIALL | AML | CMK | SEQ ID NO: 333 |
| 333 | PSF | NP_005057.1 | RNA binding protein | Y381 | NLSPyVSNELLEEAFSQFGPIER | AML CML T cell ALL | 3T3 TrkB BaF3-10ZF BaF3-4ZF CTV-1 K562 KG1-A MOLT15 | SEQ ID NO: 334 |
| 334 | PUM1 | NP_055491.1 | RNA binding protein | Y1123 | DQYANyVVQK | ALCL AML | MO-91 TS | SEQ ID NO: 335 |
| 335 | RALY | NP_057951.1 | RNA binding protein | Y109 | KRAASAlySGY | AML | CMK | SEQ ID NO: 336 |
| 336 | RBM14 | NP_006319.1 | RNA binding protein | Y226 | ASyVAPLTAQPATYR | AML | MKPL-1 | SEQ ID NO: 337 |

Figure 2

| | Protein Name | Accession No. | Protein Type | Phospho-Residue | Phosphorylation Site Sequence | Disease | Cell Line / Tissue / Patient | SEQ ID NO |
|---|---|---|---|---|---|---|---|---|
| 337 | RBM14 | NP_006319.1 | RNA binding protein | Y249 | AQPSVSLGAAyR | AML | MKPL-1 | SEQ ID NO: 338 |
| 338 | RBM14 | NP_006319.1 | RNA binding protein | Y261 | AQPSASLGVGyR | AML | MKPL-1 | SEQ ID NO: 339 |
| 339 | RBM14 | NP_006319.1 | RNA binding protein | Y273 | TQPMTAQAASyR | AML | MKPL-1 | SEQ ID NO: 340 |
| 340 | RBM15 | NP_073605.4 | RNA binding protein | Y537 | YQQQYLQPLPLTHYELVTDAFGHR | AML | MKPL-1 | SEQ ID NO: 341 |
| 341 | RBM15 | NP_073605.4 | RNA binding protein | Y546 | YQQQYLQPLPLTHyELVTDAFGHR | AML | MKPL-1 | SEQ ID NO: 342 |
| 342 | RBM30 | NP_113680.1 | RNA binding protein | Y101 | FEEyGPVIECDIVK | T cell leukemia | Jurkat | SEQ ID NO: 343 |
| 343 | RBM30 | NP_113680.1 | RNA binding protein | Y194 | VADFTEDYNEQyGAVR | T cell leukemia | Jurkat | SEQ ID NO: 344 |
| 344 | RBM30 | NP_113680.1 | RNA binding protein | Y340 | NSLyDMAR | T cell leukemia | Jurkat | SEQ ID NO: 345 |
| 345 | RBM4 | NP_002887.2 | RNA binding protein | Y327 | ATAPVPTVGEGYGyCHESELSQASA/ | T cell leukemia | Jurkat | SEQ ID NO: 346 |
| 346 | RBM5 | NP_005769.1 | RNA binding protein | Y254 | TVVDSIMTALSPy | CLL | 01364548-cll | SEQ ID NO: 347 |
| 347 | RBM6 | NP_005768.1 | RNA binding protein | Y701 | TGPMGHTyGFIDLDSHAEALR | ALCL | TS | SEQ ID NO: 348 |
| 348 | RNASE7 | NP_115961.1 | RNA binding protein | Y130 | SyVVACKPPQKK | B cell lymphoma | WSU-NHL | SEQ ID NO: 349 |
| 349 | SART3 | NP_055521.1 | RNA binding protein | Y541 | AVQCTGDyPEHVCEVLLTMER | AML | KG-1<br>KG1-A | SEQ ID NO: 350 |
| 350 | SF2 | NP_008855.1 | RNA binding protein | Y149 | EAGDVCyADVYR | T cell leukemia | Jurkat | SEQ ID NO: 351 |
| 351 | SF2 | NP_008855.1 | RNA binding protein | Y170 | KEDMTyAVR | AML<br>T cell ALL<br>T cell leukemia | CTV-1<br>Jurkat<br>MKPL-1<br>MOLT15 | SEQ ID NO: 352 |
| 352 | SF2 | NP_008855.1 | RNA binding protein | Y37 | TKDIEDVFyKYGAIR | AML | MKPL-1 | SEQ ID NO: 353 |
| 353 | SF3A3 | NP_006793.1 | RNA binding protein | Y406 | LHGLNINyNCEICGNYTYRGPK | anaplastic lymphoma | Karpas 299 | SEQ ID NO: 354 |
| 354 | SF3A3 | NP_006793.1 | RNA binding protein | Y416 | LHGLNINYNCEICGNYTyRGPK | ALCL<br>AML | MO-91<br>TS | SEQ ID NO: 355 |
| 355 | SF3A3 | NP_006793.1 | RNA binding protein | Y492 | WQPDTEEEYEDSSGNVVNKKTyEDL | T cell leukemia | Jurkat | SEQ ID NO: 356 |
| 356 | SF3B1 | NP_036565.2 | RNA binding protein | Y1295 | IYNDDKNTyIR | AML | KG-1 | SEQ ID NO: 357 |
| 357 | SF3B1 | NP_036565.2 | RNA binding protein | Y44 | AALDEAQGVGLDSTGYYDQEIyGGSI | T cell leukemia | Jurkat | SEQ ID NO: 358 |
| 358 | SF3B3 | NP_036558.3 | RNA binding protein | Y1041 | WVTTASLLDyDTVAGADKFGNICVVR | T cell ALL | CTV-1<br>MOLT15 | SEQ ID NO: 359 |
| 359 | SFRS10 | NP_004584.1 | RNA binding protein | Y235 | GYDDRDyYSR | AML<br>squamous cell carcinoma | H520<br>MKPL-1 | SEQ ID NO: 360 |
| 360 | SFRS10 | NP_004584.1 | RNA binding protein | Y260 | AAQDRDQIyRR | AML | MKPL-1 | SEQ ID NO: 361 |
| 361 | SFRS7 | NP_001026854.1 | RNA binding protein | Y33 | AFSyYGPLR | ALL<br>colon cancer | KOPT-K1<br>SW520 | SEQ ID NO: 362 |
| 362 | SFRS9 | NP_003760.1 | RNA binding protein | Y139 | EAGDVCyADVQK | T cell leukemia | Jurkat | SEQ ID NO: 363 |
| 363 | SFRS9 | NP_003760.1 | RNA binding protein | Y70 | FEDPRDAEDAIyGR | T cell ALL | MOLT15 | SEQ ID NO: 364 |
| 364 | SFRS9 | NP_003760.1 | RNA binding protein | Y75 | NGyDYGQCR | AML | MO-91 | SEQ ID NO: 365 |
| 365 | PDAP1 | NP_055706.1 | Secreted protein | Y70 | SLDSDESEDEEDDyQQKR | T cell leukemia | Jurkat<br>HL79B | SEQ ID NO: 366 |
| 366 | PSG5 | NP_002772.2 | Secreted protein | Y215 | NETGPyECEIRDR | CLL | LUC-cll patient | SEQ ID NO: 367 |
| 367 | NACA | NP_005585.1 | Transcriptional regula | Y120 | SPASDTyIVFGEAK | T cell leukemia | Jurkat | SEQ ID NO: 368 |
| 368 | NCOA7 | NP_861447.2 | Transcriptional regula | Y526 | LIEYyLTK | T cell leukemia | Jurkat | SEQ ID NO: 369 |
| 369 | NFAT1 | NP_036472.2 | Transcriptional regula | Y346 | HIyPAVEFLGPCEQGER | AML | KG-1 | SEQ ID NO: 370 |
| 370 | NFAT1 | NP_036472.2 | Transcriptional regula | Y860 | LSPGSyPTVIQQQNATSQR | AML | KG-1<br>KG1-A | SEQ ID NO: 371 |
| 371 | NFAT4 | NP_004546.1 | Transcriptional regula | Y86 | NyEGTCEIPESK | T cell leukemia | Jurkat | SEQ ID NO: 372 |
| 372 | NFAT90 | NP_004507.2 | Transcriptional regula | Y22 | HSSVyPTQEELEAVQNMVSHTER | AML<br>T cell ALL | KG-1<br>MOLT15<br>RC-K8 | SEQ ID NO: 373 |
| 373 | NFAT90 | NP_036350.2 | Transcriptional regula | Y777 | GyNHGQGSYSYSNSYNSPGGGGGS | T cell leukemia | Jurkat | SEQ ID NO: 374 |
| 374 | NFAT90 | NP_036350.2 | Transcriptional regula | Y828 | SGGNSYGSGGASyNPGSHGGYGGG | AML | MKPL-1 | SEQ ID NO: 375 |
| 375 | NFAT90 | NP_036350.2 | Transcriptional regula | Y846 | SGGNSYGSGGASYNPGSHGGYGGC | AML<br>squamous cell carcinoma | H520<br>MKPL-1 | SEQ ID NO: 376 |
| 376 | NFAT90 | NP_036350.2 | Transcriptional regula | Y891 | NADHSMNyQYR | AML | MKPL-1 | SEQ ID NO: 377 |
| 377 | NFAT90 | NP_036350.2 | Transcriptional regula | Y893 | NADHSMNYQyR | AML<br>breast cancer | HCC1806<br>MKPL-1 | SEQ ID NO: 378 |
| 378 | NFI-X | NP_002492.2 | Transcriptional regula | Y253 | VSQTPVATASGPNFSLADLESPSyYNl | AML | MKPL-1 | SEQ ID NO: 379 |
| 379 | NFkB-p105 | NP_003989.2 | Transcriptional regula | Y241 | RLEPVVSDAIyDSKAPNASNLK | ALL<br>AML<br>CML<br>T cell ALL | BaF3-4ZF<br>Baf3/E255K<br>Baf3/H396P<br>Baf3/M351T<br>Baf3/T315I<br>CTV-1<br>KOPT-K1<br>Karpas-1106p<br>MOLT15<br>VAL | SEQ ID NO: 380 |
| 380 | NFX1 | NP_002495.2 | Transcriptional regula | Y1115 | ITKEPIIDyFDVQD | T cell leukemia | Jurkat | SEQ ID NO: 381 |
| 381 | NIF3L1 | NP_068596.2 | Transcriptional regula | Y97 | VGIySPHTAYDAAPQGVNNWLAK | T cell ALL | MOLT15 | SEQ ID NO: 382 |
| 382 | NOT2 | NP_055330.1 | Transcriptional regula | Y396 | AAETDPGMVHLALGSDLTTLGLNLNS | AML<br>CML | BaF3-10ZF<br>BaF3-PRTK<br>KG1-A | SEQ ID NO: 383 |
| 383 | NR2C2 | NP_003289.2 | Transcriptional regula | Y135 | TDVQRPQVVEyCVVCGDK | ALCL | TS | SEQ ID NO: 384 |
| 384 | PCDC5RP | NP_001244.1 | Transcriptional regula | Y232 | KPALGFYDTSEEnyQALDADFRK | AML<br>T cell leukemia | Jurkat<br>MKPL-1 | SEQ ID NO: 385 |
| 385 | PCDC5RP | NP_001244.1 | Transcriptional regula | Y459 | DKLNINPEDGMAdySDPSYVK | B cell lymphoma | SuDHL5 | SEQ ID NO: 386 |
| 386 | PCDC5RP | NP_001244.1 | Transcriptional regula | Y511 | EIDDTyIEDAADVDAR | T cell leukemia | Jurkat | SEQ ID NO: 387 |
| 387 | PCDC5RP | NP_001244.1 | Transcriptional regula | Y621 | TVGFGTNNSEHITYLEHNPyEK | ALCL | TS | SEQ ID NO: 388 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 388 | PFDN5 | NP_002615.2 | Transcriptional regula | Y90 | LHDVEHVLIDVGTGyYVEK | CML | BaF3-10ZF BaF3-4ZF | SEQ ID NO: 389 |
| 389 | PIAS4 | NP_056981.2 | Transcriptional regula | Y108 | TPLAGPNIDyPVLYGK | AML | MKPL-1 | SEQ ID NO: 390 |
| 390 | PLRG1 | NP_002660.1 | Transcriptional regula | Y92 | QYPANQGQEVEyFVAGTHPYPPGPG | AML T cell leukemia | Jurkat MKPL-1 | SEQ ID NO: 391 |
| 391 | POLR2A | NP_000928.1 | Transcriptional regula | Y1383 | ELyHVISFDGSYVNYR | ALCL CML | TS DU-528 | SEQ ID NO: 392 |
| 392 | POLR2A | NP_000928.1 | Transcriptional regula | Y1916 | YSPTSPTySPTSPK | T cell ALL | K562 | SEQ ID NO: 393 |
| 393 | POLR2I | NP_006224.1 | Transcriptional regula | Y54 | NCDYQQEADNSCIyVNK | T cell leukemia | Jurkat | SEQ ID NO: 394 |
| 394 | PQBP1 | NP_005701.1 | Transcriptional regula | Y33 | HLEPEPEEEIIAEDyDDDPVDYEATR | T cell leukemia | Jurkat | SEQ ID NO: 395 |
| 395 | RDBP | NP_002895.3 | Transcriptional regula | Y133 | SLyESFVSSSDR | T cell leukemia | Jurkat | SEQ ID NO: 396 |
| 396 | REL | NP_002899.1 | Transcriptional regula | Y47 | SAGSIPGEHSTDNNRTyPSIQIMNYYC | ALCL | TS | SEQ ID NO: 397 |
| 397 | RYBP | NP_036366.3 | Transcriptional regula | Y70 | INSQLVAQQVAQQyATPPPPK | T cell leukemia | Jurkat | SEQ ID NO: 398 |
| 398 | SHARP | NP_055816.2 | Transcriptional regula | Y1399 | ASALyESSR | T cell leukemia | Jurkat | SEQ ID NO: 399 |
| 399 | Skip | NP_036377.1 | Transcriptional regula | Y292 | LAEALyIADRK | AML | MKPL-1 | SEQ ID NO: 400 |
| 400 | Skip | NP_036377.1 | Transcriptional regula | Y407 | TSNEVQyDQR | B cell ALL | SEM | SEQ ID NO: 401 |
| 401 | PAIP1 | NP_006442.2 | Translational regulato | Y397 | EATPENDPNyFMNEPTFYTSDGVPF1 | T cell leukemia | Jurkat | SEQ ID NO: 402 |
| 402 | PAIP1 | NP_006442.2 | Translational regulato | Y405 | EATPENDPNYFMNEPTFyTSDGVPF1 | T cell leukemia | Jurkat | SEQ ID NO: 403 |
| 403 | RPS10 | NP_001005.1 | Translational regulato | Y82 | DyLHLPPEIVPATLRR | AML | KG1-A | SEQ ID NO: 404 |
| 404 | RPS2 | NP_002943.2 | Translational regulato | Y248 | ATFDAISKTySYLTPDLWK | AML | KG1-A | SEQ ID NO: 405 |
| 405 | RPS3 | NP_000996.2 | Translational regulato | Y166 | FVDGLMIHSGDPVNyYVDTAVR | AML CML NSCLC T cell ALL breast cancer | BaF3-10ZF BaF3-4ZF BaF3-FLT3(D842V) BaF3-FLT3(D842Y) BaF3-FLT3(K663Q) BaF3-FLT3(WT) CTV-1 H3255 MCF-10A (Y561F) MOLT15 | SEQ ID NO: 406 |
| 406 | RPS3 | NP_000996.2 | Translational regulato | Y167 | FVDGLMIHSGDPVNYyVDTAVR | AML T cell ALL | MOLT15 MV4-11 | SEQ ID NO: 407 |
| 407 | RPS8 | NP_001003.1 | Translational regulato | Y83 | IIDVvyNASNNELVR | AML T cell ALL | MKPL-1 MOLT15 MV4-11 | SEQ ID NO: 408 |
| 408 | NF1 | NP_000258.1 | Tumor suppressor | Y1500 | IGQyLSSNR | T cell ALL | MOLT15 | SEQ ID NO: 409 |
| 409 | PSMC5 | NP_002796.4 | Ubiquitin conjugating | Y148 | ILPNKVDPLVSLMMVEKVPDSTyEMIC | T cell ALL | MOLT15 | SEQ ID NO: 410 |
| 410 | MYCT1 | NP_079383.1 | Unknown function | Y225 | VGLSTPPPPAyESIIK | AML | M-07e | SEQ ID NO: 411 |
| 411 | MYO1G | NP_149043.1 | Unknown function | Y598 | NSMVALVENLASKEPFyVR | AML T cell ALL | CTV-1 MOLT15 | SEQ ID NO: 412 |
| 412 | MYO1G | NP_149043.1 | Unknown function | Y624 | HQVAyLGLLENVR | AML | CHRF | SEQ ID NO: 413 |
| 413 | MYO1G | NP_149043.1 | Unknown function | Y737 | AIyTIMR | ALCL anaplastic lymphoma | Karpas 299 SUP-M2 TS | SEQ ID NO: 414 |
| 414 | NARFL | NP_071938.1 | Unknown function | Y239 | IyHVTVMPCYDK | B cell lymphoma | VAL | SEQ ID NO: 415 |
| 415 | NARFL | NP_071938.1 | Unknown function | Y247 | IYHVTVMPCyDK | B cell lymphoma | VAL | SEQ ID NO: 416 |
| 416 | NARFL | NP_071938.1 | Unknown function | Y49 | IEDDGSyFQINQDGGTR | T cell leukemia | Jurkat | SEQ ID NO: 417 |
| 417 | NARG2 | NP_078887.2 | Unknown function | Y108 | SyVDLLVKYAK | AML | MKPL-1 | SEQ ID NO: 418 |
| 418 | NARG2 | NP_078887.2 | Unknown function | Y115 | SYVDLLVKyAK | AML | MKPL-1 | SEQ ID NO: 419 |
| 419 | NGRN | NP_057729.1 | Unknown function | Y165 | ELQKySSDSESPRGTGSGALPSGGKI | AML | PL21 | SEQ ID NO: 420 |
| 420 | Nice-4 | NP_055662.2 | Unknown function | Y1079 | SAyNSYSWGAN | T cell leukemia | Jurkat | SEQ ID NO: 421 |
| 421 | Nice-4 | NP_055662.2 | Unknown function | Y1082 | SAYNSySWGAN | T cell leukemia | Jurkat | SEQ ID NO: 422 |

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| | | | | | | ALCL<br>ALL<br>AML<br>B cell ALL<br>CML<br>NSCLC<br>SCLC<br>T cell ALL<br>T cell leukemia<br>colon cancer<br>gastric cancer<br>glioblastoma<br>lymphoma<br>multiple myeloma<br>neuroblastoma<br>neuroepithelioma<br>osteosarcoma<br>pancreas<br>prostate cancer<br>transformed kidney | 293T TNT-TAT Silac<br>3T3 TrkB<br>3T3-TrkA<br>831/13<br>BaF3-TelVFGFR3<br>Baf3/E255K<br>Baf3/Jak2(IL-3 dep)<br>Baf3/M351T<br>Baf3/T315I<br>Baf3/Y253F<br>Baf3/p210wt<br>CHRF<br>CI-1<br>CTV-1<br>DBTRG-05MG<br>DU145<br>H1793<br>H1869<br>H1993<br>H2286<br>HCC78<br>HT29<br>Jurkat<br>K562<br>KG-1<br>KG1-A<br>KMS11<br>KMS18<br>KOPT-K1<br>KY821<br>MKPL-1<br>MNNG/MOS<br>MO-91<br>MOLT15<br>MV4-11<br>Molm 14<br>NCI-N87<br>OCI-M1<br>OCI/AML2 | |
| 422 | Nice-4 | NP_055662.2 | Unknown function | Y858 | DGSLASNPySGDLTK | | PL21 | SEQ ID NO: 423 |
| 423 | NIP30 | NP_079222.1 | Unknown function | Y49 | KPEDPEECPEEVyDPRSLyER | AML<br>T cell leukemia | Jurkat<br>MV4-11 | SEQ ID NO: 424 |
| 424 | NIP30 | NP_079222.1 | Unknown function | Y55 | KPEDPEECPEEVYDPRSLyER | AML<br>T cell leukemia | Jurkat<br>MV4-11 | SEQ ID NO: 425 |
| 425 | NIP30 | NP_079222.1 | Unknown function | Y69 | KQQEyEEQFK | T cell leukemia | Jurkat | SEQ ID NO: 426 |
| 426 | NOL10 | NP_079170.1 | Unknown function | Y289 | MGIyYIPVLGPAPR | CML | Baf3/p210wt<br>K562 | SEQ ID NO: 427 |
| 427 | NSUN2 | NP_060225.4 | Unknown function | Y609 | LAQEGIyTLYPFINSR | ALCL | 293T TNT<br>293T TNT-TAT Silac | SEQ ID NO: 428 |
| 428 | NUCKS | NP_073568.2 | Unknown function | Y13 | VVDySQFQESDDADEDYGRDSGPPT | T cell leukemia | Jurkat | SEQ ID NO: 429 |
| 429 | NUCKS | NP_073568.2 | Unknown function | Y26 | VVDYSQFQESDDADEDyGRDSGPPT | T cell leukemia | Jurkat | SEQ ID NO: 430 |
| 430 | NUDCD3 | NP_056147.2 | Unknown function | Y271 | VGEyWWNAILEGEEPIDIDKINK | AML | KG1-A | SEQ ID NO: 431 |
| 431 | NUDT15 | NP_060753.1 | Unknown function | Y92 | NSFIEKENYHy | anaplastic lymphoma | Karpas 299 | SEQ ID NO: 432 |
| 432 | optineurin | NP_098815.2 | Unknown function | Y356 | QELVyTNKKLELQVESMLSEIK | T cell ALL | MOLT15 | SEQ ID NO: 433 |
| 433 | palmdelphin | NP_060204.1 | Unknown function | Y262 | SPTEYHEPVyANPFYRPTTPQR | CML<br>umbilical vein endothelial cells | K562<br>HUVEC | SEQ ID NO: 434 |
| 434 | PCM-1 | NP_006188.3 | Unknown function | Y1757 | QTQTSEVyDGPK | T cell leukemia | Jurkat | SEQ ID NO: 435 |
| 435 | PCM-1 | NP_006188.3 | Unknown function | Y215 | LVQIRDyITK | T cell ALL | DU-528 | SEQ ID NO: 436 |
| 436 | PCM-1 | NP_006188.3 | Unknown function | Y509 | ELVHyYEQTSDMMTDAVNENR | B cell lymphoma | VAL | SEQ ID NO: 437 |
| 437 | PCM-1 | NP_006188.3 | Unknown function | Y965 | WKNNCPFSADENyRPLAK | AML<br>T cell ALL<br>T cell lymphoma<br>ALCL | DU-528<br>Karpas-1106p<br>MKPL-1<br>MV4-11<br>Mac1<br>Me-F2<br>RC-K8<br>BaF3-FLT3(WT) | SEQ ID NO: 438 |
| 438 | PELO | NP_057030.3 | Unknown function | Y99 | MGAyHTIELEPNR | AML | TS | SEQ ID NO: 439 |
| 439 | PHF8 | NP_055922.1 | Unknown function | Y178 | LGDFVKyYYSGKR | AML | MV4-11 | SEQ ID NO: 440 |
| 440 | PHF8 | NP_055922.1 | Unknown function | Y179 | LGDFVKYyYSGKR | AML | MV4-11 | SEQ ID NO: 441 |
| 441 | PHF8 | NP_055922.1 | Unknown function | Y180 | LGDFVKYYySGKR | AML | MV4-11 | SEQ ID NO: 442 |
| 442 | PLEKHG1 | NP_001025055.1 | Unknown function | Y559 | SPQENEDOEDDyQMFVPSFSSSDLN | DLBCL | OCI-ly3 | SEQ ID NO: 443 |
| 443 | PPIL4 | NP_624311.1 | Unknown function | Y39 | IKYYNyCLIHNVQR | anaplastic lymphoma | Karpas 299 | SEQ ID NO: 444 |

Figure 2

| | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 444 | PROSC | NP_009129.1 | Unknown function | Y69 | TFGENyVQELLEK | AML CML NSCLC | BaF3-10ZF BaF3-4ZF BaF3-PRTK CTV-1 H3255 KG-1 KG1-A MO-91 | SEQ ID NO: 445 |
| 445 | PSST739 | NP_940972.1 | Unknown function | Y163 | GKGCVDESGFVyAIGEK | DLBCL | OCI-ly1 | SEQ ID NO: 446 |
| 446 | PSTPIP2 | NP_077748.2 | Unknown function | Y191 | AyMLHIGTLDK | AML | MV4-11 | SEQ ID NO: 447 |
| 447 | PSTPIP2 | EAX01466.1 | Unknown function | Y241 | DIEyFVNQR | AML breast cancer | CHRF HU-3 MCF-10A(Y969F) MDA-MB-453 Me-F2 | SEQ ID NO: 448 |
| 448 | PYM | NP_115721.1 | Unknown function | Y45 | VKEGYVPQEEVPVyENKYVK | AML T cell leukemia | Jurkat MV4-11 | SEQ ID NO: 449 |
| 449 | PYM | NP_115721.1 | Unknown function | Y49 | VKEGYVPQEEVPVYENKyVK | AML T cell leukemia | Jurkat MV4-11 | SEQ ID NO: 450 |
| 450 | Q8WVJ2 | NP_660309.1 | Unknown function | Y145 | FQKENPGFDFSGAEISGNyTK | T cell leukemia | Jurkat | SEQ ID NO: 451 |
| 451 | R3HDM | NP_056176.2 | Unknown function | Y254 | yILKRDNSSFDK | AML NSCLC SCLC breast cancer cervical cancer colon cancer gastric cancer glioblastoma glioma lymphoma squamous cell carcinoma | 3T3-EGFR(del) 3T3-EGFRwt A172 H1651 H1666 H1915 H1975 H2170 H446 H810 HCC827 HL117A HL117B HL41A HL57 HL59A HL61a HL66A HL66B HL79A HL79B HL83A HT29 HeLa KG1-A LOU-NH91 MCF7 Monomac 6 NCI-N87 SCLC T1 SUPT-13 T47D U87 MG XG2 cs018 cs019 cs024 hl145a hl152a | SEQ ID NO: 452 |
| 452 | R3HDM | NP_056176.2 | Unknown function | Y354 | STNSHQSSTENELKySEPRPWSSTD | T cell leukemia | Jurkat | SEQ ID NO: 453 |
| 453 | RAB3IP | NP_071901.2 | Unknown function | Y400 | LGDSSNyYISPFCR | AML | KG1-A | SEQ ID NO: 454 |
| 454 | RAMA1 | NP_659498.2 | Unknown function | Y39 | ALDGEESDFEDyPMR | AML | KG-1 TS | SEQ ID NO: 455 |
| 455 | RAP140 | NP_056039.1 | Unknown function | Y182 | EFIMFPyDSRLDDK | ALCL | gzB1 | SEQ ID NO: 456 |
| 456 | RB1CC1 | NP_055596.3 | Unknown function | Y1564 | VMEKEyCQAKKAQNRFKVPLGTKFYI | CML | K562 | SEQ ID NO: 457 |
| 457 | RBM10 | NP_005667.2 | Unknown function | Y694 | ESATADAGyAILEK | AML | MKPL-1 | SEQ ID NO: 458 |
| 458 | RBM12B | NP_976324.2 | Unknown function | Y519 | GDHSHLFDSKDPPIySVGAFENFR | AML | MKPL-1 | SEQ ID NO: 459 |
| 459 | RBM13 | NP_115898.2 | Unknown function | Y33 | NEySLTGLCNR | ALCL AML T cell ALL | CTV-1 MOLT15 MV4-11 RC-K8 TS | SEQ ID NO: 460 |
| 460 | RBM13 | NP_115898.2 | Unknown function | Y62 | GQCyLYMK | ALCL anaplastic lymphoma | Karpas 299 SU-DHL1 TS | SEQ ID NO: 461 |
| 461 | RBM13 | NP_115898.2 | Unknown function | Y64 | GQCYLyMK | anaplastic lymphoma | Karpas 299 | SEQ ID NO: 462 |
| 462 | RBM16 | NP_055707.3 | Unknown function | Y1237 | HAQPPPIPVQNDPELyEK | T cell leukemia | Jurkat | SEQ ID NO: 463 |
| 463 | RBM34 | NP_055829.1 | Unknown function | Y66 | LASLFSSLEPQIQPVyVPVPK | AML | MKPL-1 | SEQ ID NO: 464 |

Figure 2

|   | A | B | C | D | E | F | G | H |
|---|---|---|---|---|---|---|---|---|
| 1 | Protein Name | Accession No. | Protein Type | Phospho-Residue | Phosphorylation Site Sequence | Disease | Cell Line / Tissue / Patient | SEQ ID NO |
| 464 | RCD-8 | NP_055144.3 | Unknown function | Y853 | SLAFHRPPyHLLQQR | AML | MKPL-1 | SEQ ID NO: 465 |
| 465 | RGPD8 | NP_005045.2 | Unknown function | Y1633 | NLSASFPTEESSINyTFK | AML | KG-1<br>KG1-A | SEQ ID NO: 468 |
| 466 | RGPD8 | NP_005045.2 | Unknown function | Y1711 | SAANLEyLK | AML | KG-1<br>KG1-A | SEQ ID NO: 469 |
| 467 | RGPD8 | NP_005045.2 | Unknown function | Y763 | QMLNSVMQELEDYSEGGPLyKNGSL | AML | MKPL-1 | SEQ ID NO: 470 |
| 468 | RNF138 | NP_057355.2 | Unknown function | Y145 | SETSTSDNTETyQENTSSSGHPTFK | T cell leukemia | Jurkat | SEQ ID NO: 471 |
| 469 | RNF146 | NP_112225.2 | Unknown function | Y103 | GNGEyAWYYEGR | CML | BaF3-10ZF | SEQ ID NO: 472 |
| 470 | SACS | NP_055178.2 | Unknown function | Y3220 | TANIESPTSILKALHy | T cell ALL | DU-528 | SEQ ID NO: 473 |
| 471 | SACS | NP_055178.2 | Unknown function | Y3316 | ELyEVIGCVPVDDLEVYLK | CML | K562 | SEQ ID NO: 474 |
| 472 | SACS | NP_055178.2 | Unknown function | Y3330 | ELYEVIGCVPVDDLEVyLK | CML | K562 | SEQ ID NO: 475 |
| 473 | SAFB2 | NP_055464.1 | Unknown function | Y741 | DDAyWPEGK | AML | MKPL-1 | SEQ ID NO: 476 |
| 474 | SAMHD1 | NP_056289.2 | Unknown function | Y315 | NGIDVDKWDyFAR | CML | BaF3-4ZF | SEQ ID NO: 477 |
| 475 | SC65 | NP_006446.1 | Unknown function | Y20 | MARVAWGLLWLLLGSAGAQyEKYSFI | lymphoma | SUPT-13 | SEQ ID NO: 478 |
| 476 | SC65 | NP_006446.1 | Unknown function | Y23 | MARVAWGLLWLLLGSAGAQYEKySFI | lymphoma | SUPT-13 | SEQ ID NO: 479 |
| 477 | SDCCAG1 | NP_004704.2 | Unknown function | Y117 | yDRGNIVLTDYEY | AML | CMK | SEQ ID NO: 480 |
| 478 | SDCCAG1 | NP_004704.2 | Unknown function | Y127 | YDRGNIVLTDyEY | AML | CMK | SEQ ID NO: 481 |
| 479 | SDCCAG1 | NP_004704.2 | Unknown function | Y129 | YDRGNIVLTDYEy | AML | CMK | SEQ ID NO: 482 |
| 480 | SDCCAG1 | NP_004704.2 | Unknown function | Y30 | VNNVyDVDNK | T cell ALL | MOLT15 | SEQ ID NO: 483 |
| 481 | SDCCAG1 | NP_004704.2 | Unknown function | Y883 | MKKMKEKyKDQDEEDRELIMK | AML | MV4-11 | SEQ ID NO: 484 |
| 482 | SFRS2IP | NP_004710.2 | Unknown function | Y1161 | TLPADVQNyYSR | AML | MKPL-1 | SEQ ID NO: 485 |
| 483 | SH2D5 | XP_375698.3 | Unknown function | Y619 | LGNPyCSPTLVR | CML | Baf3/H396P<br>Baf3/M351T<br>Baf3/T315I | SEQ ID NO: 486 |
| 484 | SH2D5 | XP_375698.3 | Unknown function | Y640 | SGAyRGCTYETQLQLSAR | CML | Baf3/E255K<br>Baf3/H396P<br>Baf3/M351T<br>Baf3/T315I<br>Baf3/Y253F<br>Baf3/p210wt | SEQ ID NO: 487 |
| 485 | ShcBP1 | NP_079021.2 | Unknown function | Y217 | SWDEEEEDEyDYFVR | T cell ALL | MOLT15 | SEQ ID NO: 488 |
| 486 | similar to ZFP 267 | XP_001132888.1 | Unknown function | Y163 | HKIIHNEEKPYKCKEyEK | ALCL | SU-DHL1 | SEQ ID NO: 490 |
| 487 | SKIV2L2 | NP_056175.2 | Unknown function | Y583 | VEEINPEyMLEK | AML | KG-1 | SEQ ID NO: 491 |
| 488 | SKIV2L2 | NP_056175.2 | Unknown function | Y590 | SFyQFQHYR | ALCL | TS | SEQ ID NO: 492 |
| 489 | SKIV2L2 | NP_056175.2 | Unknown function | Y694 | KSNVKPNSGELDPLyVVEVLLR | CML | BaF3-PRTK | SEQ ID NO: 493 |
| 490 | SCAMP1 | NP_004857.4 | Vesicle protein | Y37 | NVPPGLDEyNPFSDSR | T cell leukemia<br>gastric cancer<br>ALCL | Jurkat<br>NCI-N87<br>MOLT15 | SEQ ID NO: 494 |
| 491 | Sec24B | NP_006314.2 | Vesicle protein | Y1100 | LDDRVyAMCQIK | T cell ALL | TS | SEQ ID NO: 495 |
| 492 | Sec5 | NP_060773.3 | Vesicle protein | Y534 | DGEAKQyGGWEVK | T cell ALL | MOLT15 | SEQ ID NO: 496 |

14

SEQUENCE LISTING

<160> NUMBER OF SEQ ID NOS: 496

<210> SEQ ID NO 1
<211> LENGTH: 29
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 1

Val Thr Ser Val His Leu Pro Asp Tyr Ala His Tyr Tyr Thr Ile Gly
1               5                   10                  15

Pro Gly Met Phe Pro Ser Ser Gln Ile Pro Ser Trp Lys
            20                  25

<210> SEQ ID NO 2
<211> LENGTH: 29
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 2

Val Thr Ser Val His Leu Pro Asp Tyr Ala His Tyr Tyr Thr Ile Gly
1               5                   10                  15

Pro Gly Met Phe Pro Ser Ser Gln Ile Pro Ser Trp Lys
            20                  25

<210> SEQ ID NO 3
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 3

Val Gln Leu Val Asp Asn Val Tyr Cys Ile Gly Gln Arg
1               5                   10

<210> SEQ ID NO 4
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 4

Thr Gly Tyr Val Pro Ser Asn Tyr Val Glu Arg
1               5                   10

<210> SEQ ID NO 5
<211> LENGTH: 27
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr -continued

```
<400> SEQUENCE: 5

Gly Pro Asn Ala Ala Tyr Asp Phe Ser Gln Ala Thr Thr Gly Glu
1               5                   10                  15

Leu Ala Ala Asn Lys Ser Glu Met Ala Phe Lys
            20                  25

<210> SEQ ID NO 6
<211> LENGTH: 24
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 6

Val Gly Pro Asn Ala Thr Tyr Asn Phe Ser Gln Ser Leu Asn Ala Asn
1               5                   10                  15

Asp Leu Ala Asn Ser Arg Pro Lys
            20

<210> SEQ ID NO 7
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 7

Tyr Leu Met Leu Lys Asp Tyr Thr Lys Val Pro Ile Lys Arg
1               5                   10

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 8

Glu Gln Ser Gly Thr Ile Tyr Leu Gln His Ala Asp Glu Glu Arg
1               5                   10                  15

<210> SEQ ID NO 9
<211> LENGTH: 32
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 9

Thr Pro Asn Ser Thr Leu Pro Pro Ala Gly Arg Pro Ser Glu Glu Pro
1               5                   10                  15

Glu Pro Asp Tyr Glu Ala Ile Gln Thr Leu Asn Arg Glu Glu Glu Lys
            20                  25                  30

<210> SEQ ID NO 10
<211> LENGTH: 25
<212> TYPE: PRT
<213> ORGANISM: Homo sapiens
<220> FEATURE:
```

```
<221> NAME/KEY: MOD_RES
<222> LOCATION: (13)..(13)
<223> OTHER INFORMATION: Phosphorylated-Tyr

<400> SEQUENCE: 10

Gly His Ala Ala Glu Ile Ser Asp Met Ala Val Asn Tyr Glu Asn Thr
1               5                   10                  15
Met Ile Ala Ala Gly Ser Cys Asp Lys
            20                  25

<210> SEQ ID NO 11
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 11

Lys Asn Lys Ile Tyr Ser Ile Asn Pro Lys Lys
1               5                   10

<210> SEQ ID NO 12
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 12

Thr Val Phe Tyr Tyr Tyr Gly Ser Asp Lys Asp Lys
1               5                   10

<210> SEQ ID NO 13
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 13

Leu Thr Arg Asp Glu Thr Asn Tyr Gly Ile Pro Gln Arg
1               5                   10

<210> SEQ ID NO 14
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 14

Ala Lys Tyr Trp Leu Glu Arg
1               5

<210> SEQ ID NO 15
<211> LENGTH: 12
<212> TYPE: PRT
<213> ORGANISM: Homo sapiens
<220> FEATURE:
<221> NAME/KEY: MOD_RES
<222> LOCATION: (6)..(6)
```

<223> OTHER INFORMATION: Phosphorylated-Tyr

<400> SEQUENCE: 15

Ile Cys Ala Asn His Tyr Ile Ser Pro Asp Met Lys
1               5                   10

<210> SEQ ID NO 16
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 16

Ser Phe Val Trp His Ala Leu Asp Tyr Ala Asp Glu Leu Pro Lys Pro
1               5                   10                  15

Glu Gln Leu Ala Ile Arg
            20

<210> SEQ ID NO 17
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 17

Ser Thr Pro Ser Pro Thr Arg Tyr Ser Leu Ser Pro Ser Lys Ser Tyr
1               5                   10                  15

Lys Tyr Ser Pro Lys
            20

<210> SEQ ID NO 18
<211> LENGTH: 21
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 18

Ser Thr Pro Ser Pro Thr Arg Tyr Ser Leu Ser Pro Ser Lys Ser Tyr
1               5                   10                  15

Lys Tyr Ser Pro Lys
            20

<210> SEQ ID NO 19
<211> LENGTH: 21
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 19

Ser Thr Pro Ser Pro Thr Arg Tyr Ser Leu Ser Pro Ser Lys Ser Tyr
1               5                   10                  15

Lys Tyr Ser Pro Lys
            20

-continued

```
<210> SEQ ID NO 20
<211> LENGTH: 28
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 20

Ala Ser Asp Ser Met Asp Ser Leu Tyr Ser Gly Gln Ser Ser Ser
1               5                  10                  15

Gly Ile Thr Ser Cys Ser Asp Gly Thr Ser Asn Arg
            20                  25

<210> SEQ ID NO 21
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 21

Phe Ile Glu Ala Gly Gln Tyr Asn Asn His Leu Tyr Gly Thr Ser Val
1               5                  10                  15

Gln Ser Val Arg
            20

<210> SEQ ID NO 22
<211> LENGTH: 27
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 22

Thr Lys Leu Tyr Asp Met Ile Ala Asp Leu Gly Asp Asp Glu Leu Pro
1               5                  10                  15

His Ile Pro Ser Gly Ile Ile Asn Gln Ser Arg
            20                  25

<210> SEQ ID NO 23
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 23

Ala Ala Gly Glu Pro Glu Ala Gly Ser Asp Tyr Val Lys
1               5                  10

<210> SEQ ID NO 24
<211> LENGTH: 26
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 24
```

```
Gly Val Asp Tyr Ala Ser Tyr Tyr Gln Gly Leu Trp Asp Cys His Gly
1               5                   10                  15

Asp Gln Pro Asp Glu Leu Ser Phe Gln Arg
            20                  25
```

<210> SEQ ID NO 25
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 25

```
Tyr Asn Thr Gly Gly Asn Pro Thr Glu Asp Val Ser Val Asn Ser Arg
1               5                   10                  15
```

<210> SEQ ID NO 26
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 26

```
Asn Glu Glu Gly Lys Tyr Gly Tyr Val Leu Arg
1               5                   10
```

<210> SEQ ID NO 27
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 27

```
Asn Glu Glu Gly Lys Tyr Gly Tyr Val Leu Arg
1               5                   10
```

<210> SEQ ID NO 28
<211> LENGTH: 35
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 28

```
Tyr Asp Glu Glu Gly Gly Glu Glu Asp Gln Asp Tyr Asp Leu Ser
1               5                   10                  15

Gln Leu Gln Gln Pro Asp Thr Val Glu Pro Asp Ala Ile Lys Pro Val
                20                  25                  30

Gly Ile Arg
        35
```

<210> SEQ ID NO 29
<211> LENGTH: 26
<212> TYPE: PRT
<213> ORGANISM: Homo sapiens
<220> FEATURE:
<221> NAME/KEY: MOD_RES
<222> LOCATION: (7)..(7)

```
<223> OTHER INFORMATION: Phosphorylated-Tyr

<400> SEQUENCE: 29

Thr Tyr Tyr Ser Pro Val Tyr Arg Ser Pro Asn His Gly Thr Val Glu
1               5                   10                  15

Leu Gln Gly Ser Gln Thr Ala Leu Tyr Arg
            20                  25

<210> SEQ ID NO 30
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 30

Trp Tyr Lys Asp Gly Glu Arg
1               5

<210> SEQ ID NO 31
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 31

Gly Leu Ser Asn Tyr Ala Val Thr Phe Gln Arg
1               5                   10

<210> SEQ ID NO 32
<211> LENGTH: 24
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 32

Met Val Glu Pro Glu Asn Ala Val Thr Ile Thr Pro Leu Arg Pro Glu
1               5                   10                  15

Asp Asp Tyr Ser Pro Arg Glu Arg
            20

<210> SEQ ID NO 33
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 33

Asn Gly Leu Val Leu Gly Tyr Lys Val Met Tyr Lys Glu Lys
1               5                   10

<210> SEQ ID NO 34
<211> LENGTH: 24
<212> TYPE: PRT
<213> ORGANISM: Homo sapiens
<220> FEATURE:
<221> NAME/KEY: MOD_RES
```

```
<222> LOCATION: (12)..(12)
<223> OTHER INFORMATION: Phosphorylated-Tyr

<400> SEQUENCE: 34

Cys Pro Leu Asn Pro His Ser His Leu Gly Thr Tyr Gly Val Phe Thr
1               5                   10                  15

Asn Ala Ala Phe Asp Pro Ser Pro
            20

<210> SEQ ID NO 35
<211> LENGTH: 23
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 35

Lys Ser Arg Glu Pro Lys Asp Gln Glu Ala Pro Ser Thr Thr Glu Tyr
1               5                   10                  15

Ser Glu Ile Lys Thr Ser Lys
            20

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 36

Asn Ala Tyr His Ala Val Tyr Lys Gln Ser Val Thr Ser Ser Ala
1               5                   10                  15

<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 37

Asn Ala Tyr His Ala Val Tyr Lys Gln Ser Val Thr Ser Ser Ala
1               5                   10                  15

<210> SEQ ID NO 38
<211> LENGTH: 30
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 38

Val Ala Met Asn Val Tyr Glu Leu Ser Ser Ala Ala Gly Leu Pro Cys
1               5                   10                  15

Glu Ile Asp Pro Ala Leu Val Val Ala Leu Ser Ser Gln Lys
            20                  25                  30

<210> SEQ ID NO 39
<211> LENGTH: 11
```

```
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 39

Thr Pro Tyr Ile Val Leu Ser Gly Ser Gly Lys
1               5                   10

<210> SEQ ID NO 40
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 40

Glu Gln Val Tyr Asp Ala Met Gly Glu Lys
1               5                   10

<210> SEQ ID NO 41
<211> LENGTH: 14
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 41

Leu Gly Val Thr Asn Thr Ile Ile Ser His Tyr Asp Gly Arg
1               5                   10

<210> SEQ ID NO 42
<211> LENGTH: 18
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 42

Lys Leu Asp Val Glu Glu Pro Asp Ser Ala Asn Ser Ser Phe Tyr Ser
1               5                   10                  15

Thr Arg

<210> SEQ ID NO 43
<211> LENGTH: 30
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 43

Leu Gln Leu Ile Asp Asp Gln Phe Ala Asp Ala Tyr Pro Gln Arg Ile
1               5                   10                  15

Lys Phe Glu Ser Leu Glu Ile Lys Leu Asn Glu Tyr Lys Arg
            20                  25                  30

<210> SEQ ID NO 44
<211> LENGTH: 15
```

```
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 44

Gln Thr Gln Thr Ala Leu Glu Asn Glu Val Tyr Cys Asn Pro Lys
1               5                   10                  15

<210> SEQ ID NO 45
<211> LENGTH: 25
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 45

Ile Thr Asn Tyr Pro Thr Ala Trp Val Glu Gly Ser Ser Pro Asp Ser
1               5                   10                  15

Asp Leu Glu Phe Val Ala Asn Thr Lys
            20                  25

<210> SEQ ID NO 46
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 46

Ile Ala Leu His Thr Ala Leu Asn Asn Pro Tyr Tyr Tyr Leu Lys Asn
1               5                   10                  15

Glu Ala Leu Lys
            20

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 47

Ile Ala Leu His Thr Ala Leu Asn Asn Pro Tyr Tyr Tyr Leu Lys
1               5                   10                  15

<210> SEQ ID NO 48
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 48

Ser Asn Gly Tyr Glu Glu Ala Tyr Ser Val Phe Lys Lys
1               5                   10

<210> SEQ ID NO 49
```

```
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 49

Thr Ala Pro Tyr Val Val Thr Gly Ser Val Asp Gln Thr Val Lys
1               5                   10                  15

<210> SEQ ID NO 50
<211> LENGTH: 21
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 50

Phe Lys Ile Glu Asn Ser Ala Glu Glu Phe Ala Leu Tyr Val Val His
1               5                   10                  15

Thr Ser Gly Glu Lys
            20

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 51

Ser Ser Val Pro Ala Ser Asp Asp Ala Tyr Pro Glu Ile Glu Lys
1               5                   10                  15

<210> SEQ ID NO 52
<211> LENGTH: 17
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 52

Asn Leu Glu Gly Tyr Val Gly Phe Ala Asn Leu Pro Asn Gln Val Tyr
1               5                   10                  15

Arg

<210> SEQ ID NO 53
<211> LENGTH: 23
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 53

Ser Thr Leu Ile Asn Ser Leu Phe Leu Thr Asp Leu Tyr Ser Pro Glu
1               5                   10                  15

Tyr Pro Gly Pro Ser His Arg
            20
```

```
<210> SEQ ID NO 54
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 54

Lys Glu Glu Lys Pro Leu Leu Ile Met Phe Tyr Ala Pro Trp Cys Ser
1               5                   10                  15

Met Cys Lys

<210> SEQ ID NO 55
<211> LENGTH: 23
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 55

Gln Lys Ser Ser Asp Glu Ser Cys Leu Val Val Leu Phe Ala Gly Asp
1               5                   10                  15

Tyr Thr Ile Ala Asn Ala Arg
            20

<210> SEQ ID NO 56
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 56

Leu Gly Asn Tyr Ala Gly Ala Val Gln Asp Cys Glu Arg
1               5                   10

<210> SEQ ID NO 57
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 57

Ala Gly Leu Ala Leu Ser Lys His Tyr Lys Val Tyr Lys
1               5                   10

<210> SEQ ID NO 58
<211> LENGTH: 18
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 58

Val Glu Met Leu Asp Asn Leu Leu Asp Ile Glu Val Ala Tyr Ser Leu
1               5                   10                  15
```

Leu Arg

```
<210> SEQ ID NO 59
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 59

Tyr Asn Gln Pro Val Tyr Asn Gln Pro Val Gly Ala
1               5                   10

<210> SEQ ID NO 60
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 60

Glu Tyr Pro His Arg Arg Ile Asp Ile Arg Leu Ile Pro Lys
1               5                   10

<210> SEQ ID NO 61
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 61

Val Tyr Asn Ser Glu Arg Lys Lys Phe Leu Pro Leu
1               5                   10

<210> SEQ ID NO 62
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 62

Phe Phe Phe Asp Val Gly Ser Asn Lys Tyr Gly Val Phe Met Arg
1               5                   10                  15

<210> SEQ ID NO 63
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 63

Leu Asn Ala Thr Tyr Tyr Ile Thr Lys
1               5

<210> SEQ ID NO 64
```

```
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 64

Leu Asn Ala Thr Tyr Tyr Ile Thr Lys
1               5

<210> SEQ ID NO 65
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 65

Asp Asp Ala Tyr Trp Pro Glu Ala Lys Arg
1               5                   10

<210> SEQ ID NO 66
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 66

Ala Leu Leu Gly Glu Glu Asp Glu Glu Ala Leu His Tyr
1               5                   10

<210> SEQ ID NO 67
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 67

Tyr Ile Leu Leu Pro Asp Ala Met Asn Ile Glu Leu Thr Arg
1               5                   10

<210> SEQ ID NO 68
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 68

Gln Ala Tyr Asp Leu Gln Ser Asp Asn Leu Tyr Lys Ser Asp Leu Gln
1               5                   10                  15

Trp Leu Lys

<210> SEQ ID NO 69
<211> LENGTH: 19
<212> TYPE: PRT
<213> ORGANISM: Homo sapiens
```

```
<220> FEATURE:
<221> NAME/KEY: MOD_RES
<222> LOCATION: (11)..(11)
<223> OTHER INFORMATION: Phosphorylated-Tyr

<400> SEQUENCE: 69

Gln Ala Tyr Asp Leu Gln Ser Asp Asn Leu Tyr Lys Ser Asp Leu Gln
1               5                   10                  15

Trp Leu Lys

<210> SEQ ID NO 70
<211> LENGTH: 18
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 70

Asp Tyr Asp Leu Arg Ala Asp Ala Ile Ser Ile Lys Ser Ala Lys Ala
1               5                   10                  15

Ser Arg

<210> SEQ ID NO 71

<400> SEQUENCE: 71

000

<210> SEQ ID NO 72
<211> LENGTH: 16
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 72

Thr Lys Pro Pro Glu Gly Tyr Asp Thr Val Thr Leu Tyr Pro Lys Ala
1               5                   10                  15

<210> SEQ ID NO 73
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 73

Gln Gln Gly Leu Ala Ser Tyr Asp Tyr Val Arg
1               5                   10

<210> SEQ ID NO 74
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 74

Ser Ile Ile Thr Tyr Val Ser Ser Leu Tyr Asp Ala Met Pro Arg
1               5                   10                  15
```

```
<210> SEQ ID NO 75
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 75

Ser Tyr Ser Phe His Gln Ser Gln His Arg
1               5                   10

<210> SEQ ID NO 76
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 76

Tyr Tyr Ser His Val Asp Tyr Arg
1               5

<210> SEQ ID NO 77
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 77

Ser Ser Phe Tyr Val Asn Gly Leu Thr Leu Gly Gly Gln Lys
1               5                   10

<210> SEQ ID NO 78
<211> LENGTH: 21
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 78

Ser Thr Met Pro Gly Ser Val Gly Pro Gln Val Tyr Lys Val Gly Ile
1               5                   10                  15

Tyr Gly Trp Arg Lys
            20

<210> SEQ ID NO 79
<211> LENGTH: 21
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 79

Ser Thr Met Pro Gly Ser Val Gly Pro Gln Val Tyr Lys Val Gly Ile
1               5                   10                  15

Tyr Gly Trp Arg Lys
```

20

<210> SEQ ID NO 80

<400> SEQUENCE: 80

000

<210> SEQ ID NO 81
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 81

Gln Leu His Asp Asp Tyr Phe Tyr His Asp Glu Leu
1               5                   10

<210> SEQ ID NO 82
<211> LENGTH: 25
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 82

Asp Ser Asn Gln Phe His Ala Thr Cys Leu Asp Thr Phe Pro Pro Ile
1               5                   10                  15

Ser Tyr Leu Asn Ala Ile Ser Trp Arg
            20                  25

<210> SEQ ID NO 83
<211> LENGTH: 32
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Phosphorylated-Tyr

<400> SEQUENCE: 83

Gln Val Tyr Gln Ile Val Lys Pro Leu Asn Pro Asn Phe Cys Phe Leu
1               5                   10                  15

Gln Cys Thr Ser Ala Tyr Pro Leu Gln Pro Glu Asp Val Asn Leu Arg
                20                  25                  30

<210> SEQ ID NO 84
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 84

Ser His Val Cys Trp His Val Tyr Gly Leu Leu Gln Arg
1               5                   10

<210> SEQ ID NO 85
<211> LENGTH: 7
<212> TYPE: PRT
<213> ORGANISM: Homo sapiens

```
<220> FEATURE:
<221> NAME/KEY: MOD_RES
<222> LOCATION: (5)..(5)
<223> OTHER INFORMATION: Phosphorylated-Tyr

<400> SEQUENCE: 85

Asp Val Cys Leu Tyr Pro Arg
1               5

<210> SEQ ID NO 86
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 86

Ile Leu Tyr Thr Lys Ile Leu Asp Val Leu Glu Glu Ile Pro Lys
1               5                   10                  15

<210> SEQ ID NO 87
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 87

Gly Leu Leu Thr Tyr Thr Ser Trp Glu Asp Ala Leu Ser Arg
1               5                   10

<210> SEQ ID NO 88
<211> LENGTH: 19
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 88

Pro Gly Ser Asp Thr Ile Lys Pro Asn Val Asp Ser Lys Glu Tyr
1               5                   10                  15

Phe Ser Lys

<210> SEQ ID NO 89
<211> LENGTH: 34
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 89

Ala Leu Arg Pro Asp Leu Ala Asp Lys Val Ala Ser Val Tyr Glu Ala
1               5                   10                  15

Pro Gly Phe Phe Leu Asp Leu Glu Pro Ile Pro Gly Ala Leu Asp Ala
                20                  25                  30

Val Arg

<210> SEQ ID NO 90
<211> LENGTH: 8
```

```
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 90

Ser Leu Asn Ala Val Tyr Pro Arg
1               5

<210> SEQ ID NO 91
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 91

Cys Tyr Tyr Tyr Glu Asp Thr Ile Ser Thr Ile Lys
1               5                   10

<210> SEQ ID NO 92
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 92

Phe Thr Glu Ile Tyr Glu Phe His Lys
1               5

<210> SEQ ID NO 93
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 93

Val Lys Tyr Leu Pro Gln Gln Gln Lys Lys
1               5                   10

<210> SEQ ID NO 94
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 94

Phe Gly Tyr Pro Phe Val Ile Ile Ala Gly Lys
1               5                   10

<210> SEQ ID NO 95
<211> LENGTH: 12
<212> TYPE: PRT
<213> ORGANISM: Homo sapiens
<220> FEATURE:
<221> NAME/KEY: MOD_RES
<222> LOCATION: (4)..(4)
```

<223> OTHER INFORMATION: Phosphorylated-Tyr

<400> SEQUENCE: 95

Ala Ala Ala Tyr Asp Ile Ser Glu Asp Glu Glu Asp
1               5                   10

<210> SEQ ID NO 96
<211> LENGTH: 21
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 96

Ala His His Ser Ser Gln Glu Met Ser Ser Glu Tyr Arg Glu Tyr Ala
1               5                   10                  15

Asp Ser Phe Gly Lys
            20

<210> SEQ ID NO 97
<211> LENGTH: 21
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 97

Ala His His Ser Ser Gln Glu Met Ser Ser Glu Tyr Arg Glu Tyr Ala
1               5                   10                  15

Asp Ser Phe Gly Lys
            20

<210> SEQ ID NO 98
<211> LENGTH: 24
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 98

Ala Thr Phe His Thr Pro Phe Ser His Leu Gly Gln Ser Pro Glu Gly
1               5                   10                  15

Cys Ser Ser Tyr Thr Phe Pro Lys
            20

<210> SEQ ID NO 99
<211> LENGTH: 22
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 99

Arg Ser Tyr Asp Val Pro Pro Pro Met Glu Pro Asp His Pro Phe
1               5                   10                  15

Tyr Ser Asn Ile Ser Lys
            20

```
<210> SEQ ID NO 100
<211> LENGTH: 21
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 100

Ser Tyr Asp Val Pro Pro Pro Pro Met Glu Pro Asp His Pro Phe Tyr
1               5                   10                  15

Ser Asn Ile Ser Lys
            20

<210> SEQ ID NO 101
<211> LENGTH: 30
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 101

Ser Val Val Leu Met Ser His Leu Gly Arg Pro Asp Gly Val Pro Met
1               5                   10                  15

Pro Asp Lys Tyr Ser Leu Glu Pro Val Ala Val Glu Leu Lys
            20                  25                  30

<210> SEQ ID NO 102
<211> LENGTH: 14
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 102

Tyr Leu Glu Glu Val Met Lys Val Pro Val Tyr Cys Thr Lys
1               5                   10

<210> SEQ ID NO 103
<211> LENGTH: 29
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 103

Asp Ser Gly Asn Asn Ser Gly Asp Gln Ala Thr Glu Glu Glu Gly
1               5                   10                  15

Gly Tyr Ser Cys Gly Thr Ala Glu Ser His Asp Ser Lys
            20                  25

<210> SEQ ID NO 104
<211> LENGTH: 20
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 104
```

-continued

```
Val Val Glu Val Gly Ser Lys Ile Tyr Val Asp Asp Gly Leu Ile Ser
1               5                   10                  15

Leu Gln Val Lys
            20

<210> SEQ ID NO 105
<211> LENGTH: 20
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 105

Ser Leu Leu Arg Met Val Asn Val Asp Met Asn Asp Met Tyr Ala Tyr
1               5                   10                  15

Leu Leu Phe Lys
            20

<210> SEQ ID NO 106
<211> LENGTH: 20
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 106

Ser Leu Leu Arg Met Val Asn Val Asp Met Asn Asp Met Tyr Ala Tyr
1               5                   10                  15

Leu Leu Phe Lys
            20

<210> SEQ ID NO 107
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 107

Asn Met Leu Ser Gln Val Asn Tyr Arg Val Pro Asn Met Arg
1               5                   10

<210> SEQ ID NO 108
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 108

Ser Gly Asp Ile Thr Tyr Gly Gln Phe Ala Gln Leu Tyr Arg
1               5                   10

<210> SEQ ID NO 109
<211> LENGTH: 14
<212> TYPE: PRT
<213> ORGANISM: Homo sapiens
<220> FEATURE:
<221> NAME/KEY: MOD_RES
<222> LOCATION: (13)..(13)
```

-continued

<223> OTHER INFORMATION: Phosphorylated-Tyr

<400> SEQUENCE: 109

Ser Gly Asp Ile Thr Tyr Gly Gln Phe Ala Gln Leu Tyr Arg
1               5                   10

<210> SEQ ID NO 110
<211> LENGTH: 25
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 110

Cys Ile Glu Leu Asp Cys Trp Asp Gly Pro Asp Gly Met Pro Val Ile
1               5                   10                  15
Tyr His Gly His Thr Leu Thr Thr Lys
            20                  25

<210> SEQ ID NO 111
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 111

Asn Met Ala Gln Tyr Phe Lys
1               5

<210> SEQ ID NO 112
<211> LENGTH: 25
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 112

Asn Gly Ile Leu Tyr Leu Glu Asp Pro Val Asn His Glu Trp Tyr Pro
1               5                   10                  15
His Tyr Phe Val Leu Thr Ser Ser Lys
            20                  25

<210> SEQ ID NO 113
<211> LENGTH: 25
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 113

Asn Gly Ile Leu Tyr Leu Glu Asp Pro Val Asn His Glu Trp Tyr Pro
1               5                   10                  15
His Tyr Phe Val Leu Thr Ser Ser Lys
            20                  25

<210> SEQ ID NO 114
<211> LENGTH: 25
<212> TYPE: PRT

```
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 114

Asn Gly Ile Leu Tyr Leu Glu Asp Pro Val Asn His Glu Trp Tyr Pro
1               5                   10                  15
His Tyr Phe Val Leu Thr Ser Ser Lys
            20                  25

<210> SEQ ID NO 115
<211> LENGTH: 23
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 115

Ser Ala Ile Ile Gln Asn Val Glu Lys Gln Glu Gly Gly Trp Trp Arg
1               5                   10                  15
Gly Asp Tyr Gly Gly Lys Lys
            20

<210> SEQ ID NO 116
<211> LENGTH: 26
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 116

Phe Val Val Tyr Glu Glu Asp Met Phe Ser Asp Pro Asn Phe Leu Ala
1               5                   10                  15
His Ala Thr Tyr Pro Ile Lys Ala Val Lys
            20                  25

<210> SEQ ID NO 117
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 117

Gln Gln Gly Glu Leu Tyr Met Trp Asp Ser Ile Asp Gln Lys
1               5                   10

<210> SEQ ID NO 118
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 118

His Tyr Cys Ala Ile Ala Asp Ala Lys
1               5
```

```
<210> SEQ ID NO 119
<211> LENGTH: 22
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 119

Gly Ala Leu Ile His Asn Val Ser Lys Glu Pro Gly Gly Trp Trp Lys
1               5                   10                  15

Gly Asp Tyr Gly Thr Arg
            20

<210> SEQ ID NO 120
<211> LENGTH: 23
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 120

Ile Gln Gln Tyr Phe Pro Ser Asn Tyr Val Glu Asp Ile Ser Thr Ala
1               5                   10                  15

Asp Phe Glu Glu Leu Glu Lys
            20

<210> SEQ ID NO 121
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 121

Met Ser Val Asp Tyr Asn Gly Glu Gln Lys
1               5                   10

<210> SEQ ID NO 122
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 122

Ser Asn Pro Gln Val Tyr Met Asp Ile Lys
1               5                   10

<210> SEQ ID NO 123
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 123

Arg Ala Tyr Gln Cys Val Val Leu Leu Gln Gly Lys Asn Pro Asp Ile
1               5                   10                  15
```

Thr Lys

<210> SEQ ID NO 124
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 124

Ser Asp Gly Gly Tyr Thr Tyr Asp Thr Ser Asp Leu Ala Ala Ile Lys
1               5                   10                  15

<210> SEQ ID NO 125
<211> LENGTH: 17
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 125

Ser Gln Ile Asp Val Ala Leu Ser Gln Asp Ser Thr Tyr Gln Gly Glu
1               5                   10                  15

Arg

<210> SEQ ID NO 126
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 126

Ala Tyr Gln His Gly Gly Val Thr Gly Leu Ser Gln Tyr
1               5                   10

<210> SEQ ID NO 127
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 127

Ala Tyr Gln His Gly Gly Val Thr Gly Leu Ser Gln Tyr
1               5                   10

<210> SEQ ID NO 128
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 128

Ala Arg Tyr Gly Val Ile Ile Val Gly Asn Pro Lys
1               5                   10

```
<210> SEQ ID NO 129
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 129

Phe Met Thr Thr Ala Met Tyr Asp Ala Arg
1               5                   10

<210> SEQ ID NO 130
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 130

Glu Ala Ile Ile Pro Gly Ser Val Tyr Asp Arg
1               5                   10

<210> SEQ ID NO 131
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 131

Ala Lys Ala Asp Ala Leu Tyr Pro Val Val Ser Ala Ala Ser Ile Cys
1               5                   10                  15

Ala Lys

<210> SEQ ID NO 132
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 132

Leu Gln Asp Leu Asp Thr Asp Tyr Gly Ser Gly Tyr Pro Asn Asp Pro
1               5                   10                  15

Lys

<210> SEQ ID NO 133
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 133

Leu Gln Asp Leu Asp Thr Asp Tyr Gly Ser Gly Tyr Pro Asn Asp Pro
1               5                   10                  15

Lys
```

```
<210> SEQ ID NO 134
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 134

Lys Val Phe Ser Asp Val Met Glu Asp Leu Tyr Asn Tyr Ile Asn Pro
1               5                   10                  15

His Asn Gly Lys
            20

<210> SEQ ID NO 135
<211> LENGTH: 20
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 135

Lys Val Phe Ser Asp Val Met Glu Asp Leu Tyr Asn Tyr Ile Asn Pro
1               5                   10                  15

His Asn Gly Lys
            20

<210> SEQ ID NO 136
<211> LENGTH: 12
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 136

Trp Ile Gly Asp Lys Glu Ala Thr Tyr Gly Glu Arg
1               5                   10

<210> SEQ ID NO 137
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 137

Thr Thr Glu Met Glu Thr Ile Tyr Asp Leu Gly Thr Lys
1               5                   10

<210> SEQ ID NO 138
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 138

Arg Val Tyr Ser Leu Phe Leu Asp Glu Ser Arg
```

```
                           1               5                  10

<210> SEQ ID NO 139
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 139

Ile Tyr Ser Tyr Met Ser Pro Asn Lys
1               5

<210> SEQ ID NO 140
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 140

Pro Phe Phe Leu Tyr Val Ala Phe His Asp Pro His Arg
1               5                   10

<210> SEQ ID NO 141
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 141

Leu Ile Ile Ala Gly Thr Ser Ala Tyr Ala Arg
1               5                   10

<210> SEQ ID NO 142
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 142

Glu Ile Thr Phe Phe Gln Thr His Pro Tyr Phe Arg
1               5                   10

<210> SEQ ID NO 143
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 143

Ala Ala Ile Ser Arg Asp Pro Phe Tyr Glu Met Leu Ala Ala Arg
1               5                   10                  15

<210> SEQ ID NO 144
<211> LENGTH: 9
```

```
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 144

Asp Asp Glu Tyr Asp Tyr Leu Phe Lys
1               5

<210> SEQ ID NO 145
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 145

Ala Tyr Asp His Leu Phe Lys
1               5

<210> SEQ ID NO 146
<211> LENGTH: 24
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 146

Phe Arg Ala Val Thr Arg Ser Tyr Tyr Arg Gly Ala Ala Gly Ala Leu
1               5                   10                  15

Met Val Tyr Asp Ile Thr Arg Arg
            20

<210> SEQ ID NO 147
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 147

Phe Arg Ala Val Thr Arg Ser Tyr Tyr Arg Gly Ala Ala Gly Ala Leu
1               5                   10                  15

Met Val Tyr Asp Ile Thr Arg Arg
            20

<210> SEQ ID NO 148
<211> LENGTH: 7
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 148

Thr Tyr Asp Tyr Leu Phe Lys
1               5

<210> SEQ ID NO 149
```

```
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 149

Glu Phe Ile Tyr Tyr Ala Asp Val Lys Glu Pro Glu Ser Phe Pro Phe
1               5                   10                  15

Val Ile Leu Gly Asn Lys
            20

<210> SEQ ID NO 150
<211> LENGTH: 22
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 150

Glu Phe Ile Tyr Tyr Ala Asp Val Lys Glu Pro Glu Ser Phe Pro Phe
1               5                   10                  15

Val Ile Leu Gly Asn Lys
            20

<210> SEQ ID NO 151
<211> LENGTH: 21
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 151

Ile Cys Ala Asn His Tyr Ile Thr Pro Met Met Glu Leu Lys Pro Asn
1               5                   10                  15

Ala Gly Ser Asp Arg
            20

<210> SEQ ID NO 152
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 152

Ile Asn Val Asn Glu Ile Phe Tyr Asp Leu Val Arg
1               5                   10

<210> SEQ ID NO 153
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 153

Ser Lys Ile Asn Val Asn Glu Ile Phe Tyr Asp Leu Val Arg
```

<210> SEQ ID NO 154
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 154

Gln Asp Phe Asp Val Asp Cys Tyr Ala Gln Arg
1               5                   10

<210> SEQ ID NO 155
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 155

Lys Asp Leu Val Leu Tyr Cys Glu Ala Phe Leu Thr Thr Tyr Arg
1               5                   10                  15

<210> SEQ ID NO 156
<211> LENGTH: 15
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 156

Lys Asp Leu Val Leu Tyr Cys Glu Ala Phe Leu Thr Thr Tyr Arg
1               5                   10                  15

<210> SEQ ID NO 157
<211> LENGTH: 13
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 157

Lys Phe Ile Lys Ile Ala Ala His Cys Lys Glu Tyr Lys
1               5                   10

<210> SEQ ID NO 158
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 158

Ser Tyr Val Arg Gln Leu Asn Val Ile Asp Asn Gln Arg
1               5                   10

<210> SEQ ID NO 159
<211> LENGTH: 27

```
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 159

Ser Val Tyr Asp Gly Pro Glu Gln Glu Glu Tyr Ser Thr Phe Val Ile
1               5                   10                  15

Asp Asp Pro Gln Glu Thr Tyr Lys Thr Leu Lys
            20                  25

<210> SEQ ID NO 160
<211> LENGTH: 28
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 160

Met Phe Leu Met Met His Pro Trp Tyr Ile Pro Ser Ser Gln Leu Ala
1               5                   10                  15

Ala Lys Leu Leu His Ile Tyr Gln Gln Ser Arg Lys
            20                  25

<210> SEQ ID NO 161
<211> LENGTH: 28
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 161

Met Phe Leu Met Met His Pro Trp Tyr Ile Pro Ser Ser Gln Leu Ala
1               5                   10                  15

Ala Lys Leu Leu His Ile Tyr Gln Gln Ser Arg Lys
            20                  25

<210> SEQ ID NO 162
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 162

Gly Gly Gly Val Val Pro Tyr Leu Gly Thr Phe Leu Lys
1               5                   10

<210> SEQ ID NO 163
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 163

Tyr Asn Thr Tyr Val Ala Pro Gly Arg
1               5
```

<210> SEQ ID NO 164
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 164

Ser Leu Tyr Ser Tyr Ala Gly Leu Ala Pro Arg Pro Arg
1               5                   10

<210> SEQ ID NO 165
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 165

Val Arg Val Glu Ser Gly Tyr Phe Ser Leu Glu Lys
1               5                   10

<210> SEQ ID NO 166
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 166

Tyr Ala Ser Asp Lys Tyr Lys Asp Ile Tyr Thr Glu Leu Ser Ile Ala
1               5                   10                  15

Lys

<210> SEQ ID NO 167
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 167

Thr Leu Ser Asp Glu Ser Ile Tyr Asn Ser Gln Arg
1               5                   10

<210> SEQ ID NO 168
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 168

Val Ala Val Glu Ala Pro Met Arg Glu Glu Tyr Ala Asp Phe Lys Pro
1               5                   10                  15

Phe Glu Arg

```
<210> SEQ ID NO 169
<211> LENGTH: 26
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 169

Ala Pro Val Ala Gly Thr Cys Tyr Gln Ala Glu Trp Asp Asp Tyr Val
1               5                   10                  15

Pro Lys Leu Tyr Glu Gln Leu Ser Gly Lys
            20                  25

<210> SEQ ID NO 170
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 170

Leu Tyr Thr Leu Val Leu Thr Asp Pro Asp Ala Pro Ser Arg Lys Asp
1               5                   10                  15

Pro Lys Tyr Arg
            20

<210> SEQ ID NO 171
<211> LENGTH: 20
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 171

Leu Tyr Thr Leu Val Leu Thr Asp Pro Asp Ala Pro Ser Arg Lys Asp
1               5                   10                  15

Pro Lys Tyr Arg
            20

<210> SEQ ID NO 172
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 172

Met Gln Ala Ser Glu Asp Leu Leu Lys Glu His Tyr Val Asp Leu Lys
1               5                   10                  15

Asp Arg Pro Phe
            20

<210> SEQ ID NO 173
<211> LENGTH: 18
<212> TYPE: PRT
<213> ORGANISM: Homo sapiens
<220> FEATURE:
<221> NAME/KEY: MOD_RES
<222> LOCATION: (4)..(4)
```

<223> OTHER INFORMATION: Phosphorylated-Tyr

<400> SEQUENCE: 173

Ile Ser Cys Tyr Glu Ala Ser Tyr Gln Pro Leu Asp Pro Asp Lys Cys
1               5                   10                  15

Asp Arg

<210> SEQ ID NO 174
<211> LENGTH: 19
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 174

Cys His Asp Tyr Tyr Thr Thr Glu Phe Leu Tyr Asn Leu Tyr Ser Ser
1               5                   10                  15

Glu Gly Lys

<210> SEQ ID NO 175
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 175

Met Leu Ala Ile Tyr Asp Gly Phe Asp Gly Phe Ala Lys
1               5                   10

<210> SEQ ID NO 176
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 176

Ile Ile Glu Thr Met Gly Gly Tyr Cys Gly Tyr
1               5                   10

<210> SEQ ID NO 177
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 177

Ala Gln Val Tyr Asn Lys Gln Asp Tyr Asp Leu Met Val Phe Pro Glu
1               5                   10                  15

Ser Asp Ser Gln Lys Arg
            20

<210> SEQ ID NO 178
<211> LENGTH: 16
<212> TYPE: PRT
<213> ORGANISM: Homo sapiens
<220> FEATURE:

```
<221> NAME/KEY: MOD_RES
<222> LOCATION: (14)..(14)
<223> OTHER INFORMATION: Phosphorylated-Tyr

<400> SEQUENCE: 178

Gly Leu Gln Leu Leu Gln Asp Gly Asn Asp Pro Asp Pro Tyr Val Lys
1               5                   10                  15

<210> SEQ ID NO 179
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 179

Leu Cys Val Leu Glu Tyr Gln Gly Lys Tyr Ile Leu Lys
1               5                   10

<210> SEQ ID NO 180
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 180

Thr Gly Ile Tyr His Gly Gly Glu Pro Leu Cys Asp Asn Val Asn Thr
1               5                   10                  15

Gln Arg

<210> SEQ ID NO 181
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 181

Leu Leu Tyr Pro Val Ser Lys
1               5

<210> SEQ ID NO 182
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 182

Ile Phe Glu Glu Gln Cys Gln Thr Gln Glu Arg Tyr Ser Lys Glu Tyr
1               5                   10                  15

Ile Glu Lys

<210> SEQ ID NO 183
<211> LENGTH: 19
<212> TYPE: PRT
<213> ORGANISM: Homo sapiens
<220> FEATURE:
<221> NAME/KEY: MOD_RES
```

```
<222> LOCATION: (8)..(8)
<223> OTHER INFORMATION: Phosphorylated-Tyr

<400> SEQUENCE: 183

Glu Ser Ser Lys Gln Gly Cys Tyr Ala Cys Ser Val Val Val Asp Gly
1               5                   10                  15

Glu Val Lys

<210> SEQ ID NO 184
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 184

Leu Leu Tyr Pro Val Ser Lys
1               5

<210> SEQ ID NO 185
<211> LENGTH: 24
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 185

Asp Gln Tyr Leu Val Trp Leu Thr Gln Lys Gly Ala Arg Gln Lys Lys
1               5                   10                  15

Ile Asn Glu Trp Leu Gly Ile Lys
            20

<210> SEQ ID NO 186
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 186

Leu Gln Glu Tyr His Ser Gln Tyr Gln Glu Lys
1               5                   10

<210> SEQ ID NO 187
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 187

Ser Lys Glu Tyr Asp Arg Leu Tyr Glu Glu Tyr Thr Arg
1               5                   10

<210> SEQ ID NO 188
<211> LENGTH: 14
<212> TYPE: PRT
<213> ORGANISM: Homo sapiens
<220> FEATURE:
<221> NAME/KEY: MOD_RES
```

```
<222> LOCATION: (1)..(1)
<223> OTHER INFORMATION: Phosphorylated-Tyr

<400> SEQUENCE: 188

Tyr His Ser Gln Tyr His Thr Val Ala Gly Asn Asp Ile Lys
1               5                   10

<210> SEQ ID NO 189
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 189

Asp Gln Pro Tyr Tyr Asp Ile Pro Asp Ala Pro Tyr Arg
1               5                   10

<210> SEQ ID NO 190
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 190

Glu Pro Leu Ser Ser Glu Thr Gln Tyr Ser Val Asp Thr Arg
1               5                   10

<210> SEQ ID NO 191
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 191

Ala Leu Tyr Ser Thr Ala Met Glu Ser Ile Gln Gly Glu Ala Arg
1               5                   10                  15

<210> SEQ ID NO 192
<211> LENGTH: 19
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 192

Lys Glu Val Tyr Phe Met Ala Ile Ile Asp Ile Leu Thr Pro Tyr Asp
1               5                   10                  15

Thr Lys Lys

<210> SEQ ID NO 193
<211> LENGTH: 25
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr
```

-continued

```
<400> SEQUENCE: 193

Leu Leu Ser Ala Gly Ala Thr Lys Val Tyr Ala Ile Leu Thr His Gly
1               5                   10                  15

Ile Phe Ser Gly Pro Ala Ile Ser Arg
            20                  25

<210> SEQ ID NO 194
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 194

Ser Pro Lys Tyr Gly Glu Gly His Gln Ala Trp Ile Ile Gly Ile Val
1               5                   10                  15

Glu Lys

<210> SEQ ID NO 195
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 195

Ala Thr Glu Asp Gly Thr Pro Tyr Asp Pro Tyr Lys Ala Leu Trp Phe
1               5                   10                  15

Glu Arg

<210> SEQ ID NO 196
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 196

Ala Leu Ile Glu Asn Ala Asp Ala Val Tyr Glu Lys
1               5                   10

<210> SEQ ID NO 197
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 197

Ser Gln Ser His Leu Pro Tyr Phe Thr Pro Lys Pro Pro Gln Asp Ser
1               5                   10                  15

Ala Val Ile Lys
            20

<210> SEQ ID NO 198
<211> LENGTH: 10
<212> TYPE: PRT
<213> ORGANISM: Homo sapiens
```

```
<220> FEATURE:
<221> NAME/KEY: MOD_RES
<222> LOCATION: (6)..(6)
<223> OTHER INFORMATION: Phosphorylated-Tyr

<400> SEQUENCE: 198

Ala Met Tyr Pro Asp Tyr Phe Ala Lys Arg
1               5                   10

<210> SEQ ID NO 199
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 199

Thr Gly Leu Glu Asp Pro Glu Arg Tyr Leu Phe Val Asp Arg
1               5                   10

<210> SEQ ID NO 200
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 200

Ala Leu Ala Tyr Asp Lys Leu Glu Lys
1               5

<210> SEQ ID NO 201
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 201

Val Ile Gln Tyr Leu Ala His Val Ala Ser Ser His Lys
1               5                   10

<210> SEQ ID NO 202
<211> LENGTH: 16
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 202

His Glu Met Pro Pro His Ile Tyr Ala Ile Thr Asp Thr Ala Tyr Arg
1               5                   10                  15

<210> SEQ ID NO 203
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr
```

```
<400> SEQUENCE: 203

Thr Phe His Ile Phe Tyr Tyr Leu Leu Ser Gly Ala Gly Glu His Leu
1               5                   10                  15

Lys

<210> SEQ ID NO 204
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 204

Ile Leu Tyr Ser Gln Cys Gly Asp Val Met Arg
1               5                   10

<210> SEQ ID NO 205
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 205

Leu Gly Glu Leu Gln Ser Ala Tyr Asp Gly Ala Lys
1               5                   10

<210> SEQ ID NO 206
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 206

Tyr Ile Met Gln Tyr Ile Ala Ala Ile Thr Asn Pro Ser Gln Arg
1               5                   10                  15

<210> SEQ ID NO 207
<211> LENGTH: 19
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 207

His Ile Asp Tyr Phe Asn Asn Gln Ile Ile Val Asp Leu Val Glu Gln
1               5                   10                  15

Gln His Lys

<210> SEQ ID NO 208
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 208
```

Arg Ala Gln Asp Glu His Pro Gln Glu Asp Gly Tyr Tyr Phe Leu Leu
1               5                   10                  15

Gln Glu Arg

<210> SEQ ID NO 209
<211> LENGTH: 23
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 209

Glu Gln Ala Ala Tyr His Leu His Ile Tyr Pro Gln Leu Ser Thr Thr
1               5                   10                  15

Glu Ser Gln Ala Ser Cys Arg
            20

<210> SEQ ID NO 210
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 210

Thr Gly Ser Tyr Gly Ala Leu Ala Glu Ile Thr Ala Ser Lys
1               5                   10

<210> SEQ ID NO 211
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 211

Ser Tyr Leu Thr Pro Val Arg Asp Glu Glu Ser Glu Ser Gln Arg
1               5                   10                  15

<210> SEQ ID NO 212
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 212

Ser Gly Ser Tyr Ser Tyr Leu Glu Glu Arg
1               5                   10

<210> SEQ ID NO 213
<211> LENGTH: 21
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 213

-continued

```
Ile His Val Tyr Gly Tyr Ser Met Ala Tyr Gly Pro Ala Gln His Ala
1               5                   10                  15

Ile Ser Thr Glu Lys
            20

<210> SEQ ID NO 214
<211> LENGTH: 21
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 214

Ile His Val Tyr Gly Tyr Ser Met Ala Tyr Gly Pro Ala Gln His Ala
1               5                   10                  15

Ile Ser Thr Glu Lys
            20

<210> SEQ ID NO 215
<211> LENGTH: 21
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 215

Ile His Val Tyr Gly Tyr Ser Met Ala Tyr Gly Pro Ala Gln His Ala
1               5                   10                  15

Ile Ser Thr Glu Lys
            20

<210> SEQ ID NO 216
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 216

Leu Phe Glu Tyr Gly Gly Phe Pro Pro Glu Ser Asn Tyr Leu Phe Leu
1               5                   10                  15

Gly Asp Tyr Val Asp Arg
            20

<210> SEQ ID NO 217
<211> LENGTH: 14
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 217

Asn Val Val Thr Ile Phe Ser Ala Pro Asn Tyr Cys Tyr Arg
1               5                   10

<210> SEQ ID NO 218
<211> LENGTH: 13
<212> TYPE: PRT
```

-continued

```
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 218

Tyr Leu Glu Val Met Arg Lys Leu Gln Lys Thr Tyr Arg
1               5                   10

<210> SEQ ID NO 219
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 219

Leu Phe Asp Asp Cys Thr Gln Gln Tyr Lys
1               5                   10

<210> SEQ ID NO 220
<211> LENGTH: 12
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 220

Lys Ser Glu Leu Pro Gln Asp Val Tyr Thr Ile Lys
1               5                   10

<210> SEQ ID NO 221
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 221

Gly Asn His Glu Thr Asp Asn Met Asn Gln Ile Tyr Gly Phe Glu Gly
1               5                   10                  15

Glu Val Lys

<210> SEQ ID NO 222
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 222

Thr Glu Cys Tyr Gly Tyr Ala Leu Gly Asp Ala Thr Arg
1               5                   10

<210> SEQ ID NO 223
<211> LENGTH: 13
<212> TYPE: PRT
<213> ORGANISM: Homo sapiens
<220> FEATURE:
<221> NAME/KEY: MOD_RES
```

```
<222> LOCATION: (10)..(10)
<223> OTHER INFORMATION: Phosphorylated-Tyr

<400> SEQUENCE: 223

Leu Val Thr Val Trp Ser Ala Pro Asn Tyr Cys Tyr Arg
1               5                   10

<210> SEQ ID NO 224
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 224

Tyr Val Tyr Tyr Tyr Ser Tyr Leu Leu Lys
1               5                   10

<210> SEQ ID NO 225
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 225

Tyr Val Tyr Tyr Tyr Ser Tyr Leu Leu Lys
1               5                   10

<210> SEQ ID NO 226
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 226

Tyr Val Tyr Tyr Tyr Ser Tyr Leu Leu Lys
1               5                   10

<210> SEQ ID NO 227
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 227

Tyr Val Tyr Tyr Tyr Ser Tyr Leu Leu Lys
1               5                   10

<210> SEQ ID NO 228
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 228
```

```
Tyr Val Tyr Tyr Tyr Ser Tyr Leu Leu Lys
1               5                   10

<210> SEQ ID NO 229
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 229

Val Cys Asp Ala Thr Tyr Asp Lys Ala Pro Val Glu Lys
1               5                   10

<210> SEQ ID NO 230
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 230

His Gln Asp Val Met Pro Tyr Asp Ser Asn Arg
1               5                   10

<210> SEQ ID NO 231
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 231

Asn Gly Ile Ile Thr Lys Tyr Thr Leu Leu Tyr Arg
1               5                   10

<210> SEQ ID NO 232
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 232

Asn Gly Ile Ile Thr Lys Tyr Thr Leu Leu Tyr Arg
1               5                   10

<210> SEQ ID NO 233
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 233

Asn Arg Tyr Gly Asn Ile Ile Ala Tyr Asp His Ser Arg
1               5                   10

<210> SEQ ID NO 234
```

```
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 234

Tyr Gly Asn Ile Ile Ala Tyr Asp His Ser Arg
1               5                   10

<210> SEQ ID NO 235
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 235

Val Ile Leu Gln Pro Val Glu Asp Pro Ser Ser Asp Tyr Ile Asn
1               5                   10                  15

Ala Asn Tyr Ile Asp Gly Tyr Gln Arg
            20                  25

<210> SEQ ID NO 236
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 236

Asn Gln Asn Tyr Met Asn Ile Leu Arg
1               5

<210> SEQ ID NO 237
<211> LENGTH: 20
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 237

Val Phe Leu His Phe Glu Glu Glu Glu Ile Thr Phe Ala Pro Thr Tyr
1               5                   10                  15

Arg Phe Glu Arg
            20

<210> SEQ ID NO 238
<211> LENGTH: 21
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 238

Leu Lys Pro Ile Ile Ser Asp Pro Glu Tyr Leu Leu Asp Gln His Ile
1               5                   10                  15

Leu Ile Ser Ile Lys
```

```
                       20

<210> SEQ ID NO 239
<211> LENGTH: 27
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 239

Gln Thr Leu Ser Pro Asp Gln Gln Pro Thr Ala Trp Ser Tyr Asp Gln
1               5                   10                  15

Pro Pro Lys Asp Ser Pro Leu Gly Pro Cys Arg
            20                  25

<210> SEQ ID NO 240
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 240

Gly Ser Tyr Gly Leu Asp Leu Glu Ala Val Arg
1               5                   10

<210> SEQ ID NO 241
<211> LENGTH: 16
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 241

Asp Ser Asn Ile Pro Gly Ser Asp Tyr Ile Asn Ala Asn Tyr Ile Lys
1               5                   10                  15

<210> SEQ ID NO 242
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 242

Ser Gly Met Val Gln Thr Glu Ala Gln Tyr Arg
1               5                   10

<210> SEQ ID NO 243
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 243

Met Thr Glu Leu Tyr Asp Tyr Pro Lys Tyr Ser Cys His Phe Lys Lys
1               5                   10                  15
```

-continued

<210> SEQ ID NO 244
<211> LENGTH: 24
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 244

Leu Lys Arg Asp Asp Ser Asn Glu Ser Asp Val Val Glu Ser Leu Asp
1               5                   10                  15

Glu Ile Tyr His Thr Gly Thr Phe
            20

<210> SEQ ID NO 245
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 245

Ser Asn Phe Gly Tyr Asn Ile Pro Leu Lys
1               5                   10

<210> SEQ ID NO 246
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 246

Leu Tyr Gln Val Glu Tyr Ala Phe Lys
1               5

<210> SEQ ID NO 247
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 247

Gly Ala Val Tyr Ser Phe Asp Pro Val Gly Ser Tyr Gln Arg
1               5                   10

<210> SEQ ID NO 248
<211> LENGTH: 16
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 248

Phe Gly Pro Tyr Tyr Thr Glu Pro Val Ile Ala Gly Leu Asp Pro Lys
1               5                   10                  15

<210> SEQ ID NO 249

```
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 249

Arg Ala Ile Tyr Gln Ala Thr Tyr Arg
1               5

<210> SEQ ID NO 250
<211> LENGTH: 24
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Phosphorylated-Tyr

<400> SEQUENCE: 250

Val Ile Glu Ile Asn Pro Tyr Leu Leu Gly Thr Met Ser Gly Cys Ala
1               5                   10                  15

Ala Asp Cys Gln Tyr Trp Glu Arg
            20

<210> SEQ ID NO 251
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 251

Lys Gly Pro Gly Leu Tyr Tyr Val Asp Glu His Gly Thr Arg
1               5                   10

<210> SEQ ID NO 252
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 252

Gly Cys Leu Leu Tyr Gly Pro Pro Gly Thr Gly Lys
1               5                   10

<210> SEQ ID NO 253
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 253

Asp His Tyr Glu Ala Thr Ala Met His Arg
1               5                   10

<210> SEQ ID NO 254
<211> LENGTH: 13
<212> TYPE: PRT
```

```
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 254

Asn Tyr Leu His Tyr Ser Leu Tyr Asp Gln Ala Glu Lys
1               5                   10

<210> SEQ ID NO 255
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 255

Ile Val Asn Pro Lys Gly Glu Glu Lys Pro Ser Met Tyr
1               5                   10

<210> SEQ ID NO 256
<211> LENGTH: 25
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 256

Leu Lys Glu Glu Asp Met Ala Met Asn Ala Gln Gln Asp Asn Ile Leu
1               5                   10                  15

Tyr Gln Thr Val Thr Gly Leu Lys Lys
            20                  25

<210> SEQ ID NO 257
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 257

Asn Cys Leu Glu Glu Ser Glu Gly Cys Tyr Cys Arg
1               5                   10

<210> SEQ ID NO 258
<211> LENGTH: 29
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 258

Leu Tyr Ser Glu Asp Tyr Asp Asn Tyr Asp Tyr Leu Glu Ser Gly
1               5                   10                  15

Asn Trp Met Asn Asp Tyr Asp Ser Thr Ser His Ala Arg
            20                  25

<210> SEQ ID NO 259
<211> LENGTH: 29
```

```
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 259

Leu Tyr Ser Glu Asp Tyr Asp Asp Asn Tyr Asp Tyr Leu Glu Ser Gly
1               5                   10                  15

Asn Trp Met Asn Asp Tyr Asp Ser Thr Ser His Ala Arg
            20                  25

<210> SEQ ID NO 260
<211> LENGTH: 21
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 260

Arg Val Ser Val Cys Ala Glu Thr Tyr Asn Pro Asp Glu Glu Glu Glu
1               5                   10                  15

Asp Thr Asp Pro Arg
            20

<210> SEQ ID NO 261
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 261

Thr Ser Glu Val Tyr Val Trp Gly Gly Gly Lys
1               5                   10

<210> SEQ ID NO 262
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 262

Tyr Met Ser Phe Thr Asp Lys Ser Ala Glu Asp Tyr Asn Ser Ser Asn
1               5                   10                  15

Ala Leu Asn Val Lys
            20

<210> SEQ ID NO 263
<211> LENGTH: 21
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 263

Tyr Met Ser Phe Thr Asp Lys Ser Ala Glu Asp Tyr Asn Ser Ser Asn
1               5                   10                  15
```

```
Ala Leu Asn Val Lys
            20

<210> SEQ ID NO 264
<211> LENGTH: 19
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 264

Leu Arg Thr Ile Val Ser Ile Gly Asp Pro Lys Lys Tyr Thr Arg
1               5                   10                  15

Tyr Glu Lys

<210> SEQ ID NO 265
<211> LENGTH: 29
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 265

Phe Ser His Glu Glu Tyr Ser Asn Gly Ala Leu Ser Ile Leu Gln Tyr
1               5                   10                  15

Pro Tyr Asp Asn Gly Tyr Tyr Leu Pro Tyr Tyr Lys Arg
            20                  25

<210> SEQ ID NO 266
<211> LENGTH: 29
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 266

Phe Ser His Glu Glu Tyr Ser Asn Gly Ala Leu Ser Ile Leu Gln Tyr
1               5                   10                  15

Pro Tyr Asp Asn Gly Tyr Tyr Leu Pro Tyr Tyr Lys Arg
            20                  25

<210> SEQ ID NO 267
<211> LENGTH: 29
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: Phosphorylated-Tyr

<400> SEQUENCE: 267

Phe Ser His Glu Glu Tyr Ser Asn Gly Ala Leu Ser Ile Leu Gln Tyr
1               5                   10                  15

Pro Tyr Asp Asn Gly Tyr Tyr Leu Pro Tyr Tyr Lys Arg
            20                  25

<210> SEQ ID NO 268
<211> LENGTH: 29
<212> TYPE: PRT
<213> ORGANISM: Homo sapiens
```

```
<220> FEATURE:
<221> NAME/KEY: MOD_RES
<222> LOCATION: (27)..(27)
<223> OTHER INFORMATION: Phosphorylated-Tyr

<400> SEQUENCE: 268

Phe Ser His Glu Glu Tyr Ser Asn Gly Ala Leu Ser Ile Leu Gln Tyr
1               5                   10                  15
Pro Tyr Asp Asn Gly Tyr Tyr Leu Pro Tyr Tyr Lys Arg
            20                  25

<210> SEQ ID NO 269
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 269

His Lys Ala Thr Glu Gln Tyr Tyr Ala Met Lys
1               5                   10

<210> SEQ ID NO 270
<211> LENGTH: 16
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 270

Asn Leu Ile Pro Met Asp Pro Asn Gly Leu Ser Asp Pro Tyr Val Lys
1               5                   10                  15

<210> SEQ ID NO 271
<211> LENGTH: 16
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 271

Asn Leu Val Pro Met Asp Pro Asn Gly Leu Ser Asp Pro Tyr Val Lys
1               5                   10                  15

<210> SEQ ID NO 272
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 272

Thr Asn Thr Phe Cys Gly Thr Pro Asp Tyr Ile Ala Pro Glu Ile Leu
1               5                   10                  15
Leu Gly Gln Lys
            20

<210> SEQ ID NO 273
<211> LENGTH: 23
<212> TYPE: PRT
```

```
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 273

Arg Pro Pro Ser Ser Ser Ser Ser Ser Ala Ser Ser Tyr Thr Gly
1               5                   10                  15

Arg Pro Ile Glu Leu Asp Lys
            20

<210> SEQ ID NO 274
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 274

Ser Val Val Gly Thr Pro Ala Tyr Leu Ala Pro Glu Val Leu Leu Asn
1               5                   10                  15

Gln Gly Tyr Asn Arg
            20

<210> SEQ ID NO 275
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 275

Thr Leu Cys Gly Thr Pro Asn Tyr Ile Ala Pro Glu Val Leu Ser Lys
1               5                   10                  15

<210> SEQ ID NO 276
<211> LENGTH: 26
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 276

His His Thr Ile Gln Asn Ser Asp Asp Ala Tyr Val Gln Leu Asp Asn
1               5                   10                  15

Leu Pro Gly Met Ser Leu Val Ala Gly Lys
            20                  25

<210> SEQ ID NO 277
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 277

Ile Tyr Glu Ser Ile Glu Glu Ala Lys
1               5
```

```
<210> SEQ ID NO 278
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 278

Asp Val Tyr Asp Asp Gly Lys Tyr Val Tyr Val Val Thr Glu Leu Met
1               5                   10                  15

Lys

<210> SEQ ID NO 279
<211> LENGTH: 28
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 279

Tyr Gly Gln His Pro Asn Ile Ile Thr Leu Lys Asp Val Tyr Asp Asp
1               5                   10                  15

Gly Lys Tyr Val Tyr Val Val Thr Glu Leu Met Lys
            20                  25

<210> SEQ ID NO 280
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 280

Asp Val Tyr Asp Asp Gly Lys Tyr Val Tyr Val Val Thr Glu Leu Met
1               5                   10                  15

Lys

<210> SEQ ID NO 281
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 281

Thr Val Glu Tyr Leu His Ala Gln Gly Val Val His Arg
1               5                   10

<210> SEQ ID NO 282
<211> LENGTH: 24
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 282

Phe Asn Ser Tyr Asn Asn Ala Gly Met Pro Pro Phe Pro Ile Ile Ile
```

```
1               5                  10                  15

His Asp Glu Pro Thr Tyr Ala Arg
            20

<210> SEQ ID NO 283
<211> LENGTH: 24
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Phosphorylated-Tyr

<400> SEQUENCE: 283

Phe Asn Ser Tyr Asn Asn Ala Gly Met Pro Pro Phe Pro Ile Ile Ile
1               5                  10                  15

His Asp Glu Pro Thr Tyr Ala Arg
            20

<210> SEQ ID NO 284
<211> LENGTH: 30
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 284

Asp Ile Ser Leu Thr Asp Ile Gln Asp Leu Ser Ser Ile Ser Tyr Glu
1               5                  10                  15

Pro Asp Ser Ser Phe Lys Glu Ala Ser Cys Lys Thr Pro Lys
            20                  25                  30

<210> SEQ ID NO 285
<211> LENGTH: 16
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 285

Met Leu Glu Asp Ser Glu Ser Ser Tyr Glu Pro Asp Glu Leu Thr Lys
1               5                  10                  15

<210> SEQ ID NO 286
<211> LENGTH: 25
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 286

Cys Thr Lys Glu Glu Ala Thr Tyr Ile Phe Glu Val Ala Asn Ser Val
1               5                  10                  15

Gly Leu Thr Gly Tyr Gly Tyr Thr Trp
            20                  25

<210> SEQ ID NO 287
<211> LENGTH: 11
<212> TYPE: PRT
<213> ORGANISM: Homo sapiens
<220> FEATURE:
```

```
<221> NAME/KEY: MOD_RES
<222> LOCATION: (5)..(5)
<223> OTHER INFORMATION: Phosphorylated-Tyr

<400> SEQUENCE: 287

Ala Asn Tyr Glu Tyr Tyr Val Gln Gly Gln Ile
1               5                   10

<210> SEQ ID NO 288
<211> LENGTH: 31
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 288

Tyr Tyr Glu Lys Asn Arg Ser Phe Ser Asn Ala Ala Arg Val Leu Ser
1               5                   10                  15

Arg Leu Ala Asp Met His Ser Thr Glu Ile Ser Leu Gln Gln Arg
            20                  25                  30

<210> SEQ ID NO 289
<211> LENGTH: 31
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 289

Tyr Tyr Glu Lys Asn Arg Ser Phe Ser Asn Ala Ala Arg Val Leu Ser
1               5                   10                  15

Arg Leu Ala Asp Met His Ser Thr Glu Ile Ser Leu Gln Gln Arg
            20                  25                  30

<210> SEQ ID NO 290
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 290

Phe Tyr Glu Gly Val Val Glu Leu Ser Leu Thr Ala Ala Glu Lys
1               5                   10                  15

<210> SEQ ID NO 291
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 291

Asp Leu Pro Ser Ala Asp Ser Val Gln Tyr Arg
1               5                   10

<210> SEQ ID NO 292
<211> LENGTH: 20
<212> TYPE: PRT
<213> ORGANISM: Homo sapiens
```

```
<220> FEATURE:
<221> NAME/KEY: MOD_RES
<222> LOCATION: (16)..(16)
<223> OTHER INFORMATION: Phosphorylated-Tyr

<400> SEQUENCE: 292

Asn Asn Pro Ala Thr Pro Ser Thr Ala Met Gly Ser Ser Val Pro Tyr
1               5                   10                  15

Ser Thr Ala Lys
            20

<210> SEQ ID NO 293
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 293

Ser Ser Ala Thr Val Thr Gly Glu Pro Pro Ser Tyr Ser Ser Gly Ser
1               5                   10                  15

Asp Ser Ser Lys
            20

<210> SEQ ID NO 294
<211> LENGTH: 32
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 294

Ile Leu His Thr Leu Leu Ala Ser Gly Glu Asp Ala Leu Asp Phe Thr
1               5                   10                  15

Gln Glu Ser Glu Pro Ser Tyr Ile Ser Asp Val Gly Pro Pro Gly Arg
            20                  25                  30

<210> SEQ ID NO 295
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 295

Ser Ser Leu Asp Asn Ile Glu Met Ala Tyr Ala Arg
1               5                   10

<210> SEQ ID NO 296
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 296

Ala Val Tyr Cys Ile Ile Gly Arg
1               5
```

```
<210> SEQ ID NO 297
<211> LENGTH: 25
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 297

Ala Phe Ser Thr Cys Gly Ser His Leu Ile Val Val Val Leu Phe Tyr
1               5                   10                  15

Gly Ser Gly Ile Phe Thr Tyr Met Arg
            20                  25

<210> SEQ ID NO 298
<211> LENGTH: 25
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 298

Ala Phe Ser Thr Cys Gly Ser His Leu Ile Val Val Val Leu Phe Tyr
1               5                   10                  15

Gly Ser Gly Ile Phe Thr Tyr Met Arg
            20                  25

<210> SEQ ID NO 299
<211> LENGTH: 21
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 299

Asn Met Ala Leu Phe Tyr Gly Ile Leu Thr Pro Met Leu Asn Pro Leu
1               5                   10                  15

Ile Tyr Thr Leu Arg
            20

<210> SEQ ID NO 300
<211> LENGTH: 18
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 300

Ser Arg Thr Val Tyr Leu Lys Met Ala Ala Gly Ala Phe Ala Ala Gly
1               5                   10                  15

Leu Leu

<210> SEQ ID NO 301
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr
```

-continued

<400> SEQUENCE: 301

Glu Ser Ser Asp Pro Ser Ser Tyr Asn Ser Ser Gly Gln Leu Met Ala
1               5                   10                  15

Ser Lys

<210> SEQ ID NO 302
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 302

His Val Glu Ala Val Tyr Ile Asp Ile Ala Asp Arg
1               5                   10

<210> SEQ ID NO 303
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 303

Ser Ser Gly Lys His Tyr Gly Val Tyr Ser Cys Glu Gly Cys Lys
1               5                   10                  15

<210> SEQ ID NO 304
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 304

Thr Asp Phe Tyr Cys Leu Val Ser Lys Asp Asp Met
1               5                   10

<210> SEQ ID NO 305
<211> LENGTH: 23
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 305

Ala Arg Pro Gln Tyr Pro Gln Glu Gln Glu Ala Ile Gly Tyr Glu Tyr
1               5                   10                  15

Ser Glu Ile Asn Ile Pro Lys
            20

<210> SEQ ID NO 306
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

```
<400> SEQUENCE: 306

Arg Ser Ser Val Gly Glu Gly Glu Leu Gln Tyr
1               5                   10

<210> SEQ ID NO 307
<211> LENGTH: 23
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 307

Asn Leu Glu Tyr Val Ser Val Ser Pro Thr Asn Asn Thr Val Tyr Ala
1               5                   10                  15

Ser Val Thr His Ser Asn Arg
            20

<210> SEQ ID NO 308
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 308

Ser Asp Ser Tyr Val Glu Leu Ser Gln Tyr Arg
1               5                   10

<210> SEQ ID NO 309
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 309

Lys Phe Gly Tyr Val Asp Phe Glu Ser Ala Glu Asp Leu Glu Lys
1               5                   10                  15

<210> SEQ ID NO 310
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 310

Asn Leu Pro Tyr Lys Val Thr Gln Asp Glu Leu Lys Glu Val Phe Glu
1               5                   10                  15

Asp Ala Ala Glu Ile Arg
            20

<210> SEQ ID NO 311
<211> LENGTH: 17
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr
```

```
<400> SEQUENCE: 311

Ser Ile Ser Leu Tyr Tyr Thr Gly Glu Lys Gly Gln Asn Gln Asp Tyr
1               5                   10                  15

Arg

<210> SEQ ID NO 312
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 312

Ser Ile Ser Leu Tyr Tyr Thr Gly Glu Lys
1               5                   10

<210> SEQ ID NO 313
<211> LENGTH: 25
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 313

Ser Lys Gly Tyr Ala Phe Ile Glu Phe Ala Ser Phe Glu Asp Ala Lys
1               5                   10                  15

Glu Ala Leu Asn Ser Cys Asn Lys Arg
            20                  25

<210> SEQ ID NO 314
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 314

Gly Ile Asp Tyr Asp Phe Pro Ser Leu Ile Leu Gln Lys
1               5                   10

<210> SEQ ID NO 315
<211> LENGTH: 19
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 315

Thr Gly Asn Ser Lys Gly Tyr Ala Phe Val Glu Phe Glu Ser Glu Asp
1               5                   10                  15

Val Ala Lys

<210> SEQ ID NO 316
<211> LENGTH: 20
<212> TYPE: PRT
<213> ORGANISM: Homo sapiens
<220> FEATURE:
<221> NAME/KEY: MOD_RES
```

```
<222> LOCATION: (10)..(10)
<223> OTHER INFORMATION: Phosphorylated-Tyr

<400> SEQUENCE: 316

Cys Thr Thr Asp Glu Asn Lys Val Pro Tyr Phe Asn Ala Pro Val Tyr
1               5                   10                  15

Leu Glu Asn Lys
            20

<210> SEQ ID NO 317
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 317

Phe Ala Gln Pro Gly Ser Phe Glu Tyr Glu Tyr Ala Met Arg
1               5                   10

<210> SEQ ID NO 318
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 318

Thr Gln Leu Tyr Glu Tyr Leu Gln Asn Arg
1               5                   10

<210> SEQ ID NO 319
<211> LENGTH: 25
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 319

Ile Tyr Asp Asp Glu Asn Gln Lys Ile Cys Ile Phe Val Asn His Ser
1               5                   10                  15

Thr Ala Pro Tyr Ser Val Lys Asn Lys
            20                  25

<210> SEQ ID NO 320
<211> LENGTH: 25
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 320

Ile Tyr Asp Asp Glu Asn Gln Lys Ile Cys Ile Phe Val Asn His Ser
1               5                   10                  15

Thr Ala Pro Tyr Ser Val Lys Asn Lys
            20                  25

<210> SEQ ID NO 321
<211> LENGTH: 9
```

```
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 321

Tyr Gln Gly Val Asn Leu Tyr Val Lys
1               5

<210> SEQ ID NO 322
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 322

Gln Ala His Leu Thr Asn Gln Tyr Met Gln Arg
1               5                   10

<210> SEQ ID NO 323
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 323

Lys Ala His Leu Thr Asn Gln Tyr Met Gln Arg
1               5                   10

<210> SEQ ID NO 324
<211> LENGTH: 33
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 324

Gln Ile Ser Tyr Asn Tyr Ser Asp Leu Asp Gln Ser Asn Val Thr Glu
1               5                   10                  15

Glu Thr Pro Glu Gly Glu Glu His His Pro Val Ala Asp Thr Glu Asn
            20                  25                  30

Lys

<210> SEQ ID NO 325
<211> LENGTH: 33
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 325

Gln Ile Ser Tyr Asn Tyr Ser Asp Leu Asp Gln Ser Asn Val Thr Glu
1               5                   10                  15

Glu Thr Pro Glu Gly Glu Glu His His Pro Val Ala Asp Thr Glu Asn
            20                  25                  30
```

Lys

<210> SEQ ID NO 326
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 326

Cys Asp Gly Lys Cys Val Ile Cys Asp Ser Tyr Val Arg
1               5                   10

<210> SEQ ID NO 327
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 327

Ile Cys Asp Glu Cys Asn Tyr Gly Ser Tyr Gln Gly Arg
1               5                   10

<210> SEQ ID NO 328
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 328

Ala Leu Tyr Pro Val Ile Pro Arg
1               5

<210> SEQ ID NO 329
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 329

His Thr Leu Ala Tyr Asp Lys Gly Trp Arg
1               5                   10

<210> SEQ ID NO 330
<211> LENGTH: 25
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 330

Thr Val Asn Lys His Gly Asp Glu Ile Ile Thr Thr Thr Ser Asn
1               5                   10                  15

Tyr Glu Thr Gln Thr Phe Ser Ser Lys
            20                  25

<210> SEQ ID NO 331
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 331

Thr Asn His Ile Tyr Val Ser Ser Asp Asp Ile Lys
1               5                   10

<210> SEQ ID NO 332
<211> LENGTH: 22
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 332

Thr Asn His Ile Tyr Val Ser Ser Asp Asp Ile Lys Glu Thr Gly Tyr
1               5                   10                  15
Thr Tyr Ile Leu Pro Lys
            20

<210> SEQ ID NO 333
<211> LENGTH: 18
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 333

Leu Lys Asp Thr Pro Leu Tyr Thr Asp Asn Thr Ala Asn Gly Ile Ala
1               5                   10                  15
Leu Leu

<210> SEQ ID NO 334
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 334

Asn Leu Ser Pro Tyr Val Ser Asn Glu Leu Leu Glu Glu Ala Phe Ser
1               5                   10                  15
Gln Phe Gly Pro Ile Glu Arg
            20

<210> SEQ ID NO 335
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 335

Asp Gln Tyr Ala Asn Tyr Val Val Gln Lys
1               5                   10

<210> SEQ ID NO 336
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 336

Lys Arg Ala Ala Ser Ala Ile Tyr Ser Gly Tyr
1               5                   10

<210> SEQ ID NO 337
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 337

Ala Ser Tyr Val Ala Pro Leu Thr Ala Gln Pro Ala Thr Tyr Arg
1               5                   10                  15

<210> SEQ ID NO 338
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 338

Ala Gln Pro Ser Val Ser Leu Gly Ala Ala Tyr Arg
1               5                   10

<210> SEQ ID NO 339
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 339

Ala Gln Pro Ser Ala Ser Leu Gly Val Gly Tyr Arg
1               5                   10

<210> SEQ ID NO 340
<211> LENGTH: 12
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 340

Thr Gln Pro Met Thr Ala Gln Ala Ala Ser Tyr Arg
1               5                   10

<210> SEQ ID NO 341

```
<211> LENGTH: 24
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 341

Tyr Gln Gln Gln Tyr Leu Gln Pro Leu Pro Leu Thr His Tyr Glu Leu
1               5                   10                  15

Val Thr Asp Ala Phe Gly His Arg
            20

<210> SEQ ID NO 342
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 342

Tyr Gln Gln Gln Tyr Leu Gln Pro Leu Pro Leu Thr His Tyr Glu Leu
1               5                   10                  15

Val Thr Asp Ala Phe Gly His Arg
            20

<210> SEQ ID NO 343
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 343

Phe Glu Glu Tyr Gly Pro Val Ile Glu Cys Asp Ile Val Lys
1               5                   10

<210> SEQ ID NO 344
<211> LENGTH: 16
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 344

Val Ala Asp Phe Thr Glu Gln Tyr Asn Glu Gln Tyr Gly Ala Val Arg
1               5                   10                  15

<210> SEQ ID NO 345
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 345

Asn Ser Leu Tyr Asp Met Ala Arg
1               5
```

```
<210> SEQ ID NO 346
<211> LENGTH: 28
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 346

Ala Thr Ala Pro Val Pro Thr Val Gly Glu Gly Tyr Gly Tyr Gly His
1               5                   10                  15

Glu Ser Glu Leu Ser Gln Ala Ser Ala Ala Arg
            20                  25

<210> SEQ ID NO 347
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 347

Thr Val Val Asp Ser Ile Met Thr Ala Leu Ser Pro Tyr
1               5                   10

<210> SEQ ID NO 348
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 348

Thr Gly Pro Met Gly His Thr Tyr Gly Phe Ile Asp Leu Asp Ser His
1               5                   10                  15

Ala Glu Ala Leu Arg
            20

<210> SEQ ID NO 349
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 349

Ser Tyr Val Val Ala Cys Lys Pro Pro Gln Lys Lys
1               5                   10

<210> SEQ ID NO 350
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 350

Ala Val Gln Cys Thr Ser Asp Tyr Pro Glu His Val Cys Glu Val Leu
1               5                   10                  15
```

Leu Thr Met Glu Arg
            20

<210> SEQ ID NO 351
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 351

Glu Ala Gly Asp Val Cys Tyr Ala Asp Val Tyr Arg
1               5                   10

<210> SEQ ID NO 352
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 352

Lys Glu Asp Met Thr Tyr Ala Val Arg
1               5

<210> SEQ ID NO 353
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 353

Thr Lys Asp Ile Glu Asp Val Phe Tyr Lys Tyr Gly Ala Ile Arg
1               5                   10                  15

<210> SEQ ID NO 354
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 354

Leu His Gly Leu Asn Ile Asn Tyr Asn Cys Glu Ile Cys Gly Asn Tyr
1               5                   10                  15

Thr Tyr Arg Gly Pro Lys
            20

<210> SEQ ID NO 355
<211> LENGTH: 22
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 355

Leu His Gly Leu Asn Ile Asn Tyr Asn Cys Glu Ile Cys Gly Asn Tyr
1               5                   10                  15

Thr Tyr Arg Gly Pro Lys
            20

<210> SEQ ID NO 356
<211> LENGTH: 27
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Phosphorylated-Tyr

<400> SEQUENCE: 356

Trp Gln Pro Asp Thr Glu Glu Glu Tyr Glu Asp Ser Ser Gly Asn Val
1               5                   10                  15

Val Asn Lys Lys Thr Tyr Glu Asp Leu Lys Arg
            20                  25

<210> SEQ ID NO 357
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 357

Ile Tyr Asn Asp Asp Lys Asn Thr Tyr Ile Arg
1               5                   10

<210> SEQ ID NO 358
<211> LENGTH: 28
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Phosphorylated-Tyr

<400> SEQUENCE: 358

Ala Ala Leu Asp Glu Ala Gln Gly Val Gly Leu Asp Ser Thr Gly Tyr
1               5                   10                  15

Tyr Asp Gln Glu Ile Tyr Gly Gly Ser Asp Ser Arg
            20                  25

<210> SEQ ID NO 359
<211> LENGTH: 26
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 359

Trp Val Thr Thr Ala Ser Leu Leu Asp Tyr Asp Thr Val Ala Gly Ala
1               5                   10                  15

Asp Lys Phe Gly Asn Ile Cys Val Val Arg
            20                  25

<210> SEQ ID NO 360
<211> LENGTH: 10
<212> TYPE: PRT
<213> ORGANISM: Homo sapiens
<220> FEATURE:
<221> NAME/KEY: MOD_RES

```
<222> LOCATION: (7)..(7)
<223> OTHER INFORMATION: Phosphorylated-Tyr

<400> SEQUENCE: 360

Gly Tyr Asp Asp Arg Asp Tyr Tyr Ser Arg
1               5                   10

<210> SEQ ID NO 361
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 361

Ala Ala Gln Asp Arg Asp Gln Ile Tyr Arg Arg
1               5                   10

<210> SEQ ID NO 362
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 362

Ala Phe Ser Tyr Tyr Gly Pro Leu Arg
1               5

<210> SEQ ID NO 363
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 363

Glu Ala Gly Asp Val Cys Tyr Ala Asp Val Gln Lys
1               5                   10

<210> SEQ ID NO 364
<211> LENGTH: 14
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 364

Phe Glu Asp Pro Arg Asp Ala Glu Asp Ala Ile Tyr Gly Arg
1               5                   10

<210> SEQ ID NO 365
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 365
```

```
Asn Gly Tyr Asp Tyr Gly Gln Cys Arg
1               5

<210> SEQ ID NO 366
<211> LENGTH: 18
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 366

Ser Leu Asp Ser Asp Glu Ser Glu Asp Glu Glu Asp Asp Tyr Gln Gln
1               5                   10                  15

Lys Arg

<210> SEQ ID NO 367
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 367

Asn Glu Thr Gly Pro Tyr Glu Cys Glu Ile Arg Asp Arg
1               5                   10

<210> SEQ ID NO 368
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 368

Ser Pro Ala Ser Asp Thr Tyr Ile Val Phe Gly Glu Ala Lys
1               5                   10

<210> SEQ ID NO 369
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 369

Leu Ile Glu Tyr Tyr Leu Thr Lys
1               5

<210> SEQ ID NO 370
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 370

His Ile Tyr Pro Ala Val Glu Phe Leu Gly Pro Cys Glu Gln Gly Glu
1               5                   10                  15
```

-continued

Arg

<210> SEQ ID NO 371
<211> LENGTH: 19
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 371

Leu Ser Pro Gly Ser Tyr Pro Thr Val Ile Gln Gln Gln Asn Ala Thr
1               5                   10                  15

Ser Gln Arg

<210> SEQ ID NO 372
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 372

Asn Tyr Glu Gly Thr Cys Glu Ile Pro Glu Ser Lys
1               5                   10

<210> SEQ ID NO 373
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 373

His Ser Ser Val Tyr Pro Thr Gln Glu Glu Leu Glu Ala Val Gln Asn
1               5                   10                  15

Met Val Ser His Thr Glu Arg
            20

<210> SEQ ID NO 374
<211> LENGTH: 31
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 374

Gly Tyr Asn His Gly Gln Gly Ser Tyr Ser Tyr Ser Asn Ser Tyr Asn
1               5                   10                  15

Ser Pro Gly Gly Gly Gly Gly Ser Asp Tyr Asn Tyr Glu Ser Lys
            20                  25                  30

<210> SEQ ID NO 375
<211> LENGTH: 34
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr -continued

```
<400> SEQUENCE: 375

Ser Gly Gly Asn Ser Tyr Gly Ser Gly Gly Ala Ser Tyr Asn Pro Gly
1               5                   10                  15

Ser His Gly Gly Tyr Gly Gly Gly Ser Gly Gly Ser Ser Tyr Gln
            20                  25                  30

Gly Lys

<210> SEQ ID NO 376
<211> LENGTH: 34
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: Phosphorylated-Tyr

<400> SEQUENCE: 376

Ser Gly Gly Asn Ser Tyr Gly Ser Gly Gly Ala Ser Tyr Asn Pro Gly
1               5                   10                  15

Ser His Gly Gly Tyr Gly Gly Gly Ser Gly Gly Ser Ser Tyr Gln
            20                  25                  30

Gly Lys

<210> SEQ ID NO 377
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 377

Asn Ala Asp His Ser Met Asn Tyr Gln Tyr Arg
1               5                   10

<210> SEQ ID NO 378
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 378

Asn Ala Asp His Ser Met Asn Tyr Gln Tyr Arg
1               5                   10

<210> SEQ ID NO 379
<211> LENGTH: 34
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: Phosphorylated-Tyr

<400> SEQUENCE: 379

Val Ser Gln Thr Pro Val Ala Thr Ala Ser Gly Pro Asn Phe Ser Leu
1               5                   10                  15

Ala Asp Leu Glu Ser Pro Ser Tyr Tyr Asn Ile Asn Gln Val Thr Leu
            20                  25                  30

Gly Arg
```

```
<210> SEQ ID NO 380
<211> LENGTH: 22
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 380

Arg Leu Glu Pro Val Val Ser Asp Ala Ile Tyr Asp Ser Lys Ala Pro
1               5                   10                  15

Asn Ala Ser Asn Leu Lys
            20

<210> SEQ ID NO 381
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 381

Ile Thr Lys Glu Pro Ile Ile Asp Tyr Phe Asp Val Gln Asp
1               5                   10

<210> SEQ ID NO 382
<211> LENGTH: 23
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 382

Val Gly Ile Tyr Ser Pro His Thr Ala Tyr Asp Ala Ala Pro Gln Gly
1               5                   10                  15

Val Asn Asn Trp Leu Ala Lys
            20

<210> SEQ ID NO 383
<211> LENGTH: 33
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: Phosphorylated-Tyr

<400> SEQUENCE: 383

Ala Ala Glu Thr Asp Pro Gly Met Val His Leu Ala Leu Gly Ser Asp
1               5                   10                  15

Leu Thr Thr Leu Gly Leu Asn Leu Asn Ser Pro Glu Asn Leu Tyr Pro
            20                  25                  30

Lys

<210> SEQ ID NO 384
<211> LENGTH: 18
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr
```

<400> SEQUENCE: 384

Thr Asp Val Gln Arg Pro Gln Val Val Glu Tyr Cys Val Val Cys Gly
1               5                   10                  15

Asp Lys

<210> SEQ ID NO 385
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 385

Lys Pro Ala Leu Gly Phe Tyr Asp Thr Ser Glu Glu Asn Tyr Gln Ala
1               5                   10                  15

Leu Asp Ala Asp Phe Arg Lys
            20

<210> SEQ ID NO 386
<211> LENGTH: 21
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 386

Asp Lys Leu Asn Ile Asn Pro Glu Asp Gly Met Ala Asp Tyr Ser Asp
1               5                   10                  15

Pro Ser Tyr Val Lys
            20

<210> SEQ ID NO 387
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 387

Glu Ile Asp Asp Thr Tyr Ile Glu Asp Ala Ala Asp Val Asp Ala Arg
1               5                   10                  15

<210> SEQ ID NO 388
<211> LENGTH: 22
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 388

Thr Val Gly Phe Gly Thr Asn Ser Glu His Ile Thr Tyr Leu Glu
1               5                   10                  15

His Asn Pro Tyr Glu Lys
            20

<210> SEQ ID NO 389
<211> LENGTH: 19

```
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 389

Leu His Asp Val Glu His Val Leu Ile Asp Val Gly Thr Gly Tyr Tyr
1               5                   10                  15

Val Glu Lys

<210> SEQ ID NO 390
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 390

Thr Pro Leu Ala Gly Pro Asn Ile Asp Tyr Pro Val Leu Tyr Gly Lys
1               5                   10                  15

<210> SEQ ID NO 391
<211> LENGTH: 33
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 391

Gln Tyr Pro Ala Asn Gln Gly Gln Glu Val Glu Tyr Phe Val Ala Gly
1               5                   10                  15

Thr His Pro Tyr Pro Pro Gly Pro Gly Val Ala Leu Thr Ala Asp Thr
                20                  25                  30

Lys

<210> SEQ ID NO 392
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 392

Glu Leu Tyr His Val Ile Ser Phe Asp Gly Ser Tyr Val Asn Tyr Arg
1               5                   10                  15

<210> SEQ ID NO 393
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 393

Tyr Ser Pro Thr Ser Pro Thr Tyr Ser Pro Thr Ser Pro Lys
1               5                   10
```

-continued

```
<210> SEQ ID NO 394
<211> LENGTH: 17
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 394

Asn Cys Asp Tyr Gln Gln Glu Ala Asp Asn Ser Cys Ile Tyr Val Asn
1               5                   10                  15

Lys

<210> SEQ ID NO 395
<211> LENGTH: 26
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 395

His Leu Glu Pro Glu Pro Glu Glu Glu Ile Ile Ala Glu Asp Tyr Asp
1               5                   10                  15

Asp Asp Pro Val Asp Tyr Glu Ala Thr Arg
            20                  25

<210> SEQ ID NO 396
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 396

Ser Leu Tyr Glu Ser Phe Val Ser Ser Asp Arg
1               5                   10

<210> SEQ ID NO 397
<211> LENGTH: 28
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 397

Ser Ala Gly Ser Ile Pro Gly Glu His Ser Thr Asp Asn Asn Arg Thr
1               5                   10                  15

Tyr Pro Ser Ile Gln Ile Met Asn Tyr Tyr Gly Lys
            20                  25

<210> SEQ ID NO 398
<211> LENGTH: 21
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 398

Ile Asn Ser Gln Leu Val Ala Gln Gln Val Ala Gln Gln Tyr Ala Thr
```

```
                1               5                  10                 15
Pro Pro Pro Pro Lys
                20

<210> SEQ ID NO 399
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 399

Ala Ser Ala Leu Tyr Glu Ser Ser Arg
1               5

<210> SEQ ID NO 400
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 400

Leu Ala Glu Ala Leu Tyr Ile Ala Asp Arg Lys
1               5                  10

<210> SEQ ID NO 401
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 401

Thr Ser Asn Glu Val Gln Tyr Asp Gln Arg
1               5                  10

<210> SEQ ID NO 402
<211> LENGTH: 35
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 402

Glu Ala Thr Pro Glu Asn Asp Pro Asn Tyr Phe Met Asn Glu Pro Thr
1               5                  10                 15

Phe Tyr Thr Ser Asp Gly Val Pro Phe Thr Ala Ala Asp Pro Asp Tyr
                20                 25                 30

Gln Glu Lys
        35

<210> SEQ ID NO 403
<211> LENGTH: 35
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr
```

-continued

<400> SEQUENCE: 403

Glu Ala Thr Pro Glu Asn Asp Pro Asn Tyr Phe Met Asn Glu Pro Thr
1               5                   10                  15

Phe Tyr Thr Ser Asp Gly Val Pro Phe Thr Ala Ala Pro Asp Tyr
            20                  25                  30

Gln Glu Lys
        35

<210> SEQ ID NO 404
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 404

Asp Tyr Leu His Leu Pro Pro Glu Ile Val Pro Ala Thr Leu Arg Arg
1               5                   10                  15

<210> SEQ ID NO 405
<211> LENGTH: 19
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 405

Ala Thr Phe Asp Ala Ile Ser Lys Thr Tyr Ser Tyr Leu Thr Pro Asp
1               5                   10                  15

Leu Trp Lys

<210> SEQ ID NO 406
<211> LENGTH: 22
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 406

Phe Val Asp Gly Leu Met Ile His Ser Gly Asp Pro Val Asn Tyr Tyr
1               5                   10                  15

Val Asp Thr Ala Val Arg
            20

<210> SEQ ID NO 407
<211> LENGTH: 22
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 407

Phe Val Asp Gly Leu Met Ile His Ser Gly Asp Pro Val Asn Tyr Tyr
1               5                   10                  15

Val Asp Thr Ala Val Arg
            20

```
<210> SEQ ID NO 408
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 408

Ile Ile Asp Val Val Tyr Asn Ala Ser Asn Asn Glu Leu Val Arg
 1               5                  10                  15

<210> SEQ ID NO 409
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 409

Ile Gly Gln Tyr Leu Ser Ser Asn Arg
 1               5

<210> SEQ ID NO 410
<211> LENGTH: 31
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 410

Ile Leu Pro Asn Lys Val Asp Pro Leu Val Ser Leu Met Met Val Glu
 1               5                  10                  15

Lys Val Pro Asp Ser Thr Tyr Glu Met Ile Gly Gly Leu Asp Lys
                20                  25                  30

<210> SEQ ID NO 411
<211> LENGTH: 16
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 411

Val Gly Leu Ser Thr Pro Pro Pro Ala Tyr Glu Ser Ile Ile Lys
 1               5                  10                  15

<210> SEQ ID NO 412
<211> LENGTH: 19
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 412

Asn Ser Met Val Ala Leu Val Glu Asn Leu Ala Ser Lys Glu Pro Phe
 1               5                  10                  15

Tyr Val Arg
```

```
<210> SEQ ID NO 413
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 413

His Gln Val Ala Tyr Leu Gly Leu Leu Glu Asn Val Arg
1               5                   10

<210> SEQ ID NO 414
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 414

Ala Ile Tyr Thr Ile Met Arg
1               5

<210> SEQ ID NO 415
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 415

Ile Tyr His Val Thr Val Met Pro Cys Tyr Asp Lys
1               5                   10

<210> SEQ ID NO 416
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 416

Ile Tyr His Val Thr Val Met Pro Cys Tyr Asp Lys
1               5                   10

<210> SEQ ID NO 417
<211> LENGTH: 17
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 417

Ile Glu Asp Asp Gly Ser Tyr Phe Gln Ile Asn Gln Asp Gly Gly Thr
1               5                   10                  15

Arg

<210> SEQ ID NO 418
<211> LENGTH: 11
```

```
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 418

Ser Tyr Val Asp Leu Leu Val Lys Tyr Ala Lys
1               5                   10

<210> SEQ ID NO 419
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 419

Ser Tyr Val Asp Leu Leu Val Lys Tyr Ala Lys
1               5                   10

<210> SEQ ID NO 420
<211> LENGTH: 30
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 420

Glu Leu Gln Lys Tyr Ser Ser Asp Ser Glu Ser Pro Arg Gly Thr Gly
1               5                   10                  15

Ser Gly Ala Leu Pro Ser Gly Gln Lys Leu Glu Glu Leu Lys
            20                  25                  30

<210> SEQ ID NO 421
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 421

Ser Ala Tyr Asn Ser Tyr Ser Trp Gly Ala Asn
1               5                   10

<210> SEQ ID NO 422
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 422

Ser Ala Tyr Asn Ser Tyr Ser Trp Gly Ala Asn
1               5                   10

<210> SEQ ID NO 423
<211> LENGTH: 15
<212> TYPE: PRT
<213> ORGANISM: Homo sapiens
```

```
<220> FEATURE:
<221> NAME/KEY: MOD_RES
<222> LOCATION: (9)..(9)
<223> OTHER INFORMATION: Phosphorylated-Tyr

<400> SEQUENCE: 423

Asp Gly Ser Leu Ala Ser Asn Pro Tyr Ser Gly Asp Leu Thr Lys
1               5                   10                  15

<210> SEQ ID NO 424
<211> LENGTH: 21
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 424

Lys Pro Glu Asp Pro Glu Glu Cys Pro Glu Val Tyr Asp Pro Arg
1               5                   10                  15

Ser Leu Tyr Glu Arg
            20

<210> SEQ ID NO 425
<211> LENGTH: 21
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 425

Lys Pro Glu Asp Pro Glu Glu Cys Pro Glu Val Tyr Asp Pro Arg
1               5                   10                  15

Ser Leu Tyr Glu Arg
            20

<210> SEQ ID NO 426
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 426

Lys Gln Gln Glu Tyr Glu Glu Gln Phe Lys
1               5                   10

<210> SEQ ID NO 427
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 427

Met Gly Ile Tyr Tyr Ile Pro Val Leu Gly Pro Ala Pro Arg
1               5                   10

<210> SEQ ID NO 428
<211> LENGTH: 16
<212> TYPE: PRT
```

```
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 428

Leu Ala Gln Glu Gly Ile Tyr Thr Leu Tyr Pro Phe Ile Asn Ser Arg
1               5                   10                  15

<210> SEQ ID NO 429
<211> LENGTH: 27
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 429

Val Val Asp Tyr Ser Gln Phe Gln Glu Ser Asp Ala Asp Glu Asp
1               5                   10                  15

Tyr Gly Arg Asp Ser Gly Pro Pro Thr Lys Lys
            20                  25

<210> SEQ ID NO 430
<211> LENGTH: 27
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 430

Val Val Asp Tyr Ser Gln Phe Gln Glu Ser Asp Ala Asp Glu Asp
1               5                   10                  15

Tyr Gly Arg Asp Ser Gly Pro Pro Thr Lys Lys
            20                  25

<210> SEQ ID NO 431
<211> LENGTH: 23
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 431

Val Gly Glu Tyr Trp Trp Asn Ala Ile Leu Glu Gly Glu Pro Ile
1               5                   10                  15

Asp Ile Asp Lys Ile Asn Lys
            20

<210> SEQ ID NO 432
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 432

Asn Ser Phe Ile Glu Lys Glu Asn Tyr His Tyr
1               5                   10
```

```
<210> SEQ ID NO 433
<211> LENGTH: 22
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 433

Gln Glu Leu Val Tyr Thr Asn Lys Lys Leu Glu Leu Gln Val Glu Ser
1               5                   10                  15

Met Leu Ser Glu Ile Lys
            20

<210> SEQ ID NO 434
<211> LENGTH: 22
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 434

Ser Pro Thr Glu Tyr His Glu Pro Val Tyr Ala Asn Pro Phe Tyr Arg
1               5                   10                  15

Pro Thr Thr Pro Gln Arg
            20

<210> SEQ ID NO 435
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 435

Gln Thr Gln Thr Ser Glu Val Tyr Asp Gly Pro Lys
1               5                   10

<210> SEQ ID NO 436
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 436

Leu Val Gln Ile Arg Asp Tyr Ile Thr Lys
1               5                   10

<210> SEQ ID NO 437
<211> LENGTH: 21
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 437

Glu Leu Val His Tyr Tyr Glu Gln Thr Ser Asp Met Met Thr Asp Ala
1               5                   10                  15
```

```
Val Asn Glu Asn Arg
            20

<210> SEQ ID NO 438
<211> LENGTH: 18
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 438

Trp Lys Asn Asn Cys Pro Phe Ser Ala Asp Glu Asn Tyr Arg Pro Leu
1               5                   10                  15

Ala Lys

<210> SEQ ID NO 439
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 439

Met Gly Ala Tyr His Thr Ile Glu Leu Glu Pro Asn Arg
1               5                   10

<210> SEQ ID NO 440
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 440

Leu Gly Asp Phe Val Lys Tyr Tyr Tyr Ser Gly Lys Arg
1               5                   10

<210> SEQ ID NO 441
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 441

Leu Gly Asp Phe Val Lys Tyr Tyr Tyr Ser Gly Lys Arg
1               5                   10

<210> SEQ ID NO 442
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 442

Leu Gly Asp Phe Val Lys Tyr Tyr Tyr Ser Gly Lys Arg
1               5                   10
```

```
<210> SEQ ID NO 443
<211> LENGTH: 28
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 443

Ser Pro Gln Glu Asn Glu Asp Glu Asp Tyr Gln Met Phe Val
1               5                   10                  15

Pro Ser Phe Ser Ser Asp Leu Asn Ser Thr Arg
            20                  25

<210> SEQ ID NO 444
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 444

Ile Lys Tyr Tyr Asn Tyr Cys Leu Ile His Asn Val Gln Arg
1               5                   10

<210> SEQ ID NO 445
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 445

Thr Phe Gly Glu Asn Tyr Val Gln Glu Leu Leu Glu Lys
1               5                   10

<210> SEQ ID NO 446
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 446

Gly Lys Gly Cys Val Asp Glu Ser Gly Phe Val Tyr Ala Ile Gly Glu
1               5                   10                  15

Lys

<210> SEQ ID NO 447
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Phosphorylated-Tyr

<400> SEQUENCE: 447

Ala Tyr Met Leu His Ile Gly Thr Leu Asp Lys
1               5                   10
```

-continued

```
<210> SEQ ID NO 448
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 448

Asp Ile Glu Tyr Phe Val Asn Gln Arg
1               5

<210> SEQ ID NO 449
<211> LENGTH: 20
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Phosphorylated-Tyr

<400> SEQUENCE: 449

Val Lys Glu Gly Tyr Val Pro Gln Glu Glu Val Pro Val Tyr Glu Asn
1               5                   10                  15

Lys Tyr Val Lys
            20

<210> SEQ ID NO 450
<211> LENGTH: 20
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Phosphorylated-Tyr

<400> SEQUENCE: 450

Val Lys Glu Gly Tyr Val Pro Gln Glu Glu Val Pro Val Tyr Glu Asn
1               5                   10                  15

Lys Tyr Val Lys
            20

<210> SEQ ID NO 451
<211> LENGTH: 21
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Phosphorylated-Tyr

<400> SEQUENCE: 451

Phe Gln Lys Glu Asn Pro Gly Phe Asp Phe Ser Gly Ala Glu Ile Ser
1               5                   10                  15

Gly Asn Tyr Thr Lys
            20

<210> SEQ ID NO 452
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr
```

```
<400> SEQUENCE: 452

Tyr Ile Leu Lys Arg Asp Asn Ser Ser Phe Asp Lys
1               5                   10

<210> SEQ ID NO 453
<211> LENGTH: 31
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 453

Ser Thr Asn Ser His Gln Ser Ser Thr Glu Asn Glu Leu Lys Tyr Ser
1               5                   10                  15

Glu Pro Arg Pro Trp Ser Ser Thr Asp Ser Asp Ser Leu Arg
            20                  25                  30

<210> SEQ ID NO 454
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 454

Leu Gly Asp Ser Ser Asn Tyr Tyr Tyr Ile Ser Pro Phe Cys Arg
1               5                   10                  15

<210> SEQ ID NO 455
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 455

Ala Leu Asp Gly Glu Glu Ser Asp Phe Glu Asp Tyr Pro Met Arg
1               5                   10                  15

<210> SEQ ID NO 456
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 456

Glu Phe Ile Met Phe Pro Tyr Asp Ser Arg Leu Asp Asp Lys
1               5                   10

<210> SEQ ID NO 457
<211> LENGTH: 26
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 457
```

Val Met Glu Lys Glu Tyr Cys Gln Ala Lys Lys Ala Gln Asn Arg Phe
1               5                   10                  15

Lys Val Pro Leu Gly Thr Lys Phe Tyr Arg
            20                  25

<210> SEQ ID NO 458
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 458

Glu Ser Ala Thr Ala Asp Ala Gly Tyr Ala Ile Leu Glu Lys
1               5                   10

<210> SEQ ID NO 459
<211> LENGTH: 24
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 459

Gly Asp His Ser His Leu Phe Asp Ser Lys Asp Pro Pro Ile Tyr Ser
1               5                   10                  15

Val Gly Ala Phe Glu Asn Phe Arg
            20

<210> SEQ ID NO 460
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 460

Asn Glu Tyr Ser Leu Thr Gly Leu Cys Asn Arg
1               5                   10

<210> SEQ ID NO 461
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 461

Gly Gln Cys Tyr Leu Tyr Met Lys
1               5

<210> SEQ ID NO 462
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 462

```
Gly Gln Cys Tyr Leu Tyr Met Lys
1               5

<210> SEQ ID NO 463
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 463

His Ala Gln Pro Pro Pro Ile Pro Val Gln Asn Asp Pro Glu Leu Tyr
1               5                   10                  15

Glu Lys

<210> SEQ ID NO 464
<211> LENGTH: 21
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 464

Leu Ala Ser Leu Phe Ser Ser Leu Glu Pro Gln Ile Gln Pro Val Tyr
1               5                   10                  15

Val Pro Val Pro Lys
            20

<210> SEQ ID NO 465
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 465

Ser Leu Ala Phe His Arg Pro Pro Tyr His Leu Leu Gln Gln Arg
1               5                   10                  15

<210> SEQ ID NO 466

<400> SEQUENCE: 466

000

<210> SEQ ID NO 467

<400> SEQUENCE: 467

000

<210> SEQ ID NO 468
<211> LENGTH: 18
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 468
```

Asn Leu Ser Ala Ser Phe Pro Thr Glu Glu Ser Ser Ile Asn Tyr Thr
1               5                   10                  15

Phe Lys

<210> SEQ ID NO 469
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 469

Ser Ala Ala Asn Leu Glu Tyr Leu Lys
1               5

<210> SEQ ID NO 470
<211> LENGTH: 26
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr

<400> SEQUENCE: 470

Gln Met Leu Asn Ser Val Met Gln Glu Leu Glu Asp Tyr Ser Glu Gly
1               5                   10                  15

Gly Pro Leu Tyr Lys Asn Gly Ser Leu Arg
            20                  25

<210> SEQ ID NO 471
<211> LENGTH: 25
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Phosphorylated-Tyr

<400> SEQUENCE: 471

Ser Glu Thr Ser Thr Ser Asp Asn Thr Glu Thr Tyr Gln Glu Asn Thr
1               5                   10                  15

Ser Ser Ser Gly His Pro Thr Phe Lys
            20                  25

<210> SEQ ID NO 472
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 472

Gly Asn Gly Glu Tyr Ala Trp Tyr Tyr Glu Gly Arg
1               5                   10

<210> SEQ ID NO 473
<211> LENGTH: 16
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

```
<400> SEQUENCE: 473

Thr Ala Asn Ile Glu Ser Pro Thr Ser Ile Leu Lys Ala Leu His Tyr
1               5                   10                  15

<210> SEQ ID NO 474
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 474

Glu Leu Tyr Glu Val Ile Gly Cys Val Pro Val Asp Asp Leu Glu Val
1               5                   10                  15

Tyr Leu Lys

<210> SEQ ID NO 475
<211> LENGTH: 19
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Phosphorylated-Tyr

<400> SEQUENCE: 475

Glu Leu Tyr Glu Val Ile Gly Cys Val Pro Val Asp Asp Leu Glu Val
1               5                   10                  15

Tyr Leu Lys

<210> SEQ ID NO 476
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 476

Asp Asp Ala Tyr Trp Pro Glu Gly Lys
1               5

<210> SEQ ID NO 477
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 477

Asn Gly Ile Asp Val Asp Lys Trp Asp Tyr Phe Ala Arg
1               5                   10

<210> SEQ ID NO 478
<211> LENGTH: 26
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Phosphorylated-Tyr
```

```
<400> SEQUENCE: 478

Met Ala Arg Val Ala Trp Gly Leu Leu Trp Leu Leu Leu Gly Ser Ala
1               5                   10                  15

Gly Ala Gln Tyr Glu Lys Tyr Ser Phe Arg
            20                  25

<210> SEQ ID NO 479
<211> LENGTH: 26
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Phosphorylated-Tyr

<400> SEQUENCE: 479

Met Ala Arg Val Ala Trp Gly Leu Leu Trp Leu Leu Leu Gly Ser Ala
1               5                   10                  15

Gly Ala Gln Tyr Glu Lys Tyr Ser Phe Arg
            20                  25

<210> SEQ ID NO 480
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Tyr

<400> SEQUENCE: 480

Tyr Asp Arg Gly Asn Ile Val Leu Thr Asp Tyr Glu Tyr
1               5                   10

<210> SEQ ID NO 481
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated-Tyr

<400> SEQUENCE: 481

Tyr Asp Arg Gly Asn Ile Val Leu Thr Asp Tyr Glu Tyr
1               5                   10

<210> SEQ ID NO 482
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Phosphorylated-Tyr

<400> SEQUENCE: 482

Tyr Asp Arg Gly Asn Ile Val Leu Thr Asp Tyr Glu Tyr
1               5                   10

<210> SEQ ID NO 483
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr
```

<400> SEQUENCE: 483

Val Asn Asn Val Tyr Asp Val Asp Asn Lys
1               5                   10

<210> SEQ ID NO 484
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 484

Met Lys Lys Met Lys Glu Lys Tyr Lys Asp Gln Asp Glu Glu Asp Arg
1               5                   10                  15

Glu Leu Ile Met Lys
            20

<210> SEQ ID NO 485
<211> LENGTH: 12
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 485

Thr Leu Pro Ala Asp Val Gln Asn Tyr Tyr Ser Arg
1               5                   10

<210> SEQ ID NO 486
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated-Tyr

<400> SEQUENCE: 486

Leu Gly Asn Pro Tyr Cys Ser Pro Thr Leu Val Arg
1               5                   10

<210> SEQ ID NO 487
<211> LENGTH: 18
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated-Tyr

<400> SEQUENCE: 487

Ser Gly Ala Tyr Arg Gly Cys Thr Tyr Glu Thr Gln Leu Gln Leu Ser
1               5                   10                  15

Ala Arg

<210> SEQ ID NO 488
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Tyr

<400> SEQUENCE: 488

Ser Trp Asp Glu Glu Glu Asp Glu Tyr Asp Tyr Phe Val Arg
1               5                   10                  15

<210> SEQ ID NO 489

<400> SEQUENCE: 489

000

<210> SEQ ID NO 490
<211> LENGTH: 18
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Phosphorylated-Tyr

<400> SEQUENCE: 490

His Lys Ile Ile His Asn Glu Glu Lys Pro Tyr Lys Cys Lys Glu Tyr
1               5                   10                  15

Glu Lys

<210> SEQ ID NO 491
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Tyr

<400> SEQUENCE: 491

Val Glu Glu Ile Asn Pro Glu Tyr Met Leu Glu Lys
1               5                   10

<210> SEQ ID NO 492
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Tyr

<400> SEQUENCE: 492

Ser Phe Tyr Gln Phe Gln His Tyr Arg
1               5

<210> SEQ ID NO 493
<211> LENGTH: 22
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Phosphorylated-Tyr

<400> SEQUENCE: 493

Lys Ser Asn Val Lys Pro Asn Ser Gly Glu Leu Asp Pro Leu Tyr Val
1               5                   10                  15

Val Glu Val Leu Leu Arg
            20

<210> SEQ ID NO 494

-continued

```
<211> LENGTH: 16
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Tyr

<400> SEQUENCE: 494

Asn Val Pro Pro Gly Leu Asp Glu Tyr Asn Pro Phe Ser Asp Ser Arg
1               5                   10                  15

<210> SEQ ID NO 495
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Tyr

<400> SEQUENCE: 495

Leu Asp Asp Arg Val Tyr Ala Met Cys Gln Ile Lys
1               5                   10

<210> SEQ ID NO 496
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated-Tyr

<400> SEQUENCE: 496

Asp Gly Glu Ala Lys Gln Tyr Gly Gly Trp Glu Val Lys
1               5                   10
```

REAGENTS FOR THE DETECTION OF PROTEIN PHOSPHORYLATION IN SIGNALING PATHWAYS

RELATED APPLICATIONS

This is a National Stage Application of International Application No. PCT/US07/073,540 filed Jul. 13, 2007, which itself claims priority to U.S. Ser. No. 60/830,550 filed Jul. 13, 2006 now abandoned, both disclosures of which are incorporated herein, in their entirety, by reference.

TECHNICAL FIELD

The invention relates generally to a variety of moieties and tools for the detection of protein phosphorylation. Moreover, the invention relates to the use of the same for diagnostic and therapeutic purposes.

BACKGROUND

The activation of proteins by post-translational modification is an important cellular mechanism for regulating most aspects of biological organization and control, including growth, development, homeostasis, and cellular communication. Cellular signal transduction pathways involve protein kinases, protein phosphatases, and phosphoprotein-interacting domain (e.g., SH2, PTB, WW, FHA, 14-3-3) containing cellular proteins to provide multidimensional, dynamic and reversible regulation of many biological activities. See e.g., Sawyer et al., *Med. Chem.* 1(3): 293-319 (2005).

Protein phosphorylation on a proteome-wide scale is extremely complex as a result of three factors: the large number of modifying proteins, e.g. kinases, encoded in the genome, the much larger number of sites on substrate proteins that are modified by these enzymes, and the dynamic nature of protein expression during growth, development, disease states, and aging. The human genome, for example, encodes over 520 different protein kinases, making them the most abundant class of enzymes known. See Hunter, *Nature* 411: 355-65 (2001). Most kinases phosphorylate many different substrate proteins, at distinct tyrosine, serine, and/or threonine residues. Indeed, it is estimated that one-third of all proteins encoded by the human genome are phosphorylated, and many are phosphorylated at multiple sites by different kinases. See Graves et al., *Pharmacol. Ther.* 82: 11.1-21 (1999).

Many of these phosphorylation sites regulate critical biological processes and may prove to be important for diagnostic or therapeutic modalities useful in the treatment and management of many pathological conditions and diseases, including inter alia cancer, developmental disorders, as inflammatory, immune, metabolic and bone diseases.

For example, of the more than 100 dominant oncogenes identified to date, 46 are protein kinases. See Hunter, supra. Understanding which proteins are modified by these kinases will greatly expand our understanding of the molecular mechanisms underlying oncogenic transformation. Therefore, the identification of, and ability to detect, phosphorylation sites on a wide variety of cellular proteins is crucially important to understanding the key signaling proteins and pathways implicated in the progression of many disease states.

Understanding reversible protein phosphorylation and its role in the operation and interrelationship between cellular components and functions provides the opportunity to gain a finer appreciation of cellular regulation. In spite of the importance of protein modification, phosphorylation is not yet well understood due to the extraordinary complexity of signaling pathways, and the slow development of the technology necessary to unravel it.

In many instances, such knowledge is likely to provide valuable tools useful to evaluate, and possibly to manipulate target pathways, ultimately altering the functional status of a given cell for a variety of purposes.

The importance of protein kinase-regulated signal transduction pathways is underscored by a number of drugs designed to treat various cancer types by the inhibition of target protein kinases at the apex or intermediary levels of pathways implicated in cancer development. See Stern et al., *Expert Opin. Ther. Targets* 9(4):851-60 (2005).

Leukemia, a disease in which a number of underlying signal transduction events have been elucidated, has become a disease model for phosphoproteomic research and development efforts. As such, it represent a paradigm leading the way for many other programs seeking to address many classes of diseases (See, *Harrison's Principles of Internal Medicine*, McGraw-Hill, New York, N.Y.)

Depending on the cell type involved and the rate by which the disease progresses leukemia can be defined as acute or chronic myelogenous leukemia (AML or CML), or acute and chronic lymphocytic leukemia (ALL or CLL).

Most varieties of leukemia are generally characterized by genetic alterations e.g., chromosomal translocations, deletions or point mutations resulting in the constitutive activation of protein kinase genes, and their products, particularly tyrosine kinases. The most well known alteration is the oncogenic role of the chimeric BCR-Abl gene. See Nowell, *Science* 132: 1497 (1960)). The resulting BCR-Abl kinase protein is constitutively active and elicits characteristic signaling pathways that have been shown to drive the proliferation and survival of CML cells (see Daley, *Science* 247: 824-830 (1990); Raitano et al., *Biochim. Biophys. Acta.* December 9; 1333(3): F201-16 (1997)).

The recent success of Imanitib (also known as ST1571 or Gleevec®), the first molecularly targeted compound designed to specifically inhibit the tyrosine kinase activity of BCR-Abl, provided critical confirmation of the central role of BCR-Abl signaling in the progression of CML (see Schindler et al., *Science* 289: 1938-1942 (2000); Nardi et al., *Curr. Opin. Hematol.* 11: 35-43 (2003)).

The success of Gleevec® now serves as a paradigm for the development of targeted drugs designed to block the activity of other tyrosine kinases known to be involved in many diseased including leukemias and other malignancies (see, e.g., Sawyers, *Curr. Opin. Genet. Dev. February;* 12(1): 111-5 (2002); Druker, *Adv. Cancer Res.* 91:1-30 (2004)). For example, recent studies have demonstrated that mutations in the FLT3 gene occur in one third of adult patients with AML. FLT3 (Fms-like tyrosine kinase 3) is a member of the class III receptor tyrosine kinase (RTK) family including FMS, platelet-derived growth factor receptor (PDGFR) and c-KIT (see Rosnet et al., *Crit. Rev. Oncog.* 4: 595-613 (1993). In 20-27% of patients with AML, an internal tandem duplication in the juxta-membrane region of FLT3 can be detected (see Yokota et al., *Leukemia* 11: 1605-1609 (1997)). Another 7% of patients have mutations within the active loop of the second kinase domain, predominantly substitutions of aspartate residue 835 (D835), while additional mutations have been described (see Yamamoto et al., *Blood* 97: 2434-2439 (2001); Abu-Duhier et al., *Br. J. Haematol.* 113: 983-988 (2001)). Expression of mutated FLT3 receptors results in constitutive tyrosine phosphorylation of FLT3, and subsequent phosphorylation and activation of downstream molecules such as STAT5, Akt and MAPK, resulting in factor-independent growth of hematopoietic cell lines.

Altogether, FLT3 is the single most common activated gene in AML known to date. This evidence has triggered an intensive search for FLT3 inhibitors for clinical use leading to at least four compounds in advanced stages of clinical development, including: PKC412 (by Novartis), CEP-701 (by Cephalon), MLN518 (by Millenium Pharmaceuticals), and SU5614 (by Sugen/Pfizer) (see Stone et al., *Blood* (in press) (2004); Smith et al., *Blood* 103: 3669-3676 (2004); Clark et al., *Blood* 104: 2867-2872 (2004); and Spiekerman et al., *Blood* 101: 1494-1504 (2003)).

There is also evidence indicating that kinases such as FLT3, c-KIT and Abl are implicated in some cases of ALL (see Cools et al., *Cancer Res.* 64: 6385-6389 (2004); Hu, *Nat. Genet.* 36: 453-461 (2004); and Graux et al., *Nat. Genet.* 36: 1084-1089 (2004)). In contrast, very little is know regarding any causative role of protein kinases in CLL, except for a high correlation between high expression of the tyrosine kinase ZAP70 and the more aggressive form of the disease (see Rassenti et al., *N. Eng. J. Med.* 351: 893-901 (2004)).

Despite the identification of a few key molecules involved in progression of leukemia, the vast majority of signaling protein changes underlying this disease remains unknown. There is, therefore, relatively scarce information about kinase-driven signaling pathways and phosphorylation sites relevant to the different types of leukemia. This has hampered a complete and accurate understanding of how protein activation within signaling pathways is driving these complex cancers. Accordingly, there is a continuing and pressing need to unravel the molecular mechanisms of kinase-driven oncogenesis in leukemia by identifying the downstream signaling proteins mediating cellular transformation in this disease. Identifying particular phosphorylation sites on such signaling proteins and providing new reagents, such as phospho-specific antibodies and AQUA peptides, to detect and quantify them remains particularly important to advancing our understanding of the biology of this disease.

Presently, diagnosis of leukemia is made by tissue biopsy and detection of different cell surface markers. However, misdiagnosis can occur since some leukemia cases can be negative for certain markers, and because these markers may not indicate which genes or protein kinases may be deregulated. Although the genetic translocations and/or mutations characteristic of a particular form of leukemia can be sometimes detected, it is clear that other downstream effectors of constitutively active kinases having potential diagnostic, predictive, or therapeutic value, remain to be elucidated. Accordingly, identification of downstream signaling molecules and phosphorylation sites involved in different types of leukemia and development of new reagents to detect and quantify these sites and proteins may lead to improved diagnostic/prognostic markers, as well as novel drug targets, for the detection and treatment of this disease.

SUMMARY OF THE INVENTION

Several novel protein phosphorylation sites have been identified in a variety of cell lines. Such novel phosphorylation sites (tyrosine), and their corresponding parent proteins are reported (see Table 1). The elucidation of these sites at long last provides the elements necessary to attain those much needed proteomics tools and modalities.

The invention discloses novel phosphorylation sites identified in signal transduction proteins and pathways underlying various disease states including for example human leukemias. The invention thus provides new reagents, including phosphorylation-site specific antibodies and AQUA peptides, for the selective detection and quantification of these phosphorylated sites/proteins. Also provided are methods of using the reagents of the invention for the detection and quantification of the disclosed phosphorylation sites.

BRIEF DESCRIPTION OF THE DRAWINGS

FIG. 2—Is a table (corresponding to Table 1) enumerating the Leukemia signaling protein phosphorylation sites disclosed herein:
Column A=the name of the parent protein; Column B=the SwissProt accession number for the protein (human sequence); Column C=the protein type/classification; Column D=the tyrosine residue (in the parent protein amino acid sequence) at which phosphorylation occurs within the phosphorylation site; Column E=the phosphorylation site sequence encompassing the phosphorylatable residue (residue at which phosphorylation occurs (and corresponding to the respective entry in Column D) appears in lowercase; Column F=the type of leukemia in which the phosphorylation site was discovered; and Column G=the cell type(s), tissue(s) and/or patient(s) in which the phosphorylation site was discovered.

DETAILED DESCRIPTION

Figure 1:
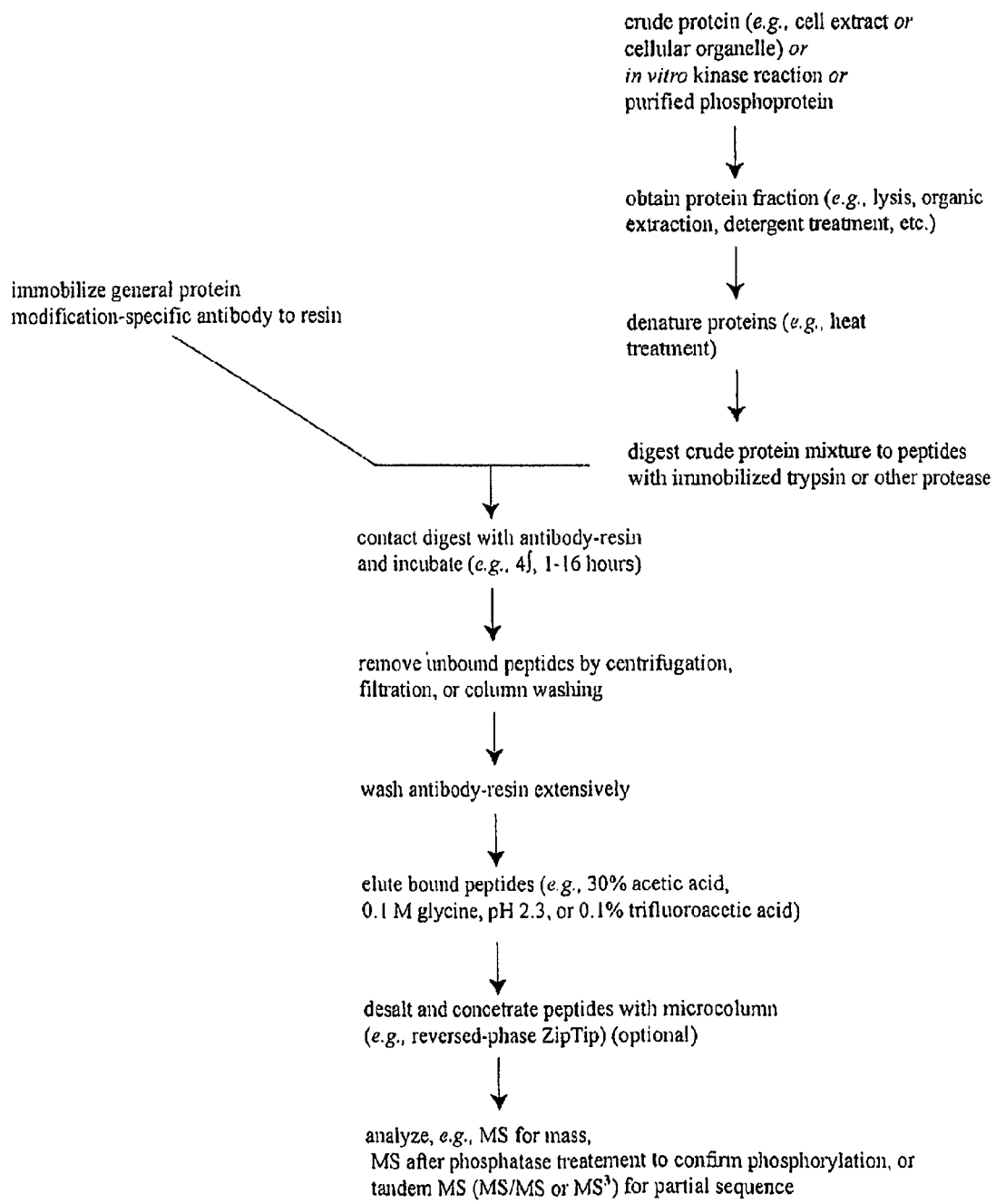
FIG. 1—Is a diagram broadly depicting the immunoaffinity isolation and mass-spectrometric characterization methodology (IAP) employed to identify the novel phosphorylation sites disclosed herein.
Figure 3:
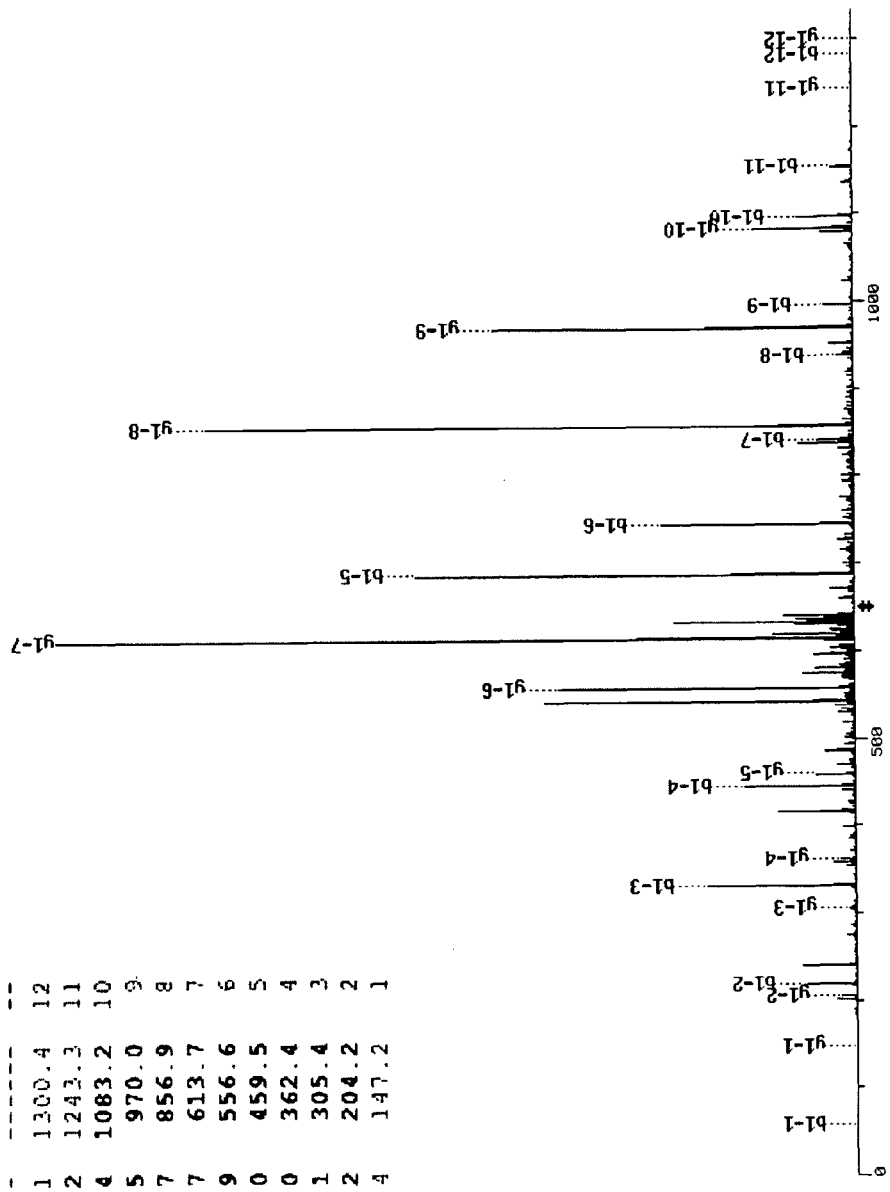
FIG. 3—is an exemplary mass spectrograph depicting the detection of the tyrosine 173 phosphorylation site in PSMC6 (see Row 251, SEQ ID NO: 252 in FIG. 2/Table 1), as further described in Example 1 (red and blue indicate ions detected in MS/MS spectrum); Y* indicates the phosphorylated serine (shown as lowercase "y" in FIG. 2).
Figure 4:
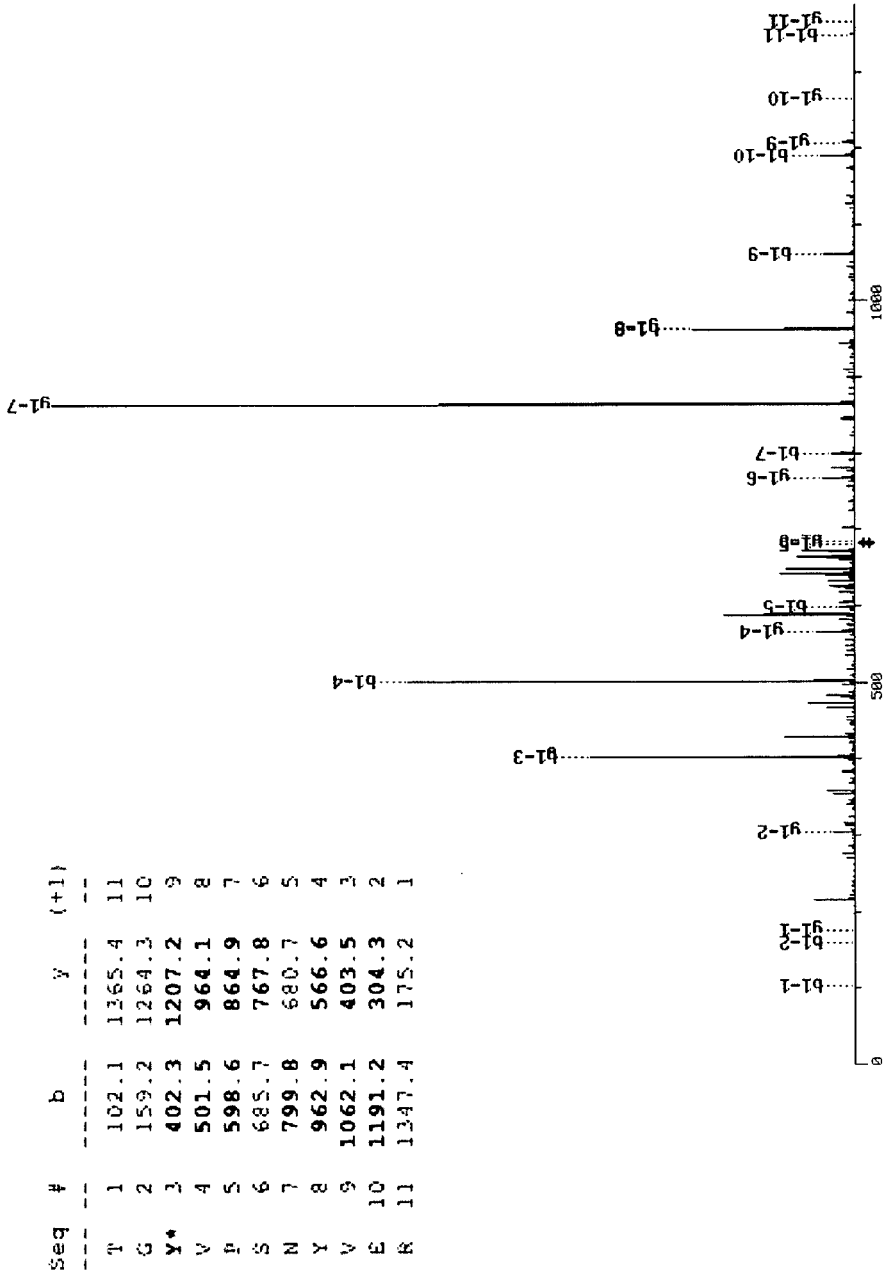
FIG. 4—is an exemplary mass spectrograph depicting the detection of the tyrosine 50 phosphorylation site in NCK2 (see Row 5, SEQ ID NO: 4 in FIG. 2/Table 1), as further described in Example 1 (red and blue indicate ions detected in MS/MS spectrum); Y* indicates the phosphorylated tyrosine (shown as lowercase "y" in FIG. 2).

Several novel protein phosphorylation sites have been identified in a variety of cell lines. Such novel phosphorylation sites (tyrosine), and their corresponding parent proteins are reported (see Table 1). The elucidation of these sites at long last provides the elements necessary to attain those much needed proteomics tools and modalities.

The disclosure of the phosphorylation sites provides the key to the production of new moieties, compositions and methods to specifically detect and/or to quantify these phosphorylated sites/proteins. Such moieties include for example reagents, such as phosphorylation site-specific antibodies and AQUA peptides (heavy-isotope labeled peptides). Such reagents are highly useful, inter alia, for studying signal transduction events underlying the progression of many diseases known or suspected to involve protein phosphorylation e.g., leukemia in a mammal. Accordingly, the invention provides novel reagents—phospho-specific antibodies and AQUA peptides—for the specific detection and/or quantification of a target signaling protein/polypeptide (e.g., a signaling protein/polypeptide implicated in leukemia) only when phosphorylated (or only when not phosphorylated) at a particular phosphorylation site disclosed herein. The invention also provides methods of detecting and/or quantifying one or more phosphorylated Target signaling protein/polypeptide using the phosphorylation-site specific antibodies and AQUA peptides of the invention.

These phosphorylation sites correspond to numerous different parent proteins (the full sequences (human) of which are all publicly available in SwissProt database and their Accession numbers listed in Column B of Table 1/FIG. 2), each of which are have been linked to specific functions in the literature and thus may be organized into discrete protein type groups, for example adaptor/scaffold proteins, cytoskeletal proteins, protein kinases, and DNA binding proteins, etc. (see Column C of Table 1), the phosphorylation of which is relevant to signal transduction activity (e.g., underlying AML, CML, CLL, and ALL), as disclosed herein.

In part, the invention provides an isolated phosphorylation site-specific antibody that specifically binds a given Target signaling protein/polypeptide only when phosphorylated (or not phosphorylated, respectively) at a particular tyrosine enumerated in Column D of Table 1/FIG. 2 comprised within the phosphorylatable peptide site sequence enumerated in corresponding Column E. In further part, the invention provides a heavy-isotope labeled peptide (AQUA peptide) for the detection and quantification of a given Target signaling protein/polypeptide, the labeled peptide comprising a particular phosphorylatable peptide site/sequence enumerated in Column E of Table 1/FIG. 2 herein. For example, among the reagents provided by the invention is an isolated phosphorylation site-specific antibody that specifically binds the NCK2 adaptor/scaffold protein only when phosphorylated (or only when not phosphorylated) at tyrosine 342 (see Row 4 (and Columns D and E) of Table 1/FIG. 2). By way of further example, among the group of reagents provided by the invention is an AQUA peptide for the quantification of phosphorylated NCKAP1 apoptosis protein, the AQUA peptide comprising the phosphorylatable peptide sequence listed in Column E, Row 38, of Table 1/FIG. 2 (which encompasses the phosphorylatable tyrosine at position 1120).

In one embodiment, the invention provides an isolated phosphorylation site-specific antibody that specifically binds a Target signaling protein/polypeptide selected from Column A of Table 1 (Row 2-492) only when phosphorylated at the tyrosine residue listed in corresponding Column D of Table 1, comprised within the phosphorylatable peptide sequence listed in corresponding Column E of Table 1 (SEQ ID NOs: 1-70, 72-79, 81-465, 468-488, 490-497), wherein said antibody does not bind said signaling protein when not phosphorylated at said tyrosine. In another embodiment, the invention provides an isolated phosphorylation site-specific antibody that specifically binds a Target signaling protein/polypeptide selected from Column A of Table 1 only when not phosphorylated at the tyrosine residue listed in corresponding Column D of Table 1, comprised within the peptide sequence listed in corresponding Column E of Table 1 (SEQ ID NOs: 1-70, 72-79, 81-465, 468-488, 490-497), wherein said antibody does not bind said signaling protein when phosphorylated at said tyrosine. Such reagents enable the specific detection of phosphorylation (or non-phosphorylation) of a novel phosphorylatable site disclosed herein. The invention further provides immortalized cell lines producing such antibodies. In one embodiment, the immortalized cell line is a rabbit or mouse hybridoma.

In another embodiment, the invention provides a heavy-isotope labeled peptide (AQUA peptide) for the quantification of a Target signaling protein/polypeptide selected from Column A of Table 1, said labeled peptide comprising the phosphorylatable peptide sequence listed in corresponding Column E of Table 1 (SEQ ID NOs: 1-70, 72-79, 81-465, 468-488, 490-497), which sequence comprises the phosphorylatable tyrosine listed in corresponding Column D of Table 1. In certain embodiments, the phosphorylatable tyrosine within the labeled peptide is phosphorylated, while in other embodiments, the phosphorylatable residue within the labeled peptide is not phosphorylated.

Reagents (antibodies and AQUA peptides) provided by the invention may conveniently be grouped by the type of Target signaling protein/polypeptide in which a given phosphorylation site (for which reagents are provided) occurs. The protein types for each respective protein (in which a phosphorylation site has been discovered) are provided in Column C of Table 1/FIG. 2, and include: adaptor/scaffold proteins, adhesion/extracellular matrix protein, apoptosis proteins, calcium binding proteins, cell cycle regulation proteins, chaperone proteins, chromatin, DNA binding/repair/replication proteins, cytoskeletal proteins, endoplasmic reticulum or golgi proteins, enzyme proteins, G/regulator proteins, inhibitor proteins, motor/contractile proteins, phosphatase, protease, Ser/Thr protein kinases, protein kinase (Tyr)s, receptor/channel/cell surface proteins, RNA binding proteins, transcriptional regulators, tumor suppressor proteins, ubiquitan conjugating system proteins and proteins of unknown function. Each of these distinct protein groups is a subset of Target signaling protein/polypeptide phosphorylation sites disclosed herein, and reagents for their detection/quantification may be considered a subset of reagents provided by the invention.

Subsets of the phosphorylation sites (and their corresponding proteins) disclosed herein are those occurring on the following protein types/groups listed in Column C of Table 1/FIG. 2 adaptor/scaffold proteins, calcium binding proteins, chromatin or DNA binding/repair/replication proteins, cytoskeletal proteins, enzyme proteins, protein kinases (Tyr), protein kinases (Ser/Thr), receptor/channel/transporter/cell surface proteins, transcriptional regulators and translational regulators. Accordingly, among subsets of reagents provided by the invention are isolated antibodies and AQUA peptides useful for the detection and/or quantification of the foregoing protein/phosphorylation site subsets.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

In one subset of embodiments, there is provided:
(i) An isolated phosphorylation site-specific antibody that specifically binds an adaptor/scaffold protein selected from Column A, Rows 2-28, of Table 1 only when phosphorylated at the tyrosine listed in corresponding Column D, Rows 2-28, of Table 1, comprised within the phosphorylatable peptide sequence listed in corresponding Column E, Rows 2-28, of Table 1 (SEQ ID NOs: 1-27), wherein said antibody does not bind said protein when not phosphorylated at said tyrosine.
(ii) An equivalent antibody to (i) above that only binds the adaptor/scaffold protein when not phosphorylated at the disclosed site (and does not bind the protein when it is phosphorylated at the site).
(iii) A heavy-isotope labeled peptide (AQUA peptide) for the quantification of an adaptor/scaffold protein selected from Column A, Rows 2-28, said labeled peptide comprising the phosphorylatable peptide sequence listed in corresponding Column E, Rows 2-28, of Table 1 (SEQ ID NOs: 1-27), which sequence comprises the phosphorylatable tyrosine listed in corresponding Column D, Rows 2-28, of Table 1.

Among this subset of reagents, antibodies and AQUA peptides for the detection/quantification of the following adaptor/scaffold protein phosphorylation sites are: NCK2 (Y50), PAG (Y387) and SAP97 (Y806) (see SEQ ID NOs: 4, 9 and 21).

In a second subset of embodiments there is provided:
(i) An isolated phosphorylation site-specific antibody that specifically binds a cell cycle regulation protein selected from Column A, Rows 41-54, of Table 1 only when phosphorylated at the tyrosine listed in corresponding Column D, Rows 41-54, of Table 1, comprised within the phosphorylatable peptide sequence listed in corresponding Column E, Rows 41-54, of Table 1 (SEQ ID NOs: 40-53), wherein said antibody does not bind said protein when not phosphorylated at said tyrosine.
(ii) An equivalent antibody to (i) above that only binds the cell cycle regulation protein when not phosphorylated at the disclosed site (and does not bind the protein when it is phosphorylated at the site).
(iii) A heavy-isotope labeled peptide (AQUA peptide) for the quantification of a signaling protein that is a cell cycle regulation protein selected from Column A, Rows 41-54, said labeled peptide comprising the phosphorylatable peptide sequence listed in corresponding Column E, Rows 41-54, of Table 1 (SEQ ID NOs: 40-53), which sequence comprises the phosphorylatable tyrosine listed in corresponding Column D, Rows 41-54, of Table 1.

Among this subset of reagents, antibodies and AQUA peptides for the detection/quantification of the following cell cycle regulation protein phosphorylation site is: securin (Y111) (see SEQ ID NO: 51).

In another subset of embodiments there is provided:
(i) An isolated phosphorylation site-specific antibody that specifically binds an enzyme protein selected from Column A, Rows 83-142, of Table 1 only when phosphorylated at the tyrosine listed in corresponding Column D, Rows 83-142, of Table 1, comprised within the phosphorylatable peptide sequence listed in corresponding Column E, Rows 83-142, of Table 1 (SEQ ID NOs: 82-141), wherein said antibody does not bind said protein when not phosphorylated at said tyrosine.
(ii) An equivalent antibody to (i) above that only binds the enzyme protein when not phosphorylated at the disclosed site (and does not bind the protein when it is phosphorylated at the site).
(iii) A heavy-isotope labeled peptide (AQUA peptide) for the quantification of a signaling protein that is an enzyme protein selected from Column A, Rows 83-142, said labeled peptide comprising the phosphorylatable peptide sequence listed in corresponding Column E, Rows 83-142, of Table 1 (SEQ ID NOs: 82-141), which sequence comprises the phosphorylatable tyrosine listed in corresponding Column D, Rows 83-142, of Table 1.

Among this subset of reagents, antibodies and AQUA peptides for the detection/quantification of the following enzyme protein phosphorylation sites are: p47phox (Y48), PLCG1 (Y379), PLCG1 (Y833) and PLCG2 (Y495) (see SEQ ID NO's: 92, 110, 115 and 118).

In still another subset of embodiments there is provided:
(i) An isolated phosphorylation site-specific antibody that specifically binds a G protein or regulator protein selected from Column A, Rows 141-166, of Table 1 only when phosphorylated at the tyrosine listed in corresponding Column D, Rows 141-166, of Table 1, comprised within the phosphorylatable peptide sequence listed in corresponding Column E, Rows 141-166, of Table 1 (SEQ ID NOs: 142-167), wherein said antibody does not bind said protein when not phosphorylated at said tyrosine.
(ii) An equivalent antibody to (i) above that only binds the G protein or regulator protein when not phosphorylated at the disclosed site (and does not bind the protein when it is phosphorylated at the site).
(iii) A heavy-isotope labeled peptide (AQUA peptide) for the quantification of a signaling protein that is a G protein or regulator protein selected from Column A, Rows 141-166, said labeled peptide comprising the phosphorylatable peptide sequence listed in corresponding Column E, Rows 141-166, of Table 1 (SEQ ID NOs: 142-167), which sequence comprises the phosphorylatable tyrosine listed in corresponding Column D, Rows 141-166, of Table 1.

Among this subset of reagents, antibodies and AQUA peptides for the detection/quantification of the following G protein or regulator protein phosphorylation sites are: Rap1a (Y159) and RAPGEF4 (Y857) (see SEQ ID NOs: 152 and 157).

In still another subset of embodiments there is provided:
(i) An isolated phosphorylation site-specific antibody that specifically binds a kinase (non-protein) selected from Column A, Rows 171-193, of Table 1 only when phosphorylated at the tyrosine listed in corresponding Column D, Rows 171-193, of Table 1, comprised within the phosphorylatable peptide sequence listed in corresponding Column E, Rows 171-193, of Table 1 (SEQ ID NOs: 172-194), wherein said antibody does not bind said protein when not phosphorylated at said tyrosine.
(ii) An equivalent antibody to (i) above that only binds the kinase (non-protein) when not phosphorylated at the disclosed site (and does not bind the protein when it is phosphorylated at the site).
(iii) A heavy-isotope labeled peptide (AQUA peptide) for the quantification of a signaling protein that is a kinase (non-protein) selected from Column A, Rows 171-193, said labeled peptide comprising the phosphorylatable peptide sequence listed in corresponding Column E, Rows 171-193, of Table 1 (SEQ ID NOs: 172-194), which sequence comprises the phosphorylatable tyrosine listed in corresponding Column D, Rows 171-193, of Table 1.

Among this subset of reagents, antibodies and AQUA peptides for the detection/quantification of the following kinase (non-protein) phosphorylation sites are: NM23 (Y52), PIK3CA (Y361), PIK3R1 (Y657), PIK3R3 (Y184) and PIK4CA (Y973) (see SEQ ID NOs: 172, 180, 183, 186 and 189).

In still another subset of embodiments there is provided:
(i) An isolated phosphorylation site-specific antibody that specifically binds a phosphatase selected from Column A, Rows 209-241, of Table 1 only when phosphorylated at the tyrosine listed in corresponding Column D, Rows 209-241, of Table 1, comprised within the phosphorylatable peptide sequence listed in corresponding Column E, Rows 209-241 of Table 1 (SEQ ID NOs: 210-242), wherein said antibody does not bind said protein when not phosphorylated at said tyrosine.
(ii) An equivalent antibody to (i) above that only binds a phosphatase when not phosphorylated at the disclosed site (and does not bind the protein when it is phosphorylated at the site).
(iii) A heavy-isotope labeled peptide (AQUA peptide) for the quantification of a signaling protein that is a phosphatase selected from Column A, Rows 209-241, said labeled peptide comprising the phosphorylatable peptide sequence listed in corresponding Column E, Rows 209-241, of Table 1 (SEQ ID NOs: 210-242), which sequence comprises the phosphorylatable tyrosine listed in corresponding Column D, Rows 209-241, of Table 1.

Among this subset of reagents, antibodies and AQUA peptides for the detection/quantification of the following phosphatase phosphorylation sites are: PHPT1 (Y93), PPP6C (Y261), PFEN (Y176), SHP-1 (Y301) and SHP-2 (Y242) (see SEQ ID NOs: 214, 223, 225, 241 and 242).

In yet another subset of embodiments, there is provided:
(i) An isolated phosphorylation site-specific antibody that specifically binds a protein kinase (Ser/Thr) selected from Column A, Rows 260-283, of Table 1 only when phosphorylated at the tyrosine listed in corresponding Column D, Rows 260-283, of Table 1, comprised within the phosphorylatable peptide sequence listed in corresponding Column E, Rows 260-283, of Table 1 (SEQ ID NOs: 261-284), wherein said antibody does not bind said protein when not phosphorylated at said tyrosine.
(ii) An equivalent antibody to (i) above that only binds the protein kinase (Ser/Thr) when not phosphorylated at the disclosed site (and does not bind the protein when it is phosphorylated at the site).
(iii) A heavy-isotope labeled peptide (AQUA peptide) for the quantification of a signaling protein that is a protein kinase (Ser/Thr) selected from Column A, Rows 260-283, said labeled peptide comprising the phosphorylatable peptide sequence listed in corresponding Column E, Rows 260-283, of Table 1 (SEQ ID NOs: 261-284), which sequence comprises the phosphorylatable tyrosine listed in corresponding Column D, Rows 260-283, of Table 1.

Among this subset of reagents, antibodies and AQUA peptides for the detection/quantification of the following protein kinase (Ser/Thr) phosphorylation sites are: PAK2 (Y252), PKCT (Y545) and PLK1 (Y217) (see SEQ ID NOs: 264, 272 and 275).

In yet another subset of embodiments, there is provided:
(i) An isolated phosphorylation site-specific antibody that specifically binds a receptor/channel/transporter/cell surface protein selected from Column A, Rows 284-306, of Table 1 only when phosphorylated at the tyrosine listed in corresponding Column D, Rows 284-306, of Table 1, comprised within the phosphorylatable peptide sequence listed in corresponding Column E, Rows 284-306, of Table 1 (SEQ ID NOs: 285-307), wherein said antibody does not bind said protein when not phosphorylated at said tyrosine.
(ii) An equivalent antibody to (i) above that only binds the receptor/channel/transporter/cell surface protein when not phosphorylated at the disclosed site (and does not bind the protein when it is phosphorylated at the site).
(iii) A heavy-isotope labeled peptide (AQUA peptide) for the quantification of a signaling protein that is a receptor/channel/transporter/cell surface protein selected from Column A, Rows 284-306, said labeled peptide comprising the phosphorylatable peptide sequence listed in corresponding Column E, Rows 284-306, of Table 1 (SEQ ID NOs: 285-307), which sequence comprises the phosphorylatable tyrosine listed in corresponding Column D, Rows 284-306, of Table 1.

Among this subset of reagents, antibodies and AQUA peptides for the detection/quantification of the following receptor/channel/transporter/cell surface protein phosphorylation sites are: NMDAR2B (Y239) and PAR1 (Y397) (see SEQ ID NOs: 286 and 301).

In still another subset of embodiments, there is provided:
(i) An isolated phosphorylation site-specific antibody that specifically binds a RNA binding protein selected from Column A, Rows 307-364, of Table 1 only when phosphorylated at the tyrosine listed in corresponding Column D, Rows 307-364, of Table 1, comprised within the phosphorylatable peptide sequence listed in corresponding Column E, Rows 307-364, of Table 1 (SEQ ID NOs: 308-365), wherein said antibody does not bind said protein when not phosphorylated at said tyrosine.
(ii) An equivalent antibody to (i) above that only binds the RNA binding protein when not phosphorylated at the disclosed site (and does not bind the protein when it is phosphorylated at the site).
(iii) A heavy-isotope labeled peptide (AQUA peptide) for the quantification of a signaling protein that is a RNA binding protein selected from Column A, Rows 307-364, said labeled peptide comprising the phosphorylatable peptide sequence listed in corresponding Column E, Rows 307-364, of Table 1 (SEQ ID NOs: 308-365), which sequence comprises the phosphorylatable tyrosine listed in corresponding Column D, Rows 307-364, of Table 1.

Among this subset of reagents, antibodies and AQUA peptides for the detection/quantification of the following a RNA binding protein phosphorylation sites are: NCL (Y402), PABP 1(Y297), PSF (Y381) and SF2 (Y149) (see SEQ ID NOs: 310, 321, 334 and 351).

In yet another subset of embodiments, there is provided:
(i) An isolated phosphorylation site-specific antibody that specifically binds a transcriptional regulator selected from Column A, Rows 367-400, of Table 1 only when phosphorylated at the tyrosine listed in corresponding Column D, Rows 367-400, of Table 1, comprised within the phosphorylatable peptide sequence listed in corresponding Column E, Rows 367-400, of Table 1 (SEQ ID NOs: 368-401), wherein said antibody does not bind said protein when not phosphorylated at said tyrosine.
(ii) An equivalent antibody to (i) above that only binds the transcriptional regulator when not phosphorylated at the disclosed site (and does not bind the protein when it is phosphorylated at the site).
(iii) A heavy-isotope labeled peptide (AQUA peptide) for the quantification of a signaling protein that is a transcriptional regulator selected from Column A, Rows 367-400, said labeled peptide comprising the phosphorylatable peptide sequence listed in corresponding Column E, Rows 367-400, of Table 1 (SEQ ID NOs: 368-401), which sequence comprises the phosphorylatable tyrosine listed in corresponding Column D, Rows 367-400, of Table 1.

Among this subset of reagents, antibodies and AQUA peptides for the detection/quantification of the following transcriptional regulator phosphorylation sites are: NFAT1 (Y860), NFkB-p105 (Y241), POLR2A (Y1916), POL2R1 (Y54) and REL (Y47) (see SEQ ID NOs: 371, 380, 393, 394 and 397).

In yet a further subset of embodiments, there is provided:
(i) An isolated phosphorylation site-specific antibody that specifically binds a protein selected from the group consisting of N-cad (Y785), PARP1 (Y775), PLCL2 (Y896), MYH10 (Y1415), RPS3 (Y166) and Nice-4 (Y858) (Column A, Rows 29, 59, 196, 299, 405 and 422 of Table 1) only when phosphorylated at the tyrosine listed in corresponding Column D of Table 1), said tyrosine comprised within the phosphorylatable peptide sequence listed in corresponding Column E of Table 1 (SEQ ID NOs: 28, 58, 196, 200, 406 and 423), wherein said antibody does not bind said protein when not phosphorylated at said tyrosine.
(ii) An equivalent antibody to (i) above that only binds a protein selected from the group consisting of N-cad (Y785), PARP1 (Y775), PLCL2 (Y896), MYH10 (Y1415), RPS3 (Y166) and Nice-4 (Y858) (Column A, Rows 29, 59, 195, 299, 405 and 422 of Table 1) when not phosphorylated at the disclosed site (and does not bind the protein when it is phosphorylated at the site).

(iii) A heavy-isotope labeled peptide (AQUA peptide) for the quantification of a protein selected from the group consisting of selected from the group consisting of N-cad (Y785), PARP1 (Y775), PLCL2 (Y896), MYH10 (Y1415), RPS3 (Y166) and Nice-4 (Y858) (Column A, Rows 29, 59, 195, 299, 405 and 422 of Table 1), said labeled peptide comprising the phosphorylatable peptide sequence listed in corresponding Column E of Table 1 (SEQ ID NOs: 28, 58, 196, 200, 406 and 423), which sequence comprises the phosphorylatable tyrosine listed in corresponding Column D, Rows 29, 59, 195, 299, 405 and 422 of Table 1.

The invention also provides an immortalized cell line producing an antibody of the invention, for example, a cell line producing an antibody within any of the foregoing subsets of antibodies. In an embodiment, the immortalized cell line is a rabbit hybridoma or a mouse hybridoma.

In other embodiments, a heavy-isotope labeled peptide (AQUA peptide) of the invention (for example, an AQUA peptide within any of the foregoing subsets of AQUA peptides) comprises a disclosed site sequence wherein the phosphorylatable tyrosine is phosphorylated. In yet other embodiments, a heavy-isotope labeled peptide of the invention comprises a disclosed site sequence wherein the phosphorylatable tyrosine is not phosphorylated.

The foregoing subsets of reagents of the invention should not be construed as limiting the scope of the invention, which, as noted above, includes reagents for the detection and/or quantification of disclosed phosphorylation sites on any of the other protein type/group subsets (each a subset) listed in Column C of Table 1/FIG. 2.

Also provided by the invention are methods for detecting or quantifying a Target signaling protein/polypeptide that is tyrosine phosphorylated, said method comprising the step of utilizing one or more of the above-described reagents of the invention to detect or quantify one or more Target Signaling Protein(s)/Polypeptide(s) selected from Column A of Table 1 only when phosphorylated at the tyrosine listed in corresponding Column D of Table 1. In certain embodiments of the methods of the invention, the reagents comprise a subset of reagents as described above. The antibodies according to the invention maybe used in standard (e.g., ELISA or conventional cytometric assays). The invention thus, provides compositions and methods for the detection and/or quantitation of a given target signaling protein or polypeptide in a sample, by contacting the sample and a control sample with one or more antibody of the invention under conditions favoring the binding and thus formation of the complex of the antibody with the protein or peptide. The formation of the complex is then detected according to methods well established and known in the art.

Also provided by the invention is a method for obtaining a phosphorylation profile of a certain protein type or group, for example adaptor/scaffold proteins or cell cycle regulation proteins (Rows 2-28 and Rows 41-54, respectively, of Table 1), that is phosphorylated in a disease signaling pathway, said method comprising the step of utilizing one or more isolated antibody that specifically binds the protein group selected from Column A of Table 1 only when phosphorylated at the tyrosine listed in corresponding Column D, of Table 1, comprised within the phosphorylation site sequence listed in corresponding Column E, to detect the phosphorylation of one or more of said protein group, thereby obtaining a phosphorylation profile for said protein group.

The invention further contemplates compositions, foremost pharmaceutical compositions, containing one or a more antibody according to the invention formulated together with a pharmaceutically acceptable carrier. One of skill will appreciate that in certain instances the composition of the invention may further comprise other pharmaceutically active moieties. The compounds according to the invention are optionally formulated in a pharmaceutically acceptable vehicle with any of the well-known pharmaceutically acceptable carriers, including diluents and excipients (see *Remington's Pharmaceutical Sciences,* 18th Ed., Gennaro, Mack Publishing Co., Easton, Pa. 1990 and Remington: *The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

The invention also provides methods of treating a mammal comprising the step of administering such a mammal a therapeutically effective amount of a composition according to the invention.

As used herein, by "treating" is meant reducing, preventing, and/or reversing the symptoms in the individual to which a compound of the invention has been administered, as compared to the symptoms of an individual not being treated according to the invention. A practitioner will appreciate that the compounds, compositions, and methods described herein are to be used in concomitance with continuous clinical evaluations by a skilled practitioner (physician or veterinarian) to determine subsequent therapy. Hence, following treatment the practitioners will evaluate any improvement in the treatment of the pulmonary inflammation according to standard methodologies. Such evaluation will aid and inform in evaluating whether to increase, reduce or continue a particular treatment dose, mode of administration, etc. The term "therapeutic composition" refers to any compounds administered to treat or prevent a disease. It will be understood that the subject to which a compound (e.g., an antibody) of the invention is administered need not suffer from a specific traumatic state. Indeed, the compounds (e.g., antibodies) of the invention may be administered prophylactically, prior to any development of symptoms. The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. See, for example, Meiner, C. L., "*Clinical Trials: Design. Conduct, and Analysis,*" *Monographs in Epidemiology and Biostatistics*, Vol. 8 Oxford University Press, USA (1986). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect.

TABLE 1

Phosphorylation Sites

| | A<br>Protein Name | B<br>Accession No. | C<br>Protein Type | D<br>Phospho-Residue | E<br>Phosphorylation Site Sequence | H<br>SEQ ID NO |
|---|---|---|---|---|---|---|
| 2 | MTSS1 | NP_055566.3 | Adaptor/scaffold | Y390 | VTSVHLPDyAHYYTIGPGMFPSSQIPSWK | SEQ ID NO: 1 |
| 3 | MTSS1 | NP_055566.3 | Adaptor/scaffold | Y393 | VTSVHLPDYAHyYTIGPGMFPSSQIPSWK | SEQ ID NO: 2 |
| 4 | NCK2 | NP_003572.2 | Adaptor/scaffold | Y342 | VQLVDNVyCIGQR | SEQ ID NO: 3 |
| 5 | NCK2 | NP_003572.2 | Adaptor/scaffold | Y50 | TGyVPSNYVER | SEQ ID NO: 4 |
| 6 | NRAGE | NP_008917.3 | Adaptor/scaffold | Y126 | GPNAAyDFSQAATTGELAANKSEMAFK | SEQ ID NO: 5 |
| 7 | NRAGE | NP_008917.3 | Adaptor/scaffold | Y161 | VGPNATyNFSQSLNANDLANSRPK | SEQ ID NO: 6 |
| 8 | NRAGE | NP_008917.3 | Adaptor/scaffold | Y481 | yLMLKDYTKVPIKR | SEQ ID NO: 7 |
| 9 | NUP62 | NP_036478.2 | Adaptor/scaffold | Y422 | EQSGTIyLQHADEER | SEQ ID NO: 8 |
| 10 | PAG | NP_060910.3 | Adaptor/scaffold | Y387 | TPNSTLPPAGRPSEEPEPDyEAIQTLNREEEK | SEQ ID NO: 9 |
| 11 | PHIP | NP_060404.3 | Adaptor/scaffold | Y235 | GHAAEISDMAVNyENTMIAAGSCDK | SEQ ID NO: 10 |
| 12 | PHIP | NP_060404.3 | Adaptor/scaffold | Y984 | KNKIySINPKK | SEQ ID NO: 11 |
| 13 | RA70 | NP_003921.2 | Adaptor/scaffold | Y152 | TVFYYyGSDKDK | SEQ ID NO: 12 |
| 14 | RACK1 | NP_006089.1 | Adaptor/scaffold | Y52 | LTRDETNyGIPQR | SEQ ID NO: 13 |
| 15 | RanBP2 | NP_006258.2 | Adaptor/scaffold | Y116 | AKyWLER | SEQ ID NO: 14 |
| 16 | RanBP2 | NP_006258.2 | Adaptor/scaffold | Y1247 | ICANHyISPDMK | SEQ ID NO: 15 |
| 17 | RanBP2 | NP_006258.2 | Adaptor/scaffold | Y1271 | SFVWHALDyADELPKPEQLAIR | SEQ ID NO: 16 |
| 18 | RanBP2 | NP_006258.3 | Adaptor/scaffold | Y785 | STPSPTRySLSPSKSYKYSPK | SEQ ID NO: 17 |
| 19 | RanBP2 | NP_006258.3 | Adaptor/scaffold | Y793 | STPSPTRYSLSPSKSyKYSPK | SEQ ID NO: 18 |
| 20 | RanBP2 | NP_006258.3 | Adaptor/scaffold | Y795 | STPSPTRYSLSPSKSYKySPK | SEQ ID NO: 19 |
| 21 | SAMSN1 | NP_071419.3 | Adaptor/scaffold | Y130 | ASDSMDSLySGQSSSSGITSCSDGTSNR | SEQ ID NO: 20 |
| 22 | SAP97 | NP_004078.1 | Adaptor/scaffold | Y806 | FIEAGQyNNHLYGTSVQSVR | SEQ ID NO: 21 |
| 23 | SG2NA | NP_001077362.1 | Adaptor/scaffold | Y374 | TKLyDMIADLGDDELPHIPSGIINQSR | SEQ ID NO: 22 |
| 24 | SHEP1 | NP_005480.1 | Adaptor/scaffold | Y26 | AAGEPEAGSDyVK | SEQ ID NO: 23 |
| 25 | SKAP55 | NP_003717.3 | Adaptor/scaffold | Y299 | GVDYASYyQGLWDCHGDQPDELSFQR | SEQ ID NO: 24 |
| 26 | SLAP-130 | NP_001456.3 | Adaptor/scaffold | Y4 | yNTGGNPTEDVSVNSR | SEQ ID NO: 25 |
| 27 | SLAP-130 | NP_001456.3 | Adaptor/scaffold | Y801 | NEEGKyGYVLR | SEQ ID NO: 26 |
| 28 | SLAP-130 | NP_001456.3 | Adaptor/scaffold | Y803 | NEEGKYGyVLR | SEQ ID NO: 27 |
| 29 | N-cad | NP_001783.2 | Adhesion or extracellular matrix protein | Y785 | YDEEGGGEEDQDyDLSQLQQPDTVEPDAIKPVGIR | SEQ ID NO: 28 |
| 30 | Plako-philin 4 | NP_003619.2 | Adhesion or extracellular matrix protein | Y425 | TYYSPVyRSPNHGTVELQGSQTALYR | SEQ ID NO: 29 |
| 31 | ROBO2 | NP_002933.1 | Adhesion or extracellular matrix protein | Y65 | WyKDGER | SEQ ID NO: 30 |
| 32 | ROBO2 | NP_002933.1 | Adhesion or extracellular matrix protein | Y893 | GLSNyAVTFQR | SEQ ID NO: 31 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 33 | Scribble | NP_056171.2 | Adhesion or extracellular matrix protein | Y834 | MVEPENAVTITPLRPEDDySPRER | SEQ ID NO: 32 |
| 34 | SDK2 | NP_061937.3 | Adhesion or extracellular matrix protein | Y914 | NGLVLGyKVMYKEK | SEQ ID NO: 33 |
| 35 | selectin P | NP_002996.1 | Adhesion or extracellular matrix protein | Y818 | CPLNPHSHLGTyGVFTNAAFDPSP | SEQ ID NO: 34 |
| 36 | SIGLEC 5 | NP_003821.1 | Adhesion or extracellular matrix protein | Y544 | KSREPKDQEAPSTVEySEIKTSK | SEQ ID NO: 35 |
| 37 | NCKAP1 | NP_038464.1 | Apoptosis | Y1116 | NAyHAVYKQSVTSSA | SEQ ID NO: 36 |
| 38 | NCKAP1 | NP_038464.1 | Apoptosis | Y1120 | NAYHAVyKQSVTSSA | SEQ ID NO: 37 |
| 39 | NCKAP1 | NP_038464.1 | Apoptosis | Y959 | VAMNVyELSSAAGLPCEIDPALWALSSQK | SEQ ID NO: 38 |
| 40 | SART1 | NP_005137.1 | Apoptosis | Y783 | TPyIVLSGSGK | SEQ ID NO: 39 |
| 41 | NASP | NP_002473.2 | Cell cycle regulation | Y148 | EQVyDAMGEK | SEQ ID NO: 40 |
| 42 | NOL1 | NP_006161.2 | Cell cycle regulation | Y438 | LGVTNTIISHyDGR | SEQ ID NO: 41 |
| 43 | NuMA-1 | NP_006176.2 | Cell cycle regulation | Y1836 | KLDVEEPDSANSSFySTR | SEQ ID NO: 42 |
| 44 | OFD1 | NP_003602.1 | Cell cycle regulation | Y187 | LQLIDDQFADAyPQRIKFESLEIKLNEYKR | SEQ ID NO: 43 |
| 45 | OFD1 | NP_003602.1 | Cell cycle regulation | Y558 | QTQTALENEVyCNPK | SEQ ID NO: 44 |
| 46 | OFD1 | NP_003602.1 | Cell cycle regulation | Y611 | ITNyPTAWVEGSSPDSDLEFVANTK | SEQ ID NO: 45 |
| 47 | ORC3L | NP_036513.2 | Cell cycle regulation | Y607 | IALHTALNNPyYYLKNEALK | SEQ ID NO: 46 |
| 48 | ORC3L | NP_036513.2 | Cell cycle regulation | Y608 | IALHTALNNPYyYLK | SEQ ID NO: 47 |
| 49 | PAFAH1 B1 | NP_000421.1 | Cell cycle regulation | Y28 | SNGYEEAySVFKK | SEQ ID NO: 48 |
| 50 | PAFAH1 B1 | NP_000421.1 | Cell cycle regulation | Y394 | TAPyVVTGSVDQTVK | SEQ ID NO: 49 |
| 51 | RASSF2 | NP_055552.1 | Cell cycle regulation | Y224 | FKIENSAEEFALyVVHTSGEK | SEQ ID NO: 50 |
| 52 | securin | NP_004210.1 | Cell cycle regulation | Y111 | SSVPASDDAyPEIEK | SEQ ID NO: 51 |
| 53 | septin 7 | NP_001779.2 | Cell cycle regulation | Y22 | NLEGYVGFANLPNQVyR | SEQ ID NO: 52 |
| 54 | septin 7 | NP_001779.2 | Cell cycle regulation | Y61 | STLINSLFLTDLYSPEyPGPSHR | SEQ ID NO: 53 |
| 55 | PDIA5 | NP_006801.1 | Chaperone | Y178 | KEEKPLLIMFyAPWCSMCK | SEQ ID NO: 54 |
| 56 | RP2 | NP_008846.1 | Chaperone | Y245 | QKSSDESCLVVLFAGDyTIANAR | SEQ ID NO: 55 |
| 57 | SGTA | NP_003012.1 | Chaperone | Y141 | LGNyAGAVQDCER | SEQ ID NO: 56 |
| 58 | NEIL3 | NP_060718.1 | Chromatin, DNA-binding, DNA repair or DNA replication protein | Y246 | AGLALSKHyKVYK | SEQ ID NO: 57 |
| 59 | PARP1 | NP_001609.1 | Chromatin, DNA-binding, DNA repair or DNA replication protein | Y775 | VEMLDNLLDIEVAySLLR | SEQ ID NO: 58 |
| 60 | PLSCR1 | NP_066928.1 | Chromatin, DNA-binding, DNA repair or DNA replication protein | Y74 | YNQPVyNQPVGA | SEQ ID NO: 59 |
| 61 | POLB | NP_002681.1 | Chromatin, DNA-binding, DNA repair or DNA replication protein | Y250 | EyPHRRIDIRLIPK | SEQ ID NO: 60 |

TABLE 1-continued

Phosphorylation Sites

| | A<br>Protein<br>1  Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 62 | POLE2 | NP_002683.2 | Chromatin, DNA-binding, DNA repair or DNA replication protein | Y99 | VyNSERKKFLPL | SEQ ID NO: 61 |
| 63 | PURA | NP_005850.1 | Chromatin, DNA-binding, DNA repair or DNA replication protein | Y240 | FFFDVGSNKyGVFMR | SEQ ID NO: 62 |
| 64 | REV3 | NP_002903.2 | Chromatin, DNA-binding, DNA repair or DNA replication protein | Y2984 | LNATyYITK | SEQ ID NO: 63 |
| 65 | REV3 | NP_002903.2 | Chromatin, DNA-binding, DNA repair or DNA replication protein | Y2985 | LNATYyITK | SEQ ID NO: 64 |
| 66 | SAFB1 | NP_002958.2 | Chromatin, DNA-binding, DNA repair or DNA replication protein | Y723 | DDAyWPEAKR | SEQ ID NO: 65 |
| 67 | SET | NP_003002.1 | Chromatin, DNA-binding, DNA repair or DNA replication protein | Y106 | ALLGEEDEEALHy | SEQ ID NO: 66 |
| 68 | NEB | NP_004534.2 | Cytoskeletal protein | Y2144 | yILLPDAMNIELTR | SEQ ID NO: 67 |
| 69 | NEB | NP_004534.2 | Cytoskeletal protein | Y2647 | QAyDLQSDNLYKSDLQWLK | SEQ ID NO: 68 |
| 70 | NEB | NP_004534.2 | Cytoskeletal protein | Y2655 | QAYDLQSDNLyKSDLQWLK | SEQ ID NO: 69 |
| 71 | NEB | NP_004534.2 | Cytoskeletal protein | Y3742 | DyDLRADAISIKSAKASR | SEQ ID NO: 70 |
| 72 | PDLIM3 | NP_055291.1 | Cytoskeletal protein | Y361 | TKPPEGYDTVTLyPKA | SEQ ID NO: 72 |
| 73 | plectin 1 | NP_000436.2 | Cytoskeletal protein | Y3667 | QQGLASyDYVR | SEQ ID NO: 73 |
| 74 | plectin 1 | NP_000436.2 | Cytoskeletal protein | Y286 | SIITYVSSLyDAMPR | SEQ ID NO: 74 |
| 75 | PPHLN1 | NP_057572.5 | Cytoskeletal protein | Y162 | SySFHQSQHR | SEQ ID NO: 75 |
| 76 | PPHLN1 | NP_057572.5 | Cytoskeletal protein | Y52 | yYSHVDYR | SEQ ID NO: 76 |
| 77 | profilin 1 | NP_005013.1 | Cytoskeletal protein | Y60 | SSFyVNGLTLGGQK | SEQ ID NO: 77 |
| 78 | SGCD | NP_000328.2 | Cytoskeletal protein | Y23 | STMPGSVGPQVyKVGIYGWRK | SEQ ID NO: 78 |
| 79 | SGCD | NP_000328.2 | Cytoskeletal protein | Y28 | STMPGSVGPQVYKVGIyGWRK | SEQ ID NO: 79 |
| 80 | RCN2 | NP_002893.1 | Endoplasmic reticulum or golgi | Y311 | QLHDDyFYHDEL | SEQ ID NO: 81 |
| 81 | MVD | NP_002452.1 | Enzyme, misc. | Y276 | DSNQFHATCLDTFPPISyLNAISWR | SEQ ID NO: 82 |
| 82 | NANS | NP_061819.2 | Enzyme, misc. | Y188 | QVYQIVKPLNPNFCFLQCTSAyPLQPEDVNLR | SEQ ID NO: 83 |
| 83 | NARG1 | NP_476516.1 | Enzyme, misc. | Y86 | SHVCWHVyGLLQR | SEQ ID NO: 84 |
| 84 | NARS | NP_004530.1 | Enzyme, misc. | Y539 | DVCLyPR | SEQ ID NO: 85 |
| 85 | NDUFA5 | NP_004991.1 | Enzyme, misc. | Y28 | ILyTKILDVLEEIPK | SEQ ID NO: 86 |
| 86 | NDUFS1 | NP_004997.4 | Enzyme, misc. | Y316 | GLLTyTSWEDALSR | SEQ ID NO: 87 |
| 87 | NKEF-B | NP_005800.3 | Enzyme, misc. | Y193 | PGSDTIKPNVDDSKEyFSK | SEQ ID NO: 88 |
| 88 | NT5C | NP_055410.1 | Enzyme, misc. | Y65 | ALRPDLADKVASVyEAPGFFLDLEPIPGALDAVR | SEQ ID NO: 89 |
| 89 | OAS3 | NP_006178.2 | Enzyme, misc. | Y376 | SLNAVyPR | SEQ ID NO: 90 |
| 90 | p40phox | NP_000622.2 | Enzyme, misc. | Y243 | CyYYEDTISTIK | SEQ ID NO: 91 |
| 91 | p41phox | NP_000256.3 | Enzyme, misc. | Y48 | FTEIyEFHK | SEQ ID NO: 92 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 92 | PARP4 | NP_006428.2 | Enzyme, misc. | Y17 | VKyLPQQQKK | SEQ ID NO: 93 |
| 93 | PARS2 | NP_689481.2 | Enzyme, misc. | Y430 | FGyPFVIIAGK | SEQ ID NO: 94 |
| 94 | PCYT1A | NP_005008.2 | Enzyme, misc. | Y359 | AAAyDISEDEED | SEQ ID NO: 95 |
| 95 | PCYT2 | NP_002852.1 | Enzyme, misc. | Y170 | AHHSSQEMSSEyREYADSFGK | SEQ ID NO: 96 |
| 96 | PCYT2 | NP_002852.1 | Enzyme, misc. | Y173 | AHHSSQEMSSEYREyADSFGK | SEQ ID NO: 97 |
| 97 | PECI | NP_006108.2 | Enzyme, misc. | Y255 | ATFHTPFSHLGQSPEGCSSyTFPK | SEQ ID NO: 98 |
| 98 | PGAM-1 | NP_002620.1 | Enzyme, misc. | Y119 | RSyDVPPPPMEPDHPFYSNISK | SEQ ID NO: 99 |
| 99 | PGAM-1 | NP_002620.1 | Enzyme, misc. | Y133 | SYDVPPPPMEPDHPFySNISK | SEQ ID NO: 100 |
| 100 | PGK1 | NP_000282.1 | Enzyme, misc. | Y76 | SVVLMSHLGRPDGVPMPDKySLEPVAVELK | SEQ ID NO: 101 |
| 101 | PGM3 | NP_056414.1 | Enzyme, misc. | Y347 | YLEEVMKVPVyCTK | SEQ ID NO: 102 |
| 102 | PIPMT | NP_079107.5 | Enzyme, misc. | Y67 | DSGNNSGDQATEEEEGGySCGTAESHDSK | SEQ ID NO: 103 |
| 103 | PKM2 | NP_002645.3 | Enzyme, misc. | Y175 | WEVGSKIyVDDGLISLQVK | SEQ ID NO: 104 |
| 104 | PLCD3 | NP_588614.1 | Enzyme, misc. | Y222 | SLLRMVNVDMNDMyAYLLFK | SEQ ID NO: 105 |
| 105 | PLCD3 | NP_588614.1 | Enzyme, misc. | Y224 | SLLRMVNVDMNDMYAyLLFK | SEQ ID NO: 106 |
| 106 | PLCG1 | NP_002651.2 | Enzyme, misc. | Y186 | NMLSQVNyRVPNMR | SEQ ID NO: 107 |
| 107 | PLCG1 | NP_002651.2 | Enzyme, misc. | Y210 | SGDITyGQFAQLYR | SEQ ID NO: 108 |
| 108 | PLCG1 | NP_002651.2 | Enzyme, misc. | Y217 | SGDITYGQFAQLyR | SEQ ID NO: 109 |
| 109 | PLCG1 | NP_002651.2 | Enzyme, misc. | Y379 | CIELDCWDGPDGMPVIyHGHTLTTK | SEQ ID NO: 110 |
| 110 | PLCG1 | NP_002651.2 | Enzyme, misc. | Y428 | NMAQyFK | SEQ ID NO: 111 |
| 111 | PLCG1 | NP_002651.2 | Enzyme, misc. | Y496 | NGILyLEDPVNHEWYPHYFVLTSSK | SEQ ID NO: 112 |
| 112 | PLCG1 | NP_002651.2 | Enzyme, misc. | Y506 | NGILYLEDPVNHEWyPHYFVLTSSK | SEQ ID NO: 113 |
| 113 | PLCG1 | NP_002651.2 | Enzyme, misc. | Y509 | NGILYLEDPVNHEWYPHyFVLTSSK | SEQ ID NO: 114 |
| 114 | PLCG1 | NP_002651.2 | Enzyme, misc. | Y833 | SAIIQNVEKQEGGWWRGDyGGKK | SEQ ID NO: 115 |
| 115 | PLCG2 | NP_002652.2 | Enzyme, misc. | Y1137 | FVVyEEDMFSDPNFLAHATYPIKAVK | SEQ ID NO: 116 |
| 116 | PLCG2 | NP_002652.2 | Enzyme, misc. | Y482 | QQGELyMWDSIDQK | SEQ ID NO: 117 |
| 117 | PLCG2 | NP_002652.2 | Enzyme, misc. | Y495 | HyCAIADAK | SEQ ID NO: 118 |
| 118 | PLCG2 | NP_002652.2 | Enzyme, misc. | Y811 | GALIHNVSKEPGGWWKGDyGTR | SEQ ID NO: 119 |
| 119 | PLCG2 | NP_002652.2 | Enzyme, misc. | Y818 | IQQyFPSNYVEDISTADFEELEK | SEQ ID NO: 120 |
| 120 | PLCL1 | NP_006217.1 | Enzyme, misc. | Y474 | MSVDyNGEQK | SEQ ID NO: 121 |
| 121 | PPIE | NP_006103.1 | Enzyme, misc. | Y143 | SNPQVyMDIK | SEQ ID NO: 122 |
| 122 | RARS | NP_002878.2 | Enzyme, misc. | Y291 | RAyQCVVLLQGKNPDITK | SEQ ID NO: 123 |
| 123 | RARS | NP_002878.2 | Enzyme, misc. | Y382 | SDGGyTYDTSDLAAIK | SEQ ID NO: 124 |
| 124 | RENT1 | NP_002902.2 | Enzyme, misc. | Y1101 | SQIDVALSQDSTyQGER | SEQ ID NO: 125 |
| 125 | RENT1 | NP_002902.2 | Enzyme, misc. | Y1107 | AyQHGGVTGLSQY | SEQ ID NO: 126 |
| 126 | RENT1 | NP_002902.2 | Enzyme, misc. | Y1118 | AYQHGGVTGLSQy | SEQ ID NO: 127 |
| 127 | RENT1 | NP_002902.2 | Enzyme, misc. | Y868 | ARyGVIIVGNPK | SEQ ID NO: 128 |
| 128 | RENT1 | NP_002902.2 | Enzyme, misc. | Y935 | FMTTAMyDAR | SEQ ID NO: 129 |
| 129 | RENT1 | NP_002902.2 | Enzyme, misc. | Y947 | EAIIPGSVyDR | SEQ ID NO: 130 |
| 130 | RNASE H2A | NP_006388.2 | Enzyme, misc. | Y172 | AKADALyPVVSAASICAK | SEQ ID NO: 131 |
| 131 | RNASE H2A | NP_006388.2 | Enzyme, misc. | Y206 | LQDLDTDyGSGYPNDPK | SEQ ID NO: 132 |
| 132 | RNASE H2A | NP_006388.2 | Enzyme, misc. | Y210 | LQDLDTDYGSGyPNDPK | SEQ ID NO: 133 |
| 133 | RRM1 | NP_001024.1 | Enzyme, misc, | Y102 | KVFSDVMEDLyNYINPHNGK | SEQ ID NO: 134 |
| 134 | RRM1 | NP_001024.1 | Enzyme, misc. | Y104 | KVFSDVMEDLYNyINPHNGK | SEQ ID NO: 135 |
| 135 | RRM2 | NP_001025.1 | Enzyme, misc. | Y221 | WIGDKEATyGER | SEQ ID NO: 136 |
| 136 | RUVBL2 | NP_006657.1 | Enzyme, misc. | Y172 | TTEMETIyDLGTK | SEQ ID NO: 137 |
| 137 | RUVBL2 | NP_006657.1 | Enzyme, misc. | Y430 | RVySLFLDESR | SEQ ID NO: 138 |
| 138 | SETD8 | NP_065115.3 | Enzyme, misc. | Y57 | IYSyMSPNK | SEQ ID NO: 139 |
| 139 | SGSH | NP_000190.1 | Enzyme, misc. | Y174 | PFFLyVAFHDPHR | SEQ ID NO: 140 |
| 140 | SHMT2 | NP_005403.2 | Enzyme, misc. | Y228 | LIIAGTSAyAR | SEQ ID NO: 141 |
| 141 | MX2 | NP_002454.1 | G protein or regulator | Y355 | EITFFQTHPyFR | SEQ ID NO: 142 |
| 142 | PSCD1 | NP_004753.1 | G protein or regulator | Y382 | AAISRDPFyEMLAAR | SEQ ID NO: 143 |
| 143 | RAB11A | NP_004654.1 | G protein or regulator | Y8 | DDEyDYLFK | SEQ ID NO: 144 |
| 144 | RAB13 | NP_002861.1 | G protein or regulator | Y5 | AyDHLFK | SEQ ID NO: 145 |
| 145 | RAB14 | NP_057406.2 | G protein or regulator | Y80 | FRAVTRSyYRGAAGALMVYDITRR | SEQ ID NO: 146 |
| 146 | RAB14 | NP_057406.2 | G protein or regulator | Y81 | FRAVTRSYyRGAAGALMVYDITRR | SEQ ID NO: 147 |
| 147 | RAB8A | NP_005361.2 | G protein or regulator | Y5 | TyDYLFK | SEQ ID NO: 148 |
| 148 | RAB9A | NP_004242.1 | G protein or regulator | Y107 | EFIyYADVKEPESFPPVILGNK | SEQ ID NO: 149 |
| 149 | RAB9A | NP_004242.1 | G protein or regulator | Y108 | EFIYyADVKEPESFPPVILGNK | SEQ ID NO: 150 |
| 150 | RanBP1 | NP_002873.1 | G protein or regulator | Y103 | ICANHyITPMMELKPNAGSDR | SEQ ID NO: 151 |
| 151 | Rap1a | NP_002875.1 | G protein or regulator | Y159 | INVNEIFyDLVR | SEQ ID NO: 152 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 152 | Rap1b | NP_056461.1 | G protein or regulator | Y159 | SKINVNEIFyDLVR | SEQ ID NO: 153 |
| 153 | RapGEF1 | NP_005303.2 | G protein or regulator | Y329 | QDFDVDCyAQR | SEQ ID NO: 154 |
| 154 | RapGEF1 | NP_005303.2 | G protein or regulator | Y715 | KDLVLyCEAFLTTYR | SEQ ID NO: 155 |
| 155 | RapGEF1 | NP_005303.2 | G protein or regulator | Y723 | KDLVLYCEAFLTTyR | SEQ ID NO: 156 |
| 156 | RAPGEF4 | NP_008954.1 | G protein or regulator | Y857 | KFIKIAAHCKEyK | SEQ ID NO: 157 |
| 157 | RAPGEF4 | NP_008954.1 | G protein or regulator | Y986 | SyVRQLNVIDNQR | SEQ ID NO: 158 |
| 158 | RasGAP3 | NP_031394.2 | G protein or regulator | Y777 | SVYDGPEQEEYSTFVIDDPQETyKTLK | SEQ ID NO: 159 |
| 159 | RASGRP2 | NP_005816.2 | G protein or regulator | Y108 | MFLMMHPWyIPSSQLAAKLLHIYQQSRK | SEQ ID NO: 160 |
| 160 | RASGRP2 | NP_005816.2 | G protein or regulator | Y122 | MFLMMHPWYIPSSQLAAKLLHIyQQSRK | SEQ ID NO: 161 |
| 161 | RGL2 | NP_004752.1 | G protein or regulator | Y431 | GGGVVPyLGTFLK | SEQ ID NO: 162 |
| 162 | RICS | NP_055530.2 | G protein or regulator | Y1188 | YNTyVAPGR | SEQ ID NO: 163 |
| 163 | RICS | NP_055530.2 | G protein or regulator | Y1355 | SLYSyAGLAPRPR | SEQ ID NO: 164 |
| 164 | RIP3 | NP_055949.2 | G protein or regulator | Y267 | VRVESGyFSLEK | SEQ ID NO: 165 |
| 165 | RIP3 | NP_055949.2 | G protein or regulator | Y945 | YASDKYKDIyTELSIAK | SEQ ID NO: 166 |
| 166 | SIPA1L1 | NP_056371.1 | G protein or regulator | Y1590 | TLSDESIyNSQR | SEQ ID NO: 167 |
| 167 | Nogo | NP_065393.1 | Inhibitor protein | Y384 | VAVEAPMREEyADFKPFER | SEQ ID NO: 168 |
| 168 | RKIP | NP_002558.1 | Inhibitor protein | Y181 | APVAGTCYQAEWDDYVPKLyEQLSGK | SEQ ID NO: 169 |
| 169 | RKIP | NP_002558.1 | Inhibitor protein | Y64 | LyTLVLTDPDAPSRKDPKYR | SEQ ID NO: 170 |
| 170 | RKIP | NP_002558.1 | Inhibitor protein | Y81 | LYTLVLTDPDAPSRKDPKyR | SEQ ID NO: 171 |
| 171 | NM23 | NP_000260.1 | Kinase (non.protein) | Y52 | MQASEDLLKEHyVDLKDRPF | SEQ ID NO: 172 |
| 172 | PFKFB3 | NP_004557.1 | Kinase (non-protein) | Y194 | ISCyEASYQPLDPDKCDR | SEQ ID NO: 173 |
| 173 | PFKL | NP_002617.3 | Kinase (non-protein) | Y640 | CHDYYTTEFLyNLYSSEGK | SEQ ID NO: 174 |
| 174 | PFKP | NP_002618.1 | Kinase (non-protein) | Y447 | MLAIyDGFDGFAK | SEQ ID NO: 175 |
| 175 | PFKP | NP_002618.1 | Kinase (non.protein) | Y586 | IIETMGGyCGY | SEQ ID NO: 176 |
| 176 | PIK3C2A | NP_002636.1 | Kinase (non-protein) | Y73 | AQVYNKQDyDLMVFPESDSQKR | SEQ ID NO: 177 |
| 177 | PIK3C2B | NP_002637.2 | Kinase (non.protein) | Y1541 | GLQLLQDGNDPDPyVK | SEQ ID NO: 178 |
| 178 | PIK3CA | NP_006209.2 | Kinase (non-protein) | Y246 | LCVLEyQGKYILK | SEQ ID NO: 179 |
| 179 | PIK3CA | NP_006209.2 | Kinase (non-protein) | Y361 | TGIyHGGEPLCDNVNTQR | SEQ ID NO: 180 |
| 180 | PIK3R1 | NP_852664.1 | Kinase (non-protein) | Y426 | LLyPVSK | SEQ ID NO: 181 |
| 181 | PIK3R1 | NP_852664.1 | Kinase (non-protein) | Y504 | IFEEQCQTQERySKEYIEK | SEQ ID NO: 182 |
| 182 | PIK3R1 | NP_852664.1 | Kinase (non-protein) | Y657 | ESSKQGCyACSVVVDGEVK | SEQ ID NO: 183 |
| 183 | PIK3R2 | NP_005018.1 | Kinase (non-protein) | Y423 | LLyPVSK | SEQ ID NO: 184 |
| 184 | PIK3R2 | NP_005018.1 | Kinase (non-protein) | Y577 | DQyLVWLTQKGARQKKINEWLGIK | SEQ ID NO: 185 |
| 185 | PIK3R3 | NP_003620.2 | Kinase (non-protein) | Y184 | LQEyHSQYQEK | SEQ ID NO: 186 |
| 186 | PIK3R3 | NP_003620.2 | Kinase (non-protein) | Y202 | SKEYDRLYEEyTR | SEQ ID NO: 187 |
| 187 | PIK4CA | NP_477352.1 | Kinase (non-protein) | Y466 | yHSQYHTVAGNDIK | SEQ ID NO: 188 |
| 188 | PIK4CA | NP_477352.1 | Kinase (non-protein) | Y973 | DQPyYDIPDAPYR | SEQ ID NO: 189 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 189 | PIP5K1A | NP_003548.1 | Kinase (non-protein) | Y333 | EPLSSETQySVDTR | SEQ ID NO: 190 |
| 190 | PIP5K1A | NP_003548.1 | Kinase (non-protein) | Y347 | ALySTAMESIQGEAR | SEQ ID NO: 191 |
| 191 | PIP5K2B | NP_003550.1 | Kinase (non.protein) | Y363 | KEVyFMAIIDILTPYDTKK | SEQ ID NO: 192 |
| 192 | PRPS2 | NP_002756.1 | Kinase (non.protein) | Y245 | LLSAGATKVyAILTHGIFSGPAISR | SEQ ID NO: 193 |
| 193 | SEPHS1 | NP_036379.2 | Kinase (non-protein) | Y345 | SPKyGEGHQAWIIGIVEK | SEQ ID NO: 194 |
| 194 | OSEP | NP_002547.1 | Lipid binding protein | Y764 | ATEDGTPyDPYKALWFER | SEQ ID NO: 195 |
| 195 | PLCL2 | NP_055999.1 | Lipid binding protein | Y896 | ALIENADAVyEK | SEQ ID NO: 196 |
| 196 | PLEKHA | NP_067635.2 | Lipid binding protein | Y181 | SQSHLPyFTPKPPQDSAVIK | SEQ ID NO: 197 |
| 197 | NDUFB9 | NP_004996.1 | Mitochondrial | Y118 | AMYPDyFAKR | SEQ ID NO: 198 |
| 198 | MYH10 | NP_005955.1 | Motor or contractile protein | Y13 | TGLEDPERyLFVDR | SEQ ID NO: 199 |
| 199 | MYH10 | NP_005955.1 | Motor or contractile protein | Y1415 | ALAyDKLEK | SEQ ID NO: 200 |
| 200 | MYH10 | NP_005955.1 | Motor or contractile protein | Y194 | VIQyLAHVASSHK | SEQ ID NO: 201 |
| 201 | MYH9 | NP_002464.1 | Motor or contractile protein | Y158 | HEMPPHIYAITDTAyR | SEQ ID NO: 202 |
| 202 | MYH9 | NP_002464.1 | Motor or contractile protein | Y278 | TFHIFyYLLSGAGEHLK | SEQ ID NO: 203 |
| 203 | MYL6 | NP_066299.2 | Motor or contractile protein | Y29 | ILySQCGDVMR | SEQ ID NO: 204 |
| 204 | MYO18B | NP_115997.5 | Motor or contractile protein | Y1564 | LGELQSAyDGAK | SEQ ID NO: 205 |
| 205 | MYO1D | NP_056009.1 | Motor or contractile protein | Y114 | yIMQYIAAITNPSQR | SEQ ID NO: 206 |
| 206 | MYO1D | NP_056009.1 | Motor or contractile protein | Y435 | HIDyFNNQIIVDLVEQQHK | SEQ ID NO: 207 |
| 207 | MYO9B | NP_004136.2 | Motor or contractile protein | Y105 | RAQDEHPQEDGyYFLLQER | SEQ ID NO: 208 |
| 208 | MYO9B | NP_004136.2 | Motor or contractile protein | Y22 | EQAAYHLHIyPQLSTTESQASCR | SEQ ID NO: 209 |
| 209 | MYPT1 | NP_002471.1 | Phosphatase | Y446 | TGSyGALAEITASK | SEQ ID NO: 210 |
| 210 | MYPT1 | NP_002471.1 | Phosphatase | Y669 | SyLTPVRDEESESQR | SEQ ID NO: 211 |
| 211 | MYPT1 | NP_002471.1 | Phosphatase | Y913 | SGSYSyLEER | SEQ ID NO: 212 |
| 212 | PHPT1 | NP_054891.2 | Phosphatase | Y91 | IHVyGYSMAYGPAQHAISTEK | SEQ ID NO: 213 |
| 213 | PHPT1 | NP_054891.2 | Phosphatase | Y93 | IHVYGySMAYGPAQHAISTEK | SEQ ID NO: 214 |
| 214 | PHPT1 | NP_054891.2 | Phosphatase | Y97 | IHVYGYSMAyGPAQHAISTEK | SEQ ID NO: 215 |
| 215 | PPP1CA | NP_002699.1 | Phosphatase | Y78 | LFEyGGFPPESNYLFLGDYVDR | SEQ ID NO: 216 |
| 216 | PPP2CA | NP_002706.1 | Phosphatase | Y265 | NVVTIFSAPNyCYR | SEQ ID NO: 217 |
| 217 | PPP2R4 | NP_066954.2 | Phosphatase | Y188 | yLEVMRKLQKTYR | SEQ ID NO: 218 |
| 218 | PPP2R5D | NP_006236.1 | Phosphatase | Y488 | LFDDCTQQyK | SEQ ID NO: 219 |
| 219 | PPP2R5D | NP_006236.1 | Phosphatase | Y580 | KSELPQDVyTIK | SEQ ID NO: 220 |
| 220 | PPP5C | NP_006238.1 | Phosphatase | Y313 | GNHETDNMNQIyGFEGEVK | SEQ ID NO: 221 |
| 221 | PPP5C | NP_006238.1 | Phosphatase | Y80 | TECYGyALGDATR | SEQ ID NO: 222 |
| 222 | PPP6C | NP_002712.1 | Phosphatase | Y261 | LVTVWSAPNyCYR | SEQ ID NO: 223 |
| 223 | PTEN | NP_000305.3 | Phosphatase | Y174 | yVYYYSYLLK | SEQ ID NO: 224 |
| 224 | PTEN | NP_000305.3 | Phosphatase | Y176 | YVyYYSYLLK | SEQ ID NO: 225 |
| 225 | PTEN | NP_000305.3 | Phosphatase | Y177 | YVYyYSYLLK | SEQ ID NO: 226 |
| 226 | PTEN | NP_000305.3 | Phosphatase | Y178 | YVYYySYLLK | SEQ ID NO: 227 |
| 227 | PTEN | NP_000305.3 | Phosphatase | Y180 | YVYYYSyLLK | SEQ ID NO: 228 |
| 228 | PTP4A2 | NP_536316.1 | Phosphatase | Y50 | VCDATyDKAPVEK | SEQ ID NO: 229 |
| 229 | PTPN23 | NP_056281.1 | Phosphatase | Y1229 | HQDVMPyDSNR | SEQ ID NO: 230 |

TABLE 1-continued

Phosphorylation Sites

| 1 | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 230 | PTPRD | NP_002830.1 | Phosphatase | Y954 | NGIITKyTLLYR | SEQ ID NO: 231 |
| 231 | PTPRD | NP_002830.1 | Phosphatase | Y958 | NGIITKYTLLyR | SEQ ID NO: 232 |
| 232 | PTPRK | NP_002835.2 | Phosphatase | Y917 | NRyGNIIAYDHSR | SEQ ID NO: 233 |
| 233 | PTPRK | NP_002835.2 | Phosphatase | Y923 | YGNIIAyDHSR | SEQ ID NO: 234 |
| 234 | PTPRK | NP_002835.2 | Phosphatase | Y941 | VILQPVEDDPSSyINANYIDGYQR | SEQ ID NO: 235 |
| 235 | SHIP | NP_005532.2 | Phosphatase | Y555 | NQNyMNILR | SEQ ID NO: 236 |
| 236 | SHIP | NP_005532.2 | Phosphatase | Y643 | VFLHFEEEEITFAPTyRFER | SEQ ID NO: 237 |
| 237 | SHIP | NP_005532.2 | Phosphatase | Y795 | LKPIISDPEyLLDQHILISIK | SEQ ID NO: 238 |
| 238 | SHIP | NP_005532.2 | Phosphatase | Y943 | QTLSPDQQPTAWSyDQPPKDSPLGPCR | SEQ ID NO: 239 |
| 239 | SHIP-2 | NP_001558.2 | Phosphatase | Y190 | GSyGLDLEAVR | SEQ ID NO: 240 |
| 240 | SHP-1 | NP_002822.2 | Phosphatase | Y301 | DSNIPGSDyINANYIK | SEQ ID NO: 241 |
| 241 | SHP-2 | NP_002825.3 | Phosphatase | Y511 | SGMVQTEAQyR | SEQ ID NO: 242 |
| 242 | PREP | NP_002717.3 | Protease | Y71 | MTELyDYPKYSCHFKK | SEQ ID NO: 243 |
| 243 | PRSS15 | NP_004784.2 | Protease | Y186 | LKRDDSNESDVVESLDEIyHTGTF | SEQ ID NO: 244 |
| 244 | PSMA3 | NP_002779.1 | Protease | Y105 | SNFGyNIPLK | SEQ ID NO: 245 |
| 245 | PSMA6 | NP_002782.1 | Protease | Y23 | LyQVEYAFK | SEQ ID NO: 246 |
| 246 | PSMB1 | NP_002784.1 | Protease | Y150 | GAVySFDPVGSYQR | SEQ ID NO: 247 |
| 247 | PSMB3 | NP_002786.2 | Protease | Y103 | FGPyYTEPVIAGLDPK | SEQ ID NO: 248 |
| 248 | PSMB5 | NP_002788.1 | Protease | Y220 | RAIyQATYR | SEQ ID NO: 249 |
| 249 | PSMB8 | NP_004150.1 | Protease | Y122 | VIEINPYLLGTMSGCAADCQyWER | SEQ ID NO: 250 |
| 250 | PSMB8 | NP_004150.1 | Protease | Y181 | KGPGLYyVDEHGTR | SEQ ID NO: 251 |
| 251 | PSMC6 | NP_002797.2 | Protease | Y173 | GCLLyGPPGTGK | SEQ ID NO: 252 |
| 252 | PSMD10 | NP_002805.1 | Protease | Y138 | DHyEATAMHR | SEQ ID NO: 253 |
| 253 | PSMD3 | NP_002800.2 | Protease | Y264 | NYLHYSLyDQAEK | SEQ ID NO: 254 |
| 254 | PSME2 | NP_002809.2 | Protease | Y239 | IVNPKGEEKPSMy | SEQ ID NO: 255 |
| 255 | RIOK1 | NP_113668.2 | Protein kinase | Y466 | LKEEDMAMNAQQDNILyQTVTGLKK | SEQ ID NO: 256 |
| 256 | RIOK2 | NP_060813.1 | Protein kinase | Y366 | NCLEESEGCyCR | SEQ ID NO: 257 |
| 257 | PHKA1 | NP_002628.1 | Protein kinase, regulatory subunit | Y636 | LYSEDYDDNyDYLESGNWMNDYDSTSHAR | SEQ ID NO: 258 |
| 258 | PHKA1 | NP_002628.1 | Protein kinase, regulatory subunit | Y638 | LYSEDYDDNYDyLESGNWMNDYDSTSHAR | SEQ ID NO: 259 |
| 259 | PKAR2A | NP_004148.1 | Protein kinase, regulatory subunit | Y105 | RVSVCAETyNPDEEEEDTDPR | SEQ ID NO: 260 |
| 260 | Nek9 | AAH93881.1 | Protein kinase, Ser/Thr (non-receptor) | Y350 | TSEVyVWGGGK | SEQ ID NO: 261 |
| 261 | PAK1 | NP_002567.3 | Protein kinase, Ser/Thr (non-receptor) | Y142 | yMSFTDKSAEDYNSSNALNVK | SEQ ID NO: 262 |
| 262 | PAK1 | NP_002567.3 | Protein kinase, Ser/Thr (non-receptor) | Y153 | YMSFTDKSAEDyNSSNALNVK | SEQ ID NO: 263 |
| 263 | PAK2 | NP_002568.2 | Protein kinase, Ser/Thr (non-receptor) | Y252 | LRTIVSIGDPKKKYTRyEK | SEQ ID NO: 264 |
| 264 | PERK | NP_004827.4 | Protein kinase, Ser/Thr (non-receptor) | Y464 | FSHEEySNGALSILQYPYDNGYYLPYYKR | SEQ ID NO: 265 |
| 265 | PERK | NP_004827.4 | Protein kinase, Ser/Thr (non-receptor) | Y481 | FSHEEYSNGALSILQYPYDNGYyLPYYKR | SEQ ID NO: 266 |
| 266 | PERK | NP_004827.4 | Protein kinase, Ser/Thr (non-receptor) | Y484 | FSHEEYSNGALSILQYPYDNGYYLPyYKR | SEQ ID NO: 267 |
| 267 | PERK | NP_004827.4 | Protein kinase, Ser/Thr (non-receptor) | Y485 | FSHEEYSNGALSILQYPYDNGYYLPYyKR | SEQ ID NO: 268 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 268 | PKACb | NP_002722.1 | Protein kinase, Ser/Thr (non-receptor) | Y69 | HKATEQyYAMK | SEQ ID NO: 269 |
| 269 | PKCA | NP_002728.1 | Protein kinase, Ser/Thr (non-receptor) | Y195 | NLIPMDPNGLSDPyVK | SEQ ID NO: 270 |
| 270 | PKCB | NP_002729.2 | Protein kinase, Ser/Thr (non-receptor) | Y195 | NLVPMDPNGLSDPyVK | SEQ ID NO: 271 |
| 271 | PKCT | NP_006248.1 | Protein kinase, Ser/Thr (non-receptor) | Y545 | TNTFCGTPDyIAPEILLGQK | SEQ ID NO: 272 |
| 272 | PKD2 | NP_057541.2 | Protein kinase, Ser/Thr (non-receptor) | Y246 | RPPSSSSSSSASSyTGRPIELDK | SEQ ID NO: 273 |
| 273 | PKD2 | NP_057541.2 | Protein kinase, Ser/Thr (non-receptor) | Y717 | SVVGTPAyLAPEVLLNQGYNR | SEQ ID NO: 274 |
| 274 | PLK1 | NP_005021.2 | Protein kinase, Ser/Thr (non-receptor) | Y217 | TLCGTPNyIAPEVLSK | SEQ ID NO: 275 |
| 275 | QSK | NP_079440.2 | Protein kinase, Ser/Thr (non-receptor) | Y1167 | HHTIQNSDDAyVQLDNLPGMSLVAGK | SEQ ID NO: 276 |
| 276 | ROCK2 | NP_004841.2 | Protein kinase, Ser/Thr (non-receptor) | Y722 | IyESIEEAK | SEQ ID NO: 277 |
| 277 | RSK2 | NP_004577.1 | Protein kinase, Ser/Thr (non-receptor) | Y483 | DVyDDGKYVYVVTELMK | SEQ ID NO: 278 |
| 278 | RSK2 | NP_004577.1 | Protein kinase, Ser/Thr (non-receptor) | Y488 | YGQHPNIITLKDVYDDGKyVYVVTELMK | SEQ ID NO: 279 |
| 279 | RSK2 | NP_004577.1 | Protein kinase, Ser/Thr (non-receptor) | Y490 | DVYDDGKYVyVVTELMK | SEQ ID NO: 280 |
| 280 | RSK2 | NP_004577.1 | Protein kinase, Ser/Thr (non-receptor) | Y529 | TVEyLHAQGVVHR | SEQ ID NO: 281 |
| 281 | SgK269 | XP_370878.3 | Protein kinase, Ser/Thr (non-receptor) | Y598 | FNSyNNAGMPPFPIIIHDEPTYAR | SEQ ID NO: 282 |
| 282 | SgK269 | XP_370878.3 | Protein kinase, Ser/Thr (non-receptor) | Y616 | FNSYNNAGMPPFPIIIHDEPTyAR | SEQ ID NO. 283 |
| 283 | SgK307 | NP_112562.3 | Protein kinase, Ser/Thr (non-receptor) | Y1141 | DISLTDIQDLSSISyEPDSSFKEASCKTPK | SEQ ID NO: 284 |
| 284 | NEO1 | NP_002490.1 | Receptor, channel, transporter or cell surface protein | Y1436 | MLEDSESSyEPDELTK | SEQ ID NO: 285 |
| 285 | NMDAR 2B | NP_000825.1 | Receptor, channel, transporter or cell surface protein | Y239 | CTKEEATyIFEVANSVGLTGYGYTW | SEQ ID NO: 286 |

TABLE 1-continued

Phosphorylation Sites

| 1 | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 286 | NUP133 | NP_060700.2 | Receptor, channel, transporter or cell surface protein | Y1150 | ANYEyYVQGQI | SEQ ID NO: 287 |
| 287 | NUP155 | NP_004289.1 | Receptor, channel, transporter or cell surface protein | Y1025 | yYEKNRSFSNAARVLSRLADMHSTEISLQQR | SEQ ID NO: 288 |
| 288 | NUP155 | NP_004289.1 | Receptor, channel, transporter or cell surface protein | Y1026 | YyEKNRSFSNAARVLSRLADMHSTEISLQQR | SEQ ID NO: 289 |
| 289 | NUP155 | NP_004289.1 | Receptor, channel, transporter or cell surface protein | Y867 | FyEGWELSLTAAEK | SEQ ID NO: 290 |
| 290 | NUP205 | NP_055950.1 | Receptor, channel, transporter or cell surface protein | Y581 | DLPSADSVQyR | SEQ ID NO: 291 |
| 291 | Nup214 | NP_005076.3 | Receptor, channel, transporter or cell surface protein | Y1145 | NNPATPSTAMGSSVPySTAK | SEQ ID NO: 292 |
| 292 | Nup214 | NP_005076.3 | Receptor, channel, transporter or cell surface protein | Y502 | SSATVTGEPPSySSGSDSSK | SEQ ID NO: 293 |
| 293 | NUP93 | NP_055484.2 | Receptor, channel, transporter or cell surface protein | Y166 | ILHTLLASGEDALDFTQESEPSyISDVGPPGR | SEQ ID NO: 294 |
| 294 | NUP93 | NP_055484.2 | Receptor, channel, transporter or cell surface protein | Y185 | SSLDNIEMAyAR | SEQ ID NO: 295 |
| 295 | NUP93 | NP_055484.2 | Receptor, channel, transporter or cell surface protein | Y391 | AVyCIIGR | SEQ ID NO: 296 |
| 296 | OR2D3 | NP_001004684.1 | Receptor, channel, transporter or cell surface protein | Y268 | AFSTCGSHLIVVVLFyGSGIFTYMR | SEQ ID NO. 297 |
| 297 | OR2D3 | NP_001004684.1 | Receptor, channel, transporter or cell surface protein | Y275 | AFSTCGSHLIVVVLFYGSGIFTyMR | SEQ ID NO: 298 |
| 298 | OR4C3 | NP_001004702.1 | Receptor, channel, transporter or cell surface protein | Y300 | NMALFyGILTPMLNPLIYTLR | SEQ ID NO: 299 |
| 299 | OR5F1 | NP_003688.1 | Receptor, channel, transporter or cell surface protein | Y141 | SRTVyLKMAAGAFAAGLL | SEQ ID NO: 300 |

TABLE 1-continued

Phosphorylation Sites

| 1 | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 300 | PAR1 | NP_001983.1 | Receptor, channel, transporter or cell surface protein | Y397 | ESSDPSSyNSSGQLMASK | SEQ ID NO: 301 |
| 301 | PITPNA | NP_006215.1 | Receptor, channel, transporter or cell surface protein | Y140 | HVEAVyIDIADR | SEQ ID NO: 302 |
| 302 | RXR-alpha | NP_002948.1 | Receptor, channel, transporter or cell surface protein | Y150 | SSGKHYGVySCEGCK | SEQ ID NO: 303 |
| 303 | SIGIRR | NP_068577.1 | Receptor, channel, transporter or cell surface protein | Y402 | TDFyCLVSKDDM | SEQ ID NO: 304 |
| 304 | SIGLEC12 | NP_201586.1 | Receptor, channel, transporter or cell surface protein | Y470 | ARPQYPQEQEAIGYEySEINIPK | SEQ ID NO: 305 |
| 305 | Siglec-9 | NP_055256.1 | Receptor, channel, transporter or cell surface protein | Y433 | RSSVGEGELQy | SEQ ID NO: 306 |
| 306 | SLAMF6 | NP_443163.1 | Receptor, channel, transporter or cell surface protein | Y273 | NLEyVSVSPTNNTVYASVTHSNR | SEQ ID NO: 307 |
| 307 | NCBP2 | NP_031388.2 | RNA binding protein | Y14 | SDSyVELSQYR | SEQ ID NO: 308 |
| 308 | NCL | NP_005372.2 | RNA binding protein | Y351 | KFGyVDFESAEDLEK | SEQ ID NO: 309 |
| 309 | NCL | NP_005372.2 | RNA binding protein | Y402 | NLPyKVTQDELKEVFEDAAEIR | SEQ ID NO: 310 |
| 310 | NCL | NP_005372.2 | RNA binding protein | Y462 | SISLyYTGEKGQNQDYR | SEQ ID NO: 311 |
| 311 | NCL | NP_005372.2 | RNA binding protein | Y463 | SISLYyTGEK | SEQ ID NO: 312 |
| 312 | NCL | NP_005372.2 | RNA binding protein | Y525 | SKGyAFIEFASFEDAKEALNSCNKR | SEQ ID NO: 313 |
| 313 | NIFK | NP_115766.2 | RNA binding protein | Y183 | GIDyDFPSLILQK | SEQ ID NO: 314 |
| 314 | NIFK | NP_115766.2 | RNA binding protein | Y88 | TGNSKGyAFVEFESEDVAK | SEQ ID NO: 315 |
| 315 | NOLA1 | NP_061856.1 | RNA binding protein | Y97 | CTTDENKVPyFNAPVYLENK | SEQ ID NO: 316 |
| 316 | NONO | NP_031389.3 | RNA binding protein | Y265 | FAQPGSFEyEYAMR | SEQ ID NO: 317 |
| 317 | NOP5 | NP_057018.1 | RNA binding protein | Y272 | TQLyEYLQNR | SEQ ID NO: 318 |
| 318 | NXF2 | NP_060279.2 | RNA binding protein | Y185 | IyDDENQKICIFVNHSTAPYSVKNK | SEQ ID NO: 319 |
| 319 | NXF2 | NP_060279.2 | RNA binding protein | Y203 | IYDDENQKICIFVNHSTAPySVKNK | SEQ ID NO: 320 |
| 320 | PABP 1 | NP_002559.2 | RNA binding protein | Y297 | YQGVNLyVK | SEQ ID NO: 321 |
| 321 | PABP 1 | NP_002559.2 | RNA binding protein | Y382 | QAHLTNQyMQR | SEQ ID NO: 322 |
| 322 | PABP 4 | NP_003810.1 | RNA binding protein | Y382 | KAHLTNQyMQR | SEQ ID NO: 323 |
| 323 | PAI-RBP1 | NP_001018077.1 | RNA binding protein | Y244 | QISyNYSDLDQSNVTEETPEGEEHHPVADTENK | SEQ ID NO: 324 |
| 324 | PAI-RBP1 | NP_001018077.1 | RNA binding protein | Y246 | QISYNySDLDQSNVTEETPEGEEHHPVADTENK | SEQ ID NO: 325 |
| 325 | PHF5A | NP_116147.1 | RNA binding protein | Y36 | CDGKCVICDSyVR | SEQ ID NO: 326 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 326 | PHF5A | NP_116147.1 | RNA binding protein | Y54 | ICDECNYGSyQGR | SEQ ID NO: 327 |
| 327 | PNPT1 | NP_149100.1 | RNA binding protein | Y459 | ALyPVIPR | SEQ ID NO: 328 |
| 328 | PRPF8 | NP_006436.3 | RNA binding protein | Y1432 | HTLAyDKGWR | SEQ ID NO: 329 |
| 329 | PRPF8 | NP_006436.3 | RNA binding protein | Y2062 | TVNKHGDEIITSTTSNyETQTFSSK | SEQ ID NO: 330 |
| 330 | PRPF8 | NP_006436.3 | RNA binding protein | Y2091 | TNHIyVSSDDIK | SEQ ID NO: 331 |
| 331 | PRPF8 | NP_006436.3 | RNA binding protein | Y2102 | TNHIYVSSDDIKETGyTYILPK | SEQ ID NO: 332 |
| 332 | PRPF8 | NP_006436.3 | RNA binding protein | Y394 | LKDTPLyTDNTANGIALL | SEQ ID NO: 333 |
| 333 | PSF | NP_005057.1 | RNA binding protein | Y381 | NLSPyVSNELLEEAFSQFGPIER | SEQ ID NO: 334 |
| 334 | PUM1 | NP_055491.1 | RNA binding protein | Y1123 | DQYANyVVQK | SEQ ID NO: 335 |
| 335 | RALY | NP_057951.1 | RNA binding protein | Y109 | KRAASAIySGY | SEQ ID NO: 336 |
| 336 | RBM14 | NP_006319.1 | RNA binding protein | Y226 | ASyVAPLTAQPATYR | SEQ ID NO: 337 |
| 337 | RBM14 | NP_006319.1 | RNA binding protein | Y249 | AQPSVSLGAAyR | SEQ ID NO: 338 |
| 338 | RBM14 | NP_006319.1 | RNA binding protein | Y261 | AQPSASLGVGyR | SEQ ID NO: 339 |
| 339 | RBM14 | NP_006319.1 | RNA binding protein | Y273 | TQPMTAQAASyR | SEQ ID NO: 340 |
| 340 | RBM15 | NP_073605.4 | RNA binding protein | Y537 | YQQQyLQPLPLTHYELVTDAFGHR | SEQ ID NO: 341 |
| 341 | RBM15 | NP_073605.4 | RNA binding protein | Y546 | YQQQYLQPLPLTHyELVTDAFGHR | SEQ ID NO: 342 |
| 342 | RBM30 | NP_113680.1 | RNA binding protein | Y101 | FEEyGPVIECDIVK | SEQ ID NO: 343 |
| 343 | RBM30 | NP_113680.1 | RNA binding protein | Y194 | VADFTEQYNEQyGAVR | SEQ ID NO: 344 |
| 344 | RBM30 | NP_113680.1 | RNA binding protein | Y340 | NSLyDMAR | SEQ ID NO: 345 |
| 345 | RBM4 | NP_002887.2 | RNA binding protein | Y327 | ATAPVPTVGEGYGyGHESELSQASAAAR | SEQ ID NO: 346 |
| 346 | RBM5 | NP_005769.1 | RNA binding protein | Y254 | TVVDSIMTALSPy | SEQ ID NO: 347 |
| 347 | RBM6 | NP_005768.1 | RNA binding protein | Y701 | TGPMGHTyGFIDLDSHAEALR | SEQ ID NO: 348 |
| 348 | RNASE7 | NP_115961.1 | RNA binding protein | Y130 | SyVVACKPPQKK | SEQ ID NO: 349 |
| 349 | SART3 | NP_055521.1 | RNA binding protein | Y541 | AVQCTSDyPEHVCEVLLTMER | SEQ ID NO: 350 |
| 350 | SF2 | NP_008855.1 | RNA binding protein | Y149 | EAGDVCyADVYR | SEQ ID NO: 351 |
| 351 | SF2 | NP_008855.1 | RNA binding protein | Y170 | KEDMTyAVR | SEQ ID NO: 352 |
| 352 | SF2 | NP_008855.1 | RNA binding protein | Y37 | TKDIEDVFyKYGAIR | SEQ ID NO: 353 |
| 353 | SF3A3 | NP_006793.1 | RNA binding protein | Y406 | LHGLNINyNCEICGNYTYRGPK | SEQ ID NO: 354 |
| 354 | SF3A3 | NP_006793.1 | RNA binding protein | Y416 | LHGLNINYNCEICGNYTyRGPK | SEQ ID NO: 355 |
| 355 | SF3A3 | NP_006793.1 | RNA binding protein | Y492 | WQPDTEEEYEDSSGNVVNKKTyEDLKR | SEQ ID NO: 356 |
| 356 | SF3B1 | NP_036565.2 | RNA binding protein | Y1295 | IYNDDKNTyIR | SEQ ID NO: 357 |
| 357 | SF3B1 | NP_036565.2 | RNA binding protein | Y44 | AALDEAQGVGLDSTGYYDQEIyGGSDSR | SEQ ID NO: 358 |
| 358 | SF3B3 | NP_036558.3 | RNA binding protein | Y1041 | WVTTASLLDyDTVAGADKFGNICVVR | SEQ ID NO: 359 |
| 359 | SFRS10 | NP_004584.1 | RNA binding protein | Y235 | GYDDRDyYSR | SEQ ID NO: 360 |
| 360 | SFRS10 | NP_004584.1 | RNA binding protein | Y260 | AAQDRDQIyRR | SEQ ID NO: 361 |
| 361 | SFRS7 | NP_001026854.1 | RNA binding protein | Y33 | AFSyYGPLR | SEQ ID NO: 362 |
| 362 | SFRS9 | NP_003760.1 | RNA binding protein | Y139 | EAGDVCyADVQK | SEQ ID NO: 363 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 363 | SFRS9 | NP_003760.1 | RNA binding protein | Y70 | FEDPRDAEDAIyGR | SEQ ID NO: 364 |
| 364 | SFRS9 | NP_003760.1 | RNA binding protein | Y75 | NGyDYGQCR | SEQ ID NO: 365 |
| 365 | PDAP1 | NP_055706.1 | Secreted protein | Y70 | SLDSDESEDEEDDyQQKR | SEQ ID NO: 366 |
| 366 | PSGS | NP_002772.2 | Secreted protein | Y215 | NETGPyECEIRDR | SEQ ID NO: 367 |
| 367 | NACA | NP_005585.1 | Transcriptional regulator | Y120 | SPASDTyIVFGEAK | SEQ ID NO: 368 |
| 368 | NCOA7 | NP_861447.2 | Transcriptional regulator | Y526 | LIEYyLTK | SEQ ID NO: 369 |
| 369 | NFAT1 | NP_036472.2 | Transcriptional regulator | Y346 | HIyPAVEFLGPCEQGER | SEQ ID NO: 370 |
| 370 | NFAT1 | NP_036472.2 | Transcriptional regulator | Y860 | LSPGSyPTVIQQQNATSQR | SEQ ID NO: 371 |
| 371 | NFAT4 | NP_004546.1 | Transcriptional regulator | Y86 | NyEGTCEIPESK | SEQ ID NO: 372 |
| 372 | NFAT90 | NP_004507.2 | Transcriptional regulator | Y22 | HSSVyPTQEELEAVQNMVSHTER | SEQ ID NO: 373 |
| 373 | NFAT90 | NP_036350.2 | Transcriptional regulator | Y777 | GyNHGQGSYSYSNSYNSPGGGGGSDYNYESK | SEQ ID NO: 374 |
| 374 | NFAT90 | NP_036350.2 | Transcriptional regulator | Y828 | SGGNSYGSGGASyNPGSHGGYGGGSGGGSSYQGK | SEQ ID NO: 375 |
| 375 | NFAT90 | NP_036350.2 | Transcriptional regulator | Y846 | SGGNSYGSGGASYNPGSHGGYGGGSGGGSSyQGK | SEQ ID NO: 376 |
| 376 | NFAT90 | NP_036350.2 | Transcriptional regulator | Y891 | NADHSMNyQYR | SEQ ID NO: 377 |
| 377 | NFAT90 | NP_036350.2 | Transcriptional regulator | Y893 | NADHSMNYQyR | SEQ ID NO: 378 |
| 378 | NFI-X | NP_002492.2 | Transcriptional regulator | Y253 | VSQTPVATASGPNFSLADLESPSyYNINQVTLGR | SEQ ID NO: 379 |
| 379 | NFkB-p105 | NP_003989.2 | Transcriptional regulator | Y241 | RLEPVVSDAIyDSKAPNASNLK | SEQ ID NO: 380 |
| 380 | NFX1 | NP_002495.2 | Transcriptional regulator | Y1115 | ITKEPIIDyFDVQD | SEQ ID NO: 381 |
| 381 | NIF3L1 | NP_068596.2 | Transcriptional regulator | Y97 | VGIySPHTAYDAAPQGVNNWLAK | SEQ ID NO: 382 |
| 382 | NOT2 | NP_055330.1 | Transcriptional regulator | Y396 | AAETDPGMVHLALGSDLTTLGLNLNSPENLyPK | SEQ ID NO: 383 |
| 383 | NR2C2 | NP_003289.2 | Transcriptional regulator | Y135 | TDVQRPQVVEyCVVCGDK | SEQ ID NO: 384 |
| 384 | PCDC5RP | NP_001244.1 | Transcriptional regulator | Y232 | KPALGFYDTSEENyQALDADFRK | SEQ ID NO: 385 |
| 385 | PCDC5RP | NP_001244.1 | Transcriptional regulator | Y459 | DKLNINPEDGMADySDPSYVK | SEQ ID NO: 386 |
| 386 | PCDC5RP | NP_001244.1 | Transcriptional regulator | Y511 | EIDDTyIEDAADVDAR | SEQ ID NO: 387 |
| 387 | PCDC5RP | NP_001244.1 | Transcriptional regulator | Y621 | TVGFGTNNSEHITYLEHNPyEK | SEQ ID NO: 388 |
| 388 | PFDN5 | NP_002615.2 | Transcriptional regulator | Y90 | LHDVEHVLIDVGTGyYVEK | SEQ ID NO: 389 |
| 389 | PIAS4 | NP_056981.2 | Transcriptional regulator | Y108 | TPLAGPNIDyPVLYGK | SEQ ID NO: 390 |
| 390 | PLRG1 | NP_002660.1 | Transcriptional regulator | Y92 | QYPANQGQEVEyFVAGTHPYPPGPGVALTADTK | SEQ ID NO: 391 |
| 391 | POLR2A | NP_000928.1 | Transcriptional regulator | Y1383 | ELyHVISFDGSYVNYR | SEQ ID NO: 392 |
| 392 | POLR2A | NP_000928.1 | Transcriptional regulator | Y1916 | YSPTSPTySPTSPK | SEQ ID NO: 393 |
| 393 | POLR2I | NP_006224.1 | Transcriptional regulator | Y54 | NCDYQQEADNSCIyVNK | SEQ ID NO: 394 |
| 394 | PQBP1 | NP_005701.1 | Transcriptional regulator | Y33 | HLEPEPEEEIIAEDyDDDPVDYEATR | SEQ ID NO: 395 |
| 395 | RDBP | NP_002895.3 | Transcriptional regulator | Y133 | SLyESFVSSSDR | SEQ ID NO: 396 |
| 396 | REL | NP_002899.1 | Transcriptional regulator | Y47 | SAGSIPGEHSTDNNRTyPSIQIMNYYGK | SEQ ID NO: 397 |
| 397 | RYBP | NP_036366.3 | Transcriptional regulator | Y70 | INSQLVAQQVAQQyATPPPK | SEQ ID NO: 398 |
| 398 | SHARP | NP_055816.2 | Transcriptional regulator | Y1399 | ASALyESSR | SEQ ID NO: 399 |
| 399 | Skip | NP_036377.1 | Transcriptional regulator | Y292 | LAEALyIADRK | SEQ ID NO: 400 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 400 | Skip | NP_036377.1 | Transcriptional regulator | Y407 | TSNEVQyDQR | SEQ ID NO: 401 |
| 401 | PAIP1 | NP_006442.2 | Translational regulator | Y397 | EATPENDPNyFMNEPTFYTSDGVPFTAADPDYQEK | SEQ ID NO: 402 |
| 402 | PAIP1 | NP_006442.2 | Translational regulator | Y405 | EATPENDPNYFMNEPTFyTSDGVPFTAADPDYQEK | SEQ ID NO: 403 |
| 403 | RPS10 | NP_001005.1 | Translational regulator | Y82 | DyLHLPPEIVPATLRR | SEQ ID NO: 404 |
| 404 | RPS2 | NP_002943.2 | Translational regulator | Y248 | ATFDAISKTySYLTPDLWK | SEQ ID NO: 405 |
| 405 | RPS3 | NP_000996.2 | Translational regulator | Y166 | FVDGLMIHSGDPVNyYVDTAVR | SEQ ID NO: 406 |
| 406 | RPS3 | NP_000996.2 | Translational regulator | Y167 | FVDGLMIHSGDPVNYyVDTAVR | SEQ ID NO: 407 |
| 407 | RPS8 | NP_001003.1 | Translational regulator | Y83 | IIDVVyNASNNELVR | SEQ ID NO: 408 |
| 408 | NF1 | NP_000258.1 | Tumor suppressor | Y1500 | IGQyLSSNR | SEQ ID NO: 409 |
| 409 | PSMC5 | NP_002796.4 | Ubiquitin conjugating system | Y148 | ILPNKVDPLVSLMMVEKVPDSTyEMIGGLDK | SEQ ID NO: 410 |
| 410 | MYCT1 | NP_079383.1 | Unknown function | Y225 | VGLSTPPPPAyESIIK | SEQ ID NO: 411 |
| 411 | MYO1G | NP_149043.1 | Unknown function | Y598 | NSMVALVENLASKEPFyVR | SEQ ID NO: 412 |
| 412 | MYO1G | NP_149043.1 | Unknown function | Y624 | HQVAyLGLLENVR | SEQ ID NO: 413 |
| 413 | MYO1G | NP_149043.1 | Unknown function | Y737 | AIyTIMR | SEQ ID NO: 414 |
| 414 | NARFL | NP_071938.1 | Unknown function | Y239 | IyHVTVMPCYDK | SEQ ID NO: 415 |
| 415 | NARFL | NP_071938.1 | Unknown function | Y247 | IYHVTVMPCyDK | SEQ ID NO: 416 |
| 416 | NARFL | NP_071938.1 | Unknown function | Y49 | IEDDGSyFQINQDGGTR | SEQ ID NO: 417 |
| 417 | NARG2 | NP_078887.2 | Unknown function | Y108 | SyVDLLVKYAK | SEQ ID NO: 418 |
| 418 | NARG2 | NP_078887.2 | Unknown function | Y115 | SYVDLLVKyAK | SEQ ID NO: 419 |
| 419 | NGRN | NP_057729.1 | Unknown function | Y165 | ELQKySSDSESPRGTGSGALPSGQKLEELK | SEQ ID NO: 420 |
| 420 | Nice-4 | NP_055662.2 | Unknown function | Y1079 | SAyNSYSWGAN | SEQ ID NO: 421 |
| 421 | Nice-4 | NP_055662.2 | Unknown function | Y1082 | SAYNSySWGAN | SEQ ID NO: 422 |
| 422 | Nice-4 | NP_055662.2 | Unknown function | Y858 | DGSLASNPySGDLTK | SEQ ID NO: 423 |
| 423 | NIP30 | NP_079222.1 | Unknown function | Y49 | KPEDPEECPEEVyDPRSLYER | SEQ ID NO: 424 |
| 424 | NIP30 | NP_079222.1 | Unknown function | Y55 | KPEDPEECPEEVYDPRSLyER | SEQ ID NO: 425 |
| 425 | NIP30 | NP_079222.1 | Unknown function | Y69 | KQQEyEEQFK | SEQ ID NO: 426 |
| 426 | NOL10 | NP_079170.1 | Unknown function | Y289 | MGIyYIPVLGPAPR | SEQ ID NO: 427 |
| 427 | NSUN2 | NP_060225.4 | Unknown function | Y609 | LAQEGIyTLYPFINSR | SEQ ID NO: 428 |
| 428 | NUCKS | NP_073568.2 | Unknown function | Y13 | VVDySQFQESDDADEDYGRDSGPPTKK | SEQ ID NO: 429 |
| 429 | NUCKS | NP_073568.2 | Unknown function | Y26 | VVDYSQFQESDDADEDyGRDSGPPTKK | SEQ ID NO: 430 |
| 430 | NUDCD3 | NP_056147.2 | Unknown function | Y271 | VGEyWWNAILEGEEPIDIDKINK | SEQ ID NO: 431 |
| 431 | NUDT15 | NP_060753.1 | Unknown function | Y92 | NSFIEKENYHy | SEQ ID NO: 432 |
| 432 | opti-neurin | NP_068815.2 | Unknown function | Y356 | QELVyTNKKLELQVESMLSEIK | SEQ ID NO: 433 |
| 433 | palm-delphin | NP_060204.1 | Unknown function | Y262 | SPTEYHEPVyANPFYRPTTPQR | SEQ ID NO: 434 |
| 434 | PCM-1 | NP_006188.3 | Unknown function | Y1757 | QTQTSEVyDGPK | SEQ ID NO: 435 |
| 435 | PCM-1 | NP_006188.3 | Unknown function | Y215 | LVQIRDyITK | SEQ ID NO: 436 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 436 | PCM-1 | NP_006188.3 | Unknown function | Y509 | ELVHyYEQTSDMMTDAVNENR | SEQ ID NO: 437 |
| 437 | PCM-1 | NP_006188.3 | Unknown function | Y965 | WKNNCPFSADENyRPLAK | SEQ ID NO: 438 |
| 438 | PELO | NP_057030.3 | Unknown function | Y99 | MGAyHTIELEPNR | SEQ ID NO: 439 |
| 439 | PHF8 | NP_055922.1 | Unknown function | Y178 | LGDFVKyYYSGKR | SEQ ID NO: 440 |
| 440 | PHF8 | NP_055922.1 | Unknown function | Y179 | LGDFVKYyYSGKR | SEQ ID NO: 441 |
| 441 | PHF8 | NP_055922.1 | Unknown function | Y180 | LGDFVKYYySGKR | SEQ ID NO: 442 |
| 442 | PLEKHG1 | NP_001025055.1 | Unknown function | Y559 | SPQENEDDEDDyQMFVPSFSSSDLNSTR | SEQ ID NO: 443 |
| 443 | PPIL4 | NP_624311.1 | Unknown function | Y39 | IKYYNyCLIHNVQR | SEQ ID NO: 444 |
| 444 | PROSC | NP_009129.1 | Unknown function | Y69 | TFGENyVQELLEK | SEQ ID NO: 445 |
| 445 | PSST739 | NP_940972.1 | Unknown function | Y163 | GKGCVDESGFVyAIGEK | SEQ ID NO: 446 |
| 446 | PSTPIP2 | NP_077748.2 | Unknown function | Y191 | AyMLHIGTLDK | SEQ ID NO: 447 |
| 447 | PSTPIP2 | EAX01466.1 | Unknown function | Y241 | DIEyFVNQR | SEQ ID NO: 448 |
| 448 | PYM | NP_115721.1 | Unknown function | Y45 | VKEGYVPQEEVPVyENKYVK | SEQ ID NO: 449 |
| 449 | PYM | NP_115721.1 | Unknown function | Y49 | VKEGYVPQEEVPVYENKyVK | SEQ ID NO: 450 |
| 450 | Q8WVJ2 | NP_660309.1 | Unknown function | Y145 | FQKENPGFDFSGAEISGNyTK | SEQ ID NO: 451 |
| 451 | R3HDM | NP_056176.2 | Unknown function | Y254 | yILKRDNSSFDK | SEQ ID NO: 452 |
| 452 | R3HDM | NP.056176.2 | Unknown function | Y354 | STNSHQSSTENELKySEPRPWSSTDSDSSLR | SEQ ID NO: 453 |
| 453 | RAB3IP | NP_071901.2 | Unknown function | Y400 | LGDSSNyYYISPFCR | SEQ ID NO: 454 |
| 454 | RAMA1 | NP_659498.2 | Unknown function | Y39 | ALDGEESDFEDyPMR | SEQ ID NO: 455 |
| 455 | RAP140 | NP_056039.1 | Unknown function | Y182 | EFIMFPyDSRLDDK | SEQ ID NO: 456 |
| 456 | RB1CC1 | NP_055596.3 | Unknown function | Y1564 | VMEKEyCQAKKAQNRFKVPLGTKFYR | SEQ ID NO: 457 |
| 457 | RBM10 | NP_005667.2 | Unknown function | Y694 | ESATADAGyAILEK | SEQ ID NO: 458 |
| 458 | RBM128 | NP_976324.2 | Unknown function | Y519 | GDHSHLFDSKDPPIySVGAFENFR | SEQ ID NO: 459 |
| 459 | RBM13 | NP_115898.2 | Unknown function | Y33 | NEySLTGLCNR | SEQ ID NO: 460 |
| 460 | RBM13 | NP_115898.2 | Unknown function | Y62 | GQCyLYMK | SEQ ID NO: 461 |
| 461 | RBM13 | NP_115898.2 | Unknown function | Y64 | GQCYLyMK | SEQ ID NO: 462 |
| 462 | RBM16 | NP_055707.3 | Unknown function | Y1237 | HAQPPPIPVQNDPELyEK | SEQ ID NO: 463 |
| 463 | RBM34 | NP_055829.1 | Unknown function | Y66 | LASLFSSLEPQIQPVyVPVPK | SEQ ID NO: 464 |
| 464 | RCD-8 | NP_055144.3 | Unknown function | Y863 | SLAFHRPPyHLLQQR | SEQ ID NO: 465 |
| 465 | RGPD8 | NP_005045.2 | Unknown function | Y1633 | NLSASFPTEESSINyTFK | SEQ ID NO: 468 |
| 466 | RGPD8 | NP_005045.2 | Unknown function | Y1711 | SAANLEyLK | SEQ ID NO: 469 |
| 467 | RGPD8 | NP_005045.2 | Unknown function | Y763 | QMLNSVMQELEDYSEGGPLyKNGSLR | SEQ ID NO: 470 |
| 468 | RNF138 | NP_057355.2 | Unknown function | Y145 | SETSTSDNTETyQENTSSSGHPTFK | SEQ ID NO: 471 |
| 469 | RNF146 | NP_112225.2 | Unknown function | Y103 | GNGEyAWYYEGR | SEQ ID NO: 472 |
| 470 | SACS | NP_055178.2 | Unknown function | Y3220 | TANIESPTSILKALHy | SEQ ID NO: 473 |
| 471 | SACS | NP_055178.2 | Unknown function | Y3316 | ELyEVIGCVPVDDLEVYLK | SEQ ID NO: 474 |
| 472 | SACS | NP_055178.2 | Unknown function | Y3330 | ELYEVIGCVPVDDLEVyLK | SEQ ID NO: 475 |

TABLE 1-continued

Phosphorylation Sites

| | A<br>Protein<br>Name | B<br>Accession<br>No. | C<br>Protein<br>Type | D<br>Phospho-<br>Residue | E<br>Phosphorylation<br>Site Sequence | H<br>SEQ ID<br>NO |
|---|---|---|---|---|---|---|
| 473 | SAFB2 | NP_055464.1 | Unknown function | Y741 | DDAyWPEGK | SEQ ID NO: 476 |
| 474 | SAMHD1 | NP_056289.2 | Unknown function | Y315 | NGIDVDKWDyFAR | SEQ ID NO: 477 |
| 475 | SC65 | NP_006446.1 | Unknown function | Y20 | MARVAWGLLWLLLGSAGAQyEKYSFR | SEQ ID NO: 478 |
| 476 | SC65 | NP_006446.1 | Unknown function | Y23 | MARVAWGLLWLLLGSAGAQYEKySFR | SEQ ID NO: 479 |
| 477 | SDCCAG1 | NP_004704.2 | Unknown function | Y117 | yDRGNIVLTDYEY | SEQ ID NO: 480 |
| 478 | SDCCAG1 | NP_004704.2 | Unknown function | Y127 | YDRGNIVLTDyEY | SEQ ID NO: 481 |
| 479 | SDCCAG1 | NP_004704.2 | Unknown function | Y129 | YDRGNIVLTDYEy | SEQ ID NO: 482 |
| 480 | SDCCAG1 | NP_004704.2 | Unknown function | Y30 | VNNVyDVDNK | SEQ ID NO: 483 |
| 481 | SDCCAG1 | NP_004704.2 | Unknown function | Y883 | MKKMKEKyKDQDEEDRELIMK | SEQ ID NO: 484 |
| 482 | SFRS2IP | NP_004710.2 | Unknown function | Y1161 | TLPADVQNyYSR | SEQ ID NO: 485 |
| 483 | SH2D5 | XP_375698.3 | Unknown function | Y619 | LGNPyCSPTLVR | SEQ ID NO: 486 |
| 484 | SH2D5 | XP_375698.3 | Unknown function | Y640 | SGAyRGCTYETQLQLSAR | SEQ ID NO: 487 |
| 485 | ShcBP1 | NP_079021.2 | Unknown function | Y217 | SWDEEEEDEyDYFVR | SEQ ID NO: 488 |
| 486 | similar to ZFP 267 | XP_001132888.1 | Unknown function | Y163 | HKIIHNEEKPYKCKEyEK | SEQ ID NO: 490 |
| 487 | SKIV2L2 | NP_056175.2 | Unknown function | Y583 | VEEINPEyMLEK | SEQ ID NO: 491 |
| 488 | SKIV2L2 | NP_056175.2 | Unknown function | Y590 | SFyQFQHYR | SEQ ID NO: 492 |
| 489 | SKIV2L2 | NP_056175.2 | Unknown function | Y694 | KSNVKPNSGELDPLyVVEVLLR | SEQ ID NO: 493 |
| 490 | SCAMP1 | NP_004857.4 | Vesicle protein | Y37 | NVPPGLDEyNPFSDSR | SEQ ID NO: 494 |
| 491 | Sec24B | NP_006314.2 | Vesicle protein | Y1100 | LDDRVyAMCQIK | SEQ ID NO: 495 |
| 492 | Sec5 | NP_060773.3 | Vesicle protein | Y534 | DGEAKQyGGWEVK | SEQ ID NO: 496 |

The short name for each protein in which a phosphorylation site has presently been identified is provided in Column A, and its SwissProt accession number (human) is provided Column B. The protein type/group into which each protein falls is provided in Column C. The identified tyrosine residue at which phosphorylation occurs in a given protein is identified in Column D, and the amino acid sequence of the phosphorylation site encompassing the tyrosine residue is provided in Column E (lower case y=the tyrosine (identified in Column D)) at which phosphorylation occurs. Table 1 above is identical to FIG. 2, except that the latter includes the disease and cell type(s) in which the particular phosphorylation site was identified (Columns F and G).

One of skill in the art will appreciate that, in many instances the utility of the instant invention is best understood in conjunction with an appreciation of the many biological roles and significance of the various target signaling proteins/polypeptides of the invention. The foregoing is illustrated in the following paragraphs summarizing the knowledge in the art relevant to a few non-limiting representative peptides containing selected phosphorylation sites according to the invention.

MYH10 (P35580), phosphorylated at Y13, Y194, Y1415, is among the proteins listed in this patent. MYH10, Myosin heavy chain 10 (non-muscle), a putative ATP- and actin-binding motor protein, expression of an alternative splice form is coincident with neuronal cell differentiation; mRNA is upregulated during coronary restenosis. (PhosphoSite®, Cell Signaling Technology (Danvers, Mass.), Human PSD™, Biobase Corporation, (Beverly, Mass.)).

NCK2 (O43639), phosphorylated at Y50, Y342, is among the proteins listed in this patent. NCK2, NCK adaptor protein 2, SH2/SH3 adaptor protein, binds PDGFR-beta (PDGFRB) and TrkB (NTRK2), inhibits EGF- and PDGF-stimulated DNA synthesis and PDGF-mediated actin polymerization, may modulate activity at promoters regulated by FOS and JUN. (PhosphoSite®, Cell Signaling Technology (Danvers, Mass.), Human PSD™, Biobase Corporation, (Beverly, Mass.)).

NFAT1 (Q13469), phosphorylated at Y346, Y860, is among the proteins listed in this patent. NFAT1, Nuclear factor of activated T-cells cytoplasmic calcineurin-dependent 2, a calcineurin-dependent transcription factor that interacts with coactivators to regulate expression of cytokines and other genes, plays a role in T-cell activation. (PhosphoSite®, Cell Signaling Technology (Danvers, Mass.), Human PSD™, Biobase Corporation, (Beverly, Mass.)).

NFkB-p105 (P19838), phosphorylated at Y240, is among the proteins listed in this patent. NFkB-p105, Nuclear factor of kappa light polypeptide gene enhancer in B-cells 1, the p50 component of the NFkB transcription factor, involved in the immune response and inflammation; increased activation is linked to HIV infections and cancer. This protein has potential diagnostic and/or therapeutic implications based on the following findings. Increased nucleus localization of NFKB1 may cause decreased induction of apoptosis by extracellular signals associated with prostatic neoplasms (Oncogene 21: 1759-67 (2002)). Increased transcription factor activity of NFKB1 may cause decreased cell death associated with squamous cell carcinoma (Cancer Res 59: 3468-74 (1999)). Increased transcription factor activity of NFKB1 correlates with arteriosclerosis (PNAS 101: 5634-9 (2004)). Increased nucleus localization of NFKB1 may cause abnormal smooth muscle cells function associated with arteriosclerosis (JBC 272: 15817-24 (1997)). Increased nucleus localization of NFKB1 correlates with advanced stage or high grade form of squamous cell carcinoma (Oncogene 22: 50-8 (2003)). Increased double-stranded DNA binding of NFKB1 may cause disease progression associated with prostatic neoplasms (MCB 22: 2862-70 (2002)). Increased transcription factor activity of NFKB1 correlates with increased cell proliferation associated with chronic B-cell leukemia (Leukemia 18: 1391-400 (2004)). Increased transcription factor activity of NFKB1 may cause inflammation associated with arteriosclerosis (Proc Natl Acad Sci USA 101: 5634-9 (2004)). Induced inhibition of the DNA binding of NFKB1 may prevent decreased response to drug associated with chronic B-cell leukemia (Blood 92: 990-5 (1998)). Induced inhibition of the DNA binding of NFKB1 may prevent decreased apoptosis associated with chronic B-cell leukemia (Blood 92: 990-5 (1998)). Increased DNA binding of NFKB1 correlates with decreased cell death associated with chronic B-cell leukemia (J Immunol 164: 2200-6 (2000)). Increased transcription factor activity of NFKB1 may cause increased interleukin-6 biosynthetic process associated with prostatic neoplasms (Cancer Res 63: 2206-15 (2003)). Increased nucleus localization of NFKB1 correlates with breast neoplasms (Oncogene 19: 1123-31 (2000)). Decreased transcription factor activity of NFKB1 may prevent decreased induction of apoptosis associated with pancreatic neoplasms (Oncogene 21: 6510-9 (2002)). Increased DNA binding of NFKB1 correlates with abnormal B-lymphocytes differentiation associated with chronic B-cell leukemia (J Immunol 164: 2200-6 (2000)). Increased DNA binding of NFKB1 correlates with increased severity of cervix neoplasms associated with squamous cell carcinoma (Oncogene 22: 50-8 (2003)). Decreased nucleus localization of NFKB1 may prevent decreased induction of apoptosis by extracellular signals associated with prostatic neoplasms (Anticancer Res 23: 3855-61 (2003)). Abnormal expression of NFKB1 in smooth muscle cells may cause increased 1-kappaB kinase/NF-kappaB cascade associated with arteriosclerosis (J Biol Chem 272: 15817-24 (1997)). Increased DNA binding of NFKB1 may correlate with head and neck neoplasms associated with squamous cell carcinoma (Cancer Res 59: 3468-74 (1999)). Increased nucleus localization of NFKB1 may cause increased 1-kappaB kinase/NF-kappaB cascade associated with melanoma (Cancer Res 59: 1372-7 (1999)). Increased transcription factor activity of NFKB1 may cause increased cytokine production associated with arteriosclerosis (Proc Natl Acad Sci USA 101: 5634-9 (2004)). Increased DNA binding of NFKB1 may cause increased cell proliferation associated with squamous cell carcinoma (Cancer Res 59: 3468-74 (1999)). Abnormal expression of NFKB1 in smooth muscle cells may cause increased inflammatory response associated with arteriosclerosis (J Biol Chem 272: 15817-24 (1997)). Increased nucleus localization of NFKB1 may cause increased positive regulation of transcription from RNA polymerase II promoter associated with melanoma (Cancer Res 59: 1372-7 (1999)). Abnormal expression of NFKB1 in smooth muscle cells may cause increased activation of NF-kappaB transcription factor associated with arteriosclerosis (J Biol Chem 272: 15817-24 (1997)). Decreased transcription factor activity of NFKB1 may prevent decreased response to drug associated with pancreatic neoplasms (Oncogene 21: 6510-9 (2002)). Abnormal expression of NFKB1 in smooth muscle cells may cause increased activation of NF-kappaB transcription factor associated with arteriosclerosis (JBC 272: 15817-24 (1997)). Increased transcription factor activity of NFKB1 may cause increased cytokine production associated with arteriosclerosis (PNAS 101: 5634-9 (2004)). Decreased nucleus localization of NFKB1 may correlate with increased response to drug associated with prostatic neoplasms (Oncogene 21: 1759-67 (2002)). Increased double-stranded DNA binding of NFKB1 may cause disease progression associated with prostatic neoplasms (Mol Cell Biol 22: 2862-70 (2002)). Increased transcription factor activity of NFKB1 may cause increased cell proliferation associated with squamous cell carcinoma (Cancer Res 59: 3468-74 (1999)). Increased DNA binding of NFKB1 may cause decreased cell death associated with squamous cell carcinoma (Cancer Res 59: 3468-74 (1999)). Increased DNA binding of NFKB1 correlates with increased cell-matrix adhesion associated with multiple myeloma (Oncogene 22: 2417-21 (2003)). Increased nucleus localization of NFKB1 may correlate with HIV infections (J Immunol 155: 4861-7 (1995)). Increased transcription factor activity of NFKB1 may cause inflammation associated with arteriosclerosis (PNAS 101: 5634-9 (2004)). Increased transcription factor activity of NFKB1 correlates with decreased apoptosis associated with chronic B-cell leukemia (Leukemia 18: 1391-400 (2004)). Abnormal expression of NFKB1 in smooth muscle cells may cause increased inflammatory response associated with arteriosclerosis (JBC 272: 15817-24 (1997)). Decreased nucleus localization of NFKB1 may prevent increased cell proliferation associated with prostatic neoplasms (Anticancer Res 23: 3855-61 (2003)). Increased transcription factor activity of NFKB1 correlates with arteriosclerosis (Proc Natl Acad Sci USA 101: 5634-9 (2004)). Increased double-stranded DNA binding of NFKB1 may cause disease progression associated with prostatic neoplasms (Mol. Cell. Biol 22: 2862-70 (2002)). Increased transcription factor activity of NFKB1 may cause thrombosis associated with arteriosclerosis (Proc Natl Acad Sci USA 101: 5634-9 (2004)). Increased nucleus localization of NFKB1 may cause increased I-kappaB kinase/NF-kappaB cascade associated with arteriosclerosis (JBC 272: 15817-24 (1997)). Increased nucleus localization of NFKB1 may cause increased inflammatory response associated with arteriosclerosis (J Biol Chem 272: 15817-24 (1997)). Increased transcription factor activity of NFKB1 may cause increased cytokine production associated with arteriosclerosis (Proc Natl Acad Sci USA 101: 5634-9 (2004)). Increased nucleus localization of NFKB1 may correlate with increased cytokine and chemokine mediated signaling pathway associated with arteriosclerosis (J Biol Chem 272: 15817-24 (1997)). Increased nitration of NFKB1 may prevent increased 1-kappaB kinase/NF-kappaB cascade associated with prostatic neoplasms (Oncogene 23: 4993-5003 (2004)). Increased transcription factor activity of NFKB1 may cause decreased occurrence of hormone-dependent neoplasms associated with prostatic neoplasms (J Cell Sci 115: 141-51 (2002)). Increased nucleus localization of NFKB1 may correlate with increased 1-kappaB kinase/NF-kappaB cascade associated with prostatic neoplasms (Mol Carcinog 39: 114-26 (2004)). Increased expression of NFKB1 in macrophages may correlate with HIV infections (J Virol 69: 1500-9 (1995)). Decreased expression of NFKB1 protein may prevent HIV infections (J Immunol 152: 4183-91

(1994)). Abnormal expression of NFKB1 in smooth muscle cells may correlate with increased cytokine and chemokine mediated signaling pathway associated with arteriosclerosis (J Biol Chem 272: 15817-24 (1997)). Increased DNA binding of NFKB1 correlates with advanced stage or high grade form of squamous cell carcinoma (Oncogene 22: 50-8 (2003)). Increased transcription factor activity of NFKB1 may correlate with head and neck neoplasms associated with squamous cell carcinoma (Cancer Res 59: 3468-74 (1999)). Increased transcription factor activity of NFKB1 may cause inflammation associated with arteriosclerosis (Proc Natl Acad Sci USA 101: 5634-9 (2004)). Increased nucleus localization of NFKB1 may cause abnormal smooth muscle cells function associated with arteriosclerosis (J Biol Chem 272: 15817-24 (1997)). Increased transcription factor activity of NFKB1 may cause increased interleukin-8 biosynthetic process associated with squamous cell carcinoma (Mol Carcinog 26: 119-29 (1999)). Increased transcription factor activity of NFKB1 may cause decreased occurrence of hormone-dependent neoplasms associated with prostatic neoplasms (J Cell Sci 115: 141-51 (2002)). Increased transcription factor activity of NFKB1 may cause thrombosis associated with arteriosclerosis (PNAS 101: 5634-9 (2004)). Increased DNA binding of NFKB1 correlates with increased release of cytoplasmic sequestered NF-kappaB associated with squamous cell carcinoma (Oncogene 22: 50-8 (2003)). Increased double-stranded DNA binding of NFKB1 may cause disease progression associated with prostatic neoplasms (Mol Cell Biol. 22: 2862-70 (2002)). Increased DNA binding of NFKB1 may cause increased cytokine production associated with squamous cell carcinoma (Cancer Res 59: 3468-74 (1999)). Increased DNA binding of NFKB1 may cause increased interleukin-8 biosynthetic process associated with squamous cell carcinoma (Mol Carcinog 26: 119-29 (1999)). Increased nucleus localization of NFKB1 may cause increased activation of NF-kappaB transcription factor associated with arteriosclerosis (J Biol Chem 272: 15817-24 (1997)). Increased nucleus localization of NFKB1 may cause increased inflammatory response associated with arteriosclerosis (JBC 272: 15817-24 (1997)). Increased transcription factor activity of NFKB1 may cause increased cytokine production associated with squamous cell carcinoma (Cancer Res 59: 3468-74 (1999)). Abnormal expression of NFKB1 in smooth muscle cells may correlate with increased cytokine and chemokine mediated signaling pathway associated with arteriosclerosis (JBC 272: 15817-24 (1997)). Increased double-stranded DNA binding of NFKB1 may cause disease progression associated with prostatic neoplasms (Mol. Cell. Biol. 22: 2862-70 (2002)). Increased expression of NFKB1 protein correlates with non-small-cell lung carcinoma (Oncogene 11: 999-1003 (1995)). Increased transcription factor activity of NFKB1 correlates with abnormal epidermal growth factor receptor signaling pathway associated with pancreatic neoplasms (Int J Cancer 105: 735-46 (2003)). Increased nucleus localization of NFKB1 may cause increased 1-kappaB kinase/NF-kappaB cascade associated with arteriosclerosis (J Biol Chem 272: 15817-24 (1997)). Increased nucleus localization of NFKB1 may cause increased activation of NF-kappaB transcription factor associated with arteriosclerosis (JBC 272: 15817-24 (1997)). Increased transcription factor activity of NFKB1 correlates with arteriosclerosis (Proc Natl Acad Sci USA 101: 5634-9 (2004)). Abnormal expression of NFKB1 in smooth muscle cells may cause increased 1-kappaB kinase/NF-kappaB cascade associated with arteriosclerosis (JBC 272: 15817-24 (1997)). Increased nucleus localization of NFKB1 correlates with increased severity of cervix neoplasms associated with squamous cell carcinoma (Oncogene 22: 50-8 (2003)). Increased expression of NFKB1 in monocytes may correlate with HIV infections (J Virol 69: 1500-9 (1995)). Increased nucleus localization of NFKB1 may correlate with increased cytokine and chemokine mediated signaling pathway associated with arteriosclerosis (JBC 272: 15817-24 (1997)). Increased nitration of NFKB1 may prevent decreased induction of apoptosis by extracellular signals associated with prostatic neoplasms (Oncogene 23: 4993-5003 (2004)). Increased DNA binding of NFKB1 may correlate with decreased induction of apoptosis associated with multiple myeloma (Blood 93: 3044-52 (1999)). Increased DNA binding of NFKB1 correlates with increased anti-apoptosis associated with multiple myeloma (Oncogene 22: 2417-21 (2003)). Increased transcription factor activity of NFKB1 may correlate with increased interleukin-1 alpha secretion associated with pancreatic neoplasms (J Biol Chem 279: 16452-62 (2004)). Increased transcription factor activity of NFKB1 may correlate with increased interleukin-1 alpha secretion associated with pancreatic neoplasms (JBC 279: 16452-62 (2004)). Increased nucleus localization of NFKB1 correlates with increased release of cytoplasmic sequestered NF-kappaB associated with squamous cell carcinoma (Oncogene 22: 50-8 (2003)). Increased DNA binding of NFKB1 may cause drug-resistant form of multiple myeloma (Blood 93: 3044-52 (1999)). Increased transcription factor activity of NFKB1 may cause thrombosis associated with arteriosclerosis (Proc Natl Acad Sci USA 101: 5634-9 (2004)). Increased nucleus localization of NFKB1 may correlate with increased 1-kappaB phosphorylation associated with melanoma (Cancer Res 61: 4901-9 (2001)). (PhosphoSite®, Cell Signaling Technology (Danvers, Mass.), Human PSD™, Biobase Corporation, (Beverly, Mass.)).

NONO (Q15233), phosphorylated at Y265, is among the proteins listed in this patent. NONO, Non-POU-domain-containing octamer-binding, transcriptional co-activator with the androgen receptor, upregulated in prostate cancer, downregulated in EBV-infected nasopharyngeal carcinoma cells, fused with TFE3 in papillary renal cell carcinoma. This protein has potential diagnostic and/or therapeutic implications based on the following findings. Translocation of the NONO gene may cause neoplastic cell transformation associated with renal cell carcinoma (Oncogene 15: 2233-9 (1997)). (PhosphoSite®, Cell Signaling Technology (Danvers, Mass.), Human PSD™, Biobase Corporation, (Beverly, Mass.)).

PABP 1 (P11940), phosphorylated at Y297, Y382, is among the proteins listed in this patent. PABP 1, Poly(A)-binding protein cytoplasmic 1, binds mRNA poly(A) tails, plays roles in regulating mRNA stability, translation, and perhaps transport from the nucleus to cytoplasm, degraded by specific viral proteases resulting in host protein synthesis shutoff. This protein has potential diagnostic and/or therapeutic implications based on the following findings. Viral exploitation of the PABPC1 protein may cause increased suppression by virus of host termination of protein biosynthetic process associated with poliomyelitis (J Virol 73: 718-27 (1999)). Increased proteolysis of PABPC1 may cause increased suppression by virus of host termination of protein biosynthetic process associated with coxsackievirus infections (J Virol 73: 709-17 (1999)). Viral exploitation of the PABPC1 protein may cause increased suppression by virus of host termination of protein biosynthetic process associated with coxsackievirus infections (J Virol 73: 709-17 (1999)). Increased proteolysis of PABPC1 may cause increased suppression by virus of host termination of protein biosynthetic process associated with poliomyelitis (J Virol 73: 718-27

(1999)). (PhosphoSite®, Cell Signaling Technology (Danvers, Mass.), Human PSD™, Biobase Corporation, (Beverly, Mass.)).

PAK1 (Q13153), phosphorylated at Y142, Y153, is among the proteins listed in this patent. PAK1, p21 activated kinase 1, a serine-threonine kinase activated by GTPases CDC42 and RAC1, serves in MAP kinase cascade regulation, cytoskeletal organization, cell migration and apoptosis, increased activity may correlate with breast cancer invasiveness. This protein has potential diagnostic and/or therapeutic implications based on the following findings. Decreased expression of PAK1 in frontal cortex correlates with encephalitis associated with HIV infections (J Neuroimmunol 157: 163-75 (2004)). Increased expression of PAK1 mRNA correlates with breast neoplasms (J Biol Chem 279: 1422-8 (2004)). Increased phosphorylation of PAK1 may cause increased severity of neoplastic cell transformation associated with breast neoplasms (J Biol Chem 276: 29403-9 (2001)). Increased expression of PAK1 mRNA correlates with breast neoplasms (JBC 279: 1422-8 (2004)). Loss of function mutation in the Protein kinase domain of PAK1 may prevent invasive form of breast neoplasms (JBC 275: 12041-50 (2000)). Loss of function mutation in the Protein kinase domain of PAK1 may prevent invasive form of breast neoplasms (J Biol Chem 275: 12041-50 (2000)). Increased protein kinase activity of PAK1 correlates with increased severity of invasive form of breast neoplasms (J Biol Chem 275: 36238-36244 (2000)). Absence of the protein kinase activity of PAK1 may cause increased actin filament polymerization associated with breast neoplasms (J Biol Chem 275: 12041-50 (2000)). Amplification of the PAK1 gene correlates with mycosis fungoides associated with skin neoplasms (Blood 101: 1513-9 (2003)). Amplification of the PAK1 gene correlates with Sezary syndrome associated with skin neoplasms (Blood 101: 1513-9 (2003)). Increased protein kinase activity of PAK1 may cause abnormal mitotic spindle organization and biogenesis associated with breast neoplasms (JBC 275: 36238-36244 (2000)). Absence of the protein kinase activity of PAK1 may prevent invasive form of breast neoplasms (JBC 275: 12041-50 (2000)). Increased phosphorylation of PAK1 may cause increased severity of neoplastic cell transformation associated with breast neoplasms (JBC 276: 29403-9 (2001)). Absence of the protein kinase activity of PAK1 may cause increased actin filament polymerization associated with breast neoplasms (JBC 275: 12041-50 (2000)). Absence of the protein kinase activity of PAK1 may prevent invasive form of breast neoplasms (J Biol Chem 275: 12041-50 (2000)). Increased protein kinase activity of PAK1 may cause abnormal mitotic spindle organization and biogenesis associated with breast neoplasms (J Biol Chem 275: 36238-36244 (2000)). Increased protein kinase activity of PAK1 may cause increased cell motility associated with breast neoplasms (J Biol Chem 275: 36238-36244 (2000)). Increased protein kinase activity of PAK1 may cause increased cell motility associated with breast neoplasms (JBC 275: 36238-36244 (2000)). Amplification of the PAK1 gene may correlate with breast neoplasms (Cytogenet Cell Genet. 79: 125-31 (1997)). Increased protein kinase activity of PAK1 correlates with increased severity of invasive form of breast neoplasms (JBC 275: 36238-36244 (2000)). (PhosphoSite®, Cell Signaling Technology (Danvers, Mass.), Human PSD™, Biobase Corporation, (Beverly, Mass.)).

PAK2 (Q13177), phosphorylated at Y252, is among the proteins listed in this patent. PAK2, p21-activated kinase 2, a protein serine-threonine kinase that autophosphorylates and autoactivates, acts as a modulator of Myc, RAC1 and myosin 2 activities, may be activated by HIV infection; gene is associated with 3q29 microdeletion syndrome. This protein has potential diagnostic and/or therapeutic implications based on the following findings. Deletion mutation in the PAK2 gene correlates with chromosome deletion associated with mental retardation (Am J Hum Genet. 77: 154-60 (2005)). (PhosphoSite®, Cell Signaling Technology (Danvers, Mass.), Human PSD™, Biobase Corporation, (Beverly, Mass.)).

PARP1 (P09874), phosphorylated at Y774, is among the proteins listed in this patent. PARP1, Poly (ADP-ribose) polymerase family member 1, catalyzes formation of ADP ribose polymers in response to DNA damage, acts transcriptional regulation of nuclear-receptor dependent promoters, increased proteolysis may be therapeutic for colon cancer. This protein has potential diagnostic and/or therapeutic implications based on the following findings. Increased cleavage of PARP1 may correlate with increased response to drug associated with prostatic neoplasms (Cancer Res 63: 4713-23 (2003)). Increased cleavage of PARP1 may correlate with increased response to drug associated with ovarian neoplasms (Oncogene 21: 4530-8 (2002)). Increased proteolysis of PARP1 may correlate with increased apoptosis associated with breast neoplasms (Exp Cell Res 255: 144-55 (2000)). Increased expression of PARP1 protein may correlate with leukemia (Cancer Lett 58: 131-5 (1991)). Increased cleavage of PARP1 may correlate with increased response to drug associated with ovarian neoplasms (Oncogene 21: 1-8 (2002)). Increased cleavage of PARP1 may correlate with increased response to drug associated with glioma (J Cell Physiol 201: 374-84 (2004)). Increased expression of PARP1 mutant protein may prevent prostatic neoplasms (Cancer Res 62: 6879-83 (2002)). Increased cleavage of PARP1 may correlate with increased apoptosis associated with prostatic neoplasms (Cancer Res 63: 4713-23 (2003)). Increased proteolysis of PARP1 may correlate with increased apoptosis associated with breast neoplasms (Oncogene 20: 8258-69 (2001)). Decreased expression of PARP1 mRNA correlates with disease progression associated with chronic lymphocytic leukemia (Leukemia 15: 1721-8 (2001)). Increased expression of PARP1 protein may correlate with ovarian neoplasms (Cancer Lett 58: 131-5 (1991)). Increased expression of PARP1 protein correlates with more severe form of B-cell lymphoma (Mol Carcinog 25: 256-61 (1999)). Increased cleavage of PARP1 may correlate with increased response to drug associated with prostatic neoplasms (Mol Carcinog 39: 114-26 (2004)). Increased proteolysis of PARP1 may correlate with increased apoptosis associated with lung neoplasms (Anticancer Res 21: 39-44 (2001)). (PhosphoSite®, Cell Signaling Technology (Danvers, Mass.), Human PSD™, Biobase Corporation, (Beverly, Mass.)).

PIK3C2A (O00443), phosphorylated at Y73, is among the proteins listed in this patent. PIK3C2A, Phosphoinositide-3-kinase class 2 alpha polypeptide, phosphorylates only PtdIns and PtdIns4P in the absence of phosphatidylserine but phosphorylates PtdIns(4,5)P2 in the presence of phosphatidylserine, exhibits insensitivity to wortmannin. (PhosphoSite®, Cell Signaling Technology (Danvers, Mass.), Human PSD™, Biobase Corporation, (Beverly, Mass.)).

PIK3C2B (O00750), phosphorylated at Y1541, is among the proteins listed in this patent. PIK3C2B, Phosphoinositide-3-kinase class 2 beta polypeptide, a nuclear enzyme catalyzing phosphorylation of phosphatidylinositol and phosphatidylinositol 4 monophosphate, altered by nitrotyrosylation in platelets from patients with systemic sclerosis. (PhosphoSite®, Cell Signaling Technology (Danvers, Mass.), Human PSD™, Biobase Corporation, (Beverly, Mass.)).

PIK3CA (P42336), phosphorylated at Y246, Y361, is among the proteins listed in this patent. PIK3CA, Phosphatidylinositol 3-kinase catalytic alpha polypeptide, heterodimerizes with an 85-kDa regulatory subunit that binds the kinase to receptors for signal transduction, altered expression and activity are involved in cancer progression. This protein has potential diagnostic and/or therapeutic implications based on the following findings. Mutation in the PIK3CA gene correlates with medulloblastoma associated with brain neoplasms (Cancer Res 64: 5048-50 (2004)). Amplification of the PIK3CA gene may cause squamous cell carcinoma (Eur J Cancer 35: 641-6 (1999)). Amplification of the PIK3CA gene correlates with carcinoma tumors associated with cervix neoplasms (Int J Cancer 101: 427-33 (2002)). Increased expression of PIK3CA mRNA correlates with squamous cell carcinoma associated with head and neck neoplasms (Gene Develop 16: 984-93 (2002)). Increased expression of PIK3CA mRNA correlates with squamous cell carcinoma associated with lung neoplasms (Genes Dev 16: 984-93 (2002)). Increased phosphatidylinositol 3-kinase activity of PIK3CA may cause increased anti-apoptosis associated with head and neck neoplasms (Cancer Res 61: 4122-9 (2001)). Amplification of the PIK3CA gene correlates with squamous cell carcinoma associated with head and neck neoplasms (Gene Develop 16: 984-93 (2002)). Amplification of the PIK3CA gene correlates with squamous cell carcinoma associated with head and neck neoplasms (Genes Dev 16: 984-93 (2002)). Increased expression of PIK3CA mRNA correlates with squamous cell carcinoma (Cancer Res 61: 4122-9 (2001)). Increased expression of PIK3CA mRNA correlates with squamous cell carcinoma associated with esophageal neoplasms (Cancer Res 63: 5691-6 (2003)). Increased expression of PIK3CA mRNA correlates with squamous cell carcinoma associated with head and neck neoplasms (Genes Dev 16: 984-93 (2002)). Increased expression of PIK3CA mRNA correlates with invasive form of ovarian neoplasms (Cancer Res 63: 4225-31 (2003)). Mutation in the PIK3CA gene correlates with carcinoma tumors associated with breast neoplasms (Cancer Res 65: 2554-9 (2005)). Increased expression of PIK3CA mRNA correlates with squamous cell carcinoma associated with lung neoplasms (Gene Develop 16: 984-93 (2002)). Increased expression of PIK3CA mRNA correlates with carcinoma tumors associated with stomach neoplasms (Int J Cancer 104: 318-27 (2003)). Increased expression of PIK3CA mRNA correlates with carcinoma tumors associated with cervix neoplasms (Int J Cancer 101: 427-33 (2002)). Increased expression of PIK3CA mRNA correlates with increased severity of carcinoma associated with ovarian neoplasms (Cancer Res 63: 4225-31 (2003)). Amplification of the PIK3CA gene correlates with squamous cell carcinoma associated with lung neoplasms (Genes Dev. 16: 984-93 (2002)). Increased expression of PIK3CA mRNA correlates with decreased apoptosis associated with ovarian neoplasms (Cancer Res 63: 4225-31 (2003)). Increased expression of PIK3CA mRNA correlates with squamous cell carcinoma associated with lung neoplasms (Genes Dev 16: 984-93 (2002)). Amplification of the PIK3CA mRNA correlates with squamous cell carcinoma associated with head and neck neoplasms (Cancer Res 61: 4122-9 (2001)). Increased expression of PIK3CA mRNA correlates with squamous cell carcinoma associated with lung neoplasms (Genes Dev. 16: 984-93 (2002)). Increased expression of PIK3CA protein may correlate with invasive form of colonic neoplasms (FASEB J 14: 2329-38 (2000)). Amplification of the PIK3CA gene correlates with squamous cell carcinoma associated with lung neoplasms (Gene Develop 16: 984-93 (2002)). Amplification of the PIK3CA gene correlates with carcinoma tumors associated with stomach neoplasms (Int J Cancer 104: 318-27 (2003)). Mutation in the PIK3CA gene correlates with lymphatic metastasis associated with breast neoplasms (Cancer Res 65: 2554-9 (2005)). Amplification of the PIK3CA gene correlates with squamous cell carcinoma associated with lung neoplasms (Genes Dev 16: 984-93 (2002)). Increased phosphatidylinositol 3-kinase activity of PIK3CA correlates with colonic neoplasms (Oncogene 19: 5083-90 (2000)). Increased expression of PIK3CA mRNA correlates with increased cell proliferation associated with ovarian neoplasms (Cancer Res 63: 4225-31 (2003)). Increased expression of PIK3CA mRNA correlates with esophageal neoplasms associated with squamous cell carcinoma (Cancer Res 63: 5691-6 (2003)). Increased expression of PIK3CA protein may cause increased cell proliferation associated with ovarian neoplasms (Nat Genet. 21: 99-102 (1999)). Increased expression of PIK3CA mRNA correlates with squamous cell carcinoma associated with head and neck neoplasms (Genes Dev 16: 984-93 (2002)). Amplification of the PIK3CA gene correlates with squamous cell carcinoma tumors associated with lung neoplasms (Eur J Cancer 35: 641-6 (1999)). Amplification of the PIK3CA gene correlates with papillomavirus infections associated with cervix neoplasms (Int J Cancer 101: 427-33 (2002)). Amplification of the PIK3CA gene correlates with ovarian neoplasms (Nat Genet. 21: 99-102 (1999)). Amplification of the PIK3CA gene correlates with squamous cell carcinoma associated with non-small-cell lung carcinoma (Cancer Res 62: 3636-40 (2002)). Amplification of the PIK3CA gene correlates with squamous cell carcinoma associated with head and neck neoplasms (Genes Dev. 16: 984-93 (2002)). Increased expression of PIK3CA mRNA may cause increased cell proliferation associated with cervix neoplasms (Oncogene 19: 2739-44 (2000)). Mutation in the PIK3CA gene correlates with glioblastoma associated with brain neoplasms (Cancer Res 64: 5048-50 (2004)). Increased phosphatidylinositol 3-kinase activity of PIK3CA may cause increased anti-apoptosis associated with squamous cell carcinoma (Cancer Res 61: 4122-9 (2001)). Increased expression of PIK3CA mRNA correlates with adenocarcinoma tumors associated with lung neoplasms (Cancer Res 61: 4122-9 (2001)). Increased expression of PIK3CA protein may correlate with invasive form of colonic neoplasms (FASEB 14: 2329-38 (2000)). Increased expression of PIK3CA mRNA correlates with squamous cell carcinoma associated with head and neck neoplasms (Genes Dev. 16: 984-93 (2002)). Increased expression of PIK3CA mRNA may cause increased angiogenesis associated with ovarian neoplasms (Cancer Res 63: 4225-31 (2003)). Increased expression of PIK3CA mRNA correlates with papillomavirus infections associated with cervix neoplasms (Int J Cancer 101: 427-33 (2002)). Increased expression of PIK3CA protein may cause increased anti-apoptosis associated with ovarian neoplasms (Nat Genet. 21: 99-102 (1999)). Increased expression of PIK3CA protein correlates with colonic neoplasms (Oncogene 19: 5083-90 (2000)). Increased phosphatidylinositol 3-kinase activity of PIK3CA may cause increased anti-apoptosis associated with lung neoplasms (Cancer Res 61: 4122-9 (2001)). Amplification of the PIK3CA gene correlates with squamous cell carcinoma associated with lung neoplasms (Genes Dev 16: 984-93 (2002)). Amplification of the PIK3CA gene correlates with squamous cell carcinoma associated with lung neoplasms (Cancer Res 62: 3636-40 (2002)). Amplification of the PIK3CA gene correlates with squamous cell carcinoma associated with head and neck neoplasms (Genes Dev 16: 984-93 (2002)). Increased expression of PIK3CA mRNA correlates with squamous cell carcinoma associated with head and neck neoplasms (Cancer Res 61:

4122-9 (2001)). Mutation in the PIK3CA gene correlates with oligodendroglioma associated with brain neoplasms (Cancer Res 64: 5048-50 (2004)). Amplification of the PIK3CA gene correlates with cervix neoplasms (Oncogene 19: 2739-44 (2000)). Increased expression of PIK3CA mRNA may cause increased anti-apoptosis associated with cervix neoplasms (Oncogene 19: 2739-44 (2000)). Mutation in the PIK3CA gene correlates with astrocytoma associated with brain neoplasms (Cancer Res 64: 5048-50 (2004)). (PhosphoSite®, Cell Signaling Technology (Danvers, Mass.), Human PSD™, Biobase Corporation, (Beverly, Mass.)).

PIK3R1 (P27986), phosphorylated at Y426, Y504, Y657, is among the proteins listed in this patent. PIK3R1, Phosphoinositide-3-kinase regulatory subunit polypeptide 1 (p85 alpha), involved in insulin receptor signaling, inhibition may be therapeutic for invasive breast cancer; mutation of corresponding gene is associated with type II diabetes and some cancers. This protein has potential diagnostic and/or therapeutic implications based on the following findings. Decreased insulin receptor signaling pathway associated with PIK3R1 correlates with type II diabetes mellitus (Diabetes 50: 1134-42 (2001)). Increased expression of PIK3R1 mutant protein may prevent increased cell motility associated with breast neoplasms (J Biol Chem 277: 3150-7 (2002)). Increased 1-kappaB kinase/NF-kappaB cascade associated with PIK3R1 may correlate with increased cell differentiation associated with colonic neoplasms (Biochem Biophys Res Commun 273: 853-8 (2000)). Deletion mutation in the PIK3R1 gene correlates with carcinoma tumors associated with colonic neoplasms (Cancer Res 61: 7426-9 (2001)). Decreased expression of PIK3R1 protein may prevent neoplasm metastasis associated with ovarian neoplasms (JBC 279: 6371-9 (2004)). Decreased expression of PIK3R1 protein may prevent neoplasm metastasis associated with ovarian neoplasms (J Biol Chem 279: 6371-9 (2004)). Decreased transmembrane receptor protein tyrosine kinase signaling pathway associated with PIK3R1 may correlate with decreased cell proliferation associated with breast neoplasms (Cancer Res 62: 4132-41 (2002)). Decreased expression of PIK3R1 protein may prevent increased cell migration associated with ovarian neoplasms (JBC 279: 6371-9 (2004)). Increased expression of PIK3R1 mutant protein may prevent increased cell motility associated with breast neoplasms (JBC 277: 3150-7 (2002)). Frameshift mutation in the PIK3R1 gene may correlate with Hodgkin's disease (Leukemia 16: 894-901 (2002)). Deletion mutation in the PIK3R1 gene correlates with carcinoma tumors associated with ovarian neoplasms (Cancer Res 61: 7426-9 (2001)). Decreased expression of PIK3R1 protein may prevent increased cell migration associated with ovarian neoplasms (J Biol Chem 279: 6371-9 (2004)). (PhosphoSite®, Cell Signaling Technology (Danvers, Mass.), Human PSD™, Biobase Corporation, (Beverly, Mass.)).

PIK3R2 (O00459), phosphorylated at Y423, Y577, is among the proteins listed in this patent. PIK3R2, Phosphoinositide-3-kinase regulatory polypeptide 2, a regulatory subunit of phosphatidylinositol 3-kinase that acts in signal transduction, cell motility and differentiation; tumorigenic fusion to USP8 gene may lead to chronic myeloproliferative disorder. (PhosphoSite®, Cell Signaling Technology (Danvers, Mass.), Human PSD™, Biobase Corporation, (Beverly, Mass.)).

PIK3R3 (Q92569), phosphorylated at Y184, Y202, is among the proteins listed in this patent. PIK3R3, Phosphoinositide-3-kinase regulatory subunit 3, binds insulin receptor (INSR) and insulin-like growth factor receptor (IGF1R), acts in cell cycle regulation, expression is induced in highly tumorigenic breast cancer cells treated with doxorubicin. (PhosphoSite®, Cell Signaling Technology (Danvers, Mass.), Human PSD™, Biobase Corporation, (Beverly, Mass.)).

PKCA (P17252), phosphorylated at Y194, is among the proteins listed in this patent. PKCA, Protein kinase C alpha isoform, important for cellular signaling, regulates cell proliferation and migration, and plays a role in RHO protein signal transduction; upregulated in liver of patients with non insulin dependent diabetes mellitus (NIDDM). This protein has potential diagnostic and/or therapeutic implications based on the following findings. Increased membrane localization of PRKCA may prevent increased cell migration associated with breast neoplasms (Biochem Biophys Res Commun 307: 839-46 (2003)). Decreased membrane localization of PRKCA may correlate with increased anti-apoptosis associated with prostatic neoplasms (Cell Growth Differ 7: 419-28 (1996)). Induced inhibition of the integrin binding of PRKCA may prevent increased cell migration associated with breast neoplasms (Mol Cell Biol. 22: 5897-911 (2002)). Decreased expression of PRKCA mRNA may cause decreased protein amino acid phosphorylation associated with breast neoplasms (J Clin Invest 95: 1906-15 (1995)). Increased expression of PRKCA protein may cause increased cell cycle arrest associated with pancreatic neoplasms (J Cell Sci 113: 3025-35 (2000)). Increased cytosol localization of PRKCA may correlate with adenoma associated with colonic neoplasms (Int J Cancer 80: 47-53 (1999)). Increased expression of PRKCA mRNA may cause increased cell proliferation associated with breast neoplasms (J Clin Invest 95: 1906-15 (1995)). Induced inhibition of the integrin binding of PRKCA may prevent increased cell migration associated with breast neoplasms (MCB 22: 5897-911 (2002)). Induced stimulation of the protein kinase C activity of PRKCA may cause increased apoptosis associated with prostatic neoplasms (J Biol Chem 278: 33753-62 (2003)). Increased expression of PRKCA protein may cause increased cell cycle arrest associated with pancreatic neoplasms (J Cell Sci 113: 3025-35 (2000)). Induced stimulation of the protein kinase C activity of PRKCA may cause drug-resistant form of colonic neoplasms (Biochem Pharmacol 48: 375-81 (1994)). Increased expression of PRKCA protein may correlate with increased Ras protein signal transduction associated with colonic neoplasms (Cancer Res 53: 2762-70 (1993)). Increased protein kinase C activity of PRKCA may correlate with increased cytokine and chemokine mediated signaling pathway associated with multiple myeloma (JBC 277: 7875-81 (2002)). Induced inhibition of the integrin binding of PRKCA may prevent increased cell migration associated with breast neoplasms (Mol Cell Biol 22: 5897-911 (2002)). Lack of expression of PRKCA protein correlates with basal cell carcinoma tumors associated with skin neoplasms (Cancer Res 63: 4692-7 (2003)). Increased expression of PRKCA mRNA correlates with drug-resistant form of breast neoplasms (Br J Cancer 88: 1400-2 (2003)). Increased proteolysis of PRKCA may correlate with Alzheimer disease (Proc Natl Acad Sci USA 95: 5562-7 (1998)). Decreased expression of PRKCA mRNA may cause drug-sensitive form of breast neoplasms (J Clin Invest 95: 1906-15 (1995)). Decreased expression of PRKCA protein may correlate with small cell carcinoma (Cancer Res 51: 5514-9 (1991)). Increased proteolysis of PRKCA may correlate with Alzheimer disease (PNAS 95: 5562-7 (1998)). Decreased expression of PRKCA protein may correlate with drug-resistant form of small cell carcinoma (Cell Growth Differ 7: 1507-12 (1996)). Decreased expression of PRKCA protein correlates with advanced stage or high grade form of colorectal neoplasms (Biochem Mol Biol Int 44: 523-8 (1998)). Induced inhibition of the integrin binding of PRKCA may prevent increased cell migration associated with breast neoplasms (Mol. Cell. Biol 22: 5897-911 (2002)). Increased membrane localization of PRKCA correlates with type II diabetes mellitus (J Clin Invest 95: 2938-44 (1995)). Decreased expression of PRKCA protein may correlate with drug-resistant form of ovarian neoplasms (Int J Cancer 62: 457-60 (1995)). Increased proteolysis of PRKCA may correlate with Alzheimer disease (Proc Natl Acad Sci USA 95: 5562-7 (1998)). Decreased expression of PRKCA protein may cause decreased cell proliferation associated with pancreatic neoplasms (Gut 39: 255-61 (1996)). Induced inhibition of the integrin binding of PRKCA may prevent increased cell migration associated with breast neoplasms (Mol. Cell. Biol. 22: 5897-911 (2002)). Induced stimulation of the protein kinase C activity of PRKCA may cause increased apoptosis associated with prostatic neoplasms (JBC 278: 33753-62 (2003)). Increased protein kinase C activity of PRKCA may correlate with increased cytokine and chemokine mediated signaling pathway associated with multiple myeloma (J Biol Chem 277: 7875-81 (2002)). Increased protein kinase C activity of PRKCA may correlate with increased cell migration associated with multiple myeloma (JBC 277: 7875-81 (2002)). Increased expression of PRKCA mRNA correlates with decreased cell proliferation associated with breast neoplasms (J Cell Physiol 172: 306-13 (1997)). Induced inhibition of the protein kinase C activity of PRKCA may correlate with drug-resistant form of colonic neoplasms (Br J Cancer 78: 1283-7 (1998)). Increased membrane localization of PRKCA may correlate with increased apoptosis associated with prostatic neoplasms (Cell Growth Differ 7: 419-28 (1996)). Increased protein kinase C activity of PRKCA may correlate with increased cell migration associated with multiple myeloma (J Biol Chem 277: 7875-81 (2002)). Increased membrane localization of PRKCA may correlate with small cell carcinoma (Cell Growth Differ 6: 1627-34 (1995)). Decreased expression of PRKCA mRNA may prevent increased cell proliferation associated with lung neoplasms (Exp Cell Res 250: 253-63 (1999)). (PhosphoSite®, Cell Signaling Technology (Danvers, Mass.), Human PSD™, Biobase Corporation, (Beverly, Mass.)).

PKCB (P05771), phosphorylated at Y194, is among the proteins listed in this patent. PKCB, Protein kinase C beta 1, serine/threonine kinase that acts in the glucose response and proliferation, expression is altered in ALS, colon adenoma, heart failure, Huntington's disease and diabetic nephropathy; rat Prkcb1 is involved in diabetic nephropathy. This protein has potential diagnostic and/or therapeutic implications based on the following findings. Increased expression of PRKCB1 protein correlates with invasive form of stomach neoplasms (J Natl Cancer Inst 85: 402-7 (1993)). Increased expression of PRKCB1 protein may cause increased caspase activation associated with myeloid leukemia (Oncogene 19: 3941-7 (2000)). Decreased expression of PRKCB1 protein may prevent stomach neoplasms (Oncogene 21: 6113-22 (2002)). Increased expression of PRKCB1 in mast cells may correlate with increased phagocytosis, engulfment associated with *Escherichia coli* infections (J Leukoc Biol 66: 1031-8 (1999)). Decreased membrane fraction localization of PRKCB1 correlates with adenoma tumors associated with colonic neoplasms (Int J Cancer 80: 47-53 (1999)). Increased expression of PRKCB1 in nephron, glomerulus correlates with defective nephron, glomerulus development associated with diabetic nephropathies (Kidney Int 66: 1107-14 (2004)). Increased protein kinase C activity of PRKCB1 may cause increased hyaluronan biosynthetic process associated with Graves' disease (J Cell Biochem 82: 58-67 (2001)). Decreased expression of PRKCB1 mRNA correlates with colonic neoplasms (Mol Carcinog 11: 197-203 (1994)). Increased expression of PRKCB1 protein correlates with non-familial form of amyotrophic lateral sclerosis (J Neurochem 85: 432-42 (2003)). Increased protein kinase C activity of PRKCB1 causes increased entry of virus into host cell associated with influenza (J Virol 77: 460-9 (2003)). Increased expression of PRKCB1 in mast cells may correlate with increased detection of bacterium associated with *Escherichia coli* infections (J Leukoc Biol 66: 1031-8 (1999)). (PhosphoSite®, Cell Signaling Technology (Danvers, Mass.), Human PSD™, Biobase Corporation, (Beverly, Mass.)).

PKCD (Q05655), phosphorylated at Y374, is among the proteins listed in this patent. PKCD, Protein kinase C delta, calcium-independent serine-threonine kinase, promotes apoptosis, phospholipid scrambling, and lamin cleavage, inhibits histamine signaling in myeloid cells, may function as a tumor suppressor. This protein has potential diagnostic and/or therapeutic implications based on the following findings. Induced inhibition of the protein kinase activity of PRKCD may prevent increased anti-apoptosis associated with non-small-cell lung carcinoma (Cancer Res 63: 780-6 (2003)). Decreased cytosol localization of PRKCD may correlate with increased cell proliferation associated with prostatic neoplasms (Biochem Biophys Res Commun 283: 806-12 (2001)). Decreased expression of PRKCD mRNA may correlate with malignant form of neuroblastoma (EMBO J. 10: 1119-25 (1991)). Increased expression of PRKCD mRNA may prevent increased cell proliferation associated with glioma (Biochem Biophys Res Commun 201: 363-72 (1994)). Increased protein binding of PRKCD may prevent increased insulin-like growth factor receptor signaling pathway associated with renal cell carcinoma (JBC 275: 20700-6 (2000)). Decreased endoproteolysis of PRKCD may prevent increased anti-apoptosis associated with prostatic neoplasms (J Clin Invest 109: 827-36 (2002)). Decreased endoproteolysis of PRKCD may prevent increased anti-apoptosis associated with prostatic neoplasms (Cancer Res 60: 6590-6 (2000)). Increased expression of PRKCD mRNA may prevent increased anti-apoptosis associated with prostatic neoplasms (J Biol Chem 275: 7574-82 (2000)). Increased protein binding of PRKCD may prevent increased insulin-like growth factor receptor signaling pathway associated with renal cell carcinoma (J Biol Chem 275: 20700-6 (2000)). Decreased membrane fraction localization of PRKCD may correlate with increased cell proliferation associated with prostatic neoplasms (Biochem Biophys Res Commun 283: 806-12 (2001)). Increased expression of PRKCD mRNA may prevent increased anti-apoptosis associated with prostatic neoplasms (JBC 275: 7574-82 (2000)). Increased membrane fraction localization of PRKCD correlates with increased response to hypoxia associated with anoxia (J Cell Physiol 188: 223-35 (2001)). Increased expression of PRKCD protein may cause decreased severity of neoplastic processes associated with colonic neoplasms (Int J Cancer 113: 42-53 (2005)). Decreased expression of PRKCD mRNA may correlate with malignant form of neuroblastoma (EMBO 10: 1119-25 (1991)). Increased proteolysis of PRKCD may cause increased cell differentiation associated with melanoma (Biochem Pharmacol 55: 1691-9 (1998)). Decreased expression of PRKCD mRNA may correlate with malignant form of neuroblastoma (EMBO J. 10: 1119-25 (1991)). (PhosphoSite®, Cell Signaling Technology (Danvers, Mass.), Human PSD™, Biobase Corporation, (Beverly, Mass.)).

PKCT (Q04759), phosphorylated at Y545, is among the proteins listed in this patent. PKCT, Protein kinase C theta, involved in T cell activation and protection from apoptosis, may play a role in insulin and multidrug resistance; rat Pkcq may play roles in hyperglycemia, hypertriglyceridemia and insulin resistance. This protein has potential diagnostic and/or therapeutic implications based on the following findings. Increased expression of PRKCQ mRNA correlates with recurrence associated with acute myelocytic leukemia (Leukemia 10: 426-33 (1996)). Decreased expression of PRKCQ protein correlates with insulin resistance associated with type II diabetes mellitus (Endocrinology 141: 2773-8 (2000)). Increased expression of PRKCQ protein correlates with sarcoma associated with gastrointestinal neoplasms (Cancer Res 64: 5127-31 (2004)). Decreased expression of PRKCQ protein correlates with decreased glycogen biosynthetic process associated with type II diabetes mellitus (Endocrinology 141: 2773-8 (2000)). Decreased expression of PRKCQ in skeletal muscle correlates with insulin resistance associated with obesity (Diabetes 49: 1353-8 (2000)). (PhosphoSite®, Cell Signaling Technology (Danvers, Mass.), Human PSD™, Biobase Corporation, (Beverly, Mass.)).

PLCG1 (P19174), phosphorylated at Y186, Y210, Y217, Y379, Y428, Y496, Y506, Y509, Y833, is among the proteins listed in this patent. PLCG1, Phospholipase C gamma 1, catalyzes phosphatidylinositol 4,5-bisphosphate hydrolysis, involved in various growth factor and T-cell antigen receptor signaling pathways, upregulated in breast and colorectal carcinomas. This protein has potential diagnostic and/or therapeutic implications based on the following findings. Increased expression of PLCG1 protein correlates with carcinoma tumors associated with colorectal neoplasms (Cancer 73: 36-41 (1994)). Increased phosphorylation of PLCG1 correlates with colorectal neoplasms associated with adenomatous polyposis coli (J Cell Biochem 55: 477-85 (1994)). Increased expression of PLCG1 protein correlates with carcinoma tumors associated with breast neoplasms (PNAS 88: 10435-9 (1991)). Increased expression of PLCG1 protein correlates with carcinoma tumors associated with breast neoplasms (Proc Natl Acad Sci USA 88: 10435-9 (1991)). Increased expression of PLCG1 protein correlates with carcinoma tumors associated with colonic neoplasms (Mol Carcinog 12: 146-52 (1995)). Increased expression of PLCG1 protein correlates with adenoma tumors associated with adenomatous polyposis coli (Cancer Res 54: 2240-4 (1994)). Increased expression of PLCG1 protein correlates with colorectal neoplasms associated with adenomatous polyposis coli (J Cell Biochem 55: 477-85 (1994)). Increased expression of PLCG1 protein correlates with carcinoma tumors associated with breast neoplasms (Proc Natl Acad Sci USA 88: 10435-9 (1991)). (PhosphoSite®, Cell Signaling Technology (Danvers, Mass.), Human PSD™, Biobase Corporation, (Beverly, Mass.)).

PLCG2 (P16885), phosphorylated at Y482, Y495, Y811, Y818, Y1137, is among the proteins listed in this patent. PLCG2, Phospholipase C gamma 2 (phosphatidylinositol-specific), hydrolyzes phosphatidyl inositol upon activation by tyrosine kinases, leading to Ca2+ release and PKC activation; plays a role in platelet activation, has a likely role in B cell receptor signaling. (PhosphoSite®, Cell Signaling Technology (Danvers, Mass.), Human PSD™, Biobase Corporation, (Beverly, Mass.)).

PLK1 (P53350), phosphorylated at Y217, is among the proteins listed in this patent. PLK1, Polo-like kinase 1, a serine-threonine protein kinase that plays a role in mitotic cell cycle control, meiotic spindle assembly, maturation of mitotic centrosomes, and cell proliferation, upregulated in a wide variety of cancers. This protein has potential diagnostic and/or therapeutic implications based on the following findings. Increased expression of PLK1 mRNA correlates with carcinoma tumors associated with stomach neoplasms (Proc Natl Acad Sci USA 91: 1736-40 (1994)). Increased expression of PLK1 mRNA correlates with leiomyosarcoma (PNAS 91: 1736-40 (1994)). Increased expression of PLK1 mRNA correlates with carcinoma tumors associated with lung neoplasms (Proc Natl Acad Sci USA 91: 1736-40 (1994)). Increased expression of PLK1 mRNA correlates with carcinoma tumors associated with esophageal neoplasms (PNAS 91: 1736-40 (1994)). Decreased expression of PLK1 mRNA may prevent increased cell proliferation associated with breast neoplasms (Anticancer Res 24: 555-62 (2004)). Increased expression of PLK1 mRNA correlates with carcinoma tumors associated with colonic neoplasms (Proc Natl Acad Sci USA 91: 1736-40 (1994)). Increased expression of PLK1 mRNA correlates with carcinoma tumors associated with lung neoplasms (PNAS 91: 1736-40 (1994)). Increased expression of PLK1 protein correlates with increased cell proliferation associated with thyroid neoplasms (Br J Cancer 90: 414-8 (2004)). Increased expression of PLK1 mRNA correlates with leiomyosarcoma (Proc Natl Acad Sci USA 91: 1736-40 (1994)). Induced inhibition of PLK1 protein may prevent prostatic neoplasms (FASEB 18: 5-7 (2004)). Increased expression of PLK1 protein correlates with more severe form of ovarian neoplasms (Br J Cancer 90: 815-21 (2004)). Increased expression of PLK1 mRNA correlates with carcinoma tumors associated with esophageal neoplasms (Proc Natl Acad Sci USA 91: 1736-40 (1994)). Increased expression of PLK1 mRNA correlates with carcinoma tumors associated with stomach neoplasms (PNAS 91: 1736-40 (1994)). Increased expression of PLK1 mRNA correlates with carcinoma tumors associated with stomach neoplasms (Proc Natl Acad Sci USA 91: 1736-40 (1994)). Decreased expression of PLK1 mRNA may prevent increased cell proliferation associated with non-small-cell lung carcinoma (Oncogene 21: 3162-71 (2002)). Increased expression of PLK1 mRNA correlates with carcinoma tumors associated with colonic neoplasms (PNAS 91: 1736-40 (1994)). Increased expression of PLK1 mRNA correlates with increased occurrence of death associated with non-small-cell lung carcinoma (Oncogene 14: 543-9 (1997)). Decreased expression of PLK1 protein may prevent increased cell proliferation associated with neoplasms (J Natl Cancer Inst 94: 1863-77 (2002)). Increased expression of PLK1 mRNA correlates with carcinoma tumors associated with esophageal neoplasms (Proc Natl Acad Sci USA 91: 1736-40 (1994)). Increased expression of PLK1 mRNA correlates with non-Hodgkin's lymphoma (PNAS 91: 1736-40 (1994)). Decreased expression of PLK1 mRNA may prevent increased cell proliferation associated with bladder neoplasms (J Clin Invest 115: 978-85 (2005)). Increased expression of PLK1 mRNA correlates with carcinoma tumors associated with lung neoplasms (Proc Natl Acad Sci USA 91: 1736-40 (1994)). Increased expression of PLK1 mRNA correlates with non-Hodgkin's lymphoma (Proc Natl Acad Sci USA 91: 1736-40 (1994)). Decreased expression of PLK1 protein may prevent increased cell proliferation associated with neoplasms (Oncogene 22: 69-80 (2003)). Increased expression of PLK1 protein correlates with carcinoma tumors associated with ovarian neoplasms (Br J Cancer 90: 815-21 (2004)). Increased expression of PLK1 protein correlates with invasive form of carcinoma (Cancer Lett 169: 41-9 (2001)). Induced inhibition of PLK1 protein may prevent prostatic neoplasms (FASEB J 18: 5-7 (2004)). Increased expression of PLK1 protein correlates with increased severity of lymphoma associated with thyroid neoplasms (Anticancer Res 24: 259-63 (2004)). Increased expression of PLK1 protein correlates with papillary carcinoma associated with thyroid neoplasms (Br J Cancer 90: 414-8 (2004)). Increased expression of PLK1 mRNA correlates with increased occurrence of death associated with hepatoblastoma (Oncogene 23: 5901-11 (2004)). Increased expression of PLK1 mRNA correlates with non-Hodgkin's lymphoma (Proc Natl Acad Sci USA 91: 1736-40 (1994)). Increased expression of PLK1 protein correlates with disease progression associated with thyroid neoplasms (Br J Cancer 90: 414-8 (2004)). Decreased expression of PLK1 protein may prevent increased anti-apoptosis associated with neoplasms (J Natl Cancer Inst 94: 1863-77 (2002)). Increased expression of PLK1 mRNA correlates with leiomyosarcoma (Proc Natl Acad Sci USA 91: 1736-40 (1994)). Increased expression of PLK1 mRNA correlates with carcinoma tumors associated with colonic neoplasms (Proc Natl Acad Sci USA 91: 1736-40 (1994)). (PhosphoSite®, Cell Signaling Technology (Danvers, Mass.), Human PSD™, Biobase Corporation, (Beverly, Mass.)).

PRPF8 (Q6P2Q9), phosphorylated at Y394, Y1432, Y2062, Y2091, Y2102, is among the proteins listed in this patent. PRPF8, PRP8 pre-mRNA processing factor 8 homolog, a component of U5 snRNP complex, involved in spliceosome assembly and mRNA splice site selection; mutation of the gene is associated with autosomal dominant retinitis pigmentosa type 13. This protein has potential diagnostic and/or therapeutic implications based on the following findings. Missense mutation in the PRPF8 gene correlates with autosomal dominant form of retinitis pigmentosa (Hum Mol Genet. 10: 1555-62 (2001)). (PhosphoSite®, Cell Signaling Technology (Danvers, Mass.), Human PSD™, Biobase Corporation, (Beverly, Mass.)).

PTEN (P60484), phosphorylated at Y174, Y176, Y177, Y178, Y180, is among the proteins listed in this patent. PTEN, Phosphatase and tensin homolog, phosphatidylinositol phosphatase that acts as tumor suppressor and is involved in cell cycle control, development, and apoptosis; associated with Cowden disease, Bannayan-Zonana syndrome, diabetes II, and various cancers. This protein has potential diagnostic and/or therapeutic implications based on the following findings. Mutation in the PTEN gene correlates with advanced stage or high grade form of renal cell carcinoma (Int J Cancer 91: 219-24 (2001)). Increased expression of PTEN mutant protein may cause decreased apoptosis associated with glioma (Br J Cancer 86: 1586-91 (2002)). Missense mutation in the PTEN gene may cause decreased apoptosis associated with glioma (Br J Cancer 86: 1586-91 (2002)). Lack of expression of PTEN protein may cause abnormal regulation of phosphoinositide 3-kinase activity associated with glioma (J Cell Physiol 201: 374-84 (2004)). Mutation in the PTEN gene correlates with breast neoplasms associated with multiple hamartoma syndrome (Am J Hum Genet. 61: 1254-60 (1997)). Increased expression of PTEN protein may cause increased cell cycle arrest associated with neuroblastoma (Proc Natl Acad Sci USA 95: 15406-11 (1998)). Mutation in the PTEN promoter correlates with multiple hamartoma syndrome (Am J Hum Genet. 73: 404-11 (2003)). Decreased expression of PTEN mRNA correlates with thyroid neoplasms (Oncogene 19: 3146-55 (2000)). Nonsense mutation in the PTEN gene correlates with chromosomal instability associated with colorectal neoplasms (Hum Mol Genet. 9: 283-7 (2000)). Decreased expression of PTEN mRNA correlates with advanced stage or high grade form of prostatic neoplasms (Proc Natl Acad Sci USA 95: 5246-50 (1998)). Mutation in the PTEN gene may cause glioblastoma (Proc Natl Acad Sci USA 95: 15587-91 (1998)). Decreased expression of PTEN mRNA correlates with advanced stage or high grade form of prostatic neoplasms (Proc Natl Acad Sci USA 95: 5246-50 (1998)). Increased expression of PTEN mutant protein may cause increased protein kinase B signaling cascade associated with glioma (Br J Cancer 86: 1586-91 (2002)). Single nucleotide polymorphism in the PTEN gene correlates with type II diabetes mellitus (FEBS Lett 554: 450-4 (2003)). Mutation in the PTEN gene may cause prostatic neoplasms (Proc Natl Acad Sci USA 95: 15587-91 (1998)). Haploinsufficiency of the PTEN gene correlates with carcinoma associated with stomach neoplasms (Int J Cancer 104: 318-27 (2003)). Loss of heterozygosity at the PTEN gene correlates with non-familial form of breast neoplasms (Br J Cancer 79: 718-23 (1999)). Decreased expression of PTEN protein may cause increased cell-cell adhesion associated with colonic neoplasms (Oncogene 21: 1450-60 (2002)). Decreased expression of PTEN protein causes increased protein kinase B signaling cascade associated with ganglioneuroma (Am J Hum Genet. 73: 1191-8 (2003)). Increased expression of PTEN protein may cause increased response to drug associated with glioma (Oncogene 18: 3936-43 (1999)). Decreased expression of PTEN protein correlates with increased occurrence of death associated with liver neoplasms (Int J Cancer 100: 152-7 (2002)). Increased expression of PTEN protein may prevent increased protein kinase B signaling cascade associated with neuroblastoma (PNAS 95: 15406-11 (1998)). Hypermethylation of the PTEN promoter correlates with increased incidence of malignant form of breast neoplasms (Int J Cancer 112: 407-10 (2004)). Splice site mutation in the PTEN gene correlates with hepatocellular carcinoma associated with liver neoplasms (Oncogene 18: 3181-5 (1999)). Increased expression of PTEN protein causes increased anoikis associated with glioma (Oncogene 20: 6669-78 (2001)). Decreased expression of PTEN protein may cause abnormal apoptosis associated with hematologic neoplasms (Hum Mol Genet. 8: 185-93 (1999)). Increased expression of PTEN protein may cause increased response to ionizing radiation associated with glioma (Oncogene 18: 3936-43 (1999)). Decreased expression of PTEN mRNA correlates with carcinoma associated with stomach neoplasms (Int J Cancer 104: 318-27 (2003)). Mutation in the PFEN promoter correlates with abnormal protein kinase B signaling cascade associated with multiple hamartoma syndrome (Am J Hum Genet. 73: 404-11 (2003)). Mutation in the PTEN gene correlates with adenocarcinoma associated with cervix neoplasms (Cancer Lett 210: 57-62 (2004)). Decreased expression of PTEN mRNA correlates with advanced stage or high grade form of prostatic neoplasms (PNAS 95: 5246-50 (1998)). Loss of function mutation in the PTEN gene correlates with chromosomal instability associated with colorectal neoplasms (Hum Mol Genet. 9: 283-7 (2000)). Decreased expression of PTEN protein correlates with hepatitis C associated with hepatocellular carcinoma (Int J Cancer 100: 152-7 (2002)). Increased expression of PTEN protein may cause increased apoptosis associated with breast neoplasms (Oncogene 18: 7034-45 (1999)). Increased expression of PTEN protein may cause increased cell death associated with breast neoplasms (Cancer Res 59: 5808-14 (1999)). Deletion mutation in the PFEN gene correlates with renal cell carcinoma (Int J Cancer 91: 219-24 (2001)). Decreased membrane localization of PTEN correlates with renal cell carcinoma (Int J Cancer 99: 53-7 (2002)). Deletion mutation in the PTEN gene correlates with non-familial form of breast neoplasms (Cancer Res 57: 3657-9 (1997)). Deletion mutation in the PFEN gene correlates with multiple hamartoma syndrome associated with breast neoplasms (Cancer Res 57: 3657-9 (1997)). Missense mutation in the PTEN gene may cause meningioma associated with glioma (Br J Cancer 86: 1586-91 (2002)). Increased expression of PTEN protein may prevent malignant form of melanoma (Mol Med 8: 451-61 (2002)). Mutation in the PTEN gene may cause glioblastoma (PNAS 95: 15587-91 (1998)). Increased expression of PTEN protein may prevent increased protein kinase B signaling cascade associated with neuroblastoma (Proc Natl Acad Sci USA 95: 15406-11 (1998)). Increased expression of PTEN protein may cause increased cell cycle arrest associated with bladder neoplasms (Oncogene 19: 5406-12 (2000)). Increased expression of PTEN protein correlates with papilloma associated with laryngeal neoplasms (Mol Med 9: 77-84 (2003)). Increased expression of PFEN protein may prevent invasive form of glioma (Cancer Lett 214: 205-13 (2004)). Mutation in the PTEN gene may cause prostatic neoplasms (Proc Natl Acad Sci USA 95: 15587-91 (1998)). Deletion mutation in the PFEN gene correlates with myelodysplastic syndromes (Leukemia 20: 230-8 (2006)). Frameshift mutation in the PTEN gene correlates with endometrial neoplasms associated with hereditary nonpolyposis colorectal neoplasms (Hum Mol Genet. 11: 445-50 (2002)). Missense mutation in the PTEN gene may cause increased protein kinase B signaling cascade associated with glioma (Br J Cancer 86: 1586-91 (2002)). Decreased expression of PTEN mRNA may correlate with small cell carcinoma associated with lung neoplasms (Oncogene 17: 1557-65 (1998)). Increased expression of PTEN protein may cause drug-resistant form of bladder neoplasms (Oncogene 19: 5406-12 (2000)). Increased expression of PTEN protein may prevent increased angiogenesis associated with melanoma (Mol Med 8: 451-61 (2002)). Decreased expression of PTEN protein correlates with non-small-cell lung carcinoma associated with lung neoplasms (Cancer 100: 1673-82 (2004)). Frameshift mutation in the PTEN gene correlates with colorectal neoplasms (Cancer Lett 174: 189-94 (2001)). Decreased expression of PTEN protein correlates with increased occurrence of death associated with hepatocellular carcinoma (Int J Cancer 100: 152-7 (2002)). Decreased expression of PTEN protein correlates with increased severity of hepatocellular carcinoma associated with liver neoplasms (Int J Cancer 100: 152-7 (2002)). Missense mutation in the PT EN gene correlates with hepatocellular carcinoma associated with liver neoplasms (Oncogene 18: 3181-5 (1999)). Decreased expression of PTEN protein correlates with liver cirrhosis associated with liver neoplasms (Int J Cancer 100: 152-7 (2002)). Increased expression of PTEN protein may prevent invasive form of bladder neoplasms (Oncogene 23: 6788-97 (2004)). Lack of expression of PTEN protein correlates with bone neoplasms associated with prostatic neoplasms (Cancer Res 62: 2942-50 (2002)). Mutation in the PTEN gene correlates with malignant form of renal cell carcinoma (Int J Cancer 91: 219-24 (2001)). Mutation in the PTEN gene may cause prostatic neoplasms (PNAS 95: 15587-91 (1998)). Missense mutation in the PTEN gene causes arteriovenous malformations associated with multiple abnormalities (Hum Mol Genet. 9: 765-8 (2000)). Decreased expression of PTEN protein correlates with non-familial form of colorectal neoplasms (Cancer Res 64: 3014-21 (2004)). Increased expression of PFEN protein may cause increased cell cycle arrest associated with endometrial neoplasms (Cancer Res 61: 4569-75 (2001)). Mutation in the PTEN gene may cause breast neoplasms (Proc Natl Acad Sci USA 95: 15587-91 (1998)). Lack of expression of PTEN protein correlates with increased protein kinase B signaling cascade associated with glioblastoma (Cancer Res 63: 2742-6 (2003)). Increased expression of PTEN protein may prevent increased protein kinase B signaling cascade associated with neuroblastoma (Proc Natl Acad Sci USA 95: 15406-11 (1998)). Decreased expression of PTEN protein causes late onset form of ganglioneuroma (Am J Hum Genet. 73: 1191-8 (2003)). Hypermethylation of the PTEN promoter correlates with non-familial form of colorectal neoplasms (Cancer Res 64: 3014-21 (2004)). Increased expression of PTEN protein may cause increased cell cycle arrest associated with neuroblastoma (Proc Natl Acad Sci USA 95: 15406-11 (1998)). Decreased expression of PTEN protein correlates with thyroid neoplasms (Oncogene 19: 3146-55 (2000)). Hypermethylation of the PTEN promoter correlates with chromosomal instability associated with colorectal neoplasms (Cancer Res 64: 3014-21 (2004)). Alternative form of PTEN mRNA correlates with non-familial form of breast neoplasms (Hum Mol Genet. 15: 777-87 (2006)). Decreased nucleus localization of PTEN may correlate with breast neoplasms (Cancer Res 63: 282-6 (2003)). Increased expression of PTEN protein may prevent decreased apoptosis associated with melanoma (Mol Med 8: 451-61 (2002)). Mutation in the PTEN gene causes late onset form of ganglioneuroma (Am J Hum Genet. 73: 1191-8 (2003)). Mutation in the PTEN gene correlates with multiple hamartoma syndrome associated with breast neoplasms (Am J Hum Genet. 61: 1254-60 (1997)). Mutation in the PTEN gene may cause breast neoplasms (Proc Natl Acad Sci USA 95: 15587-91 (1998)). Point mutation in the PTEN gene causes small cell carcinoma associated with lung neoplasms (Oncogene 17: 475-9 (1998)). Increased expression of PTEN protein may cause increased cell cycle arrest associated with neuroblastoma (PNAS 95: 15406-11 (1998)). Increased expression of PTEN protein may correlate with insulin resistance associated with type II diabetes mellitus (FEBS Lett 554: 450-4 (2003)). Loss of heterozygosity at the PTEN gene correlates with renal cell carcinoma (Int J Cancer 91: 219-24 (2001)). Mutation in the PTEN gene correlates with invasive form of renal cell carcinoma (Int J Cancer 91: 219-24 (2001)). Decreased expression of PTEN protein correlates with chromosomal instability associated with colorectal neoplasms (Cancer Res 64: 3014-21 (2004)). Nonsense mutation in the PFEN gene causes multiple hamartoma syndrome (Nat Genet. 16: 64-7 (1997)). Increased expression of PTEN protein may cause decreased cell proliferation associated with breast neoplasms (Hum Mol Genet. 10: 605-16 (2001)). Mutation in the PFEN gene may cause breast neoplasms (PNAS 95: 15587-91 (1998)). Missense mutation in the PTEN gene causes hypertrophy associated with multiple abnormalities (Hum Mol Genet. 9: 765-8 (2000)). Increased expression of PTEN protein may prevent increased protein kinase B signaling cascade associated with pancreatic neoplasms (Biochem Biophys Res Commun 301: 50-3 (2003)). Increased expression of PTEN mutant protein may cause increased cell proliferation associated with glioma (Br J Cancer 86: 1586-91 (2002)). Splice site mutation in the PTEN gene correlates with renal cell carcinoma (Int J Cancer 91: 219-24 (2001)). Alternative form of PTEN mRNA correlates with multiple hamartoma syndrome (Hum Mol Genet. 15: 777-87 (2006)). Decreased expression of PTEN protein correlates with renal cell carcinoma (Int J Cancer 99: 53-7 (2002)). Mutation in the PTEN gene may cause endometrial neoplasms (Cancer Res 57: 4736-8 (1997)). Splice site mutation in the PTEN gene correlates with hepatocellular carcinoma (Oncogene 18: 3181-5 (1999)). Deletion mutation in the PTEN gene correlates with increased incidence of advanced stage or high grade form of glioma (Oncogene 16: 3331-5 (1998)). Missense mutation in the PTEN gene causes multiple hamartoma syndrome (Nat Genet. 16: 64-7 (1997)). Decreased expression of PTEN protein correlates with liver cirrhosis associated with hepatocellular carcinoma (Int J Cancer 100: 152-7 (2002)). Increased expression of PTEN protein may cause decreased cell cycle associated with breast neoplasms (Hum Mol Genet. 10: 599-604 (2001)). Missense mutation in the PTEN gene correlates with renal cell carcinoma (Int J Cancer 91: 219-24 (2001)). Increased expression of PTEN protein may prevent increased cell proliferation associated with bladder neoplasms (Oncogene 19: 5406-12 (2000)). Missense mutation in the PTEN gene correlates with hepatocellular carcinoma (Oncogene 18: 3181-5 (1999)). Increased expression of PTEN protein may correlate with decreased insulin receptor signaling pathway associated with type II diabetes mellitus (FEBS Lett 554: 450-4 (2003)). Decreased expression of PTEN protein correlates with non-small-cell lung carcinoma (Cancer 100: 1673-82 (2004)). Decreased expression of PTEN mRNA may correlate with non-small-cell lung carcinoma associated with lung neoplasms (Oncogene 17: 1557-65 (1998)). Deletion mutation in the PTEN gene correlates with multiple hamartoma syndrome (Am J Hum Genet. 73: 404-11 (2003)). Mutation in the PTEN gene may cause glioblastoma (Proc Natl Acad Sci USA 95: 15587-91 (1998)). Decreased expression of PTEN protein correlates with multiple hamartoma syndrome (Am J Hum Genet. 73: 404-11 (2003)). Mutation in the PTEN gene correlates with non-familial form of colorectal neoplasms (Oncogene 23: 617-28 (2004)). Missense mutation in the PTEN gene causes lipomatosis associated with multiple abnormalities (Hum Mol Genet. 9: 765-8 (2000)). Increased expression of PTEN protein may prevent increased cell proliferation associated with prostatic neoplasms (Oncogene 23: 786-94 (2004)). Mutation in the PTEN gene correlates with chromosomal instability associated with colorectal neoplasms (Oncogene 23: 617-28 (2004)). Lack of expression of PTEN protein correlates with malignant form of prostatic neoplasms (Cancer Res 62: 2942-50 (2002)). (PhosphoSite®, Cell Signaling Technology (Danvers, Mass.), Human PSD™, Biobase Corporation, (Beverly, Mass.)).

Rap1a (P62834), phosphorylated at Y159, is among the proteins listed in this patent. Rap1a, RAP1A member of RAS oncogene family, a monomeric GTPase that activates Rac and inhibits cell proliferation; corresponding gene acts as a tumor suppressor and is downregulated in fibrosarcomas and the adenocarcinoma of the salivary gland. This protein has potential diagnostic and/or therapeutic implications based on the following findings. Decreased GTPase activity of RAP1A may cause tuberous sclerosis (J Biol Chem 270: 16409-14 (1995)). Decreased GTPase activity of RAP1A may cause tuberous sclerosis (JBC 270: 16409-14 (1995)). Increased expression of RAP1A mRNA may prevent drug-induced form of lung neoplasms (Mol Carcinog 17: 84-91 (1996)). (PhosphoSite®, Cell Signaling Technology (Danvers, Mass.), Human PSD™, Biobase Corporation, (Beverly, Mass.)).

RAPGEF4 (Q8WZA2), phosphorylated at Y857, Y986, is among the proteins listed in this patent. RAPGEF4, Rap guanine nucleotide exchange factor 4, may play a role in the regulation of cell growth and differentiation. (PhosphoSite®, Cell Signaling Technology (Danvers, Mass.), Human PSD™, Biobase Corporation, (Beverly, Mass.)).

RPS3 (P23396), phosphorylated at Y166, Y167, is among the proteins listed in this patent. RPS3, Ribosomal protein S3, a putative small 40S ribosomal subunit component, has DNA endonuclease activity, binds DNA base excision repair proteins APEX1 and OGG1, endonuclease activity is absent in Xeroderma pigmentosum group D patients. (PhosphoSite®, Cell Signaling Technology (Danvers, Mass.), Human PSD™, Biobase Corporation, (Beverly, Mass.)).

RSK2 (P51812), phosphorylated at Y483, Y488, Y490, Y529, is among the proteins listed in this patent. RSK2, Ribosomal protein S6 kinase 90 kDa polypeptide 3, a histone H3-S10 specific kinase that plays a role in phosphorylation of multiple proteins in response to EGF or stress; mutation of the corresponding gene is associated with Coffin-Lowry syndrome. This protein has potential diagnostic and/or therapeutic implications based on the following findings. Nonsense mutation in the RPS6KA3 gene causes multiple abnormalities associated with Coffin-Lowry syndrome (Am J Hum Genet. 63: 1631-40 (1998)). Missense mutation in the RPS6KA3 gene causes multiple abnormalities associated with Coffin-Lowry syndrome (Am J Hum Genet. 63: 1631-40 (1998)). Induced inhibition of the protein serine/threonine kinase activity of RPS6KA3 may prevent increased cell proliferation associated with prostatic neoplasms (Cancer Res 65: 3108-16 (2005)). Splice site mutation in the RPS6KA3 gene causes multiple abnormalities associated with Coffin-Lowry syndrome (Am J Hum Genet. 63: 1631-40 (1998)). Frameshift mutation in the RPS6KA3 gene causes multiple abnormalities associated with Coffin-Lowry syndrome (Am J Hum Genet. 63: 1631-40 (1998)). Increased expression of RPS6KA3 protein correlates with prostatic neoplasms (Cancer Res 65: 3108-16 (2005)). (PhosphoSite®, Cell Signaling Technology (Danvers, Mass.), Human PSD™, Biobase Corporation, (Beverly, Mass.)).

Securin (O95997), phosphorylated at Y 111, is among the proteins listed in this patent. securin, Pituitary tumor-transforming 1 (securin), transcriptional activator, promotes cell proliferation and angiogenesis, involved in sister chromatin separation and euploidy maintenance, upregulated in pituitary, colorectal, thyroid and other cancers. This protein has potential diagnostic and/or therapeutic implications based on the following findings. Increased expression of PTTG1 mRNA correlates with prolactinoma associated with pituitary neoplasms (J Clin Endocrinol Metab 84: 761-7 (1999)). Increased expression of PTTG1 mRNA correlates with adenoma (J Clin Endocrinol Metab 84: 761-7 (1999)). Increased expression of PTTG1 mRNA correlates with adenoma tumors associated with pituitary neoplasms (Oncogene 18: 5473-6 (1999)). Increased expression of PTTG1 protein correlates with invasive form of colorectal neoplasms (Lancet 355: 716-9 (2000)). Increased expression of PTTG1 mRNA correlates with adenoma tumors associated with pituitary neoplasms (J Clin Endocrinol Metab 84: 761-7 (1999)). Increased expression of PTTG1 protein correlates with pituitary neoplasms (J Clin Endocrinol Metab 85: 3409-16 (2000)). Increased expression of PTTG1 mRNA may cause abnormal fibroblast growth factor receptor signaling pathway associated with pituitary neoplasms (Mol Endocrinol 13: 156-66 (1999)). Decreased expression of PTTG1 protein may correlate with decreased adenoma tumors associated with pituitary neoplasms (J Clin Invest 109: 277-83 (2002)). Increased expression of PTTG1 mRNA correlates with adenocarcinoma tumors associated with breast neoplasms (Oncogene 18: 5473-6 (1999)). Increased expression of PTTG1 protein correlates with carcinoma tumors associated with colorectal neoplasms (Lancet 355: 716-9 (2000)). Increased expression of PTTG1 mRNA correlates with adenocarcinoma tumors associated with lung neoplasms (Oncogene 18: 5473-6 (1999)). Increased expression of PTTG1 mRNA correlates with invasive form of pituitary neoplasms (J Clin Endocrinol Metab 84: 761-7 (1999)). Increased expression of PTTG1 mRNA correlates with advanced stage or high grade form of pituitary neoplasms (J Clin Endocrinol Metab 84: 761-7 (1999)). Increased expression of PTTG1 mRNA correlates with prolactinoma (J Clin Endocrinol Metab 84: 761-7 (1999)). Increased expression of PTTG1 mRNA correlates with adenoma tumors associated with thyroid neoplasms (J Clin Endocrinol Metab 86: 5025-32 (2001)). Increased expression of PTTG1 mRNA may cause follicular papillary carcinoma associated with thyroid neoplasms (J Clin Endocrinol Metab 86: 5025-32 (2001)). Increased expression of PTTG1 mRNA correlates with carcinoma tumors associated with thyroid neoplasms (J Clin Endocrinol Metab 86: 5025-32 (2001)). (PhosphoSite®, Cell Signaling Technology (Danvers, Mass.), Human PSD™, Biobase Corporation, (Beverly, Mass.)).

SFRS10 (P62995), phosphorylated at Y235, Y260, is among the proteins listed in this patent. SFRS10, Splicing factor arginine/serine rich 10, binds splicing enhancer elements and activates pre-mRNA splicing, involved in calcitonin (CALCA) splicing, may play roles in vascular disease and the pathogenesis of tauopathies. This protein has potential diagnostic and/or therapeutic implications based on the following findings. Increased RNA splicing factor activity, transesterification mechanism of SFRS10 may cause abnormal RNA splicing associated with tauopathies (JBC 278: 18997-9007 (2003)). Increased RNA splicing factor activity, transesterification mechanism of SFRS10 may cause abnormal RNA splicing associated with tauopathies (J Biol Chem 278: 18997-9007 (2003)). (PhosphoSite®, Cell Signaling Technology (Danvers, Mass.), Human PSD™, Biobase Corporation, (Beverly, Mass.)).

SHIP (Q92835), phosphorylated at Y555, Y643, Y795, Y943, is among the proteins listed in this patent. SHIP, Inositol polyphosphate-5-phosphatase D, hydrolyzes Ins-1,3,4,5-P4 and PtdIns-3,4,5-P3, interacts with SHC1 in signal transduction pathways, may play roles in erythrocyte differentiation and basophil secretion. (PhosphoSite®, Cell Signaling Technology (Danvers, Mass.), Human PSD™, Biobase Corporation, (Beverly, Mass.)).

SHP-1 (P29350), phosphorylated at Y301, is among the proteins listed in this patent. SHP-1, Protein tyrosine phosphatase non-receptor type 6, regulates signaling by many receptors, upregulated in breast cancer, downregulated in gallbladder cancer, lymphoma, multiple myeloma and chronic cholecystitis, localization is altered in prostate cancer. This protein has potential diagnostic and/or therapeutic implications based on the following findings. Increased expression of PTPN6 protein correlates with prostatic neoplasms (J Clin Endocrinol Metab 87: 915-26 (2002)). Splice site mutation in the PTPN6 gene correlates with acute form of myeloid leukemia (Hum Mol Genet. 9: 2297-304 (2000)). Decreased expression of PTPN6 protein may correlate with Sezary syndrome associated with skin neoplasms (Leukemia 16: 1470-7 (2002)). Loss of heterozygosity at the PTPN6 gene may correlate with acute lymphocytic leukemia (Cancer Res 62: 6390-4 (2002)). Decreased expression of PTPN6 protein correlates with Burkitt Lymphoma (J Exp Med 186: 1575-83 (1997)). Increased expression of PTPN6 mRNA correlates with breast neoplasms (Int J Cancer 88: 363-8 (2000)). Increased membrane localization of PTPN6 may correlate with decreased cell proliferation associated with breast neoplasms (Endocrinology 137: 3461-8 (1996)). Increased protein tyrosine phosphatase activity of PTPN6 correlates with prostatic neoplasms (J Clin Endocrinol Metab 87: 915-26 (2002)). Increased protein tyrosine phosphatase activity of PTPN6 may cause increased response to drug associated with pancreatic neoplasms (Endocrinology 140: 765-77 (1999)). Decreased expression of PTPN6 protein may correlate with abnormal regulation of JAK-STAT cascade associated with Sezary syndrome (Leukemia 16: 1470-7 (2002)). Hypermethylation of the PTPN6 promoter correlates with multiple myeloma (Blood 103: 4630-5 (2004)). Decreased expression of PTPN6 mRNA may correlate with Sezary syndrome associated with skin neoplasms (Leukemia 16: 1470-7 (2002)). Lack of expression of PTPN6 protein correlates with invasive form of prostatic neoplasms (J Clin Endocrinol Metab 87: 915-26 (2002)). (PhosphoSite®, Cell Signaling Technology (Danvers, Mass.), Human PSD™, Biobase Corporation, (Beverly, Mass.)).

SHP-2 (Q06124), phosphorylated at Y511, is among the proteins listed in this patent. SHP-2, Protein tyrosine phosphatase non-receptor type 11, acts in many receptor tyrosine kinase and PI3-kinase signaling pathways induced by growth factors, cytokines and immunoreceptors, exploited during *Helicobacter* infections; mutations cause Noonan syndrome. This protein has potential diagnostic and/or therapeutic implications based on the following findings. Missense mutation in the PTPN11 gene causes defective several tissues development associated with Noonan syndrome (Am J Hum Genet. 70: 1555-63 (2002)). Missense mutation in the Protein-tyrosine phosphatase domain of PTPN11 causes lentigo associated with Noonan syndrome (Am J Hum Genet. 71: 389-94 (2002)). Bacterial exploitation of the protein tyrosine phosphatase activity of PTPN11 causes abnormal regulation of cell shape associated with *Helicobacter* infections (Science 295: 683-6 (2002)). Missense mutation in the PTPN11 gene causes deafness associated with Noonan syndrome (J Clin Endocrinol Metab 87: 3529-33 (2002)). Decreased protein binding of PTPN11 may cause abnormal NK cells function associated with lymphoproliferative disorders (J Immunol 165: 2932-6 (2000)). Increased protein tyrosine phosphatase activity of PTPN11 may cause neoplasm invasiveness associated with breast neoplasms (Oncogene 23: 157-67 (2004)). Missense mutation in the PTPN11 gene causes familial form of Noonan syndrome (Am J Hum Genet. 70: 1555-63 (2002)). Increased protein binding of PTPN11 may cause increased chemotaxis associated with breast neoplasms (Oncogene 23: 157-67 (2004)). Decreased protein binding of PTPN11 may cause lymphoproliferative disorders (Biochemistry 42: 14885-92 (2003)). Missense mutation in the Protein-tyrosine phosphatase domain of PTPN11 causes cafe-au-lait spots associated with Noonan syndrome (Am J Hum Genet. 71: 389-94 (2002)). Missense mutation in the PTPN11 gene causes abnormal in utero embryonic development associated with Noonan syndrome (Am J Hum Genet. 70: 1555-63 (2002)). Missense mutation in the PTPN11 gene causes pulmonary valve stenosis associated with Noonan syndrome (Am J Hum Genet. 70: 1555-63 (2002)). Increased phosphorylation of PTPN11 may cause increased chemotaxis associated with breast neoplasms (Oncogene 23: 157-67 (2004)). Increased protein tyrosine phosphatase activity of PTPN11 may cause abnormal signal transduction associated with Noonan syndrome (Nat Genet. 29: 465-8 (2001)). Missense mutation in the Protein-tyrosine phosphatase domain of PTPN11 causes multiple abnormalities associated with Noonan syndrome (Nat Genet. 29: 465-8 (2001)). Increased phosphorylation of PTPN11 may cause neoplasm invasiveness associated with breast neoplasms (Oncogene 23: 157-67 (2004)). Bacterial exploitation of the protein tyrosine phosphatase activity of PTPN11 causes abnormal signal transduction associated with *Helicobacter* infections (Science 295: 683-6 (2002)). Missense mutation in the PTPN11 gene correlates with early onset form of chronic myelomonocytic leukemia (Blood 103: 2325-31 (2004)). Increased protein binding of PTPN11 may cause neoplasm invasiveness associated with breast neoplasms (Oncogene 23: 157-67 (2004)). Missense mutation in the Protein-tyrosine phosphatase domain of PTPN11 causes multiple abnormalities associated with lentigo (Am J Hum Genet. 71: 389-94 (2002)). Missense mutation in the PTPN11 gene causes hemorrhagic disorders associated with Noonan syndrome (J Clin Endocrinol Metab 87: 3529-33 (2002)). Decreased protein binding of PTPN11 may cause abnormal cell proliferation associated with lymphoproliferative disorders (Nature 395: 462-9 (1998)). Deletion mutation in the PTPN11 gene causes Noonan syndrome (J Clin Endocrinol Metab 89: 3359-64 (2004)). Mutation in the PTPN11 gene may cause myelodysplastic syndromes (Nat Genet. 34: 148-50 (2003)). Increased protein tyrosine phosphatase activity of PTPN11 may cause increased chemotaxis associated with breast neoplasms (Oncogene 23: 157-67 (2004)). Decreased protein binding of PTPN11 may cause lymphoproliferative disorders (Biochemistry Usa 42: 14885-92 (2003)). Decreased protein binding of PTPN11 may cause abnormal natural killer cell activation associated with lymphoproliferative disorders (J Immunol 165: 2932-6 (2000)). Missense mutation in the PTPN11 gene causes Noonan syndrome (J Clin Endocrinol Metab 89: 3359-64 (2004)). Missense mutation in the Protein-tyrosine phosphatase domain of PTPN11 causes hemorrhagic disorders associated with Noonan syndrome (J Clin Endocrinol Metab 87: 3529-33 (2002)). Missense mutation in the Protein-tyrosine phosphatase domain of PTPN11 causes deafness associated with Noonan syndrome (J Clin Endocrinol Metab 87: 3529-33 (2002)). (PhosphoSite®, Cell Signaling Technology (Danvers, Mass.), Human PSD™, Biobase Corporation, (Beverly, Mass.)).

SHP-2 (Q06124), phosphorylated at Y511, is among the proteins listed in this patent. SHP-2, Protein tyrosine phosphatase non-receptor type 11, acts in many receptor tyrosine kinase and PI3-kinase signaling pathways induced by growth factors, cytokines and immunoreceptors, exploited during *Helicobacter* infections; mutations cause Noonan syndrome. This protein has potential diagnostic and/or therapeutic implications based on the following findings. Missense mutation in the PTPN11 gene causes defective several tissues development associated with Noonan syndrome (Am J Hum Genet. 70: 1555-63 (2002)). Missense mutation in the Protein-tyrosine phosphatase domain of PTPN11 causes lentigo associated with Noonan syndrome (Am J Hum Genet. 71: 389-94 (2002)). Bacterial exploitation of the protein tyrosine phosphatase activity of PTPN11 causes abnormal regulation of cell shape associated with *Helicobacter* infections (Science 295: 683-6 (2002)). Missense mutation in the PTPN11 gene causes deafness associated with Noonan syndrome (J Clin Endocrinol Metab 87: 3529-33 (2002)). Decreased protein binding of PTPN11 may cause abnormal NK cells function associated with lymphoproliferative disorders (J Immunol 165: 2932-6 (2000)). Increased protein tyrosine phosphatase activity of PTPN11 may cause neoplasm invasiveness associated with breast neoplasms (Oncogene 23: 157-67 (2004)). Missense mutation in the PTPN11 gene causes familial form of Noonan syndrome (Am J Hum Genet. 70: 1555-63 (2002)). Increased protein binding of PTPN11 may cause increased chemotaxis associated with breast neoplasms (Oncogene 23: 157-67 (2004)). Decreased protein binding of PTPN11 may cause lymphoproliferative disorders (Biochemistry 42: 14885-92 (2003)). Missense mutation in the Protein-tyrosine phosphatase domain of PTPN11 causes cafe-au-lait spots associated with Noonan syndrome (Am J Hum Genet. 71: 389-94 (2002)). Missense mutation in the PTPN11 gene causes abnormal in utero embryonic development associated with Noonan syndrome (Am J Hum Genet. 70: 1555-63 (2002)). Missense mutation in the PTPN11 gene causes pulmonary valve stenosis associated with Noonan syndrome (Am J Hum Genet. 70: 1555-63 (2002)). Increased phosphorylation of PTPN11 may cause increased chemotaxis associated with breast neoplasms (Oncogene 23: 157-67 (2004)). Increased protein tyrosine phosphatase activity of PTPN11 may cause abnormal signal transduction associated with Noonan syndrome (Nat Genet. 29: 465-8 (2001)). Missense mutation in the Protein-tyrosine phosphatase domain of PTPN11 causes multiple abnormalities associated with Noonan syndrome (Nat Genet. 29: 465-8 (2001)). Increased phosphorylation of PTPN11 may cause neoplasm invasiveness associated with breast neoplasms (Oncogene 23: 157-67 (2004)). Bacterial exploitation of the protein tyrosine phosphatase activity of PTPN11 causes abnormal signal transduction associated with *Helicobacter* infections (Science 295: 683-6 (2002)). Missense mutation in the PTPN11 gene correlates with early onset form of chronic myelomonocytic leukemia (Blood 103: 2325-31 (2004)). Increased protein binding of PTPN11 may cause neoplasm invasiveness associated with breast neoplasms (Oncogene 23: 157-67 (2004)). Missense mutation in the Protein-tyrosine phosphatase domain of PTPN11 causes multiple abnormalities associated with lentigo (Am J Hum Genet. 71: 389-94 (2002)). Missense mutation in the PTPN11 gene causes hemorrhagic disorders associated with Noonan syndrome (J Clin Endocrinol Metab 87: 3529-33 (2002)). Decreased protein binding of PTPN11 may cause abnormal cell proliferation associated with lymphoproliferative disorders (Nature 395: 462-9 (1998)). Deletion mutation in the PTPN11 gene causes Noonan syndrome (J Clin Endocrinol Metab 89: 3359-64 (2004)). Mutation in the PTPN11 gene may cause myelodysplastic syndromes (Nat Genet. 34: 148-50 (2003)). Increased protein tyrosine phosphatase activity of PTPN11 may cause increased chemotaxis associated with breast neoplasms (Oncogene 23: 157-67 (2004)). Decreased protein binding of PTPN11 may cause lymphoproliferative disorders (Biochemistry Usa 42: 14885-92 (2003)). Decreased protein binding of PTPN11 may cause abnormal natural killer cell activation associated with lymphoproliferative disorders (J Immunol 165: 2932-6 (2000)). Missense mutation in the PTPN11 gene causes Noonan syndrome (J Clin Endocrinol Metab 89: 3359-64 (2004)). Missense mutation in the Protein-tyrosine phosphatase domain of PTPN11 causes hemorrhagic disorders associated with Noonan syndrome (J Clin Endocrinol Metab 87: 3529-33 (2002)). Missense mutation in the Protein-tyrosine phosphatase domain of PTPN11 causes deafness associated with Noonan syndrome (J Clin Endocrinol Metab 87: 3529-33 (2002)). (PhosphoSite®, Cell Signaling Technology (Danvers, Mass.), Human PSD™, Biobase Corporation, (Beverly, Mass.)).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. As used herein, unless specifically indicated otherwise, the word "or" is used in the "inclusive" sense of "and/or" and not the "exclusive" sense of "either/or."

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables which are inherently discrete, and can be 0.0, 0.1, 0.01, 0.001, or any other real value for variables which are inherently continuous.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

"Antibody" or "antibodies" refers to all classes of immunoglobulins, including IgG, IgM, IgA, IgD, and IgE, including whole antibodies and any antigen biding fragment thereof (e.g., $F_{ab}$) or single chains thereof, including chimeric, polyclonal, and monoclonal antibodies. Antibodies are antigen-specific protein molecules produced by lymphocytes of the B cell lineage. Following antigenic stimulation, B cells that have surface immunoglobulin receptors that bind the antigen clonally expand, and the binding affinity for the antigen increases through a process called affinity maturation. The B cells further differentiate into plasma cells, which secrete large quantities of antibodies in to the serum. While the physiological role of antibodies is to protect the host animal by specifically binding and eliminating microbes and microbial pathogens from the body, large amounts of antibodies are also induced by intentional immunization to produce specific antibodies that are used extensively in many biomedical and therapeutic applications.

Antibody molecules are shaped somewhat like the letter "Y", and consist of 4 protein chains, two heavy (H) and two light (L) chains. Antibodies possess two distinct and spatially separate functional features. The ends of each of the two arms of the "Y" contain the variable regions (variable heavy (V(H)) and variable light (V(L)) regions), which form two identical antigen-binding sites. The variable regions undergo a process of "affinity maturation" during the immune response, leading to a rapid divergence of amino acids within these variable regions. The other end of the antibody molecule, the stem of the "Y", contains only the two heavy constant (CH) regions, interacts with effector cells to determine the effector functions of the antibody. There are five different CH region genes that encode the five different classes of immunoglobulins: IgM, IgD, IgG, IgA and IgE. These constant regions, by interacting with different effector cells and molecules, determine the immunoglobulin molecule's biological function and biological response.

Each V(H) and V(L) region contains three subregions called complementarity determining regions. These include CDR1-3 of the V(H) domain and CDR1-3 of the V(L) domain. These six CDRs generally form the antigen binding surface, and include those residues that hypermutate during the affinity maturation phase of the immune response. The CDR3 of the V(H) domain seems to play a dominant role in generating diversity of both the B cell antigen receptor (BCR) and the T cell antigen receptor systems (Xu et al., Immunity 13:37-45 (2000)).

The term "antibody" or "antibodies" refers to all classes of polyclonal or monoclonal immunoglobulins, including IgG, IgM, IgA, IgD, and IgE, including whole antibodies and any antigen binding fragment thereof. This includes any combination of immunoglobulin domains or chains that contains a variable region (V(H) or V(L)) that retains the ability to bind the immunogen. Such fragments include $F(ab)_2$ fragments (V(H)—C(H1), V(L)-C(L))$_2$; monovalent Fab fragments (V(H)—C(H1), V(L)-C(L)); Fv fragment (V(H)—V(L); single-chain Fv fragments (Kobayashi et al., Steroids July; 67(8):733-42 (2002).

Monoclonal antibodies refer to clonal antibodies produced from fusions between immunized murine, rabbit, human, or other vertebrate species, and produced by classical fusion technology Kohler G, Milstein C. Continuous cultures of fused cells secreting antibody of predefined specificity. Nature 1975 Aug. 7; 256(5517):495-7 or by alternative methods which may isolate clones of immunoglobulin secreting cells from transformed plasma cells.

When used with respect to an antibody's binding to one phospho-form of a sequence, the expression "does not bind" means that a phospho-specific antibody either does not apparently bind to the non-phospho form of the antigen as ascertained in commonly used experimental detection systems (Western blotting, IHC, Immunofluorescence, etc.). One of skill in the art will appreciate that the expression may be applicable in those instances when (1) a phospho-specific antibody either does not apparently bind to the non-phospho form of the antigen as ascertained in commonly used experimental detection systems (Western blotting, IHC, Immunofluorescence, etc.); (2) where there is some reactivity with the surrounding amino acid sequence, but that the phosphorylated residue is an immunodominant feature of the reaction. In cases such as these, there is an apparent difference in affinities for the two sequences. Dilutional analyses of such antibodies indicates that the antibodies apparent affinity for the phosphorylated form is at least 10-100 fold higher than for the non-phosphorylated form; or where (3) the phospho-specific antibody reacts no more than an appropriate control antibody would react under identical experimental conditions. A control antibody preparation might be, for instance, purified immunoglobulin from a pre-immune animal of the same species, an isotype- and species-matched monoclonal antibody. Tests using control antibodies to demonstrate specificity are recognized by one of skill in the art as appropriate and definitive.

"Target signaling protein/polypeptide" means any protein (or polypeptide derived therefrom) enumerated in Column A of Table 1/FIG. 2, which is disclosed herein as being phosphorylated in one or more cell line(s). Target signaling protein(s)/polypeptide(s) may be tyrosine kinases, such as TTN or BCR, or serine/threonine kinases, or direct substrates of such kinases, or may be indirect substrates downstream of such kinases in signaling pathways. Target signaling protein/polypeptide where elucidated in leukemia cell lines, however one of skill in the art will appreciate that a Target signaling protein/polypeptide may also be phosphorylated in other cell lines (non-leukemic) harboring activated kinase activity.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Protein" is used interchangeably with polypeptide, and includes protein fragments and domains as well as whole protein.

"Phosphorylatable amino acid" means any amino acid that is capable of being modified by addition of a phosphate group, and includes both forms of such amino acid.

"Phosphorylatable peptide sequence" means a peptide sequence comprising a phosphorylatable amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., *Molecular Cloning: A Laboratory Manual,* 2nd Ed., Cold Spring Harbor Laboratory Press, New York (1989); Kaufman et al., Eds., *Handbook of Molecular and Cellular Methods in Biology in Medicine,* CRC Press, Boca Raton (1995); McPherson, Ed., *Directed Mutagenesis: A Practical Approach,* IRL Press, Oxford (1991). Standard reference works setting forth the general principles of pharmacology include Goodman and Gilman's *The Pharmacological Basis of Therapeutics,* 11th Ed., McGraw Hill Companies Inc., New York (2006).

A. Identification of Phosphorylation Sites. The Target signaling protein/polypeptide phosphorylation sites disclosed herein and listed in Table 1/FIG. 2 were discovered by employing the modified peptide isolation and characterization techniques described in U.S. Pat. No. 7,198,896 using cellular extracts from the following human cancer cell lines, tissues and patient samples: 01364548-cll, 223-CLL, 293T, 3T3 TrkB, 3T3-Src, 3T3-TrkA, 3T3-wt, 577, A172, AML-4833, AML-6246, AML-6735, AML-7592, BaF3-10ZF, BaF3-4ZF, BaF3-APR, BaF3-FLT3(D842V), BaF3-FLT3 (D842Y), BaF3-FLT3(K663Q), BaF3-FLT3(WT), BaF3-FLT3/ITD, BaF3-PRTK, BaF3-TDII, BaF3-Tel/FGFR3, Baf3, Baf3-V617F-jak2, Baf3/E255K, Baf3/H396P, Baf3/Jak2(IL-3 dep), Baf3/M351T, Baf3/T3151, Baf3/TpoR, Baf3/TpoR-Y98F, Baf3/Tyk2, Baf3/V617F-jak2 (IL-3), Baf3/Y253F, Baf3/cc-TpoR-IV, Baf3/p210wt, CHRF, CI-1, CMK, CTV-1, DMS 53, DND41, DU-528, DU145, ELF-153, EOL-1, GDM-1, H1703, H1734, H1793, H1869, H1944, H1993, H2023, H226, H3255, H358, H520, H82, H838, HCC1428, HCC1435, HCC1806, HCC1937, HCC366, HCC827, HCT116, HEL, HL107B, HL117B, HL131A, HL131B, HL133A, HL53B, HL59b, HL60, HL61a, HL61b, HL66B, HL68A, HL75A, HL84A, HL97B, HL98A, HT29, HU-3, HUVEC, Jurkat, K562, KG-1, KG1-A, KMS11, KMS18, KMS27, KOPT-K1, KY821, Karpas 299, Karpas-1106p, M-07e, M01043, M059K, MC-116, MCF-10A (Y561F), MCF-10A(Y969F), MDA-MB-453, MDA-MB-468, MEC-2, MKPL-1, ML-1, MO-91, MOLT15, MV4-11, Me-F2, Molm 14, Monomac 6, NCI-N87, Nomo-1, OCI-M1, OCI-ly4, OCI-ly8, OCI/AML2, OPM-1, PL21, Pfeiffer, RC-K8, RI-1, SCLC T1, SEM, SK-N-AS, SK-N-MC, SKBR3, SR-786, SU-DHL1, SUP-M2, SUPT-13, SuDHL5, T17, TRE-cll patient, TS, UT-7, VAL, Verona, Verona 1, Verona 4, WSU-NHL, XG2, Z-55, cs001, cs015, cs025, cs041, cs042, gz21, gz68, gz73, gz74, gzB1, hl1144b, hl1152b, lung tumor T26, lung tumor T57, normal human lung, pancreatic xenograft, patient 1, rat brain, sw480. The isolation and identification of phosphopeptides from these cell lines, using an immobilized general phosphotyrosine-specific antibody, or an antibody recognizing the phosphorylated motif PXpSP is described in detail in Example 1 below. In addition to the protein phosphorylation sites (tyrosine) described herein, many known phosphorylation sites were also identified (not described herein). The immunoaffinity/mass spectrometric technique described in the '896 patent (the "IAP" method)—and employed as described in detail in the Examples—is briefly summarized below.

The IAP method employed generally comprises the following steps: (a) a proteinaceous preparation (e.g. a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g., Sequest) may be utilized to substantially match the spectra obtained for the isolated, modified peptide during the characterization of step (d) with the spectra for a known peptide sequence. A quantification step employing, e.g., SILAC or AQUA, may also be employed to quantify isolated peptides in order to compare peptide levels in a sample to a baseline.

In the IAP method as employed herein, a general phosphotyrosine-specific monoclonal antibody (commercially available from Cell Signaling Technology, Inc., Beverly, Mass., Cat. #9411 (p-Tyr-100)) was used in the immunoaffinity step to isolate the widest possible number of phospho-tyrosine containing peptides from the cell extracts.

Extracts from the following human cancer cell lines, tissues and patient samples were employed: 01364548-cll, 223-CLL, 293T, 3T3 TrkB, 3T3-Src, 3T3-TrkA, 3T3-wt, 577, A172, AML-4833, AML-6246, AML-6735, AML-7592, BaF3-10ZF, BaF3-4ZF, BaF3-APR, BaF3-FLT3(D842V), BaF3-FLT3(D842Y), BaF3-FLT3(K663Q), BaF3-FLT3 (WT), BaF3-FLT3/ITD, BaF3-PRTK, BaF3-TDII, BaF3-Tel/FGFR3, Baf3, Baf3-V617F-jak2, Baf3/E255K, Baf3/H396P, Baf3/Jak2(IL-3 dep), Baf3/M351T, Baf3/T3151, Baf3/TpoR, Baf3/TpoR-Y98F, Baf3/Tyk2, Baf3/V617F-jak2 (IL-3), Baf3/Y253F, Baf3/cc-TpoR-IV, Baf3/p210wt, CHRF, CI-1, CMK, CTV-1, DMS 53, DND41, DU-528, DU145, ELF-153, EOL-1, GDM-1, H1703, H1734, H1793, H1869, H1944, H1993, H2023, H226, H3255, H358, H520, H82, H838, HCC1428, HCC1435, HCC1806, HCC1937, HCC366, HCC827, HCT116, HEL, HL107B, HL117B, HL131A, HL131B, HL133A, HL53B, HL59b, HL60, HL61a, HL61b, HL66B, HL68A, HL75A, HL84A, HL97B, HL98A, HT29, HU-3, HUVEC, Jurkat, K562, KG-1, KG1-A, KMS11, KMS18, KMS27, KOPT-K1, KY821, Karpas 299, Karpas-1106p, M-07e, M01043, M059K, MC-116, MCF-10A (Y561F), MCF-10A(Y969F), MDA-MB-453, MDA-MB-468, MEC-2, MKPL-1, ML-1, MO-91, MOLT15, MV4-11, Me-F2, Molm 14, Monomac 6, NCI-N87, Nomo-1, OCI-M1, OCI-ly4, OCI-ly8, OCI/AML2, OPM-1, PL21, Pfeiffer, RC-K8, RI-1, SCLC T1, SEM, SK-N-AS, SK-N-MC, SKBR3, SR-786, SU-DHL1, SUP-M2, SUPT-13, SuDHL5, T17, TRE-cll patient, TS, UT-7, VAL, Verona, Verona 1, Verona 4, WSU-NHL, XG2, Z-55, cs001, cs015, cs025, cs041, cs042, gz21, gz68, gz73, gz74, gzB1, hl1144b, hl1152b, lung tumor T26, lung tumor T57, normal human lung, pancreatic xenograft, patient 1, rat brain and sw480.

As described in more detail in the Examples, lysates were prepared from these cells and digested with trypsin after treatment with DTT and iodoacetamide to residue and alkylate cysteine residues. Before the immunoaffinity step, peptides were pre-fractionated by reversed-phase solid phase extraction using Sep-Pak $C_{18}$ columns to separate peptides from other cellular components. The solid phase extraction cartridges were eluted with varying steps of acetonitrile. Each lyophilized peptide fraction was redissolved in MOPS IP buffer and treated with phosphotyrosine (P-Tyr-100, CST #9411) immobilized on protein G-Sepharose. Immunoaffinity-purified peptides were eluted with 0.1% TFA and a portion of this fraction was concentrated with Stage or Zip tips and analyzed by LC-MS/MS, using either a LCQ or ThermoFinnigan LTQ ion trap mass spectrometer. Peptides were eluted from a 10 cm×75 μm reversed-phase column with a 45-min linear gradient of acetonitrile. MS/MS spectra were evaluated using the program Sequest with the NCBI human protein database.

This revealed the tyrosine phosphorylation sites in signaling pathways affected by kinase activation or active in leukemia cells. The identified phosphorylation sites and their parent proteins are enumerated in Table 1/FIG. 2. The tyrosine at which phosphorylation occurs is provided in Column D, and the peptide sequence encompassing the phosphorylatable tyrosine residue at the site is provided in Column E. If a phosphorylated tyrosine was found in mouse, the orthologous site in human was identified using either Homologene or BLAST at NCBI; the sequence reported in column E is the phosphorylation site flanked by 7 amino acids on each side. FIG. 2 also shows the particular type of leukemic disease (see Column G) and cell line(s) (see Column F) in which a particular phosphorylation site was discovered.

As a result of the discovery of these phosphorylation sites, phospho-specific antibodies and AQUA peptides for the detection of and quantification of these sites and their parent proteins may now be produced by standard methods, as described below. These new reagents will prove highly useful in, e.g., studying the signaling pathways and events underlying the progression of leukemias and the identification of new biomarkers and targets for diagnosis and treatment of such diseases in a mammal.

The methods of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

B. Antibodies and Cell Lines. Isolated phosphorylation site-specific antibodies that specifically bind a Target signaling protein/polypeptide disclosed in Column A of Table 1 only when phosphorylated (or only when not phosphorylated) at the corresponding amino acid and phosphorylation site listed in Columns D and E of Table 1/FIG. 2 may be produced by standard antibody production methods, such as anti-peptide antibody methods, using the phosphorylation site sequence information provided in Column E of Table 1. The PHIP adaptor/scaffold protein phosphorylation site (tyrosine 984) (see Row 12 of Table 1/FIG. 2) is presently disclosed. Thus, an antibody that specifically binds this novel PHIP adaptor/scaffold site can now be produced, e.g. by immunizing an animal with a peptide antigen comprising all or part of the amino acid sequence encompassing the respective phosphorylated residue (e.g., a peptide antigen comprising the sequence set forth in Row 12, Column E, of Table 1, SEQ ID NO: 11, respectively) (which encompasses the phosphorylated tyrosine at position 984 in PHIP, to produce an antibody that only binds PHIP adaptor/scaffold when phosphorylated at that site.

Polyclonal antibodies of the invention may be produced according to standard techniques by immunizing a suitable animal (e.g., rabbit, goat, etc.) with a peptide antigen corresponding to the phosphorylation site of interest (i.e., a phosphorylation site enumerated in Column E of Table 1, which comprises the corresponding phosphorylatable amino acid listed in Column D of Table 1), collecting immune serum from the animal, and separating the polyclonal antibodies from the immune serum, in accordance with known procedures. For example, a peptide antigen corresponding to all or part of the novel RACK1 adaptor/scaffold phosphorylation site disclosed herein (SEQ ID NO: 13=LTRDETNyGIPQR, encompassing phosphorylated tyrosine 52 (see Row 14 of Table 1)) may be employed to produce antibodies that only bind RACK1 when phosphorylated at Tyr 52. Similarly, a peptide comprising all or part of any one of the phosphorylation site sequences provided in Column E of Table 1 may employed as an antigen to produce an antibody that only binds the corresponding protein listed in Column A of Table 1 when phosphorylated (or when not phosphorylated) at the corresponding residue listed in Column D. If an antibody that only binds the protein when phosphorylated at the disclosed site is desired, the peptide antigen includes the phosphorylated form of the amino acid. Conversely, if an antibody that only binds the protein when not phosphorylated at the disclosed site is desired, the peptide antigen includes the non-phosphorylated form of the amino acid.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)).

It will be appreciated by those of skill in the art that longer or shorter phosphopeptide antigens may be employed. See Id. For example, a peptide antigen may comprise the full sequence disclosed in Column E of Table 1/FIG. 2, or it may comprise additional amino acids flanking such disclosed sequence, or may comprise of only a portion of the disclosed sequence immediately flanking the phosphorylatable amino acid (indicated in Column E by lowercase "y"). Typically, a desirable peptide antigen will comprise four or more amino acids flanking each side of the phosphorylatable amino acid and encompassing it. Polyclonal antibodies produced as described herein may be screened as further described below.

Monoclonal antibodies of the invention may be produced in a hybridoma cell line according to the well-known technique of Kohler and Milstein. See *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal $F_{ab}$ fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferable for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods,* 74: 307 (1984)).

An epitope of a phosphorylation-site specific antibody of the invention is a peptide fragment consisting essentially of about 8 to 17 amino acids including the phosphorylatable tyrosine, wherein about 3 to 8 amino acids are positioned on each side of the phosphorylatable tyrosine (for example, the NARS tyrosine 539 phosphorylation site sequence disclosed in Row 84, Column E of Table 1), and antibodies of the invention thus specifically bind a Target Signal Protein/ Polypeptide comprising such epitopic sequence. Epitopes bound by the antibodies of the invention comprise all or part of a phosphorylatable site sequence listed in Column E of Table 1, including the phosphorylatable amino acid.

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies provided by the invention may be any type of immunoglobulins, including IgG, IgM, IgA, IgD, and IgE, including $F_{ab}$ or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 or U.S. Pat. No. 4,816,567. The antibodies may also be chemically constructed by specific antibodies made according to the method disclosed in U.S. Pat. No. 4,676,980.

The invention also provides immortalized cell lines that produce an antibody of the invention. For example, hybridoma clones, constructed as described above, that produce monoclonal antibodies to the protein phosphorylation sites disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czernik et al., *Methods in Enzymology,* 201: 264-283 (1991). For example, the antibodies may be screened against the phospho and non-phospho peptide library by ELISA to ensure specificity for both the desired antigen (i.e. that epitope including a phosphorylation site sequence enumerated in Column E of Table 1) and for reactivity only with the phosphorylated (or non-phosphorylated) form of the antigen. Peptide competition assays may be carried out to confirm lack of reactivity with other phospho-epitopes on the given Target Signal Protein/Polypeptide. The antibodies may also be tested by Western blotting against cell preparations containing the signaling protein, e.g. cell lines over-expressing the target protein, to confirm reactivity with the desired phosphorylated epitope/target.

In an exemplary embodiment, phage display libraries containing more than $10^{10}$ phage clones are used for high-throughput production of monoclonal antibodies that target post-translational modification sites (e.g., phosphorylation sites) and, for validation and quality control, high-throughput immunohistochemistry is utilized to screen the efficacy of these antibodies. Western blots, protein microarrays and flow cytometry can also be used in high-throughput screening of phosphorylation site-specific polyclonal or monoclonal antibodies of the present invention. See, e.g., Blow N., *Nature,* 447: 741-743 (2007).

Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Phosphorylation-site specific antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the Target signaling protein/polypeptide epitope for which the antibody of the invention is specific.

In certain cases, polyclonal antisera may exhibit some undesirable general cross-reactivity to phosphotyrosine or phosphoserine itself, which may be removed by further purification of antisera, e.g., over a phosphotyramine column. Antibodies of the invention specifically bind their target protein (i.e., a protein listed in Column A of Table 1) only when phosphorylated (or only when not phosphorylated, as the case may be) at the site disclosed in corresponding Columns D/E, and do not (substantially) bind to the other form (as compared to the form for which the antibody is specific).

Antibodies may be further characterized via immunohistochemical (IHC) staining using normal and diseased tissues to evaluate phosphorylation and activation status in diseased tissue. IHC may be carried out according to well-known techniques. See, e.g., *Antibodies: A Laboratory Manual*, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al.,

*Cytometry (Communications in Clinical Cytometry)* 46: 72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30 minutes on ice. Cells may then be stained with the primary phosphorylation-site specific antibody of the invention (which detects a Target Signal Protein/Polypeptide enumerated in Table 1), washed and labeled with a fluorescent-labeled secondary antibody. Additional fluorochrome-conjugated marker antibodies (e.g., CD45, CD34) may also be added at this time to aid in the subsequent identification of specific hematopoietic cell types. The cells would then be analyzed on a flow cytometer (e.g., a Beckman Coulter FC500) according to the specific protocols of the instrument used.

Antibodies of the invention may also be advantageously conjugated to fluorescent dyes (e.g., Alexa488, PE) for use in multi-parametric analyses along with other signal transduction (phospho-CrkL, phospho-Erk 1/2) and/or cell marker (CD34) antibodies.

Phosphorylation-site specific antibodies of the invention specifically bind to a target signaling protein/polypeptide only when phosphorylated at a disclosed site, but are not limited only to binding the human species, per se. The invention includes antibodies that also bind conserved and highly homologous or identical phosphorylation sites in respective target signaling protein/polypeptide from other species (e.g., mouse, rat, monkey, yeast), in addition to binding the human phosphorylation site. Highly homologous or identical sites conserved in other species can readily be identified by standard sequence comparisons, such as using BLAST, with the human target signaling protein/polypeptide phosphorylation sites disclosed herein.

C. Heavy-Isotope Labeled Peptides (AQUA Peptides). The phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, Gerber et al., *Proc. Natl. Acad. Sci. U.S.A.* 100: 6940-5 (2003).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al., supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g., 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g., trypsin, hepsin), metallo proteases (e.g., PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. A workable range is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: the mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are suitable labels. Pairs of peptide internal standards that incorporate a different isotope label may also be prepared. Amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts may be employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g., by HPLC, reverse-phase HPLC, capillary electrophoresis, ion exchange chromatography, etc.) to isolate the labeled internal standard and its corresponding target peptide from other peptides in the sample. Microcapillary LC is a method contemplated.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for any of the phosphorylation sites disclosed herein. Peptide standards for a given phosphorylation site (e.g., the tyrosine 482 in PLCG2—see Row 116 of Table 1) may be produced for both the phosphorylated and non-phosphorylated forms of the site (e.g., see RENT1 site sequence in Column E, Row 128 of Table 1 (SEQ ID NO: 129) and such standards employed in the AQUA methodology to detect and quantify both forms of such phosphorylation site in a biological sample.

AQUA peptides of the invention may comprise all, or part of, a phosphorylation site peptide sequence disclosed herein (see Column E of Table 1/FIG. 2). In an embodiment, an AQUA peptide of the invention comprises a phosphorylation site sequence disclosed herein in Table 1/FIG. 2. For example, an AQUA peptide of the invention for detection/quantification of RAB11A G protein or regulator protein when phosphorylated at tyrosine Y8 may comprise the sequence DDEyDYLFK (y=phosphotyrosine), which comprises phosphorylatable tyrosine 8 (see Row 143, Column E; (SEQ ID NO: 144)). Heavy-isotope labeled equivalents of the peptides enumerated in Table 1/FIG. 2 (both in phosphorylated and unphosphorylated form) can be readily synthesized and their unique MS and LC-SRM signature determined, so that the peptides are validated as AQUA peptides and ready for use in quantification experiments.

The phosphorylation site peptide sequences disclosed herein (see Column E of Table 1/FIG. 2) are well suited for development of corresponding AQUA peptides, since the IAP method by which they were identified (see Part A above and Example 1) inherently confirmed that such peptides are in fact produced by enzymatic digestion (trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) for the detection and/or quantification of any of the phosphorylation sites disclosed in Table 1/FIG. 2 (see Column E) and/or their corresponding parent proteins/polypeptides (see Column A). A phosphopeptide sequence comprising any of the phosphorylation sequences listed in Table 1 may be considered an AQUA peptide of the invention. For example, an AQUA peptide comprising the sequence INVNRIFyDLVR (SEQ ID NO: 152) (where y may be either phosphotyrosine or tyrosine, and where V=labeled valine (e.g., $^{14}$C)) is provided for the quantification of phosphorylated (or non-phosphorylated) diaphanous (Tyr159) in a biological sample (see Row 151 of Table 1, tyrosine 159 being the phosphorylatable residue within the site). It will be appreciated that a larger AQUA peptide comprising a disclosed phosphorylation site sequence (and additional residues downstream or upstream of it) may also be constructed. Similarly, a smaller AQUA peptide comprising less than all of the residues of a disclosed phosphorylation site sequence (but still comprising the phosphorylatable residue enumerated in Column D of Table 1/FIG. 2) may alternatively be constructed. Such larger or shorter AQUA peptides are within the scope of the present invention, and the selection and production of AQUA peptides may be carried out as described above (see Gygi et al., Gerber et al., supra.).

Certain subsets of AQUA peptides provided by the invention are described above (corresponding to particular protein types/groups in Table 1, for example, tyrosine protein kinases or adaptor/scaffold proteins). Example 4 is provided to further illustrate the construction and use, by standard methods described above, of exemplary AQUA peptides provided by the invention. For example, the above-described AQUA peptides corresponding to both the phosphorylated and non-phosphorylated forms of the disclosed RICA G protein or regulator protein tyrosine 1188 phosphorylation site (see Row 162 of Table 1/FIG. 2) may be used to quantify the amount of phosphorylated claspin (Tyr 1188) in a biological sample, e.g., a tumor cell sample (or a sample before or after treatment with a test drug).

AQUA peptides of the invention may also be employed within a kit that comprises one or multiple AQUA peptide(s) provided herein (for the quantification of a target signaling protein/polypeptide disclosed in Table 1/FIG. 2), and, optionally, a second detecting reagent conjugated to a detectable group. For example, a kit may include AQUA peptides for both the phosphorylated and non-phosphorylated form of a phosphorylation site disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be useful in the further study of signal transduction anomalies associated with diseases such as for example cancer, including leukemias, and in identifying diagnostic/bio-markers of these diseases, new potential drug targets, and/or in monitoring the effects of test compounds on target signaling proteins/polypeptides and pathways.

D. Immunoassay Formats. Antibodies provided by the invention may be advantageously employed in a variety of standard immunological assays (the use of AQUA peptides provided by the invention is described separately above). Assays may be homogeneous assays or heterogeneous assays. In a homogeneous assay the immunological reaction usually involves a phosphorylation-site specific antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phosphorylation-site specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof that may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022; U.S. Pat. No. 4,659,678; U.S. Pat. No. 4,376,110. Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of a target signaling protein/polypeptide is detectable compared to background.

Phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation. Antibodies, or other target protein or target site-binding reagents, may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Antibodies of the invention may also be optimized for use in a flow cytometry (FC) assay to determine the activation/ phosphorylation status of a target signaling protein/polypeptide in patients before, during, and after treatment with a drug targeted at inhibiting phosphorylation of such a protein at the phosphorylation site disclosed herein. For example, bone marrow cells or peripheral blood cells from patients may be analyzed by flow cytometry for target signaling protein/polypeptide phosphorylation, as well as for markers identifying various hematopoietic cell types. In this manner, activation status of the malignant cells may be specifically characterized. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 1% para-formaldehyde for 10 minutes at 37° C. followed by permeabilization in 90% methanol for 30 minutes on ice. Cells may then be stained with the primary antibody (a phospho-specific antibody of the invention), washed and labeled with a fluorescent-labeled secondary antibody. Alternatively, the cells may be stained with a fluorescent-labeled primary antibody. The cells would then be analyzed on a flow cytometer (e.g., a Beckman Coulter EPICS-XL) according to the specific protocols of the instrument used. Such an analysis would identify the presence of activated Target Signaling Protein(s)/Polypeptide(s) in the malignant cells and reveal the drug response on the targeted protein.

Alternatively, antibodies of the invention may be employed in immunohistochemical (IHC) staining to detect differences in signal transduction or protein activity using normal and diseased tissues. IHC may be carried out according to well-known techniques. See, e.g., ANTIBODIES: A LABORATORY MANUAL, supra. Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies of the invention may be also be optimized for use in other clinically-suitable applications, for example bead-based multiplex-type assays, such as IGEN, Luminex™ and/or Bioplex™ assay formats, or otherwise optimized for antibody array formats, such as reversed-phase array applications (see, e.g., Paweletz et al., *Oncogene* 20(16): 1981-89 (2001)). Accordingly, in another embodiment, the invention provides a method for the multiplex detection of phosphorylation in a biological sample, the method comprising utilizing two or more antibodies or AQUA peptides of the invention to detect the presence of two or more phosphorylated proteins enumerated in Column A of Table 1/FIG. 2. In an embodiment, two to five antibodies or AQUA peptides of the invention are employed in the method. In another embodiment, six to ten antibodies or AQUA peptides of the invention are employed, while in another embodiment eleven to twenty such reagents are employed.

Antibodies and/or AQUA peptides of the invention may also be employed within a kit that comprises at least one phosphorylation site-specific antibody or AQUA peptide of the invention (which binds to or detects a target signaling protein/polypeptide disclosed in Table 1/FIG. 2), and, optionally, a second antibody conjugated to a detectable group. In some embodies, the kit is suitable for multiplex assays and comprises two or more antibodies or AQUA peptides of the invention, and in some embodiments, comprises two to five, six to ten, or eleven to twenty reagents of the invention. The kit may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the description, numerous specific details are set forth in order to provide a thorough understanding of the present invention. The present invention may be practiced without some or all of these specific details. In other instances, well known process operations have not been described in detail, in order not to unnecessarily obscure the present invention.

The following examples are intended to further illustrate certain embodiments of the invention and are not limiting in nature. Those skilled in the art will recognize, or be able to ascertain, using no more than routine experimentation, numerous equivalents to the specific substances and procedures described herein.

Any suitable materials and/or methods known to those of skill can be utilized in carrying out the present invention. However, materials and methods are described. Materials, reagents and the like to which reference is made in the following description and examples are obtainable from commercial sources, unless otherwise noted.

Example 1

Isolation of Phosphotyrosine-Containing Peptides from Extracts of Cancer Cell Lines and Identification of Novel Phosphorylation Sites IAP isolation techniques were employed to identify phosphotyrosine containing peptides in cell extracts from the following human cancer cell lines, tissues and patient cell lines: 01364548-cll, 223-CLL, 293T, 3T3 TrkB, 3T3-Src, 3T3-TrkA, 3T3-wt, 577, A172, AML-4833, AML-6246, AML-6735, AML-7592, BaF3-10ZF, BaF3-4ZF, BaF3-APR, BaF3-FLT3(D842V), BaF3-FLT3(D842Y), BaF3-FLT3 (K663Q), BaF3-FLT3(WT), BaF3-FLT3/ITD, BaF3-PRTK, BaF3-TDII, BaF3-Tel/FGFR3, Baf3, Baf3-V617F-jak2, Baf3/E255K, Baf3/H396P, Baf3/Jak2(IL-3 dep), Baf3/M35 IT, Baf3/T3151, Baf3/TpoR, Baf3/TpoR-Y98F, Baf3/Tyk2, Baf3/V617F-jak2 (IL-3), Baf3/Y253F, Baf3/cc-TpoR-IV, Baf3/p210wt, CHRF, CI-1, CMK, CTV-1, DMS 53, DND41, DU-528, DU145, ELF-153, EOL-1, GDM-1, H1703, H1734, H1793, H1869, H1944, H1993, H2023, H226, H3255, H358, H520, H82, H838, HCC1428, HCC1435, HCC1806, HCC1937, HCC366, HCC827, HCT116, HEL, HL107B, HL117B, HL131A, HL131B, HL133A, HL53B, HL59b, HL60, HL61a, HL61b, HL66B, HL68A, HL75A, HL84A, HL97B, HL98A, HT29, HU-3, HUVEC, Jurkat, K562, KG-1, KG1-A, KMS11, KMS18, KMS27, KOPT-K1, KY821, Karpas 299, Karpas-1106p, M-07e, M01043, M059K, MC-116, MCF-10A (Y561F), MCF-10A(Y969F), MDA-MB-453, MDA-MB-468, MEC-2, MKPL-1, ML-1, MO-91, MOLT15, MV4-11, Me-F2, Molm 14, Monomac 6, NCI-N87, Nomo-1, OCI-M1, OCI-ly4, OCI-ly8, OCI/AML2, OPM-1, PL21, Pfeiffer, RC-K8, RI-1, SCLC T1, SEM, SK-N-AS, SK-N-MC, SKBR3, SR-786, SU-DHL1, SUP-M2, SUPT-13, SuDHL5, T17, TRE-cll patient, TS, UT-7, VAL, Verona, Verona 1, Verona 4, WSU-NHL, XG2, Z-55, cs001, cs015, cs025, cs041, cs042, gz21, gz68, gz73, gz74, gzB1, hl144b, hl152b, lung tumor T26, lung tumor T57, normal human lung, pancreatic xenograft, patient 1, rat brain and sw480.

Tryptic phosphotyrosine containing peptides were purified and analyzed from extracts of each of the cell lines mentioned above, as follows. Cells were cultured in DMEM medium or RPMI 1640 medium supplemented with 10% fetal bovine serum and penicillin/streptomycin.

Suspension cells were harvested by low speed centrifugation. After complete aspiration of medium, cells were resuspended in 1 mL lysis buffer per $1.25 \times 10^8$ cells (20 mM HEPES pH 8.0, 9 M urea, 1 mM sodium vanadate, supplemented or not with 2.5 mM sodium pyro-phosphate, 1 mM β-glycerol-phosphate) and sonicated.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and soluble TLCK®-trypsin (Worthington® Biochemcial Corporation, Lakewood, N.J.) was added at 10-20 μg/mL. Digestion was performed for 1-2 days at room temperature.

Trifluoroacetic acid (TFA) was added to protein digests to a final concentration of 1%, precipitate was removed by centrifugation, and digests were loaded onto Sep-Pak® $C_{18}$ columns (provided by Waters Corporation, Milford, Mass.) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble material was removed by centrifugation. IAP was performed on each peptide fraction separately. The phosphotyrosine monoclonal antibody P-Tyr-100 (Cell Signaling Technology®, Inc., Danvers, Mass. catalog number 9411) was coupled at 4 mg/ml beads to protein G or protein A agarose (Roche®, Basel, Switzerland), respectively. Immobilized antibody (15 μl, 60 μg) was added as 1:1 slurry in IAP buffer to 1.4 ml of each peptide fraction, and the mixture was incubated overnight at 40° C. with gentle rotation. The immobilized antibody beads were washed three times with 1 ml IAP buffer and twice with 1 ml water, all at 4° C. Peptides were eluted from beads by incubation with 75 μl of 0.1% TFA at room temperature for 10 minutes.

Alternatively, one single peptide fraction was obtained from Sep-Pak C18 columns by elution with 2 volumes each of 10%, 15%, 20%, 25%, 30%, 35% and 40% acetonirile in 0.1% TFA and combination of all eluates. IAP on this peptide fraction was performed as follows: After lyophilization, peptide was dissolved in 1.4 ml IAP buffer (MOPS pH 7.2, mM sodium phosphate, 50 mM NaCl) and insoluble material was removed by centrifugation. Immobilized antibody (40 μl, 160 μg) was added as 1:1 slurry in IAP buffer, and the mixture was incubated overnight at 4° C. with gentle shaking. The immobilized antibody beads were washed three times with 1 ml IAP buffer and twice with 1 ml water, all at 4° C. Peptides were eluted from beads by incubation with 40 μl of 0.15% TFA at room temperature for 10 min (eluate 1), followed by a wash of the beads (eluate 2) with 40 μl of 0.15% TFA. Both eluates were combined.

Analysis by LC-MS/MS Mass Spectrometry.

40 μl or more of IAP eluate were purified by 0.2 μl StageTips (Proxeon, Staermosegaardsvej 6,DK-5230 Odense M, Denmark) or ZipTips® (produced by Millipore®, Billerica Mass.). Peptides were eluted from the microcolumns with 1 μl of 40% MeCN, 0.1% TFA (fractions I and II) or 1 μl of 60% MeCN, 0.1% TFA (fraction III) into 7.6 μl of 0.4% acetic acid/0.005% heptafluorobutyric acid. This sample was loaded onto a 10 cm×75 μm PicoFrit® capillary column (produced by New Objective, Woburn, Mass.) packed with Michrom Magic Bullets® C18 AQ reversed-phase resin (Michrom Bioresources, Auburn Calif.) using a Famos™ autosampler with an inert sample injection valve (Dionex®, Sunnyvale, Calif.). The column was then developed with a 45-min linear gradient of acetonitrile delivered at 200 nl/min (using an Ultimate® pump, Dionex®, Sunnyvale, Calif.), and tandem mass spectra were collected in a data-dependent manner with an LTQ® (produced by Thermo® Finnigan® San, Jose, Calif.), ion trap mass spectrometer essentially as described by Gygi et al., supra.

Database Analysis & Assignments.

MS/MS spectra were evaluated using TurboSequest™ in the Sequest® (owned by Thermo® Finnigan® San Jose, Calif.) Browser package (v. 27, rev. 12) supplied as part of BioWorkS™ 3.0 (Thermo® Finnigan®, San Jose, Calif.). Individual MS/MS spectra were extracted from the raw data file using the Sequest® Browser program CreateDta™ (owned by Thermo® Finnigan® San Jose, Calif.), with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest™ and VuDta™ (owned by Thermo® Finnigan® San Jose, Calif.) programs were not used to further select MS/MS spectra for Sequest® analysis. MS/MS spectra were evaluated with the following TurboSequest™ parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (as released on Aug. 24, 2004 and containing 27, 960 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned. Furthermore, it should be noted that certain peptides were originally isolated in mouse and later normalized to human sequences as shown by Table 1/FIG. 2.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., *Mol. Cell. Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. The following Sequest scoring thresholds were used to select phosphopeptide assignments that are likely to be correct: $RSp<6$, $XCorr \geq 2.2$, and $DeltaCN>0.099$. Further, the assigned sequences could be accepted or rejected with respect to accuracy by using the following conservative, two-step process.

In the first step, a subset of high-scoring sequence assignments should be selected by filtering for XCorr values of at least 1.5 for a charge state of +1, 2.2 for +2, and 3.3 for +3, allowing a maximum RSp value of 10. Assignments in this subset should be rejected if any of the following criteria were satisfied: (i) the spectrum contains at least one major peak (at least 10% as intense as the most intense ion in the spectrum) that can not be mapped to the assigned sequence as an a, b, or y ion, as an ion arising from neutral-loss of water or ammonia from a b or y ion, or as a multiply protonated ion; (ii) the spectrum does not contain a series of b or y ions equivalent to at least six uninterrupted residues; or (iii) the sequence is not observed at least five times in all the studies conducted (except for overlapping sequences due to incomplete proteolysis or use of proteases other than trypsin).

In the second step, assignments with below-threshold scores should be accepted if the low-scoring spectrum shows a high degree of similarity to a high-scoring spectrum collected in another study, which simulates a true reference library-searching strategy.

Example 2

Production of Phospho-Specific Polyclonal Antibodies for the Detection of Target Signal Protein/Polypeptide Phosphorylation Polyclonal antibodies that specifically bind a Target Signal Protein/Polypeptide only when phosphorylated at the respective phosphorylation site disclosed herein (see Table 1/FIG. 2) are produced according to standard methods by first constructing a synthetic peptide antigen comprising the phosphorylation site sequence and then immunizing an animal to raise antibodies against the antigen, as further described below. Production of exemplary polyclonal antibodies is provided below.

A. NCK2 (Tyrosine 50).

An 11 amino acid phospho-peptide antigen, TGy*VPSNYVER (where y*=phosphotyrosine) that corresponds to the sequence encompassing the tyrosine 50 phosphorylation site in human NCK2 adaptor/scaffold protein (see Row 5 of Table 1; SEQ ID NO: 4), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific NCK2 (tyr50) polyclonal antibodies as described in Immunization/Screening below.

B. Securin (Tyrosine 111)

A 15 amino acid phospho-peptide antigen, SSVPASDDAy*PEIEK (where y*=phosphotyrosine) that corresponds to the sequence encompassing the tyrosine 261 phosphorylation site in human securin cell cycle regulation protein (see Row 52 of Table 1 (SEQ ID NO: 51)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific securin (tyr 111) polyclonal antibodies as described in Immunization/Screening below.

C. p47phox (Tyrosine 48)

A 9 amino acid phospho-peptide antigen, FTEIy*EFHK (where y*=phosphotyrosine) that corresponds to the sequence encompassing the tyrosine 48 phosphorylation site in human p47phox enzyme protein (see Row 91 of Table 1 (SEQ ID NO: 92), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific p47phox (tyr48) antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 µg antigen per rabbit). The rabbits are boosted with same antigen in incomplete Freund adjuvant (250 µg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto a non-phosphorylated synthetic peptide antigen-resin Knotes column to pull out antibodies that bind the non-phosphorylated form of the phosphorylation site. The flow through fraction is collected and applied onto a phospho-synthetic peptide antigen-resin column to isolate antibodies that bind the phosphorylated form of the site. After washing the column extensively, the bound antibodies (i.e. antibodies that bind a phosphorylated peptide described in A-C above, but do not bind the non-phosphorylated form of the peptide) are eluted and kept in antibody storage buffer.

The isolated antibody is then tested for phospho-specificity using Western blot assay using an appropriate cell line that expresses (or overexpresses) target phospho-protein (i.e. phosphorylated NCK2, securin or p47phox), for example, MO-91, Jurkat and Nomo-1 cells, respectively. Cells are cultured in DMEM or RPMI supplemented with 10% FCS. Cell are collected, washed with PBS and directly lysed in cell lysis buffer. The protein concentration of cell lysates is then measured. The loading buffer is added into cell lysate and the mixture is boiled at 100° C. for 5 minutes. 20 µl (10 µg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phospho-specific antibody is used at dilution 1:1000. Phosphorylation-site specificity of the antibody will be shown by binding of only the phosphorylated form of the target protein. Isolated phospho-specific polyclonal antibody does not (substantially) recognize the target protein when not phosphorylated at the appropriate phosphorylation site in the non-stimulated cells (e.g. NCK3 is not bound when not phosphorylated at tyrosine 50).

In order to confirm the specificity of the isolated antibody, different cell lysates containing various phosphorylated signal transduction proteins other than the target protein are prepared. The Western blot assay is performed again using these cell lysates. The phospho-specific polyclonal antibody isolated as described above is used (1:1000 dilution) to test reactivity with the different phosphorylated non-target proteins on Western blot membrane. The phospho-specific antibody does not significantly cross-react with other phosphorylated signal transduction proteins, although occasionally slight binding with a highly homologous phosphorylation-site on another protein may be observed. In such case the antibody may be further purified using affinity chromatography, or the specific immunoreactivity cloned by rabbit hybridoma technology.

Example 3

Production of Phospho-Specific Monoclonal Antibodies for the Detection of Target Signal Protein/Polypeptide Phosphorylation Monoclonal antibodies that specifically bind a Target Signal Protein/Polypeptide only when phosphorylated at the respective phosphorylation site disclosed herein (see Table 1/FIG. 2) are produced according to standard methods by first constructing a synthetic peptide antigen comprising the phosphorylation site sequence and then immunizing an animal to raise antibodies against the antigen, and harvesting spleen cells from such animals to produce fusion hybridomas, as further described below. Production of exemplary monoclonal antibodies is provided below.

A. Rap1a (Tyrosine 159)

A 12 amino acid phospho-peptide antigen, IMVNEIFy*DLVR (where y*=phosphotyrosine) that corresponds to the sequence encompassing the tyrosine 159 phosphorylation site in human Rap1a G protein or regulator protein (see Row 151 of Table 1 (SEQ ID NO: 152)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal Rap1a (tyr 159) antibodies as described in Immunization/Fusion/Screening below.

B. PIK3R3 (Tyrosine 184)

An 11 amino acid phospho-peptide antigen, LQEy*HSQYQEK (where y*=phosphotyrosine) that corresponds to the sequence encompassing the tyrosine 184 phosphorylation site in human PIK3R3 kinase (non-protein) (see Row 185 of Table 1 (SEQ ID NO: 186)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal PIK3R3 (tyr184) antibodies as described in Immunization/Fusion/Screening below.

C. PIK4CA (Tyrosine 973)

A 13 amino acid phospho-peptide antigen, DQPy*YDIPDAPYR (where y*=phosphotyrosine) that corresponds to the sequence encompassing the tyrosine 973 phosphorylation site in human PIK4CA kinase (non-protein) (see Row 188 of Table 1 (SEQ ID NO: 189)), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal PIK4CA (tyr973) antibodies as described in Immunization/Fusion/Screening below.

Immunization/Fusion/Screening.

A synthetic phospho-peptide antigen as described in A-C above is coupled to KLH, and BALB/C mice are injected intradermally (ID) on the back with antigen in complete Freunds adjuvant (e.g. 50 µg antigen per mouse). The mice are boosted with same antigen in incomplete Freund adjuvant (e.g. 25 µg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the Rap1a, PIK3R3 or PIK4CA phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target (e.g. PIK4CA phosphorylated at tyrosine 973).

Example 4

Production and Use of AQUA Peptides for the Quantification of Target Signal Protein/Polypeptide Phosphorylation Heavy-isotope labeled peptides (AQUA peptides (internal standards)) for the detection and quantification of a Target Signal Protein/Polypeptide only when phosphorylated at the respective phosphorylation site disclosed herein (see Table 1/FIG. 2) are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the MS$^n$ and LC-SRM signature of the peptide standard is validated, and the AQUA peptide is used to quantify native peptide in a biological sample, such as a digested cell extract. Production and use of exemplary AQUA peptides is provided below.

A. MYH10 (Tyrosine 1415).

An AQUA peptide comprising the sequence, ALAy*DKLEK (y*=phosphotyrosine; sequence incorporating $^{14}C/^{15}N$-labeled leucine (indicated by bold L), which corresponds to the tyrosine 1415 phosphorylation site in human MYH10 motor or contractile protein (see Row 199 in Table 1 (SEQ ID NO: 200)), is constructed according to standard synthesis techniques using, e.g., a Rainin/Protein Technologies, Inc., Symphony peptide synthesizer (see Merrifield, supra.) as further described below in Synthesis & MS/MS Signature. The MYH10 (tyr 1415) AQUA peptide is then spiked into a biological sample to quantify the amount of phosphorylated MYH10 (tyr 1415) in the sample, as further described below in Analysis & Quantification.

B. PPP6C (Tyrosine 261)

An AQUA peptide comprising the sequence LVTVWSAPNy*CYR (y*=phosphotyrosine; sequence incorporating $^{14}C/^{15}N$-labeled leucine (indicated by bold L), which corresponds to the tyrosine 261 phosphorylation site in human PPP6C phosphatase (see Row 222 in Table 1 (SEQ ID NO: 223)), is constructed according to standard synthesis techniques using, e.g., a Rainin/Protein Technologies, Inc., Symphony peptide synthesizer (see Merrifield, supra.) as further described below in Synthesis & MS/MS Signature. The PPP6C (tyr261) AQUA peptide is then spiked into a biological sample to quantify the amount of phosphorylated PPP6C (tyr261) in the sample, as further described below in Analysis & Quantification.

C. PKCT (Tyrosine 545)

An AQUA peptide comprising the sequence TNTFCGTPDy*IAPEILLGQK (y*=phosphotyrosine; sequence incorporating $^{14}C/^{15}N$-labeled phenylalanine (indicated by bold F), which corresponds to the tyrosine 545 phosphorylation site in human G-alpha-s protein kinase (Ser/Thr) (see Row 271 in Table 1 (SEQ ID NO: 272)), is constructed according to standard synthesis techniques using, e.g., a Rainin/Protein Technologies, Inc., Symphony peptide synthesizer (see Merrifield, supra.) as further described below in Synthesis & MS/MS Signature. The PKCT (tyr545) AQUA peptide is then spiked into a biological sample to quantify the amount of phosphorylated PKCT (tyr545) in the sample, as further described below in Analysis & Quantification.

D. PLK1 (Tyrosine 217)

An AQUA peptide comprising the sequence, TLCGTPNy*IAPEVLSK (y*=phosphotyrosine; sequence incorporating $^{14}C/^{15}N$-labeled proline (indicated by bold P), which corresponds to the tyrosine 217 phosphorylation site in human PLK1 receptor/channel/transporter/cell surface protein (see Row 274 in Table 1 (SEQ ID NO: 175)), is constructed according to standard synthesis techniques using, e.g., a Rainin/Protein Technologies, Inc., Symphony peptide synthesizer (see Merrifield, supra.) as further described below in Synthesis & MS/MS Signature. The PLK1 (tyr217) AQUA peptide is then spiked into a biological sample to quantify the amount of phosphorylated PLK1 (tyr217) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Pre-loaded Wang resins may be obtained from Applied Biosystems. Synthesis scales may vary from 5 to 25 µmol. Amino acids are activated in situ with 1-H-benzotriazolium, 1-bis (dimethylamino) methylene]-hexafluorophosphate (1-),3-oxide: 1-hydroxybenzotriazole hydrate and coupled at a 5-fold molar excess over peptide. Each coupling cycle is followed by capping with acetic anhydride to avoid accumulation of one-residue deletion peptide by-products. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g., a phosphorylated protein of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LTQ ion trap or TSQ Quantum triple quadrupole). On the LTQ, parent ions are isolated at 1.6 m/z width, the ion injection time being limited to 100 ms per microscan, with one microscans per peptide, and with an AGC setting of $1\times10^5$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds human signaling protein RSK2 only when phosphorylated at tyrosine 529, comprised within SEQ ID NO. 281, wherein said antibody does not bind said signaling protein RSK2 when not phosphorylated at said tyrosine.

2. An isolated phosphorylation site-specific antibody that specifically binds human signaling protein RSK2 only when not phosphorylated at the tyrosine 529, comprised within SEQ ID NO. 281, wherein said antibody does not bind said signaling protein RSK2 when phosphorylated at tyrosine 529.

* * * * *